(12) United States Patent
Huang et al.

(10) Patent No.: US 7,119,111 B2
(45) Date of Patent: Oct. 10, 2006

(54) 2-OXO-1,3,4-TRIHYDROQUINAZOLINYL DERIVATIVES AND METHODS OF USE

(75) Inventors: Qi Huang, Moorpark, CA (US); Matthew Kaller, Ventura, CA (US); Thomas Nguyen, Thousand Oaks, CA (US); Mark H. Norman, Thousand Oaks, CA (US); Robert Rzasa, Ventura, CA (US); Hui-Ling Wang, Thousand Oaks, CA (US); Wenge Zhong, Thousand Oaks, CA (US)

(73) Assignee: Amgen, Inc., Thousand Oaks, CA (US)

( * ) Notice: Subject to any disclaimer, the term of this patent is extended or adjusted under 35 U.S.C. 154(b) by 164 days.

(21) Appl. No.: 10/446,440

(22) Filed: May 27, 2003

(65) Prior Publication Data

US 2003/0229068 A1   Dec. 11, 2003

Related U.S. Application Data

(60) Provisional application No. 60/384,265, filed on May 29, 2002.

(51) Int. Cl.
*C07D 277/60* (2006.01)
*C07D 487/00* (2006.01)
*A01N 43/78* (2006.01)

(52) U.S. Cl. ............... 514/365; 548/146; 548/182; 548/190; 544/224; 544/242; 544/245; 544/253

(58) Field of Classification Search ............... 548/146, 548/182, 190; 544/224, 242, 245, 253; 514/365
See application file for complete search history.

(56) References Cited

FOREIGN PATENT DOCUMENTS

| EP | A-0569083 | * 4/1993 |
|---|---|---|
| EP | 0 569 083 | 11/1993 |
| WO | WO 00/24744 | 5/2000 |
| WO | WO-01/32649 | * 5/2001 |
| WO | WO 01/38312 | 5/2001 |
| WO | WO 01/38315 | 5/2001 |

OTHER PUBLICATIONS

Catania et al., "Expression and localization of cyclin-dependent kinase 5 in apoptotic human glioma cells", Neuro-Oncology, 3(2):89-98 (2001).
Leeson et al., "4-Amido-2-carboxytetrahydroquinolines. Structure-Activity Relationships for Antagonism at the Glycine Site of the NMDA Receptor", Journal of Medicinal Chemistry, 35:1954-1968 (1992).
Maccioni et al., "The protein kinase Cdk5: Structural aspects, roles in neurogenesis and involvement in Alzheimer's pathology", European Journal of Biochemistry, 268:1518-1527 (2001).
Noguchi et al., "Involvement of Cyclins in Cell Proliferation and Their Clinical Implications in Soft Tissue Smooth Muscle Tumors", American Journal of Pathology, 156(6):2135-2147 (2000).
Paglini et al., "The role of the Cdk5-p35 kinase in neuronal development", European Journal of Biochemistry, 268:1528-1533 (2001).
Senderowicz et al., "Preclinical and Clinical Development of Cyclin-Dependent Kinase Modulators", Journal of the National Cancer Institute, 92(5):376-387 (2000).

* cited by examiner

*Primary Examiner*—James O. Wilson
*Assistant Examiner*—Paul V. Ward
(74) *Attorney, Agent, or Firm*—Banner & Witcoff, Ltd

(57) ABSTRACT

Selected compounds are effective for treatment of diseases, such as cell proliferation or apoptosis mediated diseases. The invention encompasses novel compounds, analogs, prodrugs and pharmaceutically acceptable derivatives thereof, pharmaceutical compositions and methods for prophylaxis and treatment of diseases and other maladies or conditions involving stroke, cancer and the like. The subject invention also relates to processes for making such compounds as well as to intermediates useful in such processes.

24 Claims, No Drawings

```
                              SEQUENCE LISTING

<160> NUMBER OF SEQ ID NOS: 12

<210> SEQ ID NO 1
<211> LENGTH: 45
<212> TYPE: DNA
<213> ORGANISM: Homo sapiens

<400> SEQUENCE: 1
aagcgcgcgg aattcataaa tatggagaac ttccaaaagg tggaa              45

<210> SEQ ID NO 2
<211> LENGTH: 34
<212> TYPE: DNA
<213> ORGANISM: Homo sapiens

<400> SEQUENCE: 2
ctcgacaagc ttattagagt cgaagatggg gtac                          34

<210> SEQ ID NO 3
<211> LENGTH: 62
<212> TYPE: DNA
<213> ORGANISM: Homo sapiens

<400> SEQUENCE: 3
cccgggatct cgagataaat atgcatcatc atcatcattc aagacgaagt agccgtttac    60
aa                                                             62

<210> SEQ ID NO 4
<211> LENGTH: 39
<212> TYPE: DNA
<213> ORGANISM: Homo sapiens

<400> SEQUENCE: 4
cccggtaccg catgcttagt gttttcctgg tggtttttc                     39

<210> SEQ ID NO 5
<211> LENGTH: 23
<212> TYPE: DNA
<213> ORGANISM: Homo sapiens

<400> SEQUENCE: 5
gcgatgcaga aatacgagaa act                                      23

<210> SEQ ID NO 6
<211> LENGTH: 22
<212> TYPE: DNA
```

-continued

<213> ORGANISM: Homo sapiens

<400> SEQUENCE: 6
ccccactgtc tcaccctctc aa                                              22

<210> SEQ ID NO 7
<211> LENGTH: 22
<212> TYPE: DNA
<213> ORGANISM: Homo sapiens

<400> SEQUENCE: 7
cggtgagcgg ttttatccct cc                                              22

<210> SEQ ID NO 8
<211> LENGTH: 31
<212> TYPE: DNA
<213> ORGANISM: Homo sapiens

<400> SEQUENCE: 8
cgggatccat ggcccagccc ccaccggccc a                                    31

<210> SEQ ID NO 9
<211> LENGTH: 26
<212> TYPE: DNA
<213> ORGANISM: Homo sapiens

<400> SEQUENCE: 9
ccaagctttc accgatccag gcctag                                          26

<210> SEQ ID NO 10
<211> LENGTH: 36
<212> TYPE: DNA
<213> ORGANISM: Homo sapiens

<400> SEQUENCE: 10
cgggatccgc caccatgcag aaatacgaga aactgg                               36

<210> SEQ ID NO 11
<211> LENGTH: 27
<212> TYPE: DNA
<213> ORGANISM: Homo sapiens

<400> SEQUENCE: 11
ggactagtct agggcggaca gaagtcg                                         27

<210> SEQ ID NO 12
<211> LENGTH: 24
<212> TYPE: DNA
<213> ORGANISM: Homo sapiens

<400> SEQUENCE: 12
gcattgaatc cttgagccat gacg                                            24

2-OXO-1,3,4-TRIHYDROQUINAZOLINYL DERIVATIVES AND METHODS OF USE

This application claims the benefit of U.S. Provisional Application No. 60/384,265 filed May 29, 2002, which is hereby incorporated by reference.

FIELD OF THE INVENTION

This invention is in the field of pharmaceutical agents and specifically relates to compounds, compositions, uses and methods for treating cell proliferation-related disorders, cell death and apoptosis-related disorders.

BACKGROUND OF THE INVENTION

Identification of therapeutic agents effective in the treatment of neoplastic diseases or for the treatment of neurological disorders is the subject of significant research efforts.

Protein kinases represent a large family of proteins which play a central role in the regulation of a wide variety of cellular processes and maintaining control over cellular function. A partial list of such kinases includes abl, Akt, bcr-abl, Blk, Brk, Btk, c-kit, c-met, c-src, CDK1, CDK2, CDK3, CDK4, CDK5, CDK6, CDK7, CDK8, CDK9, CDK10, cRaf1, CSF1R, CSK, EGFR, ErbB2, ErbB3, ErbB4, Erk, Fak, fes, FGFR1, FGFR2, FGFR3, FGFR4, FGFR5, Fgr, FLK-4, flt-1, Fps, Frk, Fyn, GSK, Hck, IGF-1R, INS-R, Jak, KDR, Lck, Lyn, MEK, p38, PDGFR, PIK, PKC, PYK2, ros, tie, tie2, TRK, Yes, and Zap70. As such, inhibition of kinases has become an important therapeutic target.

Cell proliferation is the rapid reproduction of cells, such as by cell division. The cell cycle, which controls cell proliferation, is itself controlled by a family of serine-threonine kinases called cyclin dependent kinases (CDKs). The regulation of CDK activation is complex, and requires the association of the CDK with a member of the cyclin family of regulatory subunits. A further level of regulation occurs through both activating and inactivating phosphorylations of the CDK subunit. The coordinate activation and inactivation of different cyclin/CDK complexes is necessary for normal progression through the cell cycle. Both the critical G1-S and G2-M transitions are controlled by the activation of different cyclin/CDK activities. Loss of control of CDK regulation is a frequent event in hyperproliferative diseases and cancer. (T. Noguchi et al., Am. J. Pathol., 156, 2135–47 (2000)) As such, inhibition of CDKs have become an important target in the study of chemotherapeutics (A. Senderowicz and E. Sausville, J. Nat. Canc. Instit., 92, 376–87 (2000)).

Kinases have also been implicated in diseases and disorders of the central nervous system. For example, patients suffering from stroke, Alzheimer's disease or Parkinson's disease would benefit from the inhibition of kinases. Cdk5 has been shown to be involved in Alzheimer's pathology (R. Maccioni, et al., Eur. J. Biochem., 268, 1518–27 (2001)) and with neuronal development (G. Paglini and A. Caceres, Eur. J. Biochem., 268, 1528–33 (2001)).

Protein kinases also control programmed cell death, also known as apoptosis. Apoptosis is a ubiquitous physiological process used to eliminate damaged or unwanted cells in multicellular organisms. Disregulation of apoptosis is believed to be involved in the pathogenesis of many human diseases. The failure of apoptotic cell death has been implicated in various cancers, as well as autoimmune disorders. Conversely, increased apoptosis is associated with a variety of diseases involving cell loss such as neurodegenerative disorders and AIDS. As such, inhibition of apoptosis has become an important therapeutic target. Cdk5 has been shown to be involved in apoptosis pathology (A. Catania et al., Neuro-Oncology, 89–98 (April 2001)).

Cyclic ureas are known in the art. 4,4'-Diphenyl-3,4-dihydro-quinazolinone is described in U.S. Pat. No. 4,695,633, issued Sep. 22, 1987. 2-(1,2,3,4-Tetrahydroquinolinyl)-3,4-dihydro-quinazolinones are described by Leeson et al. as NMDA antagonists (J. Med. Chem., 35, 1954–68 (1992)).

However, compounds of the current invention have not been described as inhibitors of cell proliferation or apoptosis such as for the treatment of cancer or stroke.

DESCRIPTION OF THE INVENTION

A class of compounds useful in treating cell proliferative disorders, neurological disorders and apoptosis is defined by Formula I

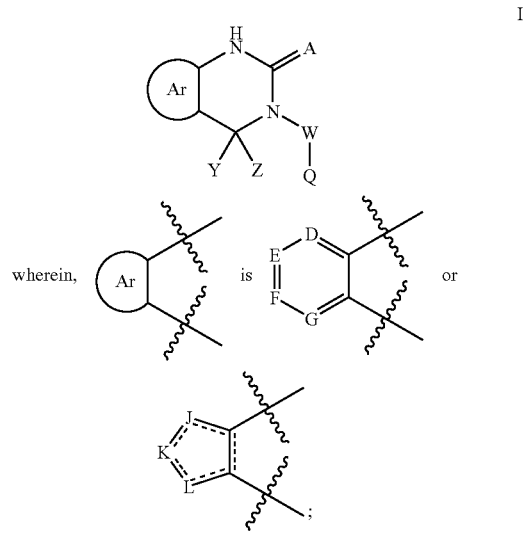

wherein, preferably phenyl, pyridyl and thiazolyl, more preferably phenyl, wherein Ar is optionally substituted with one or more radicals selected from —$OR^5$, alkylenedioxy, halo, optionally substituted aryl, alkenyl, alkynyl, —$NR^5_2$, —$(C_1–C_8)$alkyl-$N(R^5)_2$, —$S(O)_n$—$NR^5R^5$, —$S(O)_n$ $R^5$, $(C_1–C_8)$alkyl, —$(C_1–C_8)$haloalkyl, hydroxy-$(C_1–C_8)$alkyl, optionally substituted $(C_3–C_{10})$cycloalkyl, nitro, cyano, optionally substituted 4–10 membered heterocyclyl, —$C(O)R^5$, —$NR^5SO_2R^5$, —$C(O)N(R^5)_2$, —$CO_2R^5$, optionally substituted arylalkyl, optionally substituted 4–10 membered heterocyclylalkyl, —$NR^5C(O)N(R^5)_2$, —$NR^5C(O)R^5$ and —$NR^5CO_2R^5$, preferably —$OR^5$, halo, optionally substituted phenyl, $C_2–C_6$-alkenyl, $C_2–C_6$-alkynyl, —$N(R^5)_2$, —$(C_1–C_6)$alkyl-$N(R^5)_2$, —$S(O)_n$—$N(R^5)_2$, —$S(O)_nR^5$, $(C_1–C_6)$alkyl, $(C_1–C_4)$haloalkyl, hydroxy-$(C_1–C_4)$alkyl, $(C_3–C_6)$cycloalkyl, nitro, cyano, hydroxy-$(C_1–C_4)$-alkylamino, $(C_1–C_2)$-alkylamino-$(C_1–C_2)$-alkylamino, $(C_1–C_2)$-alkylamino-$(C_1–C_2)$-alkoxy, optionally substituted 4–6 membered heterocyclyl, —$C(O)R^5$, —$NR^5SO_2R^5$, —$C(O)N(R^5)_2$, —$CO_2R^5$, optionally substituted phenyl-$(C_1–C_4)$aminoalkyl, optionally substituted phenyl-$(C_1-C_6)$alkyl, optionally substituted 4–7 membered heterocyclyl-$C_1-C_6$-alkyl, —NR$^5$C(O) N(R$^5$)$_2$, —NR$^5$C(O)R$^5$ and —NR$^5$CO$_2$R$^5$;

more preferably hydroxy, $(C_1-C_4)$alkyl-O—, optionally substituted phenyl-$(C_1-C_4)$alkyl-O—, optionally substituted 4–6 membered heterocyclyl-$(C_1-C_4)$alkyl-O—, optionally substituted phenyl-O—, $C_{1-2}$-alkylenedioxy, halo, optionally substituted phenyl, —NH$_2$, —NR$^{5a}$-$(C_1-C_5)$alkyl, optionally substituted 4–6 membered heterocyclyl-NR$^{5a}$—, optionally substituted 4–6 membered heterocyclyl-$(C_1-C_4)$alkyl-NR$^{5a}$—, optionally substituted $(C_3-C_6)$cycloalkyl-$(C_1-C_4)$alkyl-NR$^{5a}$—, —$(C_1-C_2)$alkyl-NH$_2$, —$(C_1-C_2)$alkyl-NR$^{5a}$—$(C_1-C_2)$alkyl, —SO$_2$NR$^5$R$^5$, $(C_1-C_4)$alkylsulfonyl, $(C_1-C_4)$alkylthio, $(C_1-C_4)$alkyl, $(C_1-C_2)$haloalkyl, hydroxy-$(C_1-C_2)$alkyl, hydroxy-$(C_1-C_4)$-alkylamino, [(($C_1-C_2$)alkyl)$_2$N—$(C_1-C_4)$-alkyl]-NR$^{5a}$—, $(C_1-C_2)$-alkyl-NR$^{5a}$—$(C_1-C_4)$-alkyl-O—, $(C_3-C_6)$cycloalkyl, optionally substituted 4–6 membered heterocyclyl-sulfonyl, optionally substituted heterocyclyl selected from pyrrolidinyl, piperazinyl, piperidinyl, and morpholinyl, —C(O)R$^5$, —NR$^{5a}$SO$_2$R$^5$, —C(O)N(R$^5$)$_2$, —CO$_2$R$^5$, optionally substituted phenyl-$(C_1-C_4)$aminoalkyl, optionally substituted phenyl-$(C_1-C_2)$alkyl, optionally substituted 5–7 membered heterocyclyl-$C_1-C_4$-alkyl, —NR$^{5a}$C(O)R$^5$ and —NR$^{5a}$CO$_2$R$^{5a}$, even more preferably (tert-butoxycarbonyl)amino, cyclopropylmethylamino, 3-hydroxypropylamino, 2-(piperidin-1-yl)ethylamino, 2-(pyrrolidin-1-yl)ethylamino, 2-(morpholin-4-yl)ethylamino, 3-(piperidin-1-yl)propylamino, 3-(pyrrolidin-1-yl)propylamino, 3-(morpholin-4-yl)propylamino, N-methyl-N-(2-piperid-1-ylethyl)amino, N-methyl-N-(2-pyrrolidin-1-ylethyl)amino, N-methyl-N-(2-morpholin-4-ylethyl)amino, ((2S)-2-amino-3-phenylpropyl)amino, 4-methylpiperazin-1-ylamino, 4-methylpiperazin-1-yl, 3-aminopyrrolidin-1-yl, (diethylamino)ethylamino, 3,5-dimethylpiperazin-1-yl, (4-piperidylmethyl)amino, (2-methylbutyl)amino, 2-(dimethylamino)ethoxy, 2-(methylamino)ethoxy, ((2R)pyrrolidin-2-yl)methoxy, ((2R)-1-methylpyrrolidin-2-yl)methoxy, 2-(piperid-1-yl)ethoxy, 2-(piperazin-1-yl)ethoxy, 2-(morpholin-4-yl)ethoxy, 3-(N,N-diethylamino)propoxy, optionally substituted phenoxy, 3-(morpholin-4-yl)propoxy, methylenedioxy, hydroxy, benzyloxy, methoxy, chloro, fluoro, bromo, optionally substituted phenyl, amino, methylamino, diethylamino, aminomethyl, dimethylaminoethyl, N-(N',N'-diethylaminoethyl)-N-methylamino, aminosulfonyl, piperazinylsulfonyl, methylthio, methylsulfonyl, methyl, cyclopropyl, pyrrolidinyl, piperazinyl, 4-methylpiperazinyl, piperidinyl, morpholinyl, methylcarbonyl, phenylcarbonyl, piperidinylcarbonyl, trifluoromethyl, hydroxymethyl, hydroxyethyl, diethylaminocarbonyl, carboxy, methoxycarbonyl, optionally substituted benzyl, 1-azepanylmethyl, (2-methoxymethylpyrrolidin-1-yl)methyl, piperazinylmethyl, 4-methylpiperazinylmethyl, piperidinylmethyl and morpholinylmethyl;

wherein A is O or S, and preferably O;
wherein D is selected from CR$^1$, CR$^2$, CR$^3$, CR$^4$ and N;
wherein E is selected from CR$^1$, CR$^2$, CR$^3$, CR$^4$ and N;
wherein F is selected from CR$^1$, CR$^2$, CR$^3$, CR$^4$ and N;
wherein G is selected from CR$^1$, CR$^2$, CR$^3$, CR$^4$ and N;
wherein J is selected from NR$^6$, S, O, or CR$^1$, CR$^2$, CR$^3$ and CR$^4$;
wherein K is selected from CR$^6$, S, O, or CR$^1$, CR$^2$, CR$^3$ and CR$^4$;
wherein K is selected from NR$^6$, S, O, or CR$^1$, CR$^2$, CR$^3$ and CR$^4$;
wherein Q is selected from H, hydroxy, —N(R$^5$)$_2$, —NR$^5$C(O)R$^5$, —$(C_1-C_8)$alkyl-OR$^5$, —$(C_1-C_8)$alkyl-S(O)$_n$R$^5$,

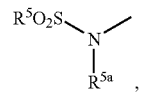

substituted aryl ring, an optionally substituted monocyclic or bicyclic, non-aromatic carbocyclic ring, an optionally substituted monocyclic or bicyclic, heteroaryl and an optionally substituted monocyclic or bicyclic, non-aromatic heterocyclic ring, preferably hydroxy, —N(R$^5$)$_2$, R$^5$SO$_2$—$(C_1-C_6)$alkyl,

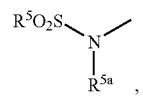

substituted phenyl, substituted or unsubstituted 5–6 membered heteroaryl, substituted or unsubstituted $(C_3-C_6)$cycloalkyl, and substituted or unsubstituted non-aromatic heterocyclyl;

more preferably —N(R$^5$)$_2$, R$^5$SO$_2$—$(C_1-C_3)$alkyl,

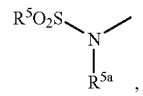

substituted phenyl, and substituted or unsubstituted 5–6-membered heteroaryl;

even more preferably —N(R$^5$)$_2$, R$^{5b}$SO$_2$—$(C_1-C_2)$alkyl,

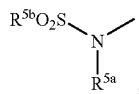

substituted phenyl and substituted or unsubstituted 6 membered heteroaryl;

particularly amino, 6-membered heteroarylamino, R$^{5b}$SO$_2$—$(C_1-C_2)$alkyl,

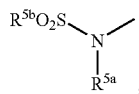

substituted phenyl, and a substituted or unsubstituted ring selected from pyridyl, pyrazinyl, pyrimidinyl and pyridazinyl;

more particularly amino, 2-pyridylamino, 3-pyridylamino, 4-pyridylamino, phenylsulfonylamino, N-methyl-N-(2-pyridylsulfonyl)amino, N-methyl-N-(3-pyridylsulfonyl)amino, N-methyl-N-(4-pyridylsulfonyl)amino, N-methyl-N-(2-thienylsulfonyl)amino, N-methyl-N-(phenylsulfonyl)amino, 2-pyridylsulfonylmethyl, 3-pyridylsulfonylmethyl, 4-pyridylsulfonylmethyl, 2-thienylsulfonylmethyl, phenylsulfonylmethyl, 2-furylmethylsulfonylmethyl, 3-trifluoromethylbenzyl-sulfonylmethyl, methylsulfonylmethyl, tert-butylsulfonylmethyl, 4-fluorophenyl-methylsulfonylmethyl, 4-chlorophenyl-methylsulfonylmethyl, phenyl substituted with one or more substituents selected from H, hydroxyl, chloro, fluoro, methoxy, amino, aminomethyl, methylsulfonyl, methyl, cyano, trifluoromethyl, and pyrrolyl, unsubstituted pyridyl, and pyridyl substituted with one or more substituents selected from chloro, fluoro, $-NH_2$, $-OH$, $-CO_2H$, methylamino, methyl, ethyl, diethylamino, pyrrolidinyl, piperazinyl, piperidinyl, morpholinyl and azetidinyl;

most particularly unsubstituted pyridyl or pyridyl substituted with one or more substituents selected from chloro, fluoro, $-NH_2$, $-OH$, $-CO_2H$, methylamino, methyl, ethyl, diethyl-amino, pyrrolidinyl, piperazinyl, piperidinyl, morpholinyl and azetidinyl;

wherein the aryl ring, carbocyclic ring, heteroaryl ring or heterocyclic rings described for Q are unsubstituted or substituted with one or more groups selected from H, halo, aryl, alkynyl, alkenyl, $-OR^5$, $-N(R^5)_2$, $-(C_1-C_8)$alkyl-$N(R^5)_2$, $-(C_1-C_8)$alkyl-$S(O)_nR^5$, $-N(R^5)_2(C_1-C_8)$alkyl-$N(R^5)_2$, lower alkoxyalkyl, $-S(O)_nR^5$, $-NR^5S(O)_nR^5$, cyano, $(C_1-C_8)$alkyl, lower cyanoalkyl, lower alkylaminoalkoxy, lower aminoalkoxyalkyl $(C_3-C_{10})$cycloalkyl, nitro, optionally substituted 4–7 membered heterocyclyl, optionally substituted phenoxyalkyl, optionally substituted heterocyclyloxyalkyl, $-SO_2NR^5R^5$, $-NR^5SO_2R^5$, $-C(O)N(R^5)_2$, $-CO_2R^5$, $-CO_2NR^5R^5$, $-SO_2NHC(O)R^5$, optionally substituted phenylalkyl, optionally substituted heterocyclylalkyl, $-NR^5C(O)N(R^5)_2$, $-NR^5C(O)R^5$, $-NR^5CO_2R^5$ and $-C(O)R^5$;

preferably H, halo, phenyl, $(C_2-C_6)$-alkynyl, $(C_2-C_6)$-alkenyl, $-OR^5$, $-N(R^5)_2$, $-(C_1-C_8)$alkyl-$N(R^5)_2$, lower alkoxyalkyl, $R^5$-sulfonyl, $R^5$-sulfonyl-$(C_1-C_6)$-alkyl, $(C_1-C_8)$alkyl, cyano, lower cyanoalkyl, lower alkylaminoalkoxy, lower aminoalkoxyalkyl $(C_3-C_{10})$ cycloalkyl, nitro, optionally substituted 4–7 membered heterocyclyl, optionally substituted phenoxyalkyl, optionally substituted heterocyclyloxyalkyl, $-SO_2NR^5R^5$, $-NR^5SO_2R^5$, $-C(O)N(R^5)_2$, $-CO_2R^5$, $-CO_2NR^5R^5$, $-SO_2NHC(O)R^5$, optionally substituted phenylalkyl, optionally substituted heterocyclylalkyl, $-NR^5C(O)N(R^5)_2$, $-NR^5C(O)R^5$, $-NR^5CO_2R^5$ and $-C(O)R^5$;

wherein W is a monocyclic or bicyclic, aromatic heterocyclic ring that is unsubstituted or substituted with one or more groups selected from halo, aryl, cycloalkyl, $-OR^5$, $(C_2-C_8)$alkenyl, $(C_2-C_8)$alkynyl, $-N(R^5)_2$, $-(C_1-C_8)$alkyl-$N(R^5)_2$, $-SO_2NR^5R^5$, $-(C_1-C_8)$alkyl-$SO_2R^5$, $-(C_1-C_8)$alkyl-$SO_2$-$(C_1-C_8)$alkyl-$R^5$, $-(C_1-C_8)$alkyl-$SO_2$-$(C_1-C_8)$aryl, $-(C_1-C_8)$alkyl-$SO_2$-$(C_1-C_8)$heteroaryl, $(C_1-C_8)$alkyl, $(C_3-C_{10})$cycloalkyl, nitro, cyano, optionally substituted 5–6 membered heterocyclyl, formyl, alkylcarbonyl, cycloalkylcarbonyl, heterocyclylcarbonyl, arylcarbonyl, $-NR^5S(O)_nR^5$, $-C(O)N(R^5)_2$, $-CO_2R^5$, optionally substituted phenylalkyl, optionally substituted heterocyclylalkyl, $-NR^5C(O)N(R^5)_2$, $-NR^5C(O)R^5$ and $-NR^5CO_2R^5$;

preferably substituted or unsubstituted 5–6 membered heteroaryl;

more preferably substituted or unsubstituted 5-membered heteroaryl;

even more preferably thienyl, thiazolyl, oxazolyl, imidazolyl, pyrrolyl, furyl, pyrazolyl, isoxazolyl, thiadiazolyl, triazolyl and isothiazolyl;

particularly thiazolyl and thiadiazolyl;

wherein Y is selected from H, $-N(R^{5a})_2$, $-SR^{5a}$, $-OR^{5a}$, and $-C(R^{5a})_3$;

preferably H, and $(C_1-C_3)$alkyl; and more preferably H;

wherein Z is selected from H, $-N(R^{5a})_2$, $-SR^{5a}$, $-OR^{5a}$, and $-C(R^{5a})_3$;

preferably H, $-N(R^{5a})_2$, $-OR^{5a}$, and $(C_1-C_3)$alkyl;

more preferably H and $(C_1-C_3)$alkyl; and even more preferably H;

wherein n is 0, 1 or 2;

preferably 2;

wherein $R^1$, $R^2$, $R^3$, and $R^4$ are independently selected from H, $-OR^5$, halo, aryl, alkenyl, alkynyl, $-NR^5_2$, $-(C_1-C_8)$alkyl-$N(R^5)_2$, $-S(O)_n-NR^5R^5$, $-S(O)_nR^5$, $(C_1-C_8)$alkyl, $(C_3-C_{10})$cycloalkyl, nitro, cyano, optionally substituted 4–10 membered heterocyclyl, $-C(O)R^5$, $-NR^5SO_2R^5$, $-C(O)N(R^5)_2$, $-CO_2R^5$, optionally substituted arylalkyl, optionally substituted 4–10 membered heterocyclylalkyl, $-NR^5C(O)N(R^5)_2$, $-NR^5C(O)R^5$ and $-NR^5CO_2R^5$; wherein $R^1$ and $R^2$ may be joined to form a 5–10 membered saturated or unsaturated carbocyclic or heterocyclic ring; wherein $R^2$ and $R^3$ may be joined to form a 5–10 membered saturated or unsaturated carbocyclic or heterocyclic ring; or wherein $R^3$ and $R^4$ may be joined to form a 5–10 membered saturated or unsaturated carbocyclic or heterocyclic ring;

wherein $R^5$ is independently selected from H, lower alkyl, lower aminoalkyl optionally substituted with optionally substituted phenyl, optionally substituted aryl, optionally substituted arylalkyl, optionally substituted heterocyclyl, optionally substituted heterocyclylalkyl, optionally substituted $C_3-C_6$ cycloalkyl, optionally substituted $C_3-C_6$ cycloalkyl-alkyl, and lower haloalkyl;

preferably H, $(C_1-C_6)$alkyl, $(C_1-C_6)$aminoalkyl optionally substituted with optionally substituted phenyl, optionally substituted phenyl, optionally substituted phenyl-$(C_1-C_4)$alkyl, optionally substituted 4–10 membered heterocyclyl, optionally substituted 4–10 membered heterocyclyl-$(C_1-C_4)$alkyl, optionally substituted $C_3-C_6$ cycloalkyl, optionally substituted $C_3-C_6$ cycloalkyl-$(C_1-C_4)$alkyl, and $(C_1-C_4)$haloalkyl;

more preferably H, $(C_1-C_6)$alkyl, $(C_1-C_6)$aminoalkyl optionally substituted with phenyl, optionally substituted $C_3-C_6$ cycloalkyl, $C_3-C_6$ cycloalkyl-$(C_1-C_4)$alkyl, optionally substituted phenyl, optionally substituted phenyl-$(C_1-C_3)$alkyl, optionally substituted 4–6 membered heterocyclyl-$(C_1-C_4)$alkyl, $(C_1-C_2)$haloalkyl, and optionally substituted 4–6 membered heterocyclyl;

even more preferably H, methyl, ethyl, propyl, tert-butyl, 2-methylbutyl, cyclopropyl, cyclopentyl, cyclobutyl, cyclohexyl, phenyl, benzyl, phenylethyl, 2-amino-3-phenylpropyl, cyclopropylmethyl, 4-piperidylmethyl, -(1-methylpyrrolidin-2-yl)methyl, (pyrrolidin-2-yl)methyl, piperidinylethyl, (pyrrolidin-1-yl)ethyl, (morpholin-4-yl)ethyl, piperidinylpropyl, (pyrrolidin-1-yl)propyl, (morpholin-4-yl)propyl, trifluoromethyl, 2-furylmethyl, pyridyl, 2-thienyl, piperazinyl, 3,5-dimethylpiperazin-1-yl, 3-aminopyrrolidin-1-yl and 4-methylpiperazin-1-yl;

wherein $R^{5a}$ is independently selected from H and $(C_1–C_6)$alkyl;
  preferably H, and $(C_1–C_2)$alkyl;
    more preferably H or methyl;

wherein $R^{5b}$ is independently selected from optionally substituted heteroaryl, optionally substituted phenyl, optionally substituted heteroaryl-$(C_1–C_4)$alkyl, optionally substituted phenyl-$(C_1–C_4)$alkyl and $(C_1–C_6)$alkyl;
  preferably optionally substituted 5–6 membered heteroaryl, optionally substituted phenyl, optionally substituted 5–6 membered heteroaryl-$(C_1–C_2)$alkyl, optionally substituted phenyl-$(C_1–C_2)$alkyl, and $(C_1–C_4)$alkyl;
    more preferably optionally substituted thienyl, optionally substituted pyridyl, optionally substituted phenyl, optionally substituted furylmethyl, optionally substituted benzyl, methyl and tert-butyl;

wherein $R^6$ is selected from H, $(C_1–C_2)$alkyl, and a lone pair of electrons;

wherein each alkyl, aryl, heteroaryl, heterocyclyl, cycloalkyl, alkynyl, alkynyl, and alkoxy moiety of any $R^1$, $R^2$, $R^3$, $R^4$, or $R^5$ can optionally join with another adjacent or vicinal $R^1$, $R^2$, $R^3$, $R^4$, or $R^5$ to form a 3–7 membered ring; and wherein each aryl, heteroaryl, cycloalkyl, and heterocyclyl, moiety of any $R^1$, $R^2$, $R^3$, $R^4$, $R^5$, Q and W is optionally substituted with one or more groups selected from halo, —$NH_2$, —OH, —$CO_2H$, $(C_1–C_4)$alkylamino, $(C_1–C_6)$alkoxy, $(C_1–C_6)$alkoxyalkyl, $(C_1–C_4)$alkyl, di$(C_1–C_4)$alkylamino, phenyl and heterocyclyl;
  preferably halo, —$NH_2$, —OH, —$CO_2H$, $(C_1–C_4)$alkylamino, $(C_1–C_4)$alkyl, di$(C_1–C_4)$alkylamino, $(C_1–C_2)$alkoxy, $(C_1–C_2)$alkoxyalkyl, pyrrolidinyl, piperazinyl, piperidinyl, morpholinyl, and azetidinyl;
    more preferably chloro, fluoro, —$NH_2$, —OH, —$CO_2H$, $(C_1–C_2)$alkylamino, $(C_1–C_2)$alkyl, di$(C_1–C_2)$alkylamino, methoxymethyl, pyrrolidinyl, piperazinyl, piperidinyl, morpholinyl, and azetidinyl;

and pharmaceutically acceptable derivatives thereof;
provided Q is not pyridinium; further provided the compound is not 3-(2-pyridin-3-yl-thiazol-4-yl)-3,4-dihydro-1H-quinazolin-2-one or 6-methyl-3-(2-pyridin-2-yl-thiazol-4-yl)-3,4-dihydro-1H-quinazolin-2-one.

The invention also relates to compounds of Formula I wherein W is

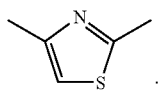

The invention also relates to compounds of Formula II

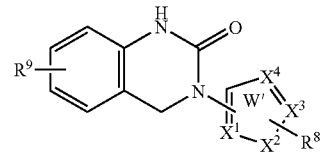

II wherein $X^1$ is C, $CR^{10}$ or N; wherein $X^2$ is selected from NH, $N(CH_3)$, S and O; wherein $X^3$ is C, $CR^{10}$ or N; wherein $X^4$ is C, $CR^{10}$ or N; provided at least one of $X^1$, $X^2$, $X^3$ and $X^4$ is not N, NH or $N(CH_3)$;
preferably $X^2$ is S;

wherein $R^8$ is selected from —$N(R^{11})_2$, $R^{11}S(O)_n$—$(C_1–C_8)$alkyl,

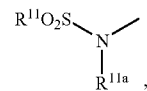

substituted phenyl, optionally substituted pyridyl, optionally substituted pyrazinyl, optionally substituted pyrimidinyl and optionally substituted pyridazinyl;
preferably amino, 2-pyridylamino, 3-pyridylamino, 4-pyridylamino, phenylsulfonylamino, N-methyl-N-(2-pyridylsulfonyl)amino, N-methyl-N-(3-pyridylsulfonyl)amino, N-methyl-N-(4-pyridylsulfonyl)amino, N-methyl-N-(2-thienylsulfonyl)amino, N-methyl-N-(phenylsulfonyl)amino, 2-pyridylsulfonylmethyl, 3-pyridylsulfonylmethyl, 4-pyridylsulfonylmethyl, 2-thienylsulfonylmethyl, phenylsulfonylmethyl, 2-furylmethylsulfonylmethyl, 3-trifluoromethylphenylmethylsulfonylmethyl, methylsulfonylmethyl, tert-butylsulfonylmethyl, 4-fluorophenyl-methylsulfonylmethyl, 4-chlorophenyl-methylsulfonylmethyl, unsubstituted phenyl, phenyl substituted with one or more substituents selected from hydroxyl, chloro, fluoro, methoxy, amino, aminomethyl, methylsulfonyl, methyl, cyano, trifluoromethyl, and pyrrolyl,
unsubstituted 4-pyridyl, and
4-pyridyl substituted with one or more substituents selected from chloro, fluoro, —$NH_2$, —OH, —$CO_2H$, methylamino, methyl, ethyl, diethylamino, pyrrolidinyl, piperazinyl, piperidinyl, morpholinyl and azetidinyl;

wherein $R^9$ is one or more radicals selected from H, hydroxy, $(C_1–C_4)$alkyl-O—, optionally substituted phenyl-$C_1–C_4)$alkyl-O—, optionally substituted 4–6 membered heterocyclyl-$(C_1–C_4)$alkyl-O—, optionally substituted phenyl-O—, $C_{1-2}$-alkylenedioxy, halo, optionally substituted phenyl, —$NH_2$, —$NR^{11a}$—$(C_1–C_5)$alkyl, optionally substituted 4–6 membered heterocyclyl-$NR^{11a}$—, optionally substituted 4–6 membered heterocyclyl-$(C_1–C_4)$alkyl-$NR^{11a}$—, optionally substituted $(C_3–C_6)$cycloalkyl-$(C_1–C_4)$alkyl-$NR^{11a}$—, —$(C_1–C_2)$alkyl-$NH_2$, —$(C_1–C_2)$alkyl-$NR^{11a}$—$(C_1–C_2)$alkyl, —$SO_2NR^{11}R^{11}$, $(C_1–C_4)$alkylsulfonyl, $(C_1–C_4)$alkylthio, $(C_1–C_4)$alkyl, $(C_1–C_2)$haloalkyl, hydroxy-$(C_1–C_2)$alkyl, hydroxy-$(C_1–C_4)$-alkylamino, [(($C_1–C_2)$alkyl)$_2$N—$(C_1–C_4)$-alkyl]-$NR^{11a}$—, $(C_1–C_2)$-alkyl$NR^{11a}$—$(C_1–C_4)$-alkyl-O—, $(C_3–C_6)$cycloalkyl, optionally substituted 4–6 membered heterocyclyl-sulfonyl, optionally substituted heterocyclyl selected from pyrrolidinyl, piperazinyl, piperidinyl, and morpholinyl, —C(O)R$^{11}$, —NR$^{11a}$SO$_2$R$^{11}$, —C(O)N(R$^{11}$)$_2$, —CO$_2$R$^{11}$, optionally substituted phenyl-(C$_1$–C$_4$)aminoalkyl, optionally substituted phenyl-(C$_1$–C$_2$)alkyl, optionally substituted 5–7 membered heterocyclyl-C$_1$–C$_4$-alkyl, —NR$^{11a}$C(O)R$^{11}$ and —NR$^{11a}$CO$_2$R$^{11a}$;

preferably H, (tert-butoxycarbonyl)amino, cyclopropylmethylamino, 3-hydroxypropylamino, 2-(piperidin-1-yl)ethylamino, 2-(pyrrolidin-1-yl)ethylamino, 2-(morpholin-4-yl)ethylamino, 3-(piperidin-1-yl)propylamino, 3-(pyrrolidin-1-yl)propylamino, 3-(morpholin-4-yl)propylamino, N-methyl-N-(2-piperid-1-ylethyl)amino, N-methyl-N-(2-pyrrolidin-1-ylethyl)amino, N-methyl-N-(2-morpholin-4-ylethyl)amino, ((2S)-2-amino-3-phenylpropyl)amino, 4-methylpiperazin-1-ylamino, 4-methylpiperazin-1-yl, 3-aminopyrrolidin-1-yl, (diethylamino)ethylamino, 3,5-dimethylpiperazin-1-yl, (4-piperidylmethyl)amino, (2-methylbutyl)amino, 2-(dimethylamino)ethoxy, 2-(methylamino)ethoxy, ((2R)pyrrolidin-2-yl)methoxy, ((2R)-1-methylpyrrolidin-2-yl)methoxy, 2-(piperid-1-yl)ethoxy, 2-(piperazin-1-yl)ethoxy, 2-morpholin-4-ylethoxy, 3-(N,N-diethylamino)propoxy, optionally substituted phenoxy, 3-(morpholin-4-yl)propoxy, methylenedioxy, hydroxy, benzyloxy, methoxy, chloro, fluoro, bromo, optionally substituted phenyl, amino, methylamino, diethylamino, aminomethyl, dimethylaminoethyl, N-(N',N'-diethylaminoethyl)-N-methylamino, aminosulfonyl, piperazinylsulfonyl, methylthio, methylsulfonyl, methyl, cyclopropyl, pyrrolidinyl, piperazinyl, 4-methylpiperazinyl, piperidinyl, morpholinyl, methylcarbonyl, phenylcarbonyl, piperidinylcarbonyl, trifluoromethyl, hydroxymethyl, hydroxyethyl, diethylaminocarbonyl, carboxy, methoxycarbonyl, optionally substituted benzyl, 1-azepanylmethyl, (2-methoxymethylpyrrolidin-1-yl)methyl, piperazinylmethyl, 4-methylpiperazinylmethyl, piperidinylmethyl, and morpholinylmethyl;

wherein R$^{10}$ is selected from H, halo, aryl, cycloalkyl, —OR$^{11}$, (C$_2$–C$_8$)alkenyl, (C$_2$–C$_8$)alkynyl, —N(R$^{11}$)$_2$, —(C$_1$–C$_8$)alkyl-N(R$^{11}$)$_2$, —SO$_2$NR$^{11}$R$^{11}$, (C$_1$–C$_8$)alkyl, cycloalkylalkyl, nitro, cyano, heteroaryl, optionally substituted 5–6 membered heterocyclyl, formyl, alkylcarbonyl, cycloalkylcarbonyl, arylcarbonyl, heterocyclylcarbonyl, —NR$^{11a}$SO$_2$R$^{11}$, optionally substituted phenylalkyl, optionally substituted heteroarylalkyl, —NR$^{11a}$C(O)N(R$^{11}$)$_2$, —NR$^{11a}$C(O)R$^{11}$ and —NR$^{11a}$CO$_2$R$^{11}$;

preferably H;

wherein n is 0, 1 or 2;

wherein each R$^{11}$ is independently selected from H, (C$_1$–C$_6$)alkyl, C$_1$–C$_6$)aminoalkyl optionally substituted with optionally substituted phenyl, optionally substituted phenyl, optionally substituted phenyl-(C$_1$–C$_4$)alkyl, optionally substituted 4–6 membered heterocyclyl, optionally substituted 4–6 membered heterocyclyl-(C$_1$–C$_4$)alkyl, (C$_3$–C$_6$)cycloalkyl, (C$_3$–C$_6$)cycloalkyl-(C$_1$–C$_4$)alkyl and (C$_1$–C$_2$)haloalkyl;

preferably H, methyl, ethyl, propyl, tert-butyl, 2-methylbutyl, cyclopropyl, cyclopentyl, cyclobutyl, cyclohexyl, phenyl, benzyl, phenylethyl, 2-amino-3-phenylpropyl, cyclopropylmethyl, 4-piperidylmethyl, -(1-methylpyrrolidin-2-yl)methyl, (pyrrolidin-2-yl)methyl, piperidinylethyl, (pyrrolidin-1-yl)ethyl, (morpholin-4-yl)ethyl, piperidinylpropyl, (pyrrolidin-1-yl)propyl, (morpholin-4-yl)propyl, trifluoromethyl, 2-furylmethyl, pyridyl, 2-thienyl, piperazinyl, 3,5-dimethylpiperazin-1-yl, 3-aminopyrrolidin-1-yl and 4-methylpiperazin-1-yl; and wherein each R$^{11a}$ is independently is selected from H and methyl;

and pharmaceutically acceptable derivatives thereof;

provided the compound is not 3-(2-pyridin-3-yl-thiazol-4-yl)-3,4-dihydro-1H-quinazolin-2-one or 6-methyl-3-(2-pyridin-2-yl-thiazol-4-yl)-3,4-dihydro-1H-quinazolin-2-one.

The invention also relates to compounds of Formula IIa and IIb

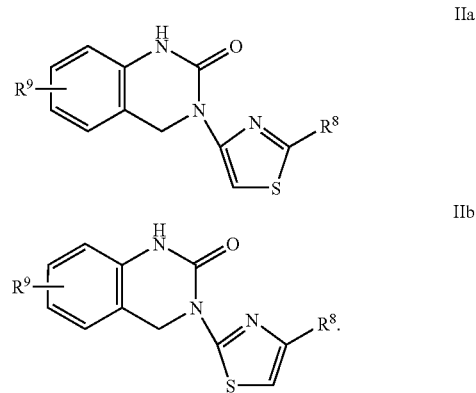

The invention also relates to compounds of Formula III

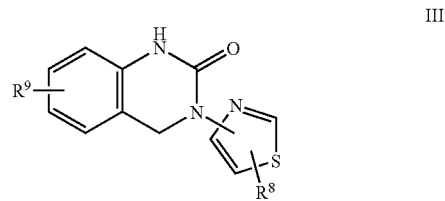

wherein the thiazole ring is substituted with R$^8$ in either positions 2 or 4;

wherein R$^8$ is selected from pyridyl, pyrazinyl, pyrimidinyl and pyridazinyl; wherein R$^8$ is unsubstituted or substituted with one or more substituents selected from chloro, fluoro, —NH$_2$, —OH, —CO$_2$H, (C$_1$–C$_2$)alkylamino, (C$_1$–C$_2$)alkyl, di(C$_1$–C$_2$)alkylamino, (C$_1$–C$_2$)alkylamino(C$_1$–C$_2$)alkyl, hydroxy-(C$_1$–C$_2$)alkylamino, 5–6-membered heterocyclyloxy, 5–6-membered heterocyclyl-(C$_1$–C$_2$)alkoxy, (C$_1$–C$_2$)alkoxy, phenyl, pyrrolidinyl, piperazinyl, piperidinyl, morpholinyl and azetidinyl;

preferably unsubstituted 4-pyridyl, and 4-pyridyl substituted with one or more substituents selected from chloro, fluoro, —NH$_2$, —OH, —CO$_2$H, methylamino, methyl, ethyl, diethyl-amino, pyrrolidinyl, piperazinyl, piperidinyl, morpholinyl and azetidinyl;

wherein R$^9$ is one or more radicals selected from H, hydroxy, (C$_1$–C$_4$)alkyl-O—, optionally substituted phenyl-C$_1$–C$_4$)alkyl-O—, optionally substituted 4–6 membered heterocyclyl-(C$_1$–C$_4$)alkyl-O—, optionally substituted phenyl-O—, C$_{1-2}$-alkylenedioxy, halo, optionally substituted phenyl, —NH$_2$, —NR$^{11a}$—

($C_1$–$C_5$)alkyl, optionally substituted 4–6 membered heterocyclyl-$NR^{11a}$—, optionally substituted 4–6 membered heterocyclyl-($C_1$–$C_4$)alkyl-$NR^{11a}$—, optionally substituted ($C_3$–$C_6$)cycloalkyl-($C_1$–$C_4$) alkyl-$NR^{11a}$—, —($C_1$–$C_2$)alkyl-$NH_2$, —($C_1$–$C_2$)alkyl-$NR^{11a}$—($C_1$–$C_2$)alkyl, —$SO_2NR^{11}R^{11}$, ($C_1$–$C_4$)alkylsulfonyl, ($C_1$–$C_4$)alkylthio, ($C_1$–$C_4$)alkyl, ($C_1$–$C_2$) haloalkyl, hydroxy-($C_1$–$C_2$)alkyl, hydroxy-($C_1$–$C_4$)-alkylamino, [(($C_1$–$C_2$)alkyl)$_2$N—($C_1$–$C_4$)-alkyl]-$NR^{11a}$—, ($C_1$–$C_2$)-alkyl$NR^{11a}$—($C_1$–$C_4$)-alkyl-O—, ($C_3$–$C_6$)cycloalkyl, optionally substituted 4–6 membered heterocyclyl-sulfonyl, optionally substituted heterocyclyl selected from pyrrolidinyl, piperazinyl, piperidinyl, and morpholinyl, —C(O)$R^{11}$, —$NR^{11a}SO_2R^{11}$, —C(O)N($R^{11}$)$_2$, —$CO_2R^{11}$, optionally substituted phenyl-($C_1$–$C_4$)aminoalkyl, optionally substituted phenyl-($C_1$–$C_2$)alkyl, optionally substituted 5–7 membered heterocyclyl-$C_1$–$C_4$-alkyl, —$NR^{11a}$C(O)$R^{11}$ and —$NR^{11a}CO_2R^{11a}$;

preferably H, (tert-butoxycarbonyl)amino, cyclopropylmethylamino, 3-hydroxypropylamino, 2-(piperidin-1-yl) ethylamino, 2-(pyrrolidin-1-yl)ethylamino, 2-(morpholin-4-yl)ethylamino, 3-(piperidin-1-yl)propylamino, 3-(pyrrolidin-1-yl)propylamino, 3-(morpholin-4-yl) propylamino, N-methyl-N-(2-piperid-1-ylethyl)amino, N-methyl-N-(2-pyrrolidin-1-ylethyl)amino, N-methyl-N-(2-morpholin-4-ylethyl)amino, ((2S)-2-amino-3-phenylpropyl)amino, 4-methylpiperazin-1-ylamino, 4-methylpiperazin-1-yl, 3-aminopyrrolidin-1-yl, (diethylamino)ethylamino, 3,5-dimethylpiperazin-1-yl, (4-piperidylmethyl)amino, (2-methylbutyl)amino, 2-(dimethylamino)ethoxy, 2-(methylamino)ethoxy, ((2R)pyrrolidin-2-yl)methoxy, ((2R)-1-methylpyrrolidin-2-yl)methoxy, 2-(piperid-1-yl)ethoxy, 2-(piperazin-1-yl)ethoxy, 2-morpholin-4-ylethoxy, 3-(N,N-diethylamino)propoxy, optionally substituted phenoxy, 3-(morpholin-4-yl)propoxy, methylenedioxy, hydroxy, benzyloxy, methoxy, chloro, fluoro, bromo, optionally substituted phenyl, amino, methylamino, diethylamino, aminomethyl, dimethylaminoethyl, N-(N',N'-diethylaminoethyl)-N-methylamino, aminosulfonyl, piperazinylsulfonyl, methylthio, methylsulfonyl, methyl, cyclopropyl, pyrrolidinyl, piperazinyl, 4-methylpiperazinyl, piperidinyl, morpholinyl, methylcarbonyl, phenylcarbonyl, piperidinylcarbonyl, trifluoromethyl, hydroxymethyl, hydroxyethyl, diethylaminocarbonyl, carboxy, methoxycarbonyl, optionally substituted benzyl, 1-azepanylmethyl, (2-methoxymethylpyrrolidin-1-yl)methyl, piperazinylmethyl, 4-methylpiperazinylmethyl, piperidinylmethyl, and morpholinylmethyl;

wherein each $R^{11}$ is independently selected from H, ($C_1$–$C_6$)alkyl, $C_1$–$C_6$aminoalkyl optionally substituted with optionally substituted phenyl, optionally substituted phenyl, optionally substituted phenyl-($C_1$–$C_4$) alkyl, optionally substituted 4–6 membered heterocyclyl, optionally substituted 4–6 membered heterocyclyl-($C_1$–$C_4$)alkyl, ($C_3$–$C_6$)cycloalkyl, ($C_3$–$C_6$)cycloalkyl-($C_1$–$C_4$)alkyl and ($C_1$–$C_2$)haloalkyl;

preferably H, methyl, ethyl, propyl, tert-butyl, 2-methylbutyl, cyclopropyl, cyclopentyl, cyclobutyl, cyclohexyl, phenyl, benzyl, phenylethyl, 2-amino-3-phenylpropyl, cyclopropylmethyl, 4-piperidylmethyl, -(1-methylpyrrolidin-2-yl)methyl, (pyrrolidin-2-yl)methyl, piperidinylethyl, (pyrrolidin-1-yl)ethyl, (morpholin-4-yl)ethyl, piperidinylpropyl, (pyrrolidin-1-yl)propyl, (morpholin-4-yl)propyl, trifluoromethyl, 2-furylmethyl, pyridyl, 2-thienyl, piperazinyl, 3,5-dimethylpiperazin-1-yl, 3-aminopyrrolidin-1-yl and 4-methylpiperazin-1-yl; and wherein each $R^{11a}$ is independently selected from H and methyl;

wherein each phenyl, cycloalkyl, and heterocyclyl moiety is optionally substituted with one or more groups selected from halo, —$NH_2$, —OH, —$CO_2H$, ($C_1$–$C_4$) alkylamino, ($C_1$–$C_4$)alkyl, di($C_1$–$C_4$)alkylamino, ($C_1$–$C_4$)haloalkyl, pyrrolidinyl, piperazinyl, piperidinyl, morpholinyl, and azetidinyl;

and pharmaceutically acceptable derivatives thereof;

provided the compound is not 3-(2-pyridin-3-yl-thiazol-4-yl)-3,4-dihydro-1H-quinazolin-2-one or 6-methyl-3-(2-pyridin-2-yl-thiazol-4-yl)-3,4-dihydro-1H-quinazolin-2-one.

The invention also relates to compounds of Formula IIIa and IIIb

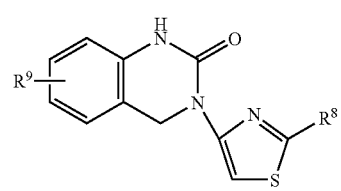

IIIa

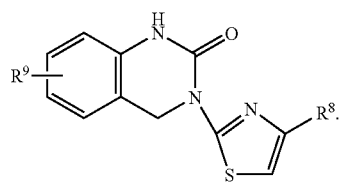

IIIb

The invention also relates to compounds of Formula IV

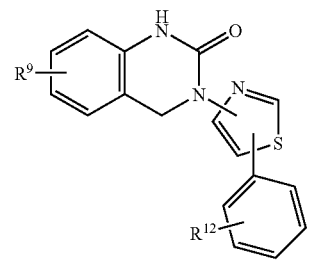

IV wherein the thiazole ring is substituted with the phenyl substituent in positions 2 or 4;

wherein $R^9$ is one or more radicals selected from H, hydroxy, ($C_1$–$C_4$)alkyl-O—, optionally substituted phenyl-$C_1$–$C_4$)alkyl-O—, optionally substituted 4–6 membered heterocyclyl-($C_1$–$C_4$)alkyl-O—, optionally substituted phenyl-O—, $C_{1-2}$-alkylenedioxy, halo, optionally substituted phenyl, —$NH_2$, —$NR^{11a}$—($C_1$–$C_5$)alkyl, optionally substituted 4–6 membered heterocyclyl-$NR^{11a}$—, optionally substituted 4–6 membered heterocyclyl-($C_1$–$C_4$)alkyl-$NR^{11a}$—, optionally substituted ($C_3$–$C_6$)cycloalkyl-($C_1$–$C_4$) alkyl-$NR^{11a}$—, —($C_1$–$C_2$)alkyl-$NH_2$, —($C_1$–$C_2$)alkyl-$R^{11a}$—($C_1$–$C_2$)alkyl, —$SO_2NR^{11}R^{11}$, ($C_1$–$C_4$)alkylsulfonyl, ($C_1$–$C_4$)alkylthio, ($C_1$–$C_4$)alkyl, ($C_1$–$C_2$)

haloalkyl, hydroxy-(C$_1$–C$_2$)alkyl, hydroxy-(C$_1$–C$_4$)-alkylamino, [((C$_1$–C$_2$)alkyl)$_2$N—(C$_1$–C$_4$)-alkyl]-NR$^{11a}$—, (C$_1$–C$_2$)-alkylNR$^{11a}$—(C$_1$–C$_4$)-alkyl-O—, (C$_3$–C$_6$)cycloalkyl, optionally substituted 4–6 membered heterocyclyl-sulfonyl, optionally substituted heterocyclyl selected from pyrrolidinyl, piperazinyl, piperidinyl, and morpholinyl, —C(O)R$^{11}$, —NR$^{11a}$SO$_2$R$^{11}$, —C(O)N(R$^{11}$)$_2$, —CO$_2$R$^{11}$, optionally substituted phenyl-(C$_1$–C$_4$)aminoalkyl, optionally substituted phenyl-(C$_1$–C$_2$)alkyl, optionally substituted 5–7 membered heterocyclyl-C$_1$–C$_4$-alkyl, —NR$^{11a}$C(O)R$^{11}$ and —NR$^{11a}$CO$_2$R$^{11a}$;

preferably H, (tert-butoxycarbonyl)amino, cyclopropylmethylamino, 3-hydroxypropylamino, 2-(piperidin-1-yl)ethylamino, 2-(pyrrolidin-1-yl)ethylamino, 2-(morpholin-4-yl)ethylamino, 3-(piperidin-1-yl)propylamino, 3-(pyrrolidin-1-yl)propylamino, 3-(morpholin-4-yl)propylamino, N-methyl-N-(2-piperid-1-ylethyl)amino, N-methyl-N-(2-pyrrolidin-1-ylethyl)amino, N-methyl-N-(2-morpholin-4-ylethyl)amino, ((2S)-2-amino-3-phenylpropyl)amino, 4-methylpiperazin-1-ylamino, 4-methylpiperazin-1-yl, 3-aminopyrrolidin-1-yl, (diethylamino)ethylamino, 3,5-dimethylpiperazin-1-yl, (4-piperidylmethyl)amino, (2-methylbutyl)amino, 2-(dimethylamino)ethoxy, 2-(methylamino)ethoxy, ((2R)pyrrolidin-2-yl)methoxy, ((2R)-1-methylpyrrolidin-2-yl)methoxy, 2-(piperid-1-yl)ethoxy, 2-(piperazin-1-yl)ethoxy, 2-morpholin-4-ylethoxy, 3-(N,N-diethylamino)propoxy, optionally substituted phenoxy, 3-(morpholin-4-yl)propoxy, methylenedioxy, hydroxy, benzyloxy, methoxy, chloro, fluoro, bromo, optionally substituted phenyl, amino, methylamino, diethylamino, aminomethyl, dimethylaminoethyl, N-(N',N'-diethylaminoethyl)-N-methylamino, aminosulfonyl, piperazinylsulfonyl, methylthio, methylsulfonyl, methyl, cyclopropyl, pyrrolidinyl, piperazinyl, 4-methylpiperazinyl, piperidinyl, morpholinyl, methylcarbonyl, phenylcarbonyl, piperidinylcarbonyl, trifluoromethyl, hydroxymethyl, hydroxyethyl, diethylaminocarbonyl, carboxy, methoxycarbonyl, optionally substituted benzyl, 1-azepanylmethyl, (2-methoxymethylpyrrolidin-1-yl)methyl, piperazinylmethyl, 4-methylpiperazinylmethyl, piperidinylmethyl, and morpholinylmethyl;

wherein each R$^{11}$ is independently selected from H, (C$_1$–C$_6$)alkyl, C$_1$–C$_6$)aminoalkyl optionally substituted with optionally substituted phenyl, optionally substituted phenyl, optionally substituted phenyl-(C$_1$–C$_4$)alkyl, optionally substituted 4–6 membered heterocyclyl, optionally substituted 4–6 membered heterocyclyl-(C$_1$–C$_4$)alkyl, (C$_3$–C$_6$)cycloalkyl, (C$_3$–C$_6$)cycloalkyl-(C$_1$–C$_4$)alkyl and (C$_1$–C$_2$)haloalkyl;

preferably H, methyl, ethyl, propyl, tert-butyl, 2-methylbutyl, cyclopropyl, cyclopentyl, cyclobutyl, cyclohexyl, phenyl, benzyl, phenylethyl, 2-amino-3-phenylpropyl, cyclopropylmethyl, 4-piperidylmethyl, -(1-methylpyrrolidin-2-yl)methyl, (pyrrolidin-2-yl)methyl, piperidinylethyl, (pyrrolidin-1-yl) ethyl, (morpholin-4-yl)ethyl, piperidinylpropyl, (pyrrolidin-1-yl)propyl, (morpholin-4-yl)propyl, trifluoromethyl, 2-furylmethyl, pyridyl, 2-thienyl, piperazinyl, 3,5-dimethylpiperazin-1-yl, 3-aminopyrrolidin-1-yl and 4-methylpiperazin-1-yl;

wherein each R$^{11a}$ is independently selected from H and methyl;

wherein R$^{12}$ is one or more substituents selected from hydroxyl, halo, aryl, (C$_2$–C$_4$)alkynyl, (C$_2$–C$_4$)alkenyl, —OR$^{11}$, —N(R$^{11}$)$_2$, —(C$_1$–C$_4$)alkyl-N(R$^{11}$)$_2$, lower alkyloxyalkyl, R$^{11}$—SO$_2$—, (C$_1$–C$_4$)alkyl, cyano, nitro, lower cyanoalkyl, lower haloalkyl, lower hydroxyalkyl, lower aminoalkyl, lower alkylaminoalkyl, lower alkylaminoalkoxy, lower aminoalkoxyalkyl, (C$_3$–C$_6$)cycloalkyl, optionally substituted 4–6 membered heterocyclyl, optionally substituted phenoxyalkyl, optionally substituted heterocyclyloxyalkyl, —SO$_2$NR$^{11}$R$^{11}$, —NR$^{11}$SO$_2$R$^{11}$, —C(O)N(R$^{11}$)$_2$, —CO$_2$R$^{11}$, —CO$_2$NR$^{11}$R$^{11}$, —SO$_2$NHC(O)R$^{11}$, optionally substituted phenyl-(C$_1$–C$_4$)alkyl, optionally substituted heterocyclyl-(C$_1$–C$_4$)alkyl, —NR$^{11}$(O)N(R$^{11}$)$_2$, —NR$^{11}$C(O)R$^{11}$, —NR$^{11}$CO$_2$R$^{11}$ and —C(O)R$^{11}$;

preferably hydroxyl, chloro, fluoro, and methoxy; and wherein each phenyl, cycloalkyl, and heterocyclyl moiety is optionally substituted with one or more groups selected from halo, —NH$_2$, —OH, —CO$_2$H, (C$_1$–C$_4$) alkylamino, (C$_1$–C$_4$)alkyl, di(C$_1$–C$_4$)alkylamino, (C$_1$–C$_4$)haloalkyl, pyrrolidinyl, piperazinyl, piperidinyl, morpholinyl, and azetidinyl;

and pharmaceutically acceptable derivatives thereof.

The invention also relates to compounds of Formula IVa and IVb

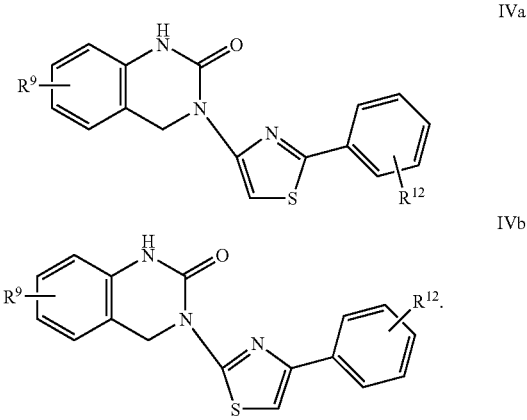

IVa

IVb

The invention also relates to compounds of Formula Va and Vb

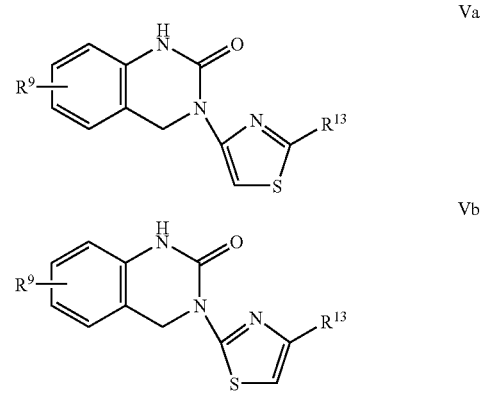

Va

Vb wherein R$^9$ is one or more radicals selected from H, hydroxy, (C$_1$–C$_4$)alkyl-O—, optionally substituted phenyl-C$_1$–C$_4$)alkyl-O—, optionally substituted 4–6 membered heterocyclyl-($C_1$–$C_4$)alkyl-O—, optionally substituted phenyl-O—, $C_{1-2}$-alkylenedioxy, halo, optionally substituted phenyl, —$NH_2$, —$NR^{11a}$—($C_1$–$C_5$)alkyl, optionally substituted 4–6 membered heterocyclyl-$NR^{11a}$—, optionally substituted 4–6 membered heterocyclyl-($C_1$–$C_4$)alkyl-$NR^{11a}$—, optionally substituted ($C_3$–$C_6$)cycloalkyl-($C_1$–$C_4$)alkyl-$NR^{11a}$—, —($C_1$–$C_2$)alkyl-$NH_2$, —($C_1$–$C_2$)alkyl-$NR^{11a}$—($C_1$–$C_2$)alkyl, —$SO_2NR^{11}R^{11}$, ($C_1$–$C_4$)alkylsulfonyl, ($C_1$–$C_4$)alkylthio, ($C_1$–$C_4$)alkyl, ($C_1$–$C_2$) haloalkyl, hydroxy-($C_1$–$C_2$)alkyl, hydroxy-($C_1$–$C_4$)-alkylamino, [(($C_1$–$C_2$)alkyl)$_2$N—($C_1$–$C_4$)-alkyl]-$NR^{11a}$—, ($C_1$–$C_2$)-alkyl$NR^{11a}$—($C_1$–$C_4$)-alkyl-O—, ($C_3$–$C_6$)cycloalkyl, optionally substituted 4–6 membered heterocyclyl-sulfonyl, optionally substituted heterocyclyl selected from pyrrolidinyl, piperazinyl, piperidinyl, and morpholinyl, —C(O)$R^{11}$, —$NR^{11a}SO_2R^{11}$, —C(O)N($R^{11}$)$_2$, —$CO_2R^{11}$, optionally substituted phenyl-($C_1$–$C_4$)aminoalkyl, optionally substituted phenyl-($C_1$–$C_2$)alkyl, optionally substituted 5–7 membered heterocyclyl-$C_1$–$C_4$-alkyl, —$NR^{11a}$C(O)$R^{11}$ and —$NR^{11a}CO_2R^{11a}$;

preferably H, (tert-butoxycarbonyl)amino, cyclopropylmethylamino, 3-hydroxypropylamino, 2-(piperidin-1-yl)ethylamino, 2-(pyrrolidin-1-yl)ethylamino, 2-(morpholin-4-yl)ethylamino, 3-(piperidin-1-yl)propylamino, 3-(pyrrolidin-1-yl)propylamino, 3-(morpholin-4-yl)propylamino, N-methyl-N-(2-piperid-1-ylethyl)amino, N-methyl-N-(2-pyrrolidin-1-ylethyl)amino, N-methyl-N-(2-morpholin-4-ylethyl)amino, ((2S)-2-amino-3-phenylpropyl)amino, 4-methylpiperazin-1-ylamino, 4-methylpiperazin-1-yl, 3-aminopyrrolidin-1-yl, (diethylamino)ethylamino, 3,5-dimethylpiperazin-1-yl, (4-piperidylmethyl)amino, (2-methylbutyl)amino, 2-(dimethylamino)ethoxy, 2-(methylamino)ethoxy, ((2R)pyrrolidin-2-yl)methoxy, ((2R)-1-methylpyrrolidin-2-yl)methoxy, 2-(piperid-1-yl)ethoxy, 2-(piperazin-1-yl)ethoxy, 2-morpholin-4-ylethoxy, 3-(N,N-diethylamino)propoxy, optionally substituted phenoxy, 3-(morpholin-4-yl)propoxy, methylenedioxy, hydroxy, benzyloxy, methoxy, chloro, fluoro, bromo, optionally substituted phenyl, amino, methylamino, diethylamino, aminomethyl, dimethylaminoethyl, N-(N',N'-diethylaminoethyl)-N-methylamino, aminosulfonyl, piperazinylsulfonyl, methylthio, methylsulfonyl, methyl, cyclopropyl, pyrrolidinyl, piperazinyl, 4-methylpiperazinyl, piperidinyl, morpholinyl, methylcarbonyl, phenylcarbonyl, piperidinylcarbonyl, trifluoromethyl, hydroxymethyl, hydroxyethyl, diethylaminocarbonyl, carboxy, methoxycarbonyl, optionally substituted benzyl, 1-azepanylmethyl, (2-methoxymethylpyrrolidin-1-yl)methyl, piperazinylmethyl, 4-methylpiperazinylmethyl, piperidinylmethyl, and morpholinylmethyl;

wherein each $R^{11}$ is independently selected from H, ($C_1$–$C_6$)alkyl, $C_1$–$C_6$ aminoalkyl optionally substituted with optionally substituted phenyl, optionally substituted phenyl, optionally substituted phenyl-($C_1$–$C_4$)alkyl, optionally substituted 4–6 membered heterocyclyl, optionally substituted 4–6 membered heterocyclyl-($C_1$–$C_4$)alkyl, ($C_3$–$C_6$)cycloalkyl, ($C_3$–$C_6$)cycloalkyl-($C_1$–$C_4$)alkyl and ($C_1$–$C_2$)haloalkyl;

preferably H, methyl, ethyl, propyl, tert-butyl, 2-methylbutyl, cyclopropyl, cyclopentyl, cyclobutyl, cyclohexyl, phenyl, benzyl, phenylethyl, 2-amino-3-phenylpropyl, cyclopropylmethyl, 4-piperidylmethyl, -(1-methylpyrrolidin-2-yl)methyl, (pyrrolidin-2-yl)methyl, piperidinylethyl, (pyrrolidin-1-yl)ethyl, (morpholin-4-yl)ethyl, piperidinylpropyl, (pyrrolidin-1-yl)propyl, (morpholin-4-yl)propyl, trifluoromethyl, 2-furylmethyl, pyridyl, 2-thienyl, piperazinyl, 3,5-dimethylpiperazin-1-yl, 3-aminopyrrolidin-1-yl and 4-methylpiperazin-1-yl; and wherein each $R^{11a}$ is independently selected from H and methyl;

wherein $R^{13}$ is selected from 6-membered nitrogen containing heteroaryl and $R^{11}$sulfonyl-($C_{1-2}$)alkyl;

preferably 4-pyridyl, 3-ethyl-4-pyridyl, 4-chlorophenylsulfonylmethyl, 2-pyridylsulfonylmethyl, 3-pyridylsulfonylmethyl, 4-pyridylsulfonylmethyl, 2-thienylsulfonylmethyl, phenylsulfonylmethyl, 2-furylmethylsulfonylmethyl, 3-trifluoromethylphenylmethyl-sulfonylmethyl, methylsulfonylmethyl, tert-butylsulfonylmethyl, 4-fluorophenylmethylsulfonylmethyl and 4-chlorophenylmethylsulfonylmethyl;

more preferably 4-pyridyl; and wherein each phenyl, cycloalkyl, and heterocyclyl moiety is optionally substituted with one or more groups selected from halo, —$NH_2$, —OH, —$CO_2H$, ($C_1$–$C_4$)alkylamino, ($C_1$–$C_4$)alkyl, di($C_1$–$C_4$)alkylamino, ($C_1$–$C_4$)haloalkyl, pyrrolidinyl, piperazinyl, piperidinyl, morpholinyl, and azetidinyl;

and pharmaceutically acceptable derivatives thereof;

provided the compound is not 3-(2-pyridin-3-yl-thiazol-4-yl)-3,4-dihydro-1H-quinazolin-2-one or 6-methyl-3-(2-pyridin-2-yl-thiazol-4-yl)-3,4-dihydro-1H-quinazolin-2-one.

The invention also relates to compounds of Formula Va and Formula Vb wherein $R^{13}$ is selected from $R^{11}$sulfonyl-($C_{1-2}$)alkyl.

The invention also relates to compounds of Formula Va and Formula Vb wherein $R^{13}$ is selected from 4-chlorophenylsulfonylmethyl, 2-pyridylsulfonylmethyl, 3-pyridylsulfonylmethyl, 4-pyridylsulfonylmethyl, 2-thienylsulfonylmethyl, phenylsulfonylmethyl, 2-furylmethylsulfonylmethyl, 3-trifluoromethylphenylmethyl-sulfonylmethyl, methylsulfonylmethyl, tert-butylsulfonylmethyl, 4-fluorophenylmethylsulfonylmethyl and 4-chlorophenyl-methylsulfonylmethyl.

A family of specific compounds of particular interest within Formula I consists of compounds and pharmaceutically-acceptable salts thereof as follows:

3-(2-(4-pyridyl)-1,3-thiazol-4-yl)-1,3,4-trihydroquinazolin-2-one;

methyl 2-oxo-3-(2-(4-pyridyl)(1,3-thiazol-4-yl))-1,3,4-trihydroquinazoline-5-carboxylate;

2-oxo-3-(2-(4-pyridyl)(1,3-thiazol-4-yl))-1,3,4-trihydroquinazoline-5-carboxylic acid;

N,N-diethyl[2-oxo-3-(2-(4-pyridyl)(1,3-thiazol-4-yl))(1,3,4-trihydroquinazolin-5-yl)]carboxamide;

5-methoxy-3-(2-(4-pyridyl)(1,3-thiazol-4-yl))-1,3,4-trihydroquinazolin-2-one;

5-bromo-3-(2-(4-pyridyl)(1,3-thiazol-4-yl))-1,3,4-trihydroquinazolin-2-one;

6-methyl-3-(2-(4-pyridyl)(1,3-thiazol-4-yl))-1,3,4-trihydroquinazolin-2-one;

5-methyl-3-(2-(4-pyridyl)(1,3-thiazol-4-yl))-1,3,4-trihydroquinazolin-2-one;

7-fluoro-3-(2-(4-pyridyl)(1,3-thiazol-4-yl))-1,3,4-trihydroquinazolin-2-one;

6-fluoro-3-(2-(4-pyridyl)(1,3-thiazol-4-yl))-1,3,4-trihydroquinazolin-2-one;

5-chloro-3-(2-(4-pyridyl)(1,3-thiazol-4-yl))-1,3,4-trihydroquinazolin-2-one;

7-phenyl-3-(2-(4-pyridyl)(1,3-thiazol-4-yl))-1,3,4-trihydroquinazolin-2-one;
5-fluoro-3-(2-(4-pyridyl)(1,3-thiazol-4-yl))-1,3,4-trihydroquinazolin-2-one;
5-(morpholin-4-ylmethyl)-3-(2-(4-pyridyl)(1,3-thiazol-4-yl))-1,3,4-trihydroquinazolin-2-one;
5-(piperidylmethyl)-3-(2-(4-pyridyl)(1,3-thiazol-4-yl))-1,3,4-trihydroquinazolin-2-one;
3-(4-(4-pyridyl)-1,3-thiazol-2-yl)-1,3,4-trihydroquinazolin-2-one;
3-(4-(2-pyridyl)-1,3-thiazol-2-yl)-1,3,4-trihydroquinazolin-2-one;
3-(4-(3-pyridyl)-1,3-thiazol-2-yl)-1,3,4-trihydroquinazolin-2-one;
3-(6-methoxybenzimidazol-2-yl)-1,3,4-trihydroquinazolin-2-one;
7-(2-(4-pyridyl)-1,3-thiazol-4-yl)-5,7,8-trihydro-2H-1,3-dioxolano[4,5-g]quinazolin-6-one;
methyl 2-oxo-3-(2-(4-pyridyl)(1,3-thiazol-4-yl))-1,3,4-trihydroquinazoline-7-carboxylate;
6-(3-morpholin-4-ylpropoxy)-3-(2-(4-pyridyl)(1,3-thiazol-4-yl))-1,3,4-trihydroquinazolin-2-one;
5-fluoro-3-(2-(3-pyridyl)(1,3-thiazol-4-yl))-1,3,4-trihydroquinazolin-2-one;
7-(2-(4-pyridyl)-1,3-thiazol-4-yl)-6,7,9-trihydro-2H-1,3-dioxoleno[4,5-h]quinazolin-8-one;
6-[3-(diethylamino)propoxy]-3-(2-(4-pyridyl)(1,3-thiazol-4-yl))-1,3,4-trihydroquinazolin-2-one;
7-bromo-3-(2-(4-pyridyl)(1,3-thiazol-4-yl))-1,3,4-trihydroquinazolin-2-one;
7-(morpholin-4-ylmethyl)-3-(2-(4-pyridyl)(1,3-thiazol-4-yl))-1,3,4-trihydroquinazolin-2-one;
7-amino-3-(2-(4-pyridyl)(1,3-thiazol-4-yl))-1,3,4-trihydroquinazolin-2-one;
5-(azaperhydroepinylmethyl)-3-(2-(4-pyridyl)(1,3-thiazol-4-yl))-1,3,4-trihydroquinazolin-2-one;
7-(3-methoxyphenyl)-3-(2-(4-pyridyl)(1,3-thiazol-4-yl))-1,3,4-trihydroquinazolin-2-one;
7-(3-hydroxyphenyl)-3-(2-(4-pyridyl)(1,3-thiazol-4-yl))-1,3,4-trihydroquinazolin-2-one;
7-[3-(2-piperidylethoxy)phenyl]-3-(2-(4-pyridyl)(1,3-thiazol-4-yl))-1,3,4-trihydroquinazolin-2-one;
7-(piperidylmethyl)-3-(2-(4-pyridyl)(1,3-thiazol-4-yl))-1,3,4-trihydroquinazolin-2-one;
5-phenyl-3-(2-(4-pyridyl)(1,3-thiazol-4-yl))-1,3,4-trihydroquinazolin-2-one;
3-[2-(2-ethyl-4-pyridyl)-1,3-thiazol-4-yl]-1,3,4-trihydroquinazolin-2-one;
6-piperidyl-3-(4-(4-pyridyl)(1,3-thiazol-2-yl))-1,3,4-trihydroquinazolin-2-one;
6-{[2-(dimethylamino)ethyl]methylamino}-3-(4-(4-pyridyl)(1,3-thiazol-2-yl))-1,3,4-trihydroquinazolin-2-one;
6-(4-methylpiperazinyl)-3-(4-(4-pyridyl)(1,3-thiazol-2-yl))-1,3,4-trihydroquinazolin-2-one;
3-[4-(3,4-difluorophenyl)-1,3-thiazol-2-yl]-1,3,4-trihydroquinazolin-2-one;
6-(2,4-dimethylphenoxy)-3-(4-(4-pyridyl)(1,3-thiazol-2-yl))-1,3,4-trihydroquinazolin-2-one;
3-[4-(2,4-dimethoxyphenyl)-1,3-thiazol-2-yl]-1,3,4-trihydroquinazolin-2-one;
3-[4-(2-hydroxy-4-methoxyphenyl)-1,3-thiazol-2-yl]-1,3,4-trihydroquinazolin-2-one;
5-chloro-3-(4-(4-pyridyl)(1,3-thiazol-2-yl))-1,3,4-trihydroquinazolin-2-one;
3-[4-(3,4-dichlorophenyl)-1,3-thiazol-2-yl]-1,3,4-trihydroquinazolin-2-one;
5-fluoro-3-(4-(4-pyridyl)(1,3-thiazol-2-yl))-1,3,4-trihydroquinazolin-2-one;
3-(3-(4-pyridyl)-1,2,4-thiadiazol-5-yl)-1,3,4-trihydroquinazolin-2-one;
3-(5-(4-pyridyl)-2-thienyl)-1,3,4-trihydroquinazolin-2-one;
3-[4-(4-methoxyphenyl)-1,3-thiazol-2-yl]-1,3,4-trihydroquinazolin-2-one;
3-[4-(4-hydroxyphenyl)-1,3-thiazol-2-yl]-1,3,4-trihydroquinazolin-2-one;
6,7-dimethoxy-3-(3-(4-pyridyl)(1,2,4-thiadiazol-5-yl))-1,3,4-trihydroquinazolin-2-one;
5-(2-morpholin-4-ylethoxy)-3-(3-(4-pyridyl)(1,2,4-thiadiazol-5-yl))-1,3,4-trihydroquinazolin-2-one;
3-(3-(4-pyridyl)(1,2,4-thiadiazol-5-yl))-7-(trifluoromethyl)-1,3,4-trihydroquinazolin-2-one;
5-morpholin-4-yl-3-(3-(4-pyridyl)(1,2,4-thiadiazol-5-yl))-1,3,4-trihydroquinazolin-2-one;
6-[((2S)-1-methylpyrrolidin-2-yl)methoxy]-3-(3-(4-pyridyl)(1,2,4-thiadiazol-5-yl))-1,3,4-trihydroquinazolin-2-one;
5-[((2S)-1-methylpyrrolidin-2-yl)methoxy]-3-(3-(4-pyridyl)(1,2,4-thiadiazol-5-yl))-1,3,4-trihydroquinazolin-2-one;
7-fluoro-6-piperidyl-3-(2-(4-pyridyl)(1,3-thiazol-4-yl))-1,3,4-trihydroquinazolin-2-one;
5-(3-methoxyphenyl)-3-(2-(4-pyridyl)(1,3-thiazol-4-yl))-1,3,4-trihydroquinazolin-2-one;
7-hydroxy-3-(2-(4-pyridyl)(1,3-thiazol-4-yl))-1,3,4-trihydroquinazolin-2-one;
6-(4-methylpiperazinyl)-3-(2-(4-pyridyl)(1,3-thiazol-4-yl))-1,3,4-trihydro-quinazolin-2-one;
7-{[(2S)-2-(methoxymethyl)pyrrolidinyl]methyl}-3-(2-(4-pyridyl)(1,3-thiazol-4-yl))-1,3,4-trihydroquinazolin-2-one;
7-{[(2R)-2-(methoxymethyl)pyrrolidinyl]methyl}-3-(2-(4-pyridyl)(1,3-thiazol-4-yl))-1,3,4-trihydroquinazolin-2-one;
3-(2-{[(4-chlorophenyl)sulfonyl]methyl}(1,3-thiazol-4-yl))-7-(morpholin-4-ylmethyl)-1,3,4-trihydroquinazolin-2-one; and
3-benzimidazol-2-yl-1,3,4-trihydroquinazolin-2-one.

Indications

Compounds of the present invention would be useful for, but not limited to, the treatment of cell proliferative diseases, cell death or of apoptosis.

The compounds of the invention are endowed with serine-threonine kinase inhibitory activity, such as CDK/cyclin kinase inhibitory activity.

The compounds of the invention are useful in therapy as antineoplasia agents.

Compounds of the invention would be useful for the treatment of neoplasia including cancer, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-Lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

Preferably, the compounds are useful for the treatment of neoplasia selected from lung cancer, colon cancer and breast cancer.

Due to the key role of CDKs in the regulation of cellular proliferation, these compounds are also useful in the treatment of a variety of cell proliferative disorders such as, for instance, blood vessel proliferative disorders including arthritis and restenosis; fibrotic disorders including hepatic cirrhosis and atherosclerosis; mesangial cell proliferative disorders including glomerulonephritis, diabetic nephropathy, malignant nephrosclerosis, thrombotic microangiopathy syndromes, transplant rejection and glomerulopathies; metabolic disorders including psoriasis, diabetes mellitus, chronic wound healing, inflammation, and diabetic retinopathy and other vision disorders; and others including benign prostate hyperplasia, familial adenomatosis polyposis, neuro-fibromatosis, pulmonary fibrosis, angiogenesis, metastasis, vascular smooth cell proliferation, post-surgical stenosis and hypertrophic scar formation, eczema, inflammatory bowel disease, endotoxic shock, and fungal infections.

The compounds of the invention are useful to prevent the phosphorylation of tau protein.

The compounds of the invention are useful in the treatment of neurological disorders, including neurological injuries and neurodegenerative diseases, such as, but not limited to, stroke, brain trauma, epilepsy, spinal cord injury, ischemia, multiple sclerosis, vision related disorders including but not limited to glaucoma and macular degeneration, hearing loss, AIDS-related dementia, retinitis pigmentosa, spinal muscular atrophy, cerebellar degeneration, amyotrophic lateral sclerosis, Parkinson's disease, Huntington's disease and Alzheimer's disease.

Compounds of Formula I–V, as inhibitors of the CDKs, can modulate the level of cellular RNA and DNA synthesis. These agents would therefore be useful in the treatment of viral infections, including but not limited to HIV, human papilloma virus, herpesvirus, poxvirus, Epstein-Barr virus, Sindbis virus and adenovirus.

The compounds of this invention may also act as inhibitors of other protein kinases, e.g. GSK and KDR, and thus be effective in the treatment of diseases associated with other protein kinases.

Besides being useful for human treatment, these compounds are also useful for veterinary treatment of companion animals, exotic animals and farm animals, including mammals, rodents, and the like. More preferred animals include horses, dogs, and cats.

Inhibitors of certain kinases may have utility in the treatment of diseases when the kinase is not misregulated, but is nonetheless essential for maintenance of the disease state. In this case, inhibition of the kinase activity would act either as a cure or palliative for these diseases. For example, many viruses, such as human papilloma virus, disrupt the cell cycle and drive cells into the S-phase of the cell cycle. Preventing cells from entering DNA synthesis after viral infection by inhibition of essential S-phase initiating activities such as CDK2, may disrupt the virus life cycle by preventing virus replication. This same principle may be used to protect normal cells of the body from toxicity of cycle-specific chemotherapeutic agents. Inhibition of CDK2 or CDK4 will prevent progression into the cycle in normal cells and limit the toxicity of cytotoxics which act in S-phase, G2 or mitosis. Furthermore, CDK2/cyclin E activity has also been shown to regulate NF-κB: Inhibition of CDK2 activity stimulates NF-κB-dependent gene expression, an event mediated through interactions with the p300 coactivator. NF-κB regulates genes involved in inflammatory responses, (such as hematopoietic growth factors chemokines and leukocyte adhesion molecules) and may be involved in the suppression of apoptotic signals within the cell. Thus, inhibition of CDK2 may suppress apoptosis induced by cytotoxic drugs via a mechanism which involves NF-κB. Inhibition of CDK2 activity may also have utility in other cases where regulation of NF-κB plays a role in etiology of disease. A further example may be taken from fungal infections: Inhibition of the *Aspergillus* kinases Cdc2/CDC28 or Nim A may cause arrest or death in the fungi, improving the therapeutic outcome for patients with these infections.

The compounds of the invention are useful as modulators of apoptosis. As such they are useful in the prevention of AIDS development in HIV-infected individuals, autoimmune diseases (including but not limited to systemic lupus, erythematosus, autoimmune mediated glomerulonephritis, rheumatoid arthritis and autoimmune diabetes mellitus), myelodysplastic syndromes, aplastic anemia, ischemic injury associated with myocardial infarctions, stroke and reperfusion injury, vision related disorders including but not limited to glaucoma and macular degeneration, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis) aspirin-sensitive rhinosinusitis, cystic fibrosis, kidney diseases and cancer pain.

Definitions

The phrase "therapeutically-effective" is intended to qualify the amount of each agent, which will achieve the goal of improvement in disorder severity and the frequency of incidence over treatment of each agent by itself, while avoiding adverse side effects typically associated with alternative therapies. For example, effective neoplastic therapeutic agents prolong the survivability of the patient, inhibit the rapidly-proliferating cell growth associated with the neoplasm, or effect a regression of the neoplasm. Alternatively, effective therapeutic agents for the treatment of neurological disorders minimize the damage from injury, improve cognitive functions, and the like.

The term "treatment" includes therapeutic treatment as well as prophylactic treatment (either preventing the onset of disorders altogether or delaying the onset of a preclinically evident stage of disorders in individuals).

The term "H" denotes a single hydrogen atom. This radical may be attached, for example, to an oxygen atom to form a hydroxyl radical.

Where the term "alkyl" is used, either alone or within other terms such as "haloalkyl", "cyanoalkyl" and "alkylamino", it embraces linear or branched radicals having one to about twenty carbon atoms or, preferably, one to about twelve carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. Even more preferred are lower alkyl radicals having one to four carbon atoms. The term "alkylenyl" embraces bridging divalent alkyl radicals such as methylenyl and ethyleneyl.

The term "alkenyl" embraces linear or branched radicals having at least one carbon-carbon double bond of two to about twenty carbon atoms or, preferably, two to about twelve carbon atoms. More preferred alkenyl radicals are "lower alkenyl" radicals having two to about four carbon atoms. Examples of alkenyl radicals include ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations.

The term "alkynyl" denotes linear or branched radicals having at least one carbon-carbon triple bond and having two to about twenty carbon atoms or, preferably, two to about twelve carbon atoms. More preferred alkynyl radicals are "lower alkynyl" radicals having two to about ten carbon atoms. Most preferred are lower alkynyl radicals having two to about four carbon atoms. Examples of such radicals include propargyl, butynyl, and the like.

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1–6 carbon atoms. Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "alkoxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. The "alkoxy" radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy, and fluoropropoxy.

The term "aryl", alone or in combination, means a carbocyclic aromatic system containing one or two rings wherein such rings may be attached together in a pendent manner or may be fused. The term "aryl" embraces aromatic radicals such as phenyl, naphthyl, tetrahydronaphthyl, indane and biphenyl. More preferred aryl is phenyl. Said "aryl" group may have 1 to 3 substituents such as lower alkyl, hydroxyl, halo, haloalkyl, nitro, cyano, alkoxy, and lower alkylamino. Benzodioxolyl is considered aryl.

The term "heterocyclyl" embraces saturated, partially saturated and unsaturated heteroatom-containing ring radicals, where the heteroatoms may be selected from nitrogen, sulfur and oxygen. It does not include rings containing —O—O—, —O—S— or —S—S— portions. Said "heterocyclyl" group may have 1 to 3 substituents such as hydroxyl, halo, haloalkyl, cyano, lower alkyl, lower aralkyl, oxo, lower alkoxy, amino, and lower alkylamino.

Examples of saturated heterocyclic radicals include saturated 3 to 6-membered heteromonocyclic group containing 1 to 4 nitrogen atoms [e.g. pyrrolidinyl, imidazolidinyl, piperidino, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothiophene, dihydropyran, dihydrofuran and dihydrothiazole.

Examples of unsaturated heterocyclic radicals, also termed "heteroaryl" radicals, include unsaturated 5 to 6 membered heteromonocyclyl groups containing 1 to 4 nitrogen atoms, for example, pyrrolyl, pyrrolinyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 3 to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl].

The term also includes bridged, spiro and oxo-containing heterocyclic rings, such as 1,4-dioxa-8-aza-spiro[4.5]decyl, phthalimidyl, 1,4-dioxa-8-aza-spiro[4.5]decyl, and (1-azabicyclo[2.2.2]oct-3-yl).

Preferred heterocyclic radicals include five to ten membered fused or unfused radicals. More preferred examples of heteroaryl radicals include quinolyl, isoquinolyl, imidazolyl, pyridyl, thienyl, thiazolyl, oxazolyl, furyl, and pyrazinyl. Even more preferred heteroaryl radicals are 5- or 6-membered heteroaryl, containing one or two heteroatoms selected from sulfur nitrogen and oxygen, selected from thienyl, furanyl, pyrrolyl, thiazolyl, oxazolyl, imidazolyl, pyrazolyl, isoxazolyl, isothiazolyl, pyridyl, piperidinyl and pyrazinyl.

The term "sulfonyl", whether used alone or linked to other terms such as alkylsulfonyl, denotes respectively divalent radicals —$SO_2$—.

The terms "sulfamyl," "aminosulfonyl" and "sulfonamidyl," whether alone or used with terms such as "N-alkylaminosulfonyl", "N-arylaminosulfonyl", "N,N-dialkylaminosulfonyl" and "N-alkyl-N-arylaminosulfonyl", denotes a sulfonyl radical substituted with an amine radical, forming a sulfonamide (—$SO_2NH_2$).

The term "alkylaminosulfonyl" includes "N-alkylaminosulfonyl" and "N,N-dialkylaminosulfonyl" where sulfamyl radicals are independently substituted, respectively, with one alkyl radical, or two alkyl radicals. More preferred alkylaminosulfonyl radicals are "lower alkylaminosulfonyl" radicals having one to six carbon atoms. Even more preferred are lower alkylaminosulfonyl radicals having one to three carbon atoms. Examples of such lower alkylaminosulfonyl radicals include N-methylaminosulfonyl, N-ethylaminosulfonyl and N-methyl-N-ethylaminosulfonyl.

The terms "N-arylaminosulfonyl" and "N-alkyl-N-arylaminosulfonyl" denote sulfamyl radicals substituted, respectively, with one aryl radical, or one alkyl and one aryl radical. More preferred N-alkyl-N-arylaminosulfonyl radicals are "lower N-alkyl-N-arylsulfonyl" radicals having alkyl radicals of one to six carbon atoms. Even more preferred are lower N-alkyl-N-arylsulfonyl radicals having one to three carbon atoms. Examples of such lower N-alkyl-N-aryl-aminosulfonyl radicals include N-methyl-N-phenylaminosulfonyl and N-ethyl-N-phenylaminosulfonyl. Examples of such N-aryl-aminosulfonyl radicals include N-phenylaminosulfonyl.

The term "arylalkylaminosulfonyl" embraces aralkyl radicals as described above, attached to an aminosulfonyl radical. More preferred are lower arylalkylaminosulfonyl radicals having one to three carbon atoms.

The term "heterocyclylaminosulfonyl" embraces heterocyclyl radicals as described above, attached to an aminosulfonyl radical.

The terms "carboxy" or "carboxyl", whether used alone or with other terms, such as "carboxyalkyl", denotes —$CO_2H$.

The term "carbonyl", whether used alone or with other terms, such as "aminocarbonyl", denotes —(C=O)—.

The terms "alkylcarbonyl" denotes carbonyl radicals which have been substituted with an alkyl radical. More preferred are "lower alkylcarbonyl" having lower alkyl radicals as described above attached to a carbonyl radical.

The terms "arylcarbonyl" denotes carbonyl radicals substituted with an aryl radical. More preferred are "optionally substituted phenylcarbonyl" radicals.

The terms "cycloalkylcarbonyl" denotes carbonyl radicals substituted with an cycloalkyl radical. More preferred are "optionally substituted cycloalkylcarbonyl" radicals, even more preferably containing $C_{3-6}$ cycloalkyl.

The terms "heterocyclylcarbonyl" denotes carbonyl radicals substituted with an heterocyclyl radical. More preferred are "optionally substituted 5–6 membered heterocyclylcarbonyl" radicals.

The term "aminocarbonyl" when used by itself or with other terms such as "aminocarbonylalkyl", "N-alkylaminocarbonyl", "N-arylaminocarbonyl", "N,N-dialkylaminocarbonyl", "N-alkyl-N-arylaminocarbonyl", "N-alkyl-N-hydroxyaminocarbonyl" and "N-alkyl-N-hydroxyaminocarbonylalkyl", denotes an amide group of the formula —C(=O)$NH_2$.

The terms "N-alkylaminocarbonyl" and "N,N-dialkylaminocarbonyl" denote aminocarbonyl radicals which have been substituted with one alkyl radical and independently with two alkyl radicals, respectively. More preferred are "lower alkylaminocarbonyl" having lower alkyl radicals as described above attached to an aminocarbonyl radical.

The terms "N-arylaminocarbonyl" and "N-alkyl-N-arylaminocarbonyl" denote aminocarbonyl radicals substituted, respectively, with one aryl radical, or one alkyl and one aryl radical.

The term "aminoalkyl" embraces linear or branched alkyl radicals having one to about ten carbon atoms any one of which may be substituted with one or more amino radicals. More preferred aminoalkyl radicals are "lower aminoalkyl" radicals having one to six carbon atoms and one or more amino radicals. Examples of such radicals include aminomethyl, aminoethyl, aminopropyl, aminobutyl and aminohexyl. Even more preferred are lower aminoalkyl radicals having one to three carbon atoms.

The term "alkylaminoalkyl" embraces aminoalkyl radicals having the nitrogen atom independently substituted with an alkyl radical. More preferred alkylaminoalkyl radicals are "lower alkylaminoalkyl" radicals having alkyl radicals of one to six carbon atoms. Even more preferred are lower alkylaminoalkyl radicals having alkyl radicals of one to three carbon atoms. Suitable alkylaminoalkyl radicals may be mono or dialkyl substituted, such as N-methylaminomethyl, N,N-dimethyl-aminoethyl, N,N-diethylaminomethyl and the like.

The term "heterocyclylalkyl" embraces heterocyclic-substituted alkyl radicals. More preferred heterocyclylalkyl radicals are "5- or 6-membered heteroarylalkyl" radicals having alkyl portions of one to six carbon atoms and a 5- or 6-membered heteroaryl radical. Even more preferred are lower heteroarylalkyl radicals having alkyl portions of one to three carbon atoms. Examples include such radicals as pyridylmethyl and thienylmethyl.

The term "aralkyl" embraces aryl-substituted alkyl radicals. Preferable aralkyl radicals are "lower aralkyl" radicals having aryl radicals attached to alkyl radicals having one to six carbon atoms. Even more preferred are lower aralkyl radicals phenyl attached to alkyl portions having one to three carbon atoms. Examples of such radicals include benzyl, diphenylmethyl and phenylethyl. The aryl in said aralkyl may be additionally substituted with halo, alkyl, alkoxy, halkoalkyl and haloalkoxy.

The term "arylalkenyl" embraces aryl-substituted alkenyl radicals. Preferable arylalkenyl radicals are "lower arylalkenyl" radicals having aryl radicals attached to alkenyl radicals having two to six carbon atoms. Examples of such radicals include phenylethenyl. The aryl in said arylalkenyl may be additionally substituted with halo, alkyl, alkoxy, halkoalkyl and haloalkoxy.

The term "arylalkynyl" embraces aryl-substituted alkynyl radicals. Preferable arylalkynyl radicals are "lower arylalkynyl" radicals having aryl radicals attached to alkynyl radicals having two to six carbon atoms. Examples of such radicals include phenylethynyl. The aryl in said aralkyl may be additionally substituted with halo, alkyl, alkoxy, halkoalkyl and haloalkoxy. The terms benzyl and phenylmethyl are interchangeable.

The term "alkylthio" embraces radicals containing a linear or branched alkyl radical, of one to ten carbon atoms, attached to a divalent sulfur atom. Even more preferred are lower alkylthio radicals having one to three carbon atoms. An example of "alkylthio" is methylthio, ($CH_3S$—).

The term "haloalkylthio" embraces radicals containing a haloalkyl radical, of one to ten carbon atoms, attached to a divalent sulfur atom. Even more preferred are lower haloalkylthio radicals having one to three carbon atoms. An example of "haloalkylthio" is trifluoromethylthio.

The term "alkylsulfinyl" embraces radicals containing a linear or branched alkyl radical, of one to ten carbon atoms, attached to a divalent —S(=O)— atom. More preferred are lower alkylsulfinyl radicals having one to three carbon atoms.

The term "arylsulfinyl" embraces radicals containing an aryl radical, attached to a divalent —S(=O)— atom. Even more preferred are optionally substituted phenylsulfinyl radicals.

The term "haloalkylsulfinyl" embraces radicals containing a haloalkyl radical, of one to ten carbon atoms, attached to a divalent —S(=O)— atom. Even more preferred are lower haloalkylsulfinyl radicals having one to three carbon atoms.

The term "alkylamino" denotes amino groups which have been substituted with one alkyl radical and with two alkyl radicals, including terms "N-alkylamino" and "N,N-dialkylamino". More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable "alkylamino" may be mono or dialkylamino such as N-methylamino, N-ethylamino, N,N-dimethylamino, N,N-diethylamino and the like.

The term "arylamino" denotes amino groups which have been substituted with one or two aryl radicals, such as N-phenylamino. The "arylamino" radicals may be further substituted on the aryl ring portion of the radical.

The term "heteroarylamino" denotes amino groups which have been substituted with one or two heteroaryl radicals, such as N-thienylamino. The "heteroarylamino" radicals may be further substituted on the heteroaryl ring portion of the radical.

The term "aralkylamino" denotes amino groups which have been substituted with one or two aralkyl radicals. More preferred are phenyl-$C_1$–$C_3$-alkylamino radicals, such as N-benzylamino. The "aralkylamino" radicals may be further substituted on the aryl ring portion of the radical.

The term "alkylaminoalkylamino" denotes alkylamino groups which have been substituted with one or two alkylamino radicals. More preferred are $C_1$–$C_3$-alkylamino-$C_1$–$C_3$-alkylamino radicals.

The term "alkylaminoalkoxy" embraces alkoxy radicals substituted with alkylamino radicals. More preferred alkylaminoalkoxy radicals are "lower alkylaminoalkoxy" radicals having alkoxy radicals of one to six carbon atoms. Even more preferred are lower alkylaminoalkoxy radicals having alkyl radicals of one to three carbon atoms. Suitable alkylaminoalkoxy radicals may be mono or dialkyl substituted, such as N-methylaminoethoxy, N,N-dimethylaminoethoxy, N,N-diethylaminoethoxy and the like.

The terms "N-alkyl-N-arylamino" and "N-aralkyl-N-alkylamino" denote amino groups which have been substituted with one aralkyl and one alkyl radical, or one aryl and one alkyl radical, respectively, to an amino group.

The term "arylthio" embraces aryl radicals of six to ten carbon atoms, attached to a divalent sulfur atom. An example of "arylthio" is phenylthio.

The term "aralkylthio" embraces aralkyl radicals as described above, attached to a divalent sulfur atom. More preferred are phenyl-$C_1$–$C_3$-alkylthio radicals. An example of "aralkylthio" is benzylthio.

The term "aryloxy" embraces optionally substituted aryl radicals, as defined above, attached to an oxygen atom. Examples of such radicals include phenoxy.

The term "aralkoxy" embraces oxy-containing aralkyl radicals attached through an oxygen atom to other radicals. More preferred aralkoxy radicals are "lower aralkoxy" radicals having optionally substituted phenyl radicals attached to lower alkoxy radical as described above.

The term "heterocyclylalkoxy" embraces oxy-containing heterocyclylalkyl radicals attached through an oxygen atom to other radicals. More preferred heterocyclylalkoxy radicals are "lower heteroarylalkoxy" radicals having optionally substituted heteroaryl radicals attached to lower alkoxy radical as described above.

The term "heterocyclyloxyalkyl" embraces heteroaryl radicals attached through an ether oxygen atom to an alkyl radical. More preferred heterocyclyloxyalkyl radicals are "lower heteroaryloxyalkyl" radicals having optionally substituted heteroaryl radicals attached to an —O—$C_{1-6}$ alkyl radical.

The term "cycloalkyl" includes saturated carbocyclic groups. Preferred cycloalkyl groups include $C_3$–$C_6$ rings. More preferred compounds include, cyclopentyl, cyclopropyl, and cyclohexyl.

The term "cycloalkenyl" includes carbocyclic groups have one or more carbon-carbon double bonds. "Cycloalkenyl" and "cycloalkyldienyl" compounds are included. Preferred cycloalkenyl groups include $C_3$–$C_6$ rings. More preferred compounds include, for example, cyclopentenyl, cyclopentadienyl, cyclohexenyl and cycloheptadienyl.

The term "comprising" is meant to be open ended, including the indicated component but not excluding other elements.

The phrase "Formula I–V" includes any and all subformulas such as IIa, IIb, IIIa, IIIb, IVa, IVb, Va and Vb.

The present invention preferably includes compounds that selectively inhibit CDK2 and/or CDK5.

The present invention also comprises the use of a compound of the invention, or pharmaceutically acceptable salt thereof, in the manufacture of a medicament for the treatment either acutely or chronically of a cell proliferation or apoptosis mediated disease state, including those described previously. The compounds of the present invention are also useful in the manufacture of an anti-cancer medicament. The compounds of the present invention are also useful in the manufacture of a medicament to attenuate or prevent disorders through inhibition of CDKs and other kinases. The compounds of the present invention are also useful in the manufacture of a medicament to treat neurological disorders.

The present invention comprises a pharmaceutical composition comprising a therapeutically-effective amount of a compound of Formulas I–V in association with a least one pharmaceutically-acceptable carrier, adjuvant or diluent.

The present invention also comprises a method of treating cell proliferative disorders, apoptosis mediated disorders, cancer, CDK mediated disorder or neurological disorders, in a subject, the method comprising treating the subject having or susceptible to such disorder with a therapeutically-effective amount of a compound of Formulas I–V.

Combinations

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the treatment of neoplasia, such as with radiation therapy or with cytostatic or cytotoxic agents; or in the treatment of neurological disorders, such as with thrombolytic and anticoagulant agents, anti-inflammatory agents, NMDA inhibitors, anti-Parkinsonian agents, and inhibitors of lipid peroxidation.

If formulated as a fixed dose, such combination products employ the compounds of this invention within the accepted dosage ranges. Compounds of Formula I–V may also be administered sequentially with known agents when a combination formulation is inappropriate. The invention is not limited in the sequence of administration; compounds of the invention may be administered either prior to, at the same time with or after administration of the other agent.

Currently, standard treatment of primary tumors consists of surgical excision followed by either radiation or IV administered chemotherapy. The typical chemotherapy regime consists of either DNA alkylating agents, DNA intercalating agents or microtubule poisons. The chemotherapy doses used are just below the maximal tolerated dose and therefore dose limiting toxicities typically include, nausea, vomiting, diarrhea, hair loss, neutropenia and the like. Experiments performed in in vivo animal models and in in vitro cell based assays have demonstrated that combining chemotherapeutic agents with cell cycle inhibitors, such as CDK inhibitors, typically results in either decreased rate of tumor growth or, in some cases, tumor regression. Combining chemotherapy with a CDK inhibitor typically results in an increased therapeutic index and lower levels of both agents are required. This ultimately results in a decrease in toxicity and an increase in efficacy.

Schwartz et al, Clin. Can. Res., 3, 1467–1472 (1997) have demonstrated that combining the CDK inhibitor flavopiridol with mitomycin-C (DNA alkylating agent) resulted in an increased rate of apoptosis in gastric and breast cancer cells. Bible et al (Bible et al., Cancer Res., 57, 3375–3380 (1997) have also demonstrated therapeutic synergy exists between flavopiridol and paclitaxel, cytarabine, topotecan, doxorubicin, and etoposide (all standard chemotherapeutic agents) when tested in cell based assays using human non-small cell lung cancer cells. Preclinical models (cell culture) suggest that a cell cycle inhibitor potentiates the effect of a cytotoxic agent when administered after the chemotherapeutic agent. The chemotherapeutic agent will induce specific DNA/ mitotic damage checkpoints in normal cells which in combination with a CDK inhibitor will cause a cell cycle arrest or cytostatic effect. In contrast, tumor cells will be driven into apoptosis or cell death when a chemotherapeutic agent and a CDK inhibitor are combined due to tumor cells attempting to activate defective DNA damage and cell cycle checkpoints. In addition, scheduling of a CDK inhibitor for clinical trials should include a rest period to allow the patients normal cells to recover and reduce the potential for cytotoxic side effects.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents which may be used in combination with compounds of the present invention consists of antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine protein kinase inhibitors, Taiho UFT and uricytin.

A second family of antineoplastic agents which may be used in combination with compounds of the present invention consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP (Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SR1 International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celecoxib, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-la, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofuran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Alternatively, the present compounds may also be used in co-therapies with other anti-neoplastic agents, such as other kinase inhibitors including KDR inhibitors, p38 inhibitors, TNF inhibitors, metallomatrix proteases inhibitors (MMP), COX-2 inhibitors, NSAID's, SOD mimics or $\alpha_v\beta_3$ inhibitors.

Alternatively, the present compounds may also be used in co-therapies with other treatments for neurological treatments such as thrombolytic and anticoagulant agents including tPA, urokinase and inhibitors of platelet aggregation, p38 inhibitors, IL1ra, NMDA inhibitors, anti-Parkinsonian agents including carbidopa and levodopa, and inhibitors of lipid peroxidation, for example.

The present invention comprises a process for the preparation of a compound of Formula I–V.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt.

Compounds of the present invention can possess, in general, tautomeric forms, which are included in the family of compounds in Formula I–V.

Also included in the family of compounds of Formula I–V are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I–V may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid. Suitable pharmaceutically-acceptable base addition salts of compounds of Formula I–V include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, histidine, glucamine, isopropylamine, lysine, morpholine, N-ethylmorpholine, piperazine, piperidine, triethylamine, trimethylamine. All of these salts may be prepared by conventional means from the corresponding compound of the invention by reacting, for example, the appropriate acid or base with the compound of Formula I–V.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as HCl, $H_2SO_4$ and $H_3PO_4$ and such organic acids as oxalic acid, maleic acid, succinic acid and citric acid. Other examples include salts with alkali metals or alkaline earth metals, such as sodium, potassium, calcium or magnesium or with organic bases.

Additional examples of such salts can be found in Berge et al., J. Pharm. Sci., 66, 1 (1977). leaving group, e.g. halo, OTs, etc.) such as in the presence of a base, preferably NaH, in a suitable dry, unreactive solvent, preferably DMF, at a temperature above RT, preferably above about 50° C., more preferably at about 80° C. The prop-2-enyl formate group is removed from 3, such as by using (Ph$_3$P)$_4$Pd in the presence of a nucleophile, such as morpholine, in a suitable dry, unreactive solvent, preferably THF, at a temperature of about RT. Reduction of the nitro moiety, such as by reaction with iron powder in the presence of NH$_4$Cl, in an aqueous protic solvent, such as EtOH, provides amine 4 which can be converted into the bicyclic urea 8, such as by treatment with CDI and base, preferably NaH, in a suitable dry, unreactive solvent, preferably DMF, at a temperature of about RT.

Substituted bicyclic urea or thiourea 8 can also be prepared via Route B from coupling triflate 6 with benzyl amine 5 under thermal conditions (preferably reflux in dioxane). Sequential urea or thiourea formation, ester hydrolysis and de-carboxylation leads to compounds of formula 8.

Alternatively, urea or thiourea formation of arylamine 5 followed by acylation with 2-bromoacetyl bromide provides bromoacetyl derivative 10 which reacts with an appropriate thioamide 11 to obtain substituted bicyclic urea or thiourea 8 (Route C).

Substituted bicyclic urea or thiourea 15 can be prepared from thiourea 12 such as by condensation with α-ketobromide 13 in an aqueous solvent, such as 50% aqueous MeOH, at a temperature above RT, preferably at about 40° C., followed by reduction, such as in the presence of iron dust and NH$_4$Cl, in an aqueous protic solvent, such as EtOH, at a temperature above RT, preferably above about 50° C., more preferably at about reflux. Urea formation of thiazole 14 by treatment with 4-nitrophenyl chloroformate and base General Synthetic Procedures The compounds of the invention can be synthesized according to the following procedures of Schemes 1–6, wherein the substituents are as defined above, except where further noted.

Scheme 1

Route A

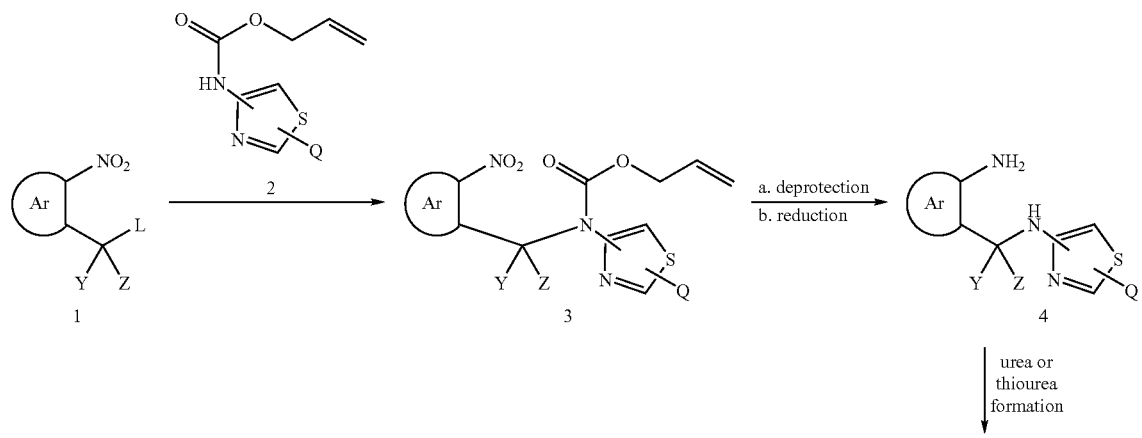

Route B

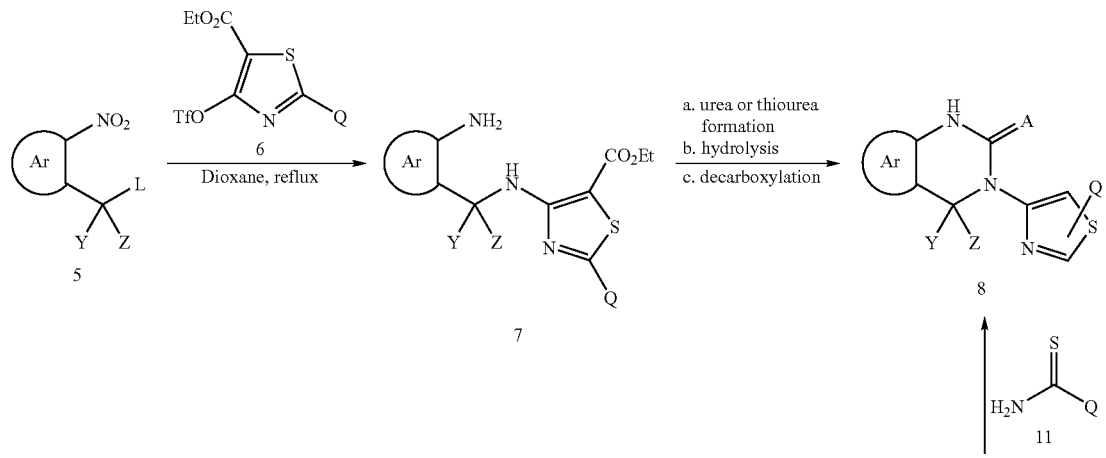

Route C

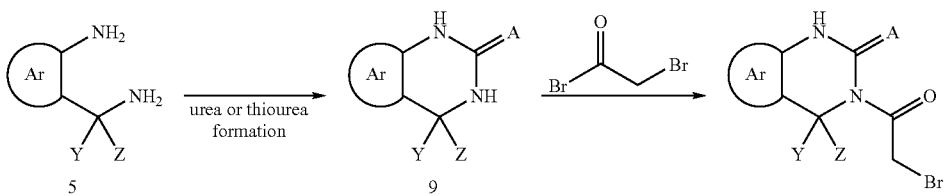

Route D

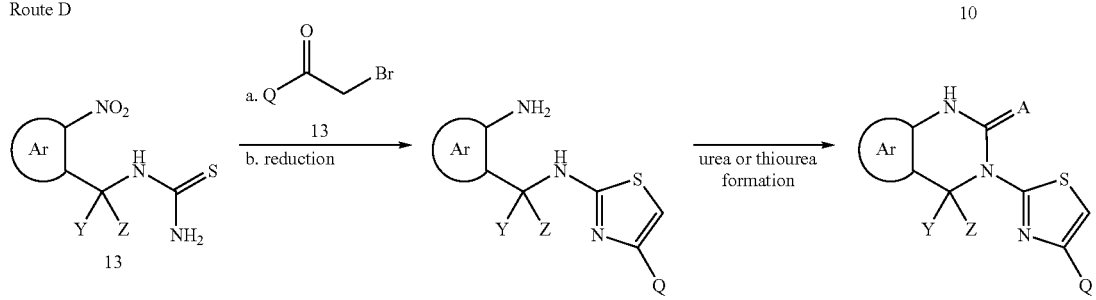

Route E

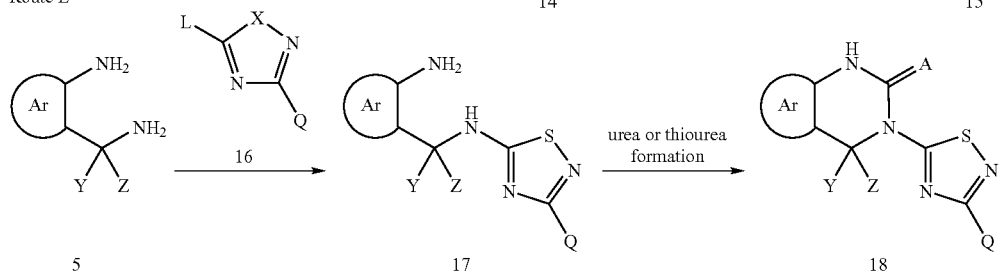

Substituted bicyclic ureas 8, 15, and 18 can be synthesized according to the methods set out in Scheme 1. Following Route A, carboxamide 2 may be N-alkylated such as by treatment with a nitro aryl compound 1 (where L is a (preferably TEA) in anhydrous solvent, such as THF, at a temperature above RT, preferably above about 50° C., more preferably at about reflux, preferably by treatment with CDI or thiocarbonyldiimidazole and base, such as NaH, in a suitable dry, unreactive solvent, such as DMF, at a temperature of about RT, provides substituted bicyclic urea or thiourea 15 (Route D).

Substituted bicyclic urea or thiourea 18 can be prepared from arylamine 5 by treatment with formula 16 (where L is CCl$_3$, or Cl) in anhydrous solvent, such as THF, at a temperature above RT, preferably above about 50° C., more preferably at about 60° C., followed by urea or thiourea formation (Route E).

Scheme 2

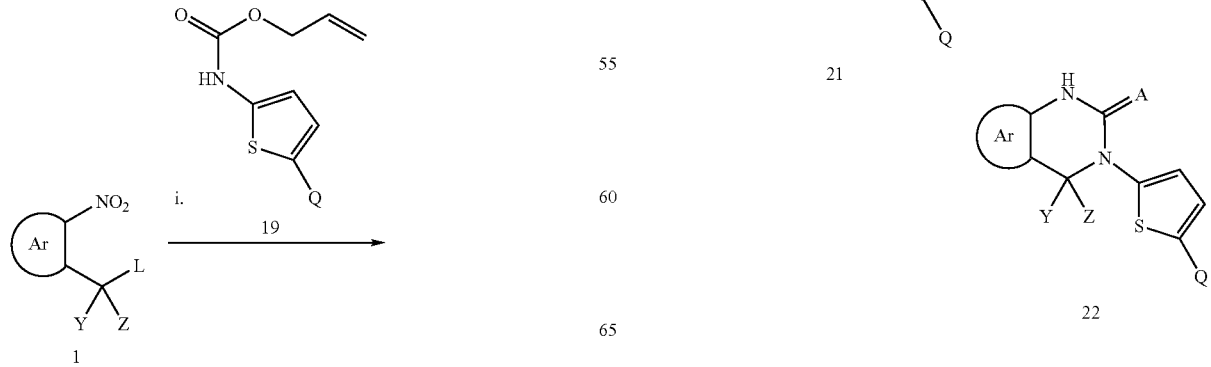

Substituted bicyclic ureas 22 can be synthesized according to the method set out in Scheme 2. Carbamate 19 may be N-alkylated by treatment with a nitro-aryl 1 (where L is a leaving group, e.g. halo, OTs, etc.) in the presence of a base (preferably NaH) in a suitable dry, unreactive solvent (preferably DMF) at a temperature above RT, preferably above about 50° C., more preferably at about 80° C. The prop-2-enyl formate group can be removed from 20 such as by using $(Ph_3P)_4Pd$ in the presence of nucleophile, such as morpholine, in a suitable dry, unreactive solvent (preferably THF) at a temperature of about RT. Reduction of the nitro moiety such as by reaction with iron powder in the presence of $NH_4Cl$ in aqueous solvent, such as 70% aqueous EtOH, at a temperature above RT, preferably above about 50° C., more preferably at a temperature about 80° C. provides the amine 21 which can be converted into bicyclic urea or thiourea 22 such as by treatment with CDI or thiocarbonyldiimidazole and base (preferably NaH) in a suitable dry, unreactive solvent (preferably DMF) at a temperature of about RT.

Scheme 3

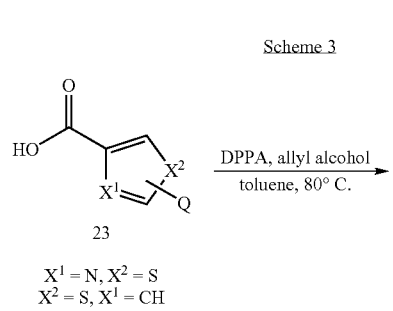

23

$X^1 = N, X^2 = S$
$X^2 = S, X^1 = CH$

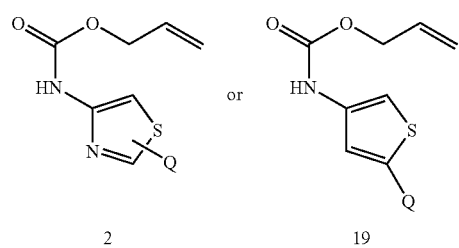

2    19

Carbamates 2 and 19 can be synthesized according to the method set out in Scheme 3. The corresponding acids 23 are treated with DPPA in the presence of base, such as TEA, in an anhydrous solvent, such as toluene, at a temperature above RT, preferably above about 50° C., more preferably at a temperature about 80° C., followed by introduction of allyl alcohol to provide the carbamates 2 and 19.

Scheme 4

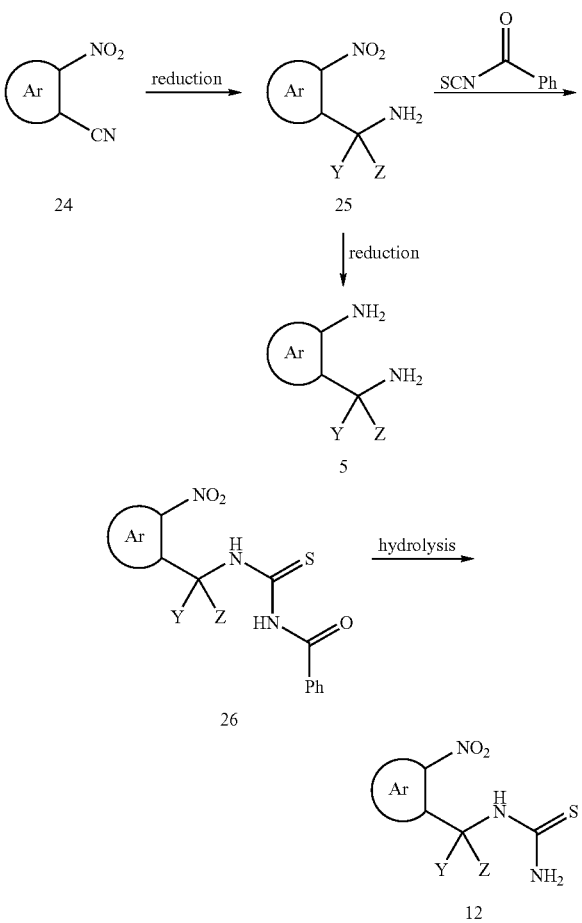

Arylamine 5 and thiourea 12 can be synthesized according to the method set out in Scheme 4. The corresponding nitrile 24 is reduced, such as with borane, in an anhydrous solvent, such as THF, at a temperature below RT and preferably at about 0° C. to provide the arylmethylamine 25. The arylmethylamine 25 may be reduced by metal catalytic reduction (preferably iron dust) in the presence of $NH_4Cl$ in aqueous solvent, such as 70% aqueous EtOH, at a temperature above RT, preferably above about 50° C., more preferably at a temperature about 80° C. to afford arylamines 5. The amine 25 can also be converted into thiourea 12 such as by treatment with benzoyl isothiocyanate at a temperature above RT, preferably above about 50° C., more preferably at a temperature about 60° C., followed by hydrolysis in the presence of base, such as $K_2CO_3$.

Scheme 5

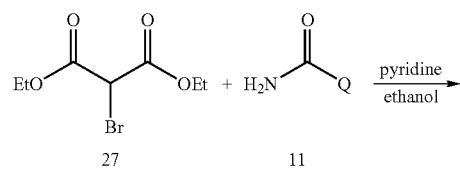

27    11

-continued

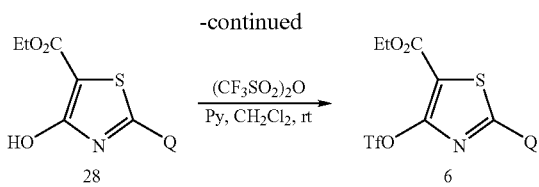

Triflate 6 can be prepared according to the method set out in Scheme 5. Condensation of diethyl bromomalonate 27 with appropriate thioamides 11 in a polar protic solvent, such as EtOH, at a temperature above RT, preferably above about 50° C., more preferably at a temperature about 80° C. provides the thiazole 28 which can be treated with trifluoromethanesulfonic anhydride in the presence of base, such as pyridine, in the anhydrous solvent, such as $CH_2Cl_2$, at a temperature above about 0° C., preferably at about RT to yield triflate 6.

Scheme 6

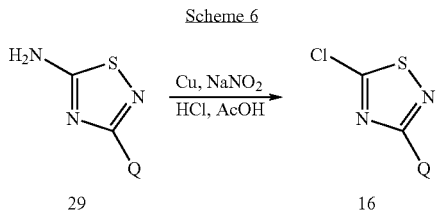

5-Chlorothiadiazole 16 can be prepared from the corresponding amine 29 (EP 0641797 A1, 1995) such as by treatment with $NaNO_2$ and copper turnings in the presence of HCl and glacial HOAc.

In the preparation of starting materials, existing functional groups, for example carboxy, hydroxy, amino, or mercapto, which do not participate in the reaction should, if necessary, be protected. Such protecting groups are those or similar to those usually used in the synthesis of peptide compounds, cephalosporins, penicillins, nucleic acid derivatives or sugars. Preferred protecting groups, their introduction and their removal are described above or in the examples.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves to ready removal, i.e. without undesired secondary reactions, typically by solvolysis, reduction, photolysis or also by enzyme activity, for example under conditions analogous to physiological conditions, and that they are not present in the end-products. One skilled in the art knows, or can easily establish, which protecting groups are suitable with the reactions mentioned above and hereinafter.

The protection of such functional groups by such protecting groups, the protecting groups themselves, and their removal reactions are described for example in standard reference works, such as J. F. W. McOmie, "Protective Groups in Organic Chemistry", Plenum Press, London and New York 1973; in T. W. Greene, "Protective Groups in Organic Synthesis", Wiley, New York 1981; in "The Peptides"; Volume 3 (editors: E. Gross and J. Meienhofer), Academic Press, London and New York 1981; in "Methoden der organischen Chemie" (Methods of organic chemistry), Houben Weyl, 4th edition, Volume 15/1, Georg Thieme Verlag, Stuttgart 1974; in H.-D. Jakubke and H. Jescheit, "Aminosauren, Peptide, Proteine" (Amino acids, peptides, proteins), Verlag Chemie, Weinheim, Deerfield Beach, and Basel 1982; and in Jochen Lehmann, "Chemie der Kohlenhydrate: Monosaccharide und Derivate" (Chemistry of carbohydrates: monosaccharides and derivatives), Georg Thieme Verlag, Stuttgart 1974.

In the additional process steps, carried out as desired, functional groups of the starting compounds which should not take part in the reaction may be present in unprotected form or may be protected for example by one or more of the protecting groups mentioned above. The protecting groups are then wholly or partly removed according to one of the methods previously described.

In certain cases, typically in hydrogenation processes, it is possible to achieve stereoselective reactions, allowing for example easier recovery of individual isomers.

The solvents from which those can be selected which are suitable for the reaction in question include, for example, water, esters, typically lower alkyl-lower alkanoates, e.g. EtOAc, ethers, typically aliphatic ethers, e.g. $Et_2O$, or cyclic ethers, e.g. THF, liquid aromatic hydrocarbons, typically benzene or toluene, alcohols, typically MeOH, EtOH or 1-propanol or iPrOH, nitriles, typically $CH_3CN$, halogenated hydrocarbons, typically $CH_2Cl_2$, acid amides, typically DMF, bases, typically heterocyclic nitrogen bases, e.g. pyridine, carboxylic acids, typically lower alkanecarboxylic acids, e.g. AcOH, carboxylic acid anhydrides, typically lower alkyl acid anhydrides, e.g. $Ac_2O$, cyclic, linear, or branched hydrocarbons, typically cyclohexane, hexane, or isopentane, or mixtures of these solvents, e.g. aqueous solutions, unless otherwise stated in the description of the process.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described above as preferred.

The compounds of Formula I–V, including their salts, are also obtainable in the form of hydrates, or their crystals can include for example the solvent used for crystallization (present as solvates).

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of the invention, are known, are commercially available, or can be synthesized in analogy to or according to methods that are known in the art.

All remaining starting materials are known, capable of being prepared according to known processes, or commercially obtainable; in particular, they can be prepared using processes as described above or as in the examples.

The compounds of this invention may contain one or more asymmetric centers and thus occur as racemates and racemic mixtures, scalemic mixtures, single enantiomers, individual diastereomers and diastereomeric mixtures. All such isomeric forms of these compounds are expressly included in the present invention.

The compounds of this invention may also be represented in multiple tautomeric forms, for example, as illustrated below:

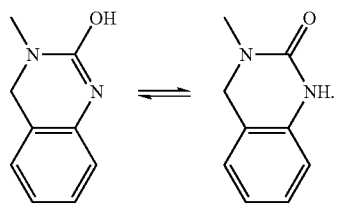

The invention expressly includes all tautomeric forms of the compounds described herein.

The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thiazolyl, etc.) may be attached to specific atoms, whereby they are intended to be fixed to that atom, or they may be drawn unattached to a specific atom, whereby they are intended to be attached at any available atom that is not already substituted by an atom other than H (hydrogen).

The compounds of this invention may contain heterocyclic ring systems attached to another ring system. Such heterocyclic ring systems may be attached through a carbon atom or a heteroatom in the ring system.

A compound of any of the formulas delineated herein may be synthesized according to any of the processes delineated herein. In the processes delineated herein, the steps may be performed in an alternate order and may be preceded, or followed, by additional protection/deprotection steps as necessary. The processes may further comprise use of appropriate reaction conditions, including inert solvents, additional reagents, such as bases (e.g., LDA, DIEA, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase), extraction, distillation, trituration, reverse phase HPLC and the like. Reactions conditions such as temperature, duration, pressure, and atmosphere (inert gas, ambient) are known in the art and may be adjusted as appropriate for the reaction. Additionally, the compounds can be produced metabolically.

As can be appreciated by one skilled in the art, the above synthetic schemes are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds. Synthetic chemistry transformations and protecting group methodologies (protection and deprotection) useful in synthesizing the inhibitor compounds described herein are known in the art and include, for example, those such as described in R. Larock, *Comprehensive Organic Transformations*, VCH Publishers (1989); T. Greene and P. Wuts, *Protective Groups in Organic Synthesis*, 3rd. Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995); P. Lopez et al., Synthesis 2, 186 (1998); A. Mikhalev, et al., Khim. Geterotsikl Soedin, 5, 697 (1997); M. Fernandez, et al., Synthesis, 11, 1362 (1995); P. Desos, et al., J. Med. Chem, 39, 197 (1996); G. Timari, et al., Synlett, 9, 1067 (1997); Y. Tagawa, et al., J. Heterocycl. Chem., 34, 1677 (1997); A. Fuerstner, et al., Chem. Sci. 50, 326 (1995); and A. Katritzky and A. Pozharski, Handbook of Heterocyclic Chemistry, $2^{nd}$ Ed. (2001).

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

The following examples contain detailed descriptions of the methods of preparation of compounds of Formulas I–V. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated. All compounds showed NMR spectra consistent with their assigned structures.

The following abbreviations are used:

| | |
|---|---|
| AcOH | acetic acid |
| $Ac_2O$ | acetic anhydride |
| $CH_3CN$ | acetonitrile |
| ATP | adenosine triphosphate |
| $NH_3$ | ammonia |
| $NH_4Cl$ | ammonium chloride |
| $NH_4OH$ | ammonium hydroxide |
| AIBN | 2,2'-azobisisobutyronitrile |
| $PdCl_2$(dppf) | 1,1'-bis(diphenylphosphino)ferrocene palladium chloride |
| $BH_3$ | borane |
| BSA | bovine serum albumin |
| $CCl_4$ | carbon tetrachloride |
| CDI | 1,1'-carbonyl diimidazole |
| $CHCl_3$ | chloroform |
| d | day |
| $CH_2Cl_2$ | dichloromethane |
| $Et_2O$ | diethyl ether |
| DEA, $Et_2NH$ | diethylamine |
| DIBAL-H | diisobutylaluminum hydride |
| DIEA | diisopropylethylamine |
| DME | 1,2-dimethoxyethane |
| DMAP | 4-(diethylamino)pyridine |
| DPPA | diphenylphosphoryl azide |
| EDCI | 1-(3-dimethylaminopropyl)-3-ethylcarbodiimide hydrochloride |
| DMF | dimethylformamide |
| DMSO | dimethylsulfoxide |
| DTT | dithiothreitol |
| EtOH | ethanol |
| EtOAc | ethyl acetate |
| EGTA | ethylene glycol-bis(β-aminoethyl ether)-N,N,N',N'-tetraacetic acid |
| EDTA | ethylenediaminetetraacetic acid |
| g | gram |
| h | hour |
| HCl | hydrochloric acid |
| $H_2$ | hydrogen |
| $H_2S$ | hydrogen sulfide |
| HOBt | hydroxybenzotriazole |
| HEPES | [4-(2-hydroxyethyl)-1-piperzine ethanesulfonic acid |

| | |
|---|---|
| Fe | iron |
| iPrOH | isopropanol |
| IPEA | isopropylethylamine |
| LiBH₄ | lithium borohydride |
| LDA | lithium dissopropylamide |
| LiOH | lithium hydroxide |
| LHMDS | lithium bis(trimethylsilyl)amide |
| MgSO₄ | magnesium sulfate |
| MgCl₂ | magnesium chloride |
| MnCl₂ | manganese chloride |
| MnO₂ | manganese oxide |
| MeOH | methanol |
| mg | milligram |
| mL | milliliter |
| min | minutes |
| NBS | N-bromosuccinimide |
| N₂ | nitrogen |
| Pd/C | palladium on carbon |
| Pd(Ph₃P)₄ | palladium (0) tetrakistriphenylphosphine |
| H₃PO₄ | phosphoric acid |
| P₂O₅ | phosphorous pentoxide |
| PBr₃ | phosphorous tribromide |
| K₂CO₃ | potassium carbonate |
| KSCN | potassium thiocyanide |
| RT | room temperature |
| NaN₃ | sodium azide |
| Na₂SO₄ | sodium sulfate |
| NaHCO₃ | sodium bicarbonate |
| NaBH(OAc)₃ | sodium triacetoxyborohydride |
| NaCl | sodium chloride |
| NaH | sodium hydride |
| NaI | sodium iodide |
| Na₂SO₄ | sodium sulfate |
| SOV | sodium orthovanadate |
| H₂SO₄ | sulfuric acid |
| TBS-Cl | tert-butyldimethylsilyl chloride |
| TBAF | tetra-n-butylammonium fluoride |
| THF | tetrahydrofuran |
| TPAP | tetrapropylammonium perruthenate |
| SOCl₂ | thionyl chloride |
| TEA, Et₃N | triethylamine |
| TFA | trifluoroacetic acid |
| Tris-HCl | tris(hydroxymethyl)aminomethane hydrochloride salt |
| H₂O | water |

EXAMPLE 1

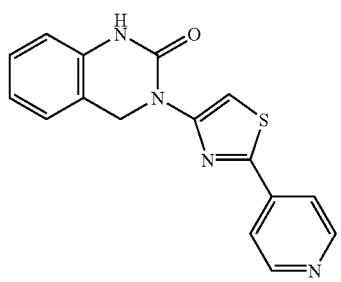

3-(2-(4-Pyridyl)-1,3-thiazol-4-yl)-1,3,4-trihydroquinazolin-2-one (a) Preparation of prop-2-enyloxy-N-(2-(4-pyridyl)(1,3-thiazol-4-yl))carboxamide. To a stirred mixture of 2-(4-pyridyl)-5-thiazole carboxylic acid (Avocado, 10 g, 48.52 mmol) and Et₃N (24.6 g, 242.6 mmol) in anhydrous toluene (200 mL) was added DPPA (Aldrich, 14 g, 50.95 mmol). The reaction mixture was stirred at RT for 2 h, and heated at 80° C. for 2 h. Allyl alcohol was added and heating was continued at 80° C. for 24 h. The mixture was cooled and concentrated. The residue was triturated in Et₂O, and the yellow solid was filtered and air-dried.

(b) Preparation of N-[(2-nitrophenyl)methyl]prop-2-enyloxy-N-(2-(4-pyridyl)(1,3-thiazol-4-yl))carboxamide. To a stirred suspension of NaH (0.148 g, 3.68 mmol) in anhydrous DMF (10 mL) was added prop-2-enyloxy-N-(2-(4-pyridyl)(1,3-thiazol-4-yl))carboxamide (Step a) (0.8 g, 3.06 mmol). After stirring at RT for 1 h, 2-nitrobenzyl bromide (0.7 g, 3.216 mmol) was added. The reaction mixture was stirred at RT for 14 h. The mixture was concentrated, dissolved in H₂O, and extracted with CH₂Cl₂ (3×). The organic extracts were combined, dried over MgSO₄, concentrated, and purified by flash column chromatography (1.3% MeOH/CH₂Cl₂) to afford a light-yellow solid.

(c) Preparation of [(2-nitrophenyl)methyl](2-(4-pyridyl)(1,3-thiazol-4-yl))amine. To a stirred mixture of N-[(2-nitrophenyl)methyl]prop-2-enyloxy-N-(2-(4-pyridyl)(1,3-thiazol-4-yl))carboxamide (Step b) (0.7 g, 1.77 mmol) and morpholine (1.54 g, 17.7 mmol) in anhydrous THF (10 mL) was added (Ph₃P)₄Pd. The mixture was stirred at RT for 2 h. The mixture was concentrated, dissolved in H₂O, extracted with CH₂Cl₂ (3×). The combined extracts were dried over MgSO₄, concentrated, and purified by flash column chromatography (1.5% MeOH/CH₂Cl₂) to afford an orange solid.

(d) Preparation of [(2-aminophenyl)methyl](2-(4-pyridyl)(1,3-thiazol-4-yl))amine. A mixture of [(2-nitrophenyl)methyl](2-(4-pyridyl)(1,3-thiazol-4-yl))amine (Step c) (0.53 g, 1.69 mmol), NH₄Cl (0.05 g, 0.85 mmol), and iron powder (0.47 g, 8.45 mmol) in EtOH/H₂O (1:1, 20 mL) was heated at reflux for 1 h. The mixture was filtered hot. The filtrate was concentrated, dissolved in H₂O, and extracted with CH₂Cl₂ (3×). The combined organic extracts were washed with brine, dried over MgSO₄, concentrated, and purified by flash column chromatography (2% MeOH/CH₂Cl₂) to afford a brown oil.

(e) Preparation of 3-(2-(4-pyridyl)-1,3-thiazol-4-yl)-1,3,4-trihydroquinazolin-2-one. To a stirred mixture of [(2-aminophenyl)methyl](2-(4-pyridyl)(1,3-thiazol-4-yl))amine (Step d)(0.32 g, 1.13 mmol) and TEA (0.15 g, 1.47 mmol) in anhydrous p-dioxane (5 mL) was added p-nitrophenyl chloroformate (0.23 g, 1.25 mmol). The reaction mixture was stirred at RT for 1 h and heated at reflux for 4 h. The mixture was cooled and concentrated in vacuo. The residue was suspended in H₂O and extracted with CH₂Cl₂ (3×). The organic extracts were washed with brine, dried over MgSO₄, concentrated, and the crude material was purified by flash column chromatography (1.5% MeOH/CH₂Cl₂) to afford a tan solid. This material was dissolved in MeOH, and 4M HCl in dioxane was added. The solution was concentrated and dried to give a yellow solid. Anal. Calc'd for C₁₆H₁₂N₄OS.HCl: C, 55.59; H, 3.76; N, 16.20; Found: C, 55.61; H, 3.93; N, 16.03.

EXAMPLE 2

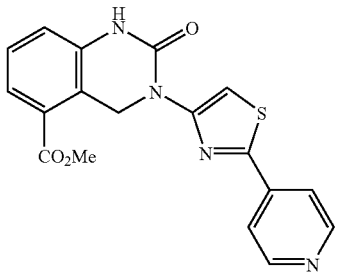

Methyl 2-oxo-3-(2-(4-pyridyl)(1,3-thiazol-4-yl))-1,
3,4-trihydroquinazoline-5-carboxylate (a) Preparation of methyl 2-(bromomethyl)-3-nitrobenzoate. A mixture of methyl 2-methyl-3-nitrobenzoate (Aldrich) (10 g, 51 mmol), AIBN (0.84 g, 5 mmol), and NBS (10.9 g, 61 mmol) in anhydrous CCl$_4$ (200 mL) was heated at reflux for 36 h. The mixture was cooled and the resulting solid was filtered. The filtrate was concentrated to afford a light brown oil, which solidified upon standing at RT. This material was taken on to the next step without purification.

(b) Preparation of methyl 3-nitro-2-{[prop-2-enyloxy-N-(2-(4-pyridyl)(1,3-thiazol-4-yl))carbonylamino]methyl}benzoate. To a stirred suspension of NaH (1.5 g, 37 mmol) in anhydrous DMF (100 mL) was added methyl 2-(bromomethyl)-3-nitrobenzoate (Step a) (8 g, 31 mmol). After stirring at RT for 1 h, prop-2-enyloxy-N-(2-(4-pyridyl)(1,3-thiazol-4-yl))carboxamide (9.24 g, 31 mmol) was added and the reaction mixture was stirred at RT for 14 h. The mixture was concentrated, dissolved in H$_2$O, and extracted with CH$_2$Cl$_2$ (3×). The organic extracts were combined, dried over MgSO$_4$, concentrated, and the crude material was purified by flash column chromatography (1.3% MeOH/CH$_2$Cl$_2$) to afford a light-yellow solid.

(c) Preparation of methyl 3-amino-2-{[prop-2-enyloxy-N-(2-(4-pyridyl)(1,3-thiazol-4-yl))carbonylamino]methyl}benzoate. A mixture of methyl 3-nitro-2-{[prop-2-enyloxy-N-(2-(4-pyridyl)(1,3-thiazol-4-yl))carbonylamino]methyl}benzoate (Step b) (5 g, 11 mmol), NH$_4$Cl (0.3 g, 6 mmol), and iron powder (3.08 g, 55 mmol) in EtOH/H$_2$O (1:1, 140 mL) was heated at reflux for 1 h. The mixture was filtered hot, and the filtrate was concentrated, dissolved in H$_2$O, and extracted with CH$_2$Cl$_2$ (3×). The combined extracts were washed with brine, dried over MgSO$_4$, and concentrated to give a light-yellow solid.

(d) Preparation of methyl 3-amino-2-{[(2-(4-pyridyl)(1,3-thiazol-4-yl))amino]methyl}benzoate. A mixture of methyl 3-amino-2-{[prop-2-enyloxy-N-(2-(4-pyridyl)(1,3-thiazol-4-yl))carbonylamino]methyl}benzoate (Step c) (4.6 g, 11 mmol), morpholine (9.5 g, 108 mmol), and (Ph$_3$P)$_4$Pd (1.25 g, 1 mmol) in anhydrous THF (70 mL) was stirred at RT overnight. The precipitated solid was filtered. The filtrate was concentrated, dissolved in H$_2$O, extracted with CH$_2$Cl$_2$ (3×). The combined extracts were dried over MgSO$_4$, concentrated, and the crude material was purified by flash column chromatography (1.5% MeOH/CH$_2$Cl$_2$) to afford a light brown oil.

(e) Preparation of methyl 2-oxo-3-(2-(4-pyridyl)(1,3-thiazol-4-yl))-1,3,4-trihydroquinazoline-5-carboxylate. To a stirred mixture of methyl 3-amino-2-{[(2-(4-pyridyl)(1,3-thiazol-4-yl))amino]methyl}benzoate (Step d) (1.8 g, 5 mmol), Et$_3$N (2.7 g, 26 mmol), DMAP (0.07 g) in anhydrous THF (30 mL) was added p-nitrophenyl chloroformate (Aldrich, 1.98 g, 11 mmol). After stirring at RT for 1 h, the reaction mixture was heated at 70° C. overnight. The mixture was cooled, concentrated, dissolved in H$_2$O, and extracted with CH$_2$Cl$_2$ (3×). The combined extracts were dried over MgSO$_4$, concentrated and the crude material was purified by flash column chromatography (1.5% MeOH/CH$_2$Cl$_2$) to afford a light-yellow solid. MS m/z: 367 (M+H) Calc'd for C$_{18}$H$_{14}$N$_4$O$_3$S—366.08.

EXAMPLE 3

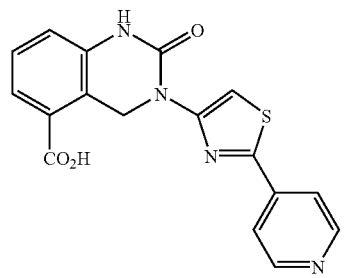

2-Oxo-3-(2-(4-pyridyl)(1,3-thiazol-4-yl))-1,3,4-trihydroquinazoline-5-carboxylic acid A mixture of methyl 2-oxo-3-(2-(4-pyridyl)(1,3-thiazol-4-yl))-1,3,4-trihydroquinazoline-5-carboxylate (Example 2) (0.25 g, 0.68 mmol) and 1N NaOH (1.4 ml, 1.37 mmol) in dioxane (3 mL) was stirred at RT overnight. The mixture was concentrated, dissolved in H$_2$O, and acidified with 2N HCl. The light yellow solid was filtered, and triturated in EtOAc to afford a light-yellow solid. This material was dissolved in MeOH and 4M HCl in dioxane was added. The solution was concentrated to give the HCl salt as a light-yellow solid. MS m/z=353 (M+1) Calc'd for C$_{17}$H$_{12}$N$_4$O$_3$S—352.06.

EXAMPLE 4

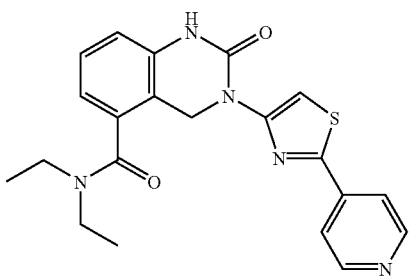

N,N-Diethyl[2-oxo-3-(2-(4-pyridyl)(1,3-thiazol-4-yl))(1,3,4-trihydroquinazolin-5-yl)]carboxamide A mixture of 2-oxo-3-(2-(4-pyridyl)(1,3-thiazol-4-yl))-1,3,4-trihydroquinazoline-5-carboxylic acid hydrochloride (Example 3) (0.020 g, 0.57 mmol) and SOCl$_2$ (0.5 mL, 5.7 mmol) was heated at reflux for 1 h. The reaction mixture was cooled and concentrated. To the residue was added an excess of Et₂NH and the solution was stirred at RT overnight. The mixture was concentrated, dissolved in water, extracted with CH₂Cl₂ (3×). The organic extracts were dried over MgSO₄ and concentrated. The crude material was purified by preparative TLC to afford a light-yellow solid. MS m/z—408 (M+1). Calc'd for $C_{21}H_{21}N_5O_2S$—407.14

EXAMPLE 5

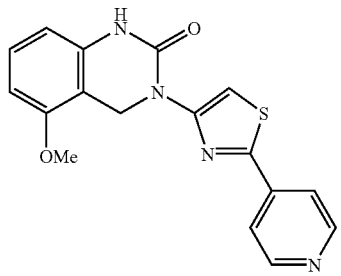

5-Methoxy-3-(2-(4-pyridyl)(1,3-thiazol-4-yl))-1,3,4-trihydroquinazolin-2-one (a) Preparation of 2-(bromomethyl)-3-methoxy-1-nitrobenzene. A mixture of 3-methoxyl-2-methyl-1-nitrobenzene (Aldrich, 10 g, 51 mmol), AIBN (0.84 g, 5 mmol), and NBS (10.9 g, 61 mmol) in anhydrous CCl₄ (200 mL) was heated at reflux for 36 h. The mixture was cooled and the resulting solid was filtered. The filtrate was concentrated to afford a light brown oil, which solidified upon standing at RT. This material was employed in the next step without purification.

(b) Preparation of N-[(6-methoxy-2-nitrophenyl)methyl]prop-2-enyloxy-N-(2-(4-pyridyl)(1,3-thiazol-4-yl))carboxamide. To a stirred suspension of NaH (0.54 g, 13.6 mmol) in anhydrous DMF (10 mL) was added prop-2-enyloxy-N-(2-(4-pyridyl)(1,3-thiazol-4-yl))carboxamide (Example 1, Step a) (3 g, 11.29 mmol). After stirring at RT for 1 h, 2-(bromomethyl)-3-methoxy-1-nitrobenzene (Example 5, Step a) (2.91 g, 11.86 mmol) was added. The reaction mixture was stirred at RT for 14 h. The mixture was concentrated, dissolved in H₂O, and extracted with CH₂Cl₂ (3×). The organic extracts were combined, dried over MgSO₄, concentrated, and the crude material was purified by flash column chromatography (1.3% MeOH/CH₂Cl₂) to afford a tan solid.

(c) Preparation of [(6-methoxy-2-nitrophenyl)methyl](2-(4-pyridyl)(1,3-thiazol-4-yl))amine. To a stirred mixture of N-[(6-methoxy-2-nitrophenyl)methyl]prop-2-enyloxy-N-(2-(4-pyridyl)(1,3-thiazol-4-yl))carboxamide (Step b) (4.13 g, 9.69 mmol) and morpholine (8.44 g, 96.9 mmol) in anhydrous THF (10 mL) was added (Ph₃P)₄Pd (0.56 g, 0.5 mmol). The mixture was stirred at RT for 2 h. The mixture was concentrated, dissolved in H₂O, extracted with CH₂Cl₂ (3×) The combined organic extracts were dried over MgSO₄, concentrated, and the crude material was purified by flash column chromatography (1.5% MeOH/CH₂Cl₂) to afford an orange solid.

(d) Preparation of [(2-amino-6-methoxyphenyl)methyl](2-(4-pyridyl)(1,3-thiazol-4-yl))amine. A mixture of [(6-methoxy-2-nitrophenyl)methyl](2-(4-pyridyl)(1,3-thiazol-4-yl))amine (Step c) (3.31 g, 9.67 mmol), NH₄Cl (0.3 g, 4.85 mmol), and iron powder (2.7 g, 48.4 mmol) in EtOH/H₂O (1:1, 20 mL) was heated at reflux for 1 h. The mixture was filtered hot. The filtrate was concentrated, dissolved in H₂O, extracted with CH₂Cl₂ (3×). The combined organic extracts were washed with brine, dried over MgSO₄, concentrated, and the crude material was purified by flash column chromatography (2% MeOH/CH₂Cl₂) to afford a brown solid.

(e) Preparation of 5-methoxy-3-(2-(4-pyridyl)(1,3-thiazol-4-yl))-1,3,4-trihydroquinazolin-2-one. To a stirred mixture of [(2-amino-6-methoxyphenyl)methyl](2-(4-pyridyl)(1,3-thiazol-4-yl))amine (Step d) (0.40 g, 1.28 mmol) and CDI (0.62 g, 3.84 mmol) in anhydrous DMF (5 mL) was added NaH (60% oil dispersion, 0.18 g, 4.49 mmol) in portions. After stirring at RT overnight, the reaction mixture was quenched by H₂O. The tan solid was filtered, dried, and triturated in Et₂O to afford a light tan solid. A portion (0.10 g) of the product was dissolved in MeOH and 4M HCl (0.075 mL) in p-dioxane was added. The solution was concentrated and dried to give a tan solid. MS m/z: 339 (M+1). Calc'd for $C_{17}H_{14}N_4O_2S$—338.08.

EXAMPLE 6

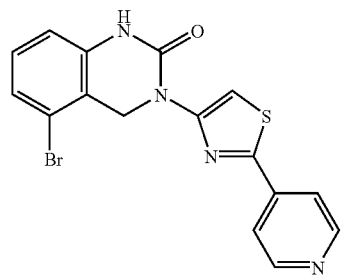

5-Bromo-3-(2-(4-pyridyl)(1,3-thiazol-4-yl))-1,3,4-trihydroquinazolin-2-one (a) Preparation of ethyl 2-(4-pyridyl)-1,3-thiazole-4-carboxylate. Thioisonicotinamide (Pfaltz-Bauer) (20.0 g, 144.7 mmol) and ethyl bromopyruvate (Aldrich) (19.0 mL, 151.4 mmol) were dissolved in 250 mL of EtOH. The solution was heated at 80° C. and stirred overnight. The reaction mixture was cooled to RT and filtered. The filtrate was concentrated and filtered once more. The combined solids were combined and dried in vacuo to give a yellow solid.

(b) Preparation of 2-(4-pyridyl)-1,3-thiazole-4-carboxylic acid. Ethyl 2-(4-pyridyl)-1,3-thiazole-4-carboxylic acid (Step a) (23.1 g, 98.5 mmol) was dissolved in 250 mL of EtOH. A solution of NaOH (9.6 g, 240.0 mmol, 75 mL H₂O) was slowly added to the reaction. The solution was heated at 80° C. and stirred overnight. The solution was cooled to RT and then concentrated in vacuo. The residue was dissolved in H₂O (50 mL) and acidified with 1N HCl (aq). The resulting precipitate was filtered and dried to give a gray-brown solid. MS m/z: 207 (M+1). Calc'd for $C_9H_6N_2O_2S$—206.01.

(c) Preparation of prop-2-enyloxy-N-(2-(4-pyridyl)(1,3-thiazol-4-yl))carboxamide. 2-(4-Pyridyl)-1,3-thiazole-4-carboxylic acid (Step b) (14.84 g, 71.9 mmol) was suspended in 250 mL of toluene and Et₃N (Aldrich) (10.2 mL, 73.2 mmol) was added. The reaction mixture was allowed to stir at RT for 1 h. DPPA (Aldrich) (23.5 mL, 108.9 mmol) was added and the reaction mixture was stirred for an additional 1 h. The reaction mixture was then heated at 80° C. for 1 h before allyl alcohol (Aldrich) (49 mL, 720.5 mmol) was introduced. After stirring overnight, the mixture was cooled to RT and concentrated in vacuo. The residue was dissolved in CH$_2$Cl$_2$ and Et$_2$O was added until a yellow precipitate came out of solution. The precipitate was filtered and the filtrate was concentrated in vacuo. The filtrate residue was again dissolved in CH$_2$Cl$_2$ and Et$_2$O was added until a yellow precipitate came out of solution. The precipitate was filtered. The combined yellow solids were dried to give a solid. The filtrate was concentrated in vacuo and purified by flash chromatography on silica gel using 6:4 CH$_2$Cl$_2$:EtOAc as the eluant to afford an additional compound. MS m/z: 262 (M+1). Calc'd for C$_{12}$H$_{11}$N$_3$O$_2$S—261.06.

(d) Preparation of 3-bromo-2-(bromomethyl)-1-nitrobenzene. 2-Bromo-6-nitrotoluene (Aldrich) (3.33 g, 15.4 mmol) was dissolved in 20 mL of CCl$_4$. The solution was heated at 80° C., then NBS (Aldrich) (3.38 g, 19.0 mmol) and AIBN (Aldrich) (296 mg, 1.80 mmol) were added and the reaction mixture was stirred overnight at 80° C. The reaction mixture was cooled to RT and filtered. The filtrate was concentrated in vacuo to give a brown oil that was a mixture of starting material:desired compound (1:2). This mixture was used without further purification.

(e) Preparation of N-[(6-bromo-2-nitrophenyl)methyl] prop-2-enyloxy-N-(2-(4-pyridyl)(1,3-thiazol-4-yl))carboxamide. Prop-2-enyloxy-N-(2-(4-pyridyl)(1,3-thiazol-4-yl)) carboxamide (Step c) (1.02 g, 3.9 mmol) was dissolved in 20 mL of dry DMF. NaH (Aldrich, 60% in mineral oil) was added to the solution portion-wise. The reaction was stirred for 45 min at RT and then a solution of 3-bromo-2-(bromomethyl)-1-nitrobenzene (Step d) (2.3 g, 5.14) in 5 mL of DMF was added dropwise. The reaction was heated at 80° C. for 4 h. The reaction was cooled to RT and then partitioned between EtOAc:H$_2$O. The aqueous layer was extracted with EtOAc (3×). The combined EtOAc layers were washed with H$_2$O and brine, then dried over MgSO$_4$, and concentrated in vacuo to an oil. The crude oil was purified by flash chromatography on silica gel using 97:3 CH$_2$Cl$_2$:MeOH as the eluant to afford a brown oil. MS m/z: 476 (M+1). Calc'd for C$_{19}$H$_{15}$BrN$_4$O$_4$S—474.00.

(f) Preparation of [(6-bromo-2-nitrophenyl)methyl](2-(4-pyridyl)(1,3-thiazol-4-yl))amine. N-[(6-Bromo-2-nitrophenyl)methyl]prop-2-enyloxy-N-(2-(4-pyridyl)(1,3-thiazol-4-yl))carboxamide (Step e) (936 mg, 2.0 mmol) was dissolved in 20 mL of CH$_3$CN. Morpholine (Aldrich) (1.71 mL, 19.6 mmol) and Pd(PPh$_3$)$_4$ (205 mg, 0.2 mmol) were added and the reaction mixture was stirred at RT overnight. The reaction mixture was concentrated in vacuo. The residue was dissolved in EtOAc and washed with H$_2$O. The aqueous layer was extracted with EtOAc (2×). The combined EtOAc layers were washed with brine, dried over MgSO$_4$, and concentrated in vacuo to a brown oil. The crude oil was purified by flash chromatography on silica gel using 6:4 CH$_2$Cl$_2$:EtOAc as the eluant to afford a brown oil. MS m/z: 392 (M+1). Calc'd for C$_{15}$H$_{11}$BrN$_4$O$_2$S—389.98.

(g) Preparation of [(2-amino-6-bromophenyl)methyl](2-(4-pyridyl)(1,3-thiazol-4-yl))amine. [(6-Bromo-2-nitrophenyl)methyl](2-(4-pyridyl)(1,3-thiazol-4-yl))amine (Step f) (400 mg, 1.0 mmol) was dissolved in 25 mL of EtOH/10 mL of H$_2$O. Iron powder (Aldrich) (255 mg, 4.6 mmol) and NH$_4$Cl (Aldrich) (28 mg, 0.5 mmol) were added and the mixture was heated to 80° C. After stirring for 3 h, the reaction mixture was filtered while hot through a bed of Celite®, and the Celite® was rinsed liberally with EtOAc. The filtrate was concentrated in vacuo, and the residue was partitioned between EtOAc:H$_2$O. The aqueous layer was extracted with EtOAc (2×). The combined EtOAc layers were washed with brine, dried over MgSO$_4$, and concentrated in vacuo to give a brown oil. MS m/z: 362 (M+1). Calc'd for C$_{15}$H$_{13}$BrN$_4$S—360.00.

(h) Preparation of 5-bromo-3-(2-(4-pyridyl)(1,3-thiazol-4-yl))-1,3,4-trihydroquinazolin-2-one. [(2-Amino-6-bromophenyl)methyl](2-(4-pyridyl)(1,3-thiazol-4-yl))amine (Step g) (296 mg, 0.8 mmol), p-nitrophenyl chloroformate (175 mg, 0.9 mmol), and Et$_3$N (0.12 mL, 0.9 mmol) were dissolved in 10 mL of toluene/10 mL of THF and stirred for 1 h at RT. The reaction mixture was heated at 80° C. overnight. The reaction mixture was cooled to RT and then concentrated in vacuo. The residue was dissolved in CH$_2$Cl$_2$ and washed with H$_2$O. The aqueous layer was extracted with CH$_2$Cl$_2$ (2×). The combined CH$_2$Cl$_2$ layers were washed with brine, dried over MgSO$_4$, and concentrated in vacuo to a yellow solid. The crude solid was purified by flash chromatography on silica gel using 99:1 to 97:3 CH$_2$Cl$_2$: MeOH as the eluant to afford an off-white solid. MP 283–284° C. MS m/z: 388 (M+1). Anal. Calc'd for C$_{16}$H$_{11}$BrN$_4$OS: C, 49.63; H, 2.86; N, 14.47. Found: C, 49.61; H, 2.99; N, 14.26.

EXAMPLE 7

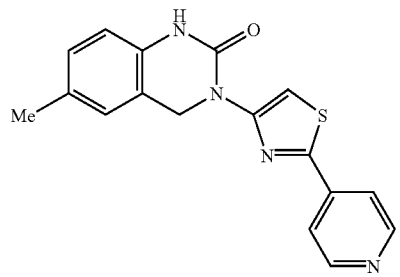

6-Methyl-3-(2-(4-pyridyl)(1,3-thiazol-4-yl))-1,3,4-trihydroquinazolin-2-one (a) Preparation of 2-(bromomethyl)-4-methyl-1-nitrobenzene. 5-Methyl-2-nitrobenzyl alcohol (Aldrich) (2.16 g, 12.9 mmol) was dissolved in 40 mL of dry CH$_2$Cl$_2$. PBr$_3$ (Aldrich) (1.25 mL, 13.3 mmol) was added dropwise. The reaction mixture was stirred overnight. Saturated NaHCO$_3$ (aq) was cautiously added until the pH was 6. The reaction mixture was partitioned and the aqueous layer was extracted with CH$_2$Cl$_2$ (2×). The combined CH$_2$Cl$_2$ layers were washed with brine, dried over MgSO$_4$, and concentrated in vacuo to give a yellow oil which crystallized upon standing.

(b) Preparation of prop-2-enyl 3-(5-methyl-2-nitrophenyl)-2-(2-(4-pyridyl)(1,3-thiazol-4-yl))propanoate. This compound was prepared according to the method described in Example 6e from prop-2-enyloxy-N-(2-(4-pyridyl)(1,3-thiazol-4-yl))carboxamide (Example 6, Step c) (1.01 g, 3.9 mmol), NaH (193 mg, 4.8 mmol), and 2-(bromomethyl)-4-methyl-1-nitrobenzene (Step a) (938 mg, 4.1) to give a red-brown oil.

(c) Preparation of [(5-methyl-2-nitrophenyl)methyl](2-(4-pyridyl)(1,3-thiazol-4-yl))amine. This compound was prepared according to the method described in Example 6f from prop-2-enyl 3-(5-methyl-2-nitrophenyl)-2-(2-(4-pyridyl)(1, 3-thiazol-4-yl))propanoate (Step b) (1.4 g, 3.4 mmol), morpholine (1.5 mL, 17.2 mmol), and Pd (PPh$_3$)$_4$ (275 mg, 0.2 mmol) to give a dark red solid.

(d) Preparation of [(2-amino-5-methylphenyl)methyl](2-(4-pyridyl)(1,3-thiazol-4-yl))amine. This compound was prepared according to the method described in Example 6g using [(5-methyl-2-nitrophenyl)methyl](2-(4-pyridyl)(1,3-thiazol-4-yl))amine (Step c) (350 mg, 1.1 mmol), iron powder (350 mg, 6.3 mmol), and NH$_4$Cl (55 mg, 1.0 mmol). The crude oil was purified by flash chromatography on silica gel using 98:2 CH$_2$Cl$_2$:MeOH as the eluant to afford a dark oil. MS m/z: 297 (M+1). Calc'd for C$_{16}$H$_{16}$N$_4$S—296.11.

(e) Preparation of 6-methyl-3-(2-(4-pyridyl)(1,3-thiazol-4-yl))-1,3,4-trihydroquinazolin-2-one. This compound was prepared according to the method described in Example 6h using [(2-amino-5-methylphenyl)methyl](2-(4-pyridyl)(1,3-thiazol-4-yl))amine (296 mg, 0.4 mmol), p-nitrophenyl chloroformate (172 mg, 0.9 mmol), TEA (0.27 mL, 1.9 mmol), and DMAP (5 mg, 0.04 mmol). The crude solid was purified by flash chromatography on silica gel using 98:2 CH$_2$Cl$_2$:MeOH as the eluant to afford an off-white solid. MP 259–261° C. MS m/z: 323 (M+1). Anal. Calc'd for C$_{17}$H$_{14}$N$_4$OS.0.3H$_2$O: C, 62.29; H, 4.53; N, 17.09. Found: C, 62.49; H, 4.53; N, 16.50.

EXAMPLE 8

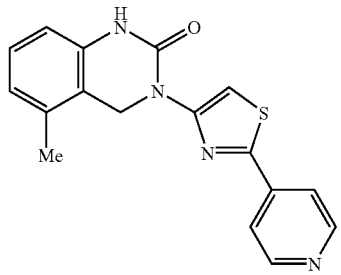

5-Methyl-3-(2-(4-pyridyl)(1,3-thiazol-4-yl))-1,3,4-trihydroquinazolin-2-one (a) Preparation of 2-(bromomethyl)-3-methyl-1-nitrobenzene. This compound was prepared according to the method described in Example 7a, by employing 6-methyl-2-nitrobenzyl alcohol (Aldrich) (2.16 g, 12.9 mmol) and PBr$_3$ (1.25 mL, 13.3 mmol) to give a light orange oil that crystallized upon standing.

(b) Preparation of N-[(6-methyl-2-nitrophenyl)methyl]prop-2-enyloxy-N-(2-(4-pyridyl)(1,3-thiazol-4-yl))carboxamide. This compound was prepared according to the method described in Example 6e from prop-2-enyloxy-N-(2-(4-pyridyl)(1,3-thiazol-4-yl))carboxamide (Example 6, Step c) (1.07 g, 4.1 mmol), NaH (210 mg, 5.3 mmol), and 2-(bromomethyl)-3-methyl-1-nitrobenzene (Step a) (984 mg, 4.3) to give a crude dark brown oil.

(c) Preparation of [(6-methyl-2-nitrophenyl)methyl](2-(4-pyridyl)(1,3-thiazol-4-yl))amine. This compound was prepared according to the method described in Example 6f from N-[(6-methyl-2-nitrophenyl)methyl]prop-2-enyloxy-N-(2-(4-pyridyl)(1,3-thiazol-4-yl))carboxamide (Step b) (1.26 g, 3.1 mmol), morpholine (1.5 mL, 17.2 mmol), and Pd(PPh$_3$)$_4$ (350 mg, 0.3 mmol) to give a dark red solid.

(d) Preparation of [(2-amino-6-methylphenyl)methyl](2-(4-pyridyl)(1,3-thiazol-4-yl))amine. This compound was prepared according to the method described in Example 6g from [(6-methyl-2-nitrophenyl)methyl](2-(4-pyridyl)(1,3-thiazol-4-yl))amine (Step c) (630 mg, 1.9 mmol), iron powder (595 mg, 10.7 mmol), and NH$_4$Cl (54 mg, 1.0 mmol). The crude oil was purified by flash chromatography on silica gel using 98:2 CH$_2$Cl$_2$:MeOH as the eluant to afford a dark oil. MS m/z: 297 (M+1). Calc'd for C$_{16}$H$_{16}$N$_4$S—296.11.

(e) Preparation of 5-methyl-3-(2-(4-pyridyl)(1,3-thiazol-4-yl))-1,3,4-trihydroquinazolin-2-one. This compound was prepared according to the method described in Example 6h from [(2-amino-6-methylphenyl)methyl](2-(4-pyridyl)(1,3-thiazol-4-yl))amine (418 mg, 1.4 mmol), p-nitrophenyl chloroformate (580 mg, 2.9 mmol), triethylamine (0.41 mL, 2.9 mmol), and DMAP (25 mg, 0.2 mmol). The crude solid was purified by flash chromatography on silica gel using 99:1 CH$_2$Cl$_2$:MeOH as the eluant to afford an off-white solid. MS m/z: 323 (M+1). Calc'd for: C$_{17}$H$_{14}$N$_4$OS—322.09.

EXAMPLE 9

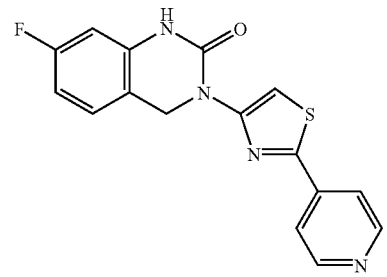

7-Fluoro-3-(2-(4-pyridyl)(1,3-thiazol-4-yl))-1,3,4-trihydroquinazolin-2-one (a) Preparation of 1-(bromomethyl)-4-fluoro-2-nitrobenzene. This compound was prepared according to the method described in Example 6d using 4-fluoro-2-nitrotoluene (Aldrich) (4.91 g, 31.7 mmol), NBS (7.45 g, 41.9 mmol), and AIBN (0.55 g, 3.4 mmol). The crude compound was purified by flash chromatography on silica gel using 5% EtOAc/Hexane to afford an orange oil.

(b) Preparation of N-[(4-fluoro-2-nitrophenyl)methyl]prop-2-enyloxy-N-(2-(4-pyridyl)(1,3-thiazol-4-yl))carboxamide. This compound was prepared according to the method described in Example 6e using prop-2-enyloxy-N-(2-(4-pyridyl)(1,3-thiazol-4-yl))carboxamide (Example 6, Step c) (1.07 g, 4.1 mmol), 60% NaH (208 mg, 5.2 mmol), and 1-(bromomethyl)-4-fluoro-2-nitrobenzene (Step a) (1.06 g, 4.5 mmol) to give crude compound which was used without further purification. MS m/z: 415 (M+1). Calc'd for C$_{19}$H$_{15}$FN$_4$O$_4$S—414.08.

(c) Preparation of [(4-fluoro-2-nitrophenyl)methyl](2-(4-pyridyl)(1,3-thiazol-4-yl))amine. This compound was prepared according to the method described in Example 6f using allyl N-[(4-fluoro-2-nitrophenyl)methyl]prop-2-enyloxy-N-(2-(4-pyridyl)(1,3-thiazol-4-yl))carboxamide (Step b) (1.6 g, 3.9 mmol), morpholine (1.5 mL, 17.1 mmol), and Pd(PPh$_3$)$_4$ (475 mg, 0.4 mmol). The crude oil was purified by flash chromatography on silica gel using 98:2 CH$_2$Cl$_2$:MeOH to afford a brownish-orange solid that was contaminated with P(O)Ph$_3$. MS m/z: 331 (M+1). Calc'd for C$_{15}$H$_{11}$FN$_4$O$_2$S—330.06.

(d) Preparation of [(2-amino-4-fluorophenyl)methyl](2-(4-pyridyl)(1,3-thiazol-4-yl))amine. This compound was prepared according to the method described in Example 6g using [(4-fluoro-2-nitrophenyl)methyl](2-(4-pyridyl)(1,3-thiazol-4-yl))amine (Step c) (1.1 g, 3.3 mmol), Fe powder (1.03 g, 18.4 mmol), and NH$_4$Cl (96 mg, 1.8 mmol). The crude oil was purified by flash chromatography on silica gel using 98:2 CH$_2$Cl$_2$:MeOH to afford a light brown oil. MS m/z: 301 (M+1). Calc'd for C$_{15}$H$_{13}$FN$_4$S—300.08.

(e) Preparation of 7-fluoro-3-(2-(4-pyridyl)(1,3-thiazol-4-yl))-1,3,4-trihydroquinazolin-2-one. This material was prepared according to the method described in Example 6h using [(2-amino-4-fluorophenyl)methyl](2-(4-pyridyl)(1,3-thiazol-4-yl))amine (Step d) (330 mg, 1.1 mmol), p-nitrophenyl chloroformate (450 mg, 2.2 mmol), TEA (0.46 mL, 3.3 mmol), and DMAP (Aldrich) (32 mg, 0.26 mmol). The crude solid was purified by flash chromatography on silica gel using 7:3 CH$_2$Cl$_2$:EtOAc to afford a white solid. MP: 285–286° C. MS m/z: 327 (M+1). Anal. Calc'd for C$_{16}$H$_{11}$FN$_4$OS: C, 58.89; H, 3.40; N, 17.17. Found: C, 58.90; H, 3.47; N, 16.88.

EXAMPLE 10

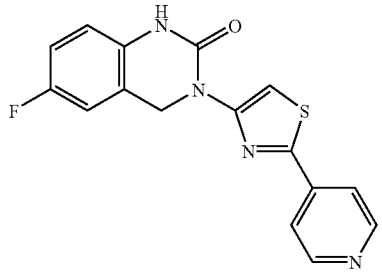

6-Fluoro-3-(2-(4-pyridyl)(1,3-thiazol-4-yl))-1,3,4-trihydroquinazolin-2-one (a) Preparation of 2-(bromomethyl)-4-fluoro-1-nitrobenzene. This compound was prepared according to the method described in Example 6d using 5-fluoro-2-nitrotoluene (Aldrich) (5.30 g, 34.2 mmol), NBS (7.31 g, 41.1 mmol), and AIBN (0.60 g, 3.7 mmol) were used. The crude compound was purified by flash chromatography on silica gel using 2% EtOAc/Hexane to afford an orange oil.

(b) Preparation of N-[(5-fluoro-2-nitrophenyl)methyl]prop-2-enyloxy-N-(2-(4-pyridyl)(1,3-thiazol-4-yl))carboxamide. This compound was prepared according to the method described in Example 6e using prop-2-enyloxy-N-(2-(4-pyridyl)(1,3-thiazol-4-yl))carboxamide (Example 6, Step c) (1.03 g, 3.9 mmol), 60% NaH (211 mg, 5.3 mmol), and 2-(bromomethyl)-4-fluoro-1-nitrobenzene (Step a) (919 mg, 3.9 mmol). The crude oil was purified by flash chromatography on silica gel using 98:2 CH$_2$Cl$_2$:MeOH as the eluant to afford a light orange oil. MS m/z: 415 (M+1). Calc'd for C$_{19}$H$_{15}$FN$_4$O$_4$S—414.08.

(c) Preparation of N-[(2-amino-5-fluorophenyl)methyl]prop-2-enyloxy-N-(2-(4-pyridyl)(1,3-thiazol-4-yl))carboxamide. N-[(5-Fluoro-2-nitrophenyl)methyl]prop-2-enyloxy-N-(2-(4-pyridyl)(1,3-thiazol-4-yl))carboxamide (Step b) (949 mg, 2.3 mmol), iron powder (680 mg, 12.2 mmol), and NH$_4$Cl (79 mg, 1.5 mmol) were dissolved in 60 mL of CH$_3$CN and 30 mL of H$_2$O. The solution was stirred at 80° C. for 2 h, and filtered while hot through a bed of Celite®. The filtrate was concentrated in vacuo to an aqueous solution. The aqueous solution was extracted with EtOAc (3×). The combined EtOAc layers were washed with brine, dried over MgSO$_4$, and concentrated in vacuo to afford a tan solid. MS m/z: 385 (M+1). Calc'd for C$_{19}$H$_{17}$FN$_4$O$_2$S—384.11.

(d) Preparation of [(2-amino-5-fluorophenyl)methyl](2-(4-pyridyl)(1,3-thiazol-4-yl))amine. N-[(2-Amino-5-fluorophenyl)methyl]prop-2-enyloxy-N-(2-(4-pyridyl)(1,3-thiazol-4-yl))carboxamide (Step c) (850 mg, 2.2 mmol), morpholine (4 mL, 45.7 mmol), and Pd(PPh$_3$)$_4$ (260 mg, 0.2 mmol) were dissolved in 30 mL of THF. The solution was stirred for 4 h and concentrated in vacuo to remove THF and morpholine. The residue was partitioned between EtOAc:H$_2$O. The aqueous layer was extracted with EtOAc (2×). The combined EtOAc layers were washed 1N HCl (aq) (2×). The combined acidic aqueous layers were neutralized with 5N NaOH (aq) and the extracted with EtOAc (3×). The combined EtOAc layers were washed with brine, dried over MgSO$_4$, and concentrated in vacuo to afford a light brown oil. MS m/z: 301 (M+1). Calc'd for C$_{15}$H$_{13}$FN$_4$S—300.08.

(e) Preparation of 6-fluoro-3-(2-(4-pyridyl)(1,3-thiazol-4-yl))-1,3,4-trihydroquinazolin-2-one. [(2-Amino-5-fluorophenyl)methyl](2-(4-pyridyl)(1,3-thiazol-4-yl))amine (Step d) (610 mg, 2.0 mmol) and CDI (995 mg, 6.1 mmol) were dissolved in 20 mL of anhydrous DMF. NaH (60% in mineral oil) (290 mg, 7.3 mmol) was added portion-wise and the reaction was stirred for 4 h. The reaction mixture was diluted with H$_2$O and after stirring for 0.5 h was filtered. The precipitate was washed with H$_2$O (2×10 mL), then stirred in a solution of H$_2$O:Hexane (1:1) to remove any remaining mineral oil. The precipitate was again filtered and dried in vacuo at 60° C. to afford a white solid. MP: 290–291° C. MS m/z: 327 (M+1). Anal. Calc'd for C$_{16}$H$_{11}$FN$_4$OS.0.1H$_2$O: C, 58.56; H, 3.44; N, 17.07. Found: C, 58.31; H, 3.56; N, 16.82.

EXAMPLE 11

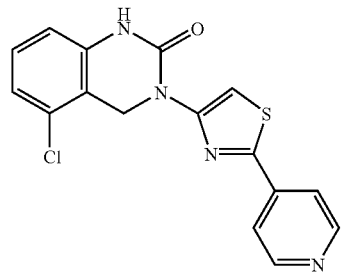

5-Chloro-3-(2-(4-pyridyl)(1,3-thiazol-4-yl))-1,3,4-trihydroquinazolin-2-one (a) Preparation of 2-(bromomethyl)-3-chloro-1-nitrobenzene. This compound was prepared according to the method described in Example 6d using 2-chloro-6-nitrotoluene (Aldrich) (4.06 g, 23.6 mmol), NBS (5.07 g, 28.5 mmol), and AIBN (0.45 g, 2.7 mmol). The crude compound was purified by flash chromatography on silica gel using 2% EtOAc/Hexane to afford a white solid.

(b) Preparation of N-[(6-chloro-2-nitrophenyl)methyl]prop-2-enyloxy-N-(2-(4-pyridyl)(1,3-thiazol-4-yl))carboxamide. This compound was prepared according to the method described in Example 6e using prop-2-enyloxy-N-(2-(4-pyridyl)(1,3-thiazol-4-yl))carboxamide (Example 6, Step c) (1.24 g, 4.8 mmol), 60% NaH (260 mg, 6.5 mmol), and 2-(bromomethyl)-3-chloro-1-nitrobenzene (Step a) (1.19 g, 4.8 mmol) to give crude compound. MS m/z: 431 (M+1). Calc'd for $C_{19}H_{15}ClN_4O_4S$—430.05.

(c) Preparation of [(2-chloro-6-nitrophenyl)methyl](2-(4-pyridyl)(1,3-thiazol-4-yl))amine. This compound was prepared according to the method described in Example 6f using N-[(6-chloro-2-nitrophenyl)methyl]prop-2-enyloxy-N-(2-(4-pyridyl)(1,3-thiazol-4-yl))carboxamide (Step b) (1.5 g), morpholine (5 mL, 57.2 mmol), and Pd(PPh$_3$)$_4$ (366 mg, 0.3 mmol) to give a brown-orange solid. MS m/z: 347 (M+1). Calc'd for $C_{15}H_{11}ClN_4O_2S$—346.03.

(d) Preparation of [(2-amino-6-chlorophenyl)methyl](2-(4-pyridyl)(1,3-thiazol-4-yl))amine. This compound was prepared according to the method described in Example 6g using [(2-chloro-6-nitrophenyl)methyl](2-(4-pyridyl)(1,3-thiazol-4-yl))amine (Step c) (1.05 g, 3.0 mmol), iron powder (935 mg, 16.7 mmol), and NH$_4$Cl (87 mg, 1.6 mmol) to give a light brown oil. MS m/z: 317 (M+1). Calc'd for $C_{15}H_{13}ClN_4S$—316.05.

(e) Preparation of 5-chloro-3-(2-(4-pyridyl)(1,3-thiazol-4-yl))-1,3,4-trihydroquinazolin-2-one. This compound was prepared according to the method described in Example 10e using [(2-amino-6-chlorophenyl)methyl](2-(4-pyridyl)(1,3-thiazol-4-yl))amine (Step d) (740 mg, 2.3 mmol), 60% NaH (342 mg, 8.6 mmol), and CDI (1.16 g, 7.1 mmol). The crude solid was purified by flash chromatography on silica gel using 95:5 CH$_2$Cl$_2$:MeOH to afford an off-white solid. MP: 292–293° C. MS m/z: 343 (M+1). Anal. Calc'd for $C_{16}H_{11}ClN_4OS \cdot 0.2H_2O$: C, 55.48; H, 3.32; N, 16.17. Found: C, 55.24; H, 3.47; N, 15.90.

EXAMPLE 12

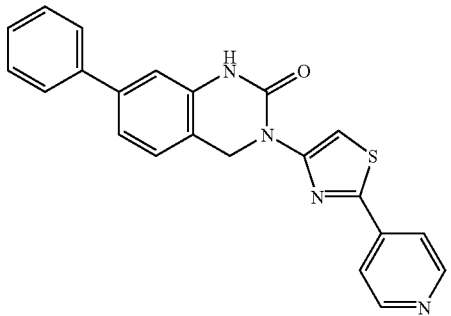

7-Phenyl-3-(2-(4-pyridyl)(1,3-thiazol-4-yl))-1,3,4-trihydroquinazolin-2-one (a) Preparation of 1-methyl-2-nitro-4-phenylbenzene. Bromobenzene (Aldrich) (3.3 mL, 29.6 mmol), 3-nitro-4-methylbenzene boronic acid (Avocado) (5.11 g, 28.3 mmol), and 2M Na$_2$CO$_3$ (63 mL, 126.0 mmol) were dissolved in 100 mL of toluene/15 mL of EtOH. Pd(PPh$_3$)$_4$ (2.04 g, 1.8 mmol) was added and the mixture was stirred at 80° C. for 4 h. The reaction was cooled to RT, and partitioned between EtOAc:H$_2$O. The aqueous layer was extracted with EtOAc (3×). The combined EtOAc layers were washed with brine, dried over MgSO$_4$, and concentrated in vacuo. The crude solid was purified by flash chromatography on silica gel using 98:2 Hexane:EtOAc to afford a light orange solid.

(b) Preparation of 1-(bromomethyl)-2-nitro-4-phenylbenzene. This compound was prepared according to the method described in Example 6d using 1-methyl-2-nitro-4-phenylbenzene (Step a) (4.68 g, 22.0 mmol), NBS (4.73 g, 26.5 mmol), and AIBN (0.43 g, 2.6 mmol). The crude compound was purified by flash chromatography on silica gel using 2% EtOAc/Hexane to afford a white solid.

(c) Preparation of N-[(2-nitro-4-phenylphenyl)methyl]prop-2-enyloxy-N-(2-(4-pyridyl)(1,3-thiazol-4-yl))carboxamide. This compound was prepared according to the method described in Example 6e using prop-2-enyloxy-N-(2-(4-pyridyl)(1,3-thiazol-4-yl))carboxamide (Example 6, Step c) (960 mg, 3.7 mmol), 60% NaH (190 mg, 4.8 mmol), and 1-(bromomethyl)-2-nitro-4-phenylbenzene (Step b) (1.30 g, 4.4 mmol). The crude oil was purified by flash chromatography on silica gel using 98:2 CH$_2$Cl$_2$: MeOH as the eluant to afford a brown oil. MS m/z: 473 (M+1). Calc'd for $C_{25}H_{20}N_4O_4S$—472.12.

(d) Preparation of [(2-nitro-4-phenylphenyl)methyl](2-(4-pyridyl)(1,3-thiazol-4-yl))amine. This compound was prepared according to the method described in Example 6f using N-[(2-nitro-4-phenylphenyl)methyl]prop-2-enyloxy-N-(2-(4-pyridyl)(1,3-thiazol-4-yl))carboxamide (Step c) (800 mg, 1.7 mmol), morpholine (4.5 mL, 51.4 mmol), and Pd(PPh$_3$)$_4$ (270 mg, 2.3 mmol) to give a brown oil. MS m/z: 389 (M+1). Calc'd for $C_{21}H_{16}N_4O_2S$—388.10.

(e) Preparation of [(2-amino-4-phenylphenyl)methyl](2-(4-pyridyl)(1,3-thiazol-4-yl))amine. This compound was prepared according to the method described in Example 6g using [(2-nitro-4-phenylphenyl)methyl](2-(4-pyridyl)(1,3-thiazol-4-yl))amine (Step d) (499 mg, 1.3 mmol), Fe powder (420 mg, 7.5 mmol), and NH$_4$Cl (40 mg, 0.8 mmol) to give a light-brown oil. MS m/z: 359 (M+1). Calc'd for $C_{21}H_{18}N_4S$—358.13.

(f) Preparation of 7-phenyl-3-(2-(4-pyridyl)(1,3-thiazol-4-yl))-1,3,4-trihydroquinazolin-2-one. This compound was prepared according to the method described in Example 10e using [(2-amino-4-phenylphenyl)methyl](2-(4-pyridyl)(1,3-thiazol-4-yl))amine (Step e) (80 mg, 0.22 mmol), 60% NaH (27 mg, 1.1 mmol), and CDI (105 mg, 0.65 mmol) to give an off-white solid. MP: 248–250° C. MS m/z: 385 (M+1). Anal. Calc'd for $C_{22}H_{16}N_4OS \cdot 0.4H_2O$: C, 67.47; H, 4.32; N, 14.31. Found: C, 67.86; H, 4.71; N, 13.77.

EXAMPLE 13

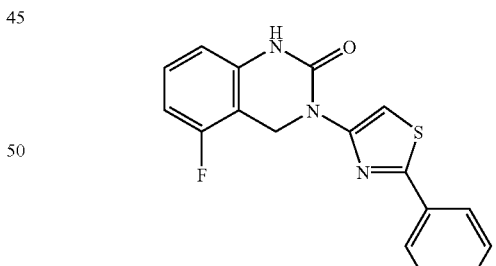

5-Fluoro-3-(2-(4-pyridyl)(1,3-thiazol-4-yl))-1,3,4-trihydroquinazolin-2-one (a) Preparation of 2-(bromomethyl)-3-fluoro-1-nitrobenzene. This compound was prepared according to the method described in Example 6d from 2-fluoro-6-nitrotoluene (Aldrich) (4.05 g, 26.1 mmol), NBS (5.61 g, 31.5 mmol), and AIBN (443 mg, 2.7 mmol). The crude compound was purified by flash chromatography on silica gel using 2% EtOAc/Hexane to afford a white solid.

(b) Preparation of N-[(6-fluoro-2-nitrophenyl)methyl]prop-2-enyloxy-N-(2-(4-pyridyl)(1,3-thiazol-4-yl))carboxamide. This compound was prepared according to the method described in Example 6e from prop-2-enyloxy-N-(2-(4-pyridyl)(1,3-thiazol-4-yl))carboxamide (Example 6, Step c) (1.07 g, 4.1 mmol), 60% NaH (199 mg, 5.0 mmol), and 2-(bromomethyl)-3-fluoro-1-nitrobenzene (Step a) (980 mg, 4.8 mmol) to give a dark oil.

(c) Preparation of [(2-fluoro-6-nitrophenyl)methyl](2-(4-pyridyl)(1,3-thiazol-4-yl))amine. This compound was prepared according to the method described in Example 6f from N-[(6-fluoro-2-nitrophenyl)methyl]prop-2-enyloxy-N-(2-(4-pyridyl)(1,3-thiazol-4-yl))carboxamide (Step b) (1.4 g), morpholine (5 mL, 57.2 mmol), and Pd(PPh$_3$)$_4$ (470 mg, 0.4 mmol) to give a brown oil. MS m/z: 331 (M+1). Calc'd for $C_{15}H_{11}FN_4O_2S$—330.06.

(d) Preparation of [(2-amino-6-fluorophenyl)methyl](2-(4-pyridyl)(1,3-thiazol-4-yl))amine. This compound was prepared according to the method described in Example 6g from [(2-fluoro-6-nitrophenyl)methyl](2-(4-pyridyl)(1,3-thiazol-4-yl))amine (Step c) (760 mg, 2.3 mmol), iron powder (680 mg, 12.2 mmol), and NH$_4$Cl (64 mg, 1.2 mmol) to give a light brown oil.

(e) Preparation of 5-fluoro-3-(2-(4-pyridyl)(1,3-thiazol-4-yl))-1,3,4-trihydroquinazolin-2-one. This compound was prepared according to the method described in Example 10e from [(2-amino-6-fluorophenyl)methyl](2-(4-pyridyl)(1,3-thiazol-4-yl))amine (Step d) (230 mg, 0.8 mmol), 60% NaH (115 mg, 2.9 mmol), and CDI (372 mg, 2.3 mmol) gave an off-white solid. MP: 247–249° C. MS m/z: 327 (M+1). Anal. Calc'd for $C_{16}H_{11}FN_4OS$: C, 58.89; H, 3.40; N, 17.17. Found: C, 59.35; H, 3.58; N, 16.90.

EXAMPLE 14

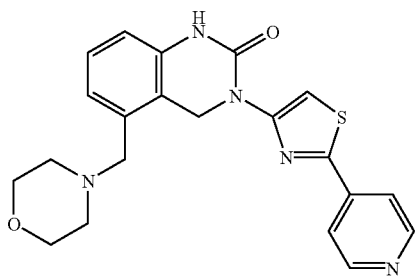

5-(Morpholin-4-ylmethyl)-3-(2-(4-pyridyl)(1,3-thiazol-4-yl))-1,3,4-trihydroquinazolin-2-one (a) Preparation of 6-(bromomethyl)-2-nitrobenzenecarbonitrile. This compound was prepared according to the method described in Example 6d from 6-nitro-o-tolunitrile (Aldrich) (5.67 g, 34.9 mmol), NBS (7.87 g, 31.5 mmol), and AIBN (788 mg, 4.8 mmol). The crude compound was purified by flash chromatography on silica gel using 15% EtOAc/Hexane to afford a light yellow solid.

(b) Preparation of 6-(morpholin-4-ylmethyl)-2-nitrobenzenecarbonitrile. 6-(Bromomethyl)-2-nitrobenzenecarbonitrile (Step a) (126 mg, 0.5 mmol) was dissolved in 7 mL of DMF. Morpholine (0.21 mL, 2.4 mmol) was added and the reaction changed immediately from a light yellow to an orange-tan color. The reaction mixture was partitioned between EtOAc:H$_2$O. The aqueous layer was extracted with EtOAc (3×). The combined EtOAc layers were washed with H$_2$O and brine, then dried over MgSO$_4$ and concentrated in vacuo to give a yellow solid. MS m/z: 248 (M+1). Calc'd from $C_{12}H_{13}N_3O_3$—247.10.

(c) Preparation of [6-(morpholin-4-ylmethyl)-2-nitrophenyl]methylamine. 6-(Morpholin-4-ylmethyl)-2-nitrobenzenecarbonitrile (Step b) (1.59 g, 6.4 mmol) was added as a solid to a cooled solution (0° C.) of 1M BH$_3$.THF (35 mL, 35 mmol). The solution was warmed to RT and stirred overnight. The mixture was concentrated to half its volume, carefully poured into 40 mL of 10% HCl (aq), and stirred at reflux for 3 h. The mixture was cooled to RT and concentrated in vacuo to remove any remaining THF. The resulting aqueous solution was washed with benzene (2×) and neutralized with 1N NaOH. The aqueous solution was extracted with CH$_2$Cl$_2$ (2×). The combined CH$_2$Cl$_2$ layers were washed with brine, dried over MgSO$_4$ and concentrated in vacuo to give a light brown oil. MS m/z: 252 (M+1). Calc'd for $C_{12}H_{17}N_3O_3$—251.13.

(d) Preparation of ethyl 4-hydroxy-2-(4-pyridyl)-1,3-thiazole-5-carboxylate. Thioisonicotinamide (Lancaster Synthesis, Ltd.) (16.0 g, 115.9 mmol) was dissolved in 300 mL of EtOH. Diethyl bromomalonate (Aldrich) (19.8 mL, 116.1 mmol) and pyridine (37.5 mL, 463.7 mmol) were added and the solution was stirred at 80° C. overnight. The reaction was cooled to RT and filtered. The filtrate was concentrated to approximately half its volume and again filtered. The combined solids were air dried to give a yellow solid. MS m/z: 251 (M+1). Calc'd for $C_{11}H_{10}N_2O_3S$—250.04.

(e) Preparation of ethyl 2-(4-pyridyl)-4-[(trifluoromethyl)sulfonyloxy]-1,3-thiazole-5-carboxylate. Triflouromethanesulfonic anhydride (Aldrich) (20 g, 70.9 mmol) was added slowly to a cooled solution (0° C.) of ethyl 4-hydroxy-2-(4-pyridyl)-1,3-thiazole-5-carboxylate (Step d) (12.7 g, 50.8 mmol) and pyridine (12.5 mL, 154.6 mmol) in 200 mL of anhydrous CH$_2$Cl$_2$. The reaction was warmed to RT and stirred overnight. The reaction was concentrated in vacuo and purified by flash chromatography on silica gel using 2:1 to 6:4 Hexane:EtOAc as the eluant to give a light yellow solid. MS m/z: 383 (M+1). Calc'd for $C_{12}H_9F_3N_2O_5S_2$—381.99.

(f) Preparation of ethyl 4-({[6-(morpholin-4-ylmethyl)-2-nitrophenyl]methyl}amino)-2-(4-pyridyl)-1,3-thiazole-5-carboxylate. Ethyl 2-(4-pyridyl)-4-[(trifluoromethyl)sulfonyloxy]-1,3-thiazole-5-carboxylate (Step e) (1.49 g, 3.9 mmol) and [6-(morpholin-4-ylmethyl)-2-nitrophenyl]-methylamine (Step c) (975 mg, 3.9 mmol) were dissolved in 25 mL of dioxane. The solution was stirred at 80° C. for 6 h and cooled to RT. The mixture was concentrated in vacuo, and purified by flash chromatography on silica gel using 7:3 to 1:1 CH$_2$Cl$_2$:EtOAc as the eluant to give an orange-yellow solid. MS m/z: 484 (M+1). Calc'd for $C_{23}H_{25}N_5O_5S$—483.16.

(g) Preparation of ethyl 4-({[2-amino-6-(morpholin-4-ylmethyl)phenyl]methyl}amino)-2-(4-pyridyl)-1,3-thiazole-5-carboxylate. Ethyl 4-({[6-(morpholin-4-ylmethyl)-2-nitrophenyl]methyl}amino)-2-(4-pyridyl)-1,3-thiazole-5-carboxylate (Step f) (660 mg, 1.4 mmol) was dissolved in 30 mL of CH$_3$CN/15 mL of H$_2$O. Iron powder (460 mg, 8.2 mmol) and NH$_4$Cl (90 mg, 1.7 mmol) were added and the solution was heated at 80° C. for 2 h. The reaction was filtered while hot and concentrated to an aqueous solution, which was extracted with EtOAc (3×). The combined EtOAc layers were washed with brine, dried over MgSO$_4$, and concentrated in vacuo to give a light brown oil. MS m/z: 454 (M+1). Calc'd for $C_{23}H_{27}N_5O_3S$—453.18.

(h) Preparation of ethyl 4-[5-(morpholin-4-ylmethyl)-2-oxo(1,3,4-trihydroquinazolin-3-yl)]-2-(4-pyridyl)-1,3-thiazole-5-carboxylate. This compound was prepared according to the method described in Example 10e from ethyl 4-({[6-(morpholin-4-ylmethyl)-2-nitrophenyl]methyl}amino)-2-(4-pyridyl)-1,3-thiazole-5-carboxylate (Step g) (530 mg, 1.2 mmol), 60% NaH (170 mg, 4.3 mmol), and CDI (570 mg, 3.5 mmol). The crude solid was purified by flash chromatography on silica gel using 96:4 to 90:10 $CH_2Cl_2$:MeOH as the eluant to give a white solid. MP: 115–117° C. MS m/z: 480 (M+1). Calc'd for $C_{21}H_{21}N_5O_2S$—407.14.

(i) Preparation of 5-(morpholin-4-ylmethyl)-3-(2-(4-pyridyl)(1,3-thiazol-4-yl))-1,3,4-trihydroquinazolin-2-one Ethyl 4-[5-(morpholin-4-ylmethyl)-2-oxo(1,3,4-trihydroquinazolin-3-yl)]-2-(4-pyridyl)-1,3-thiazole-5-carboxylate (Step h) (320 mg, 0.7 mmol) was dissolved in 5:1 MeOH:$CH_2Cl_2$. NaOH (1N, 15 mL) was added and the reaction was stirred at RT for 1 h. The reaction was concentrated in vacuo to a residue. Concentrated $H_2SO_4$ (20 mL) was added and the solution was heated at 120° C. for 2 h. The reaction was cooled to RT, and carefully basified with 5N NaOH while cooling in an ice bath. The aqueous solution was extracted with EtOAc (3×) and the combined EtOAc layers were washed with brine, dried over $MgSO_4$, and concentrated in vacuo. The crude solid was purified by flash chromatography on silica gel using 98:2 to 95:5 $CH_2Cl_2$:MeOH as the eluant to give a light yellow solid. MS m/z: 408 (M+1). The free base was dissolved in $CH_2Cl_2$ (15 mL) and of MeOH (6 mL), and 1N ethereal HCl (Aldrich) (0.36 mL, 0.4 mmol) was added. After stirring for 2 h, the mixture was concentrated in vacuo. The resulting residue was stirred in $Et_2O$ and the resulting precipitate was filtered and washed with $Et_2O$ to give an orange solid. MP: 261–263° C. MS m/z: 408 (M+1). Anal. Calc'd for $C_{21}H_{21}N_5O_2S \cdot 1.0HCl \cdot 2H_2O$: C, 52.55; H, 5.46; N, 14.59. Found C, 52.52; H 5.30; N, 14.42.

EXAMPLE 15

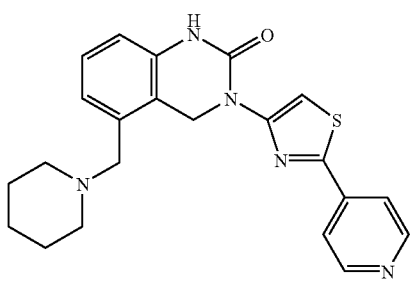

5-(Piperidylmethyl)-3-(2-(4-pyridyl)(1,3-thiazol-4-yl))-1,3,4-trihydroquinazolin-2-one (a) Preparation of 2-nitro-6-(piperidylmethyl)benzenecarbonitrile. This compound was prepared according to the method described in Example 14b from 6-(bromomethyl)-2-nitrobenzenecarbonitrile (Example 14a) (1.85 g, 7.8 mmol), piperidine (Aldrich) (0.85 mL, 8.6 mmol), and 20 mL of $CH_3CN$. The crude solid was purified by flash chromatography on silica gel using 6:4 hexanes:EtOAc as the eluant to afford a light-brown solid. MS m/z: 246 (M+1). Calc'd for $C_{13}H_{15}N_3O_2$—245.12

(b) Preparation of [2-nitro-6-(piperidylmethyl)phenyl]-methylamine. This compound was prepared according to the method described in Example 14c from 2-nitro-6-(piperidylmethyl)-benzenecarbonitrile (Step a) (1.26 g, 5.1 mmol) and 1M $BH_3 \cdot THF$ (25 mL, 25 mmol) to give a light brown oil. MS m/z: 250 (M+1). Calc'd for $C_{13}H_{19}N_3O_2$—249.15.

(c) Preparation of ethyl 4-({[2-nitro-6-(piperidylmethyl)-phenyl]methyl}amino)-2-(4-pyridyl)-1,3-thiazole-5-carboxylate. This compound was prepared according to the method described in Example 14f from ethyl 2-(4-pyridyl)-4-[(trifluoromethyl)sulfonyloxy]-1,3-thiazole-5-carboxylate (Example 14e) (1.62 g, 4.2 mmol) and [2-nitro-6-(piperidylmethyl)phenyl]-methylamine (Step b) (1.06 g, 4.3 mmol). The crude oil was purified by flash chromatography on silica gel using 7:3 $CH_2Cl_2$:EtOAc as the eluant to give a light-brown oil. MS m/z: 482 (M+1). Calc'd for $C_{24}H_{27}N_5O_4S$—481.18.

(d) Preparation of ethyl 4-({[2-amino-6-(piperidylmethyl)phenyl]methyl}amino)-2-(4-pyridyl)-1,3-thiazole-5-carboxylate. This compound was prepared according to the method described in Example 14g from ethyl 4-({[2-nitro-6-(piperidylmethyl)phenyl]methyl}-amino)-2-(4-pyridyl)-1,3-thiazole-5-carboxylate (Step d) (800 mg, 1.7 mmol), iron powder (465 mg, 8.3 mmol), and $NH_4Cl$ (48 mg, 0.9 mmol) to give a yellow solid. MS m/z: 452 (M+1). Calc'd for $C_{24}H_{29}N_5O_2S$—451.20.

(e) Preparation of ethyl 4-[2-oxo-5-(piperidylmethyl)(1,3,4-trihydroquinazolin-3-yl)]-2-(4-pyridyl)-1,3-thiazole-5-carboxylate. The compound was prepared according to the method described in Example 10e from ethyl 4-({[2-amino-6-(piperidylmethyl)phenyl]methyl}-amino)-2-(4-pyridyl)-1,3-thiazole-5-carboxylate (Step d) (630 mg, 1.4 mmol), 60% NaH (195 mg, 4.9 mmol), and CDI (680 mg, 4.2 mmol) to give a yellow solid. MS m/z: 478 (M+1). Calc'd for $C_{25}H_{27}N_5O_3S$—477.18.

(f) Preparation of 5-(piperidylmethyl)-3-(2-(4-pyridyl)(1,3-thiazol-4-yl))-1,3,4-trihydroquinazolin-2-one. This compound was prepared according to the method described in Example 14; from ethyl 4-[2-oxo-5-(piperidylmethyl)(1,3,4-trihydroquinazolin-3-yl)]-2-(4-pyridyl)-1,3-thiazole-5-carboxylate (Step e) (609 mg, 1.3 mmol), 15 mL of 1N NaOH, and 20 mL of concentrated $H_2SO_4$. The crude solid was purified by flash chromatography on silica gel using 98:2 to 96:4 $CH_2Cl_2$:MeOH as the eluant to give a light yellow solid. MS m/z: 406 (M+1). The free base was dissolved in 15 mL of $CH_2Cl_2$/6 mL of MeOH, then 1N ethereal HCl (Aldrich) (0.65 mL, 0.65 mmol) was added. After stirring for 2 h, the mixture was concentrated in vacuo. The residue was stirred in $Et_2O$ and the resulting precipitate was filtered and washed with $Et_2O$ to give an orange solid. MP: 278–280° C. MS m/z: 406 (M+1). Anal. Calc'd for $C_{22}H_{23}N_5OS \cdot 2HCl \cdot 2H_2O$: C, 51.36; H, 5.68; N, 13.61. Found C, 51.21; H 5.67; N, 13.33.

EXAMPLE 16

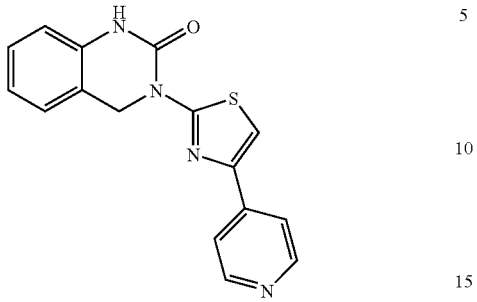

3-(4-(4-Pyridyl)-1,3-thiazol-2-yl)-1,3,4-trihydro-quinazolin-2-one (a) Preparation of amino{[(2-nitrophenyl)methyl]amino}methane-1-thione. To a solution of 2-nitrobenzylamine hydrochloride (Avocado) (4.93 g, 26.1 mmol) and Et$_3$N (10 mL, 71.8 mmol) in CHCl$_3$ (300 mL) was added benzoyl isothiocyanate (Aldrich) (3.4 mL, 25.3 mmol) and the resulting yellow solution was heated to 61° C. After 1.5 h the solvent was removed in vacuo and the residue was dissolved in 70% aqueous MeOH. To the solution was added K$_2$CO$_3$ (4.06 g, 29.4 mmol) and the reaction was heated at reflux for 0.5 h. The yellow-orange mixture was cooled to RT and the crude material was purified by flash chromatography on silica gel with Hexanes:EtOAc (4:1, 1:1, 1:3) as eluant to afford a purple solid. Mp: 228–229° C. MS m/z: 212 (M+1). Calc'd for C$_8$H$_9$N$_3$O$_2$S—211.04.

(b) Preparation of [(2-nitrophenyl)methyl](4-(4-pyridyl)(1,3-thiazol-2-yl))amine. To a heated (45° C.) slurry of amino{[(2-nitrophenyl)methyl]amino}methane-1-thione (Step a) (841 mg, 4.0 mmol) in 50% aqueous MeOH (50 mL) was added 4-(bromoacetyl)pyridine hydrobromide (Aust. J. Chem. 1989, 42, 1735; 1.16 g, 4.1 mmol) and the reaction was stirred at 45° C. for 1.5 h. The reaction was cooled to RT and the solids were filtered and washed with water. Drying over P$_2$O$_5$ overnight gave a pale yellow powder. MS m/z: 313 (M+1), 311 (M−1). Calc'd for C$_{15}$H$_{12}$N$_4$O$_2$S—312.07.

(c) Preparation of 3-(4-(4-pyridyl)-1,3-thiazol-2-yl)-1,3,4-trihydroquinazolin-2-one. A slurry of [(2-nitrophenyl)methyl](4-(4-pyridyl)(1,3-thiazol-2-yl))amine (Step b) (924 mg, 3.0 mmol), iron dust (872 mg, 15.6 mmol), and NH$_4$Cl (119 mg, 2.2 mmol) in 50% aqueous EtOH (30 mL) was heated to 75° C. for 1.5 h. The reaction was cooled to RT and was concentrated in vacuo. The aqueous solution was extracted successively with EtOAc, CH$_2$Cl$_2$ and the combined organics were washed with brine and dried over Na$_2$SO$_4$. Concentration in vacuo gave a solid that was dissolved in THF (10 mL) and to this solution was added 4-nitrophenyl chloroformate (Aldrich) (398 mg, 2.0 mmol) followed by Et$_3$N (0.4 mL, 2.9 mmol). The reaction mixture was heated at reflux and after 9 h, cooled to RT and purified by flash chromatography on silica gel with hexanes:EtOAc (4:1, 1:1) to CH$_2$Cl$_2$:MeOH (19:1, 9:1) as eluant to give a white solid. Mp: >267° C. MS m/z: 309 (M+1); 307 (M−1). Anal. Calc'd for C$_{16}$H$_{12}$N$_4$OS.0.06 MeOH: C, 62.16; H, 3.98; N, 18.06. Found: C, 62.21; H, 4.05; N, 18.04.

EXAMPLE 17

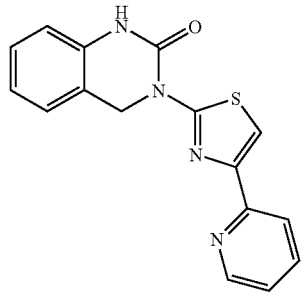

3-(4-(2-Pyridyl)-1,3-thiazol-2-yl)-1,3,4-trihydro-quinazolin-2-one

[(2-Nitrophenyl)methyl](4-(2-pyridyl)(1,3-thiazol-2-yl))amine was prepared according to the method described in Example 16 (Step b) by employing amino{[(2-nitrophenyl)methyl]amino}-methane-1-thione (Example 16, Step a) (1.04 g, 4.9 mmol), 2-(bromoacetyl)pyridine hydrobromide (Aust. J. Chem. 1989, 42, 1735; 1.34 g, 4.9 mmol), and 50% MeOH (10 mL). After 2 h, the reaction was cooled to RT and the solvent was removed in vacuo. The crude material was dissolved in 50% aqueous EtOH and iron dust (Aldrich) (1.419 g, 25.2 mmol) and NH$_4$Cl (190 mg, 3.5 mmol) was added. The reaction was heated to reflux for 1 h, then concentrated in vacuo. The residue was dissolved in THF (20 mL) and to this solution was added 4-nitrophenyl chloroformate (1.17 g, 5.8 mmol) followed by Et$_3$N (1 mL, 7.2 mmol). The reaction was heated at reflux for 2.5 h then cooled to RT. The solvent was removed in vacuo and the crude material was purified by flash chromatography on silica gel with Hexanes:EtOAc (4:1, 1:1, 0:1) as eluant to give a tan solid. Mp: >275° C. MS m/z: 309 (M+1); 307 (M−1). Anal. Calc'd for C$_{16}$H$_{12}$N$_4$OS.0.5H$_2$O: C, 60.55; H, 4.13; N, 17.65. Found: C, 60.20; H, 4.17; N, 16.92.

EXAMPLE 18

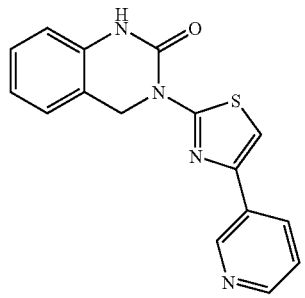

3-(4-(3-Pyridyl)-1,3-thiazol-2-yl)-1,3,4-trihydro-quinazolin-2-one

[(2-Nitrophenyl)methyl](4-(3-pyridyl)(1,3-thiazol-2-yl))amine was prepared according to the method described in Example 16 (Step b) by employing amino{[(2-nitrophenyl)methyl]amino}methane-1-thione (1.03 g, 4.9 mmol) (Example 16, Step a), 3-(bromoacetyl)pyridine hydrobromide (*Aust. J. Chem.* 1989, 42, 1735; 1.37 g, 4.9 mmol), and 50% MeOH (50 mL). The crude yellow oil, iron dust (Aldrich) (1.39 g, 24.9 mmol) and $NH_4Cl$ (198 mg, 3.7 mmol) in 50% EtOH (50 mL) was heated at reflux. After 1 h the solvent was removed in vacuo. The residue was dissolved in THF (20 mL) and to this solution was added 4-nitrophenyl chloroformate (Aldrich) (860 mg, 4.2 mmol) followed by $Et_3N$ (0.85 mL, 6.1 mmol) and the reaction was heated at reflux. After 1 h the reaction was cooled to RT and stirred overnight. The solvent was removed in vacuo and purified by flash chromatography on silica gel with Hexanes:EtOAc (1:1) to $CH_2Cl_2$:MeOH (39:1, 19:1) as eluant to give an off-white solid. Mp: 269–272° C. MS m/z: 309 (M+1). Calc'd for $C_{16}H_{12}N_4OS$—308.07.

EXAMPLE 19

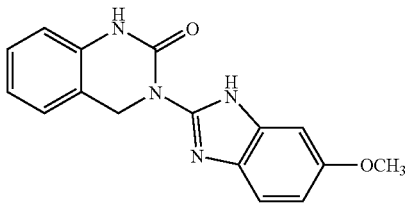

3-(6-Methoxybenzimidazol-2-yl)-1,3,4-trihydroquinazolin-2-one

A mixture of 2-aminobenzylamine (500 mg, 4.1 mmol) and 2-chloro-5-methoxybenzoimidazole (210 mg, 1.2 mmol) was heated at 120° C. for 18 h. The resulting oily residue was dissolved in $CH_2Cl_2$ (30 mL) and washed with $H_2O$ (30 mL). The organic layer was separated, dried over $Na_2SO_4$, and concentrated to provide crude benzimidazole amine as a solid which was treated with CDI (1.0 g, 6.0 mmol) in anhydrous DMF (15 mL). After stirring at RT for 18 h, the reaction mixture was concentrated. The residue was purified by prep TLC to give an oil which was triturated from $CH_2Cl_2$ and hexane to yield a solid. Further purification by prep HPLC provided the title compound as white solid. MS m/z: 295 (M+H$^+$); MALDI FTMS (DHB) m/z: 295.1184 (M+H; Calc'd for $C_{16}H_{15}N_4O_2$, 295.1189).

EXAMPLE 20

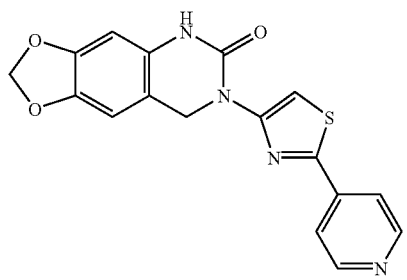

7-(2-(4-Pyridyl)-1,3-thiazol-4-yl)-5,7,8-trihydro-2H-1,3-dioxolano[4,5-g]quinazolin-6-one (a) Preparation of (6-nitro-2H-benzo[3,4-d]1,3-dioxolan-5-yl)methyl methylsulfonate. To a stirred mixture of 6-nitropiperonyl alcohol (Aldrich, 2.0 g, 10.14 mmol) and TEA (1.70 mL, 12.25 mmol) in dried $CH_2Cl_2$ was added methanesulfonyl chloride (1.30 g, 11.16 mmol) dropwise. After stirring at RT for 2 h, the reaction mixture was quenched by the addition of $H_2O$, and the layers were separated. The organic layer was washed with brine, dried over MgSO4, and concentrated to give a brown oil which solidified upon standing.

(b) Preparation of N-[(6-nitro(2H-benzo[d]1,3-dioxolan-5-yl))methyl]prop-2-enyloxy-N-(2-(4-pyridyl)(1,3-thiazol-4-yl))carboxamide. To a stirred suspension of NaH (60% oil dispersion, 0.18 g, 4.60 mmol) in anhydrous DMF (10 mL) was added prop-2-enyloxy-N-(2-(4-pyridyl)(1,3-thiazol-4-yl))carboxamide (Example 6c) (1.0 g, 3.83 mmol). After stirring at RT for 1 h, (6-nitro-2H-benzo[3,4-d]1,3-dioxolan-5-yl)methyl methylsulfonate (Step a) (1.05 g, 3.83 mmol) was added. The reaction mixture was stirred at RT for 14 h. The mixture was concentrated, dissolved in $H_2O$, and extracted with $CH_2Cl_2$ (3×). The organic extracts were combined, dried over $MgSO_4$, concentrated, and purified by flash column chromatography (1.3% MeOH/$CH_2Cl_2$) to afford a light-yellow solid. MS (m/z): 441.2 (M+1). Calc'd for $C_{20}H_{16}N_4O_6S$—440.08.

(c) Preparation of [(6-nitro(2H-benzo[d]1,3-dioxolan-5-yl))methyl](2-(4-pyridyl)(1,3-thiazol-4-yl))amine. To a stirred mixture of N-[(6-nitro(2H-benzo[d]1,3-dioxolan-5-yl))methyl]prop-2-enyloxy-N-(2-(4-pyridyl)(1,3-thiazol-4-yl))carboxamide (Step b) (1.20 g, 2.73 mmol) and morpholine (2.40 g, 27.30 mmol) in anhydrous THF (20 mL) was added $(Ph_3P)_4Pd$ (0.160 g, 0.14 mmol). The mixture was stirred at RT for 2 h then concentrated, dissolved in $H_2O$, and extracted with $CH_2Cl_2$ (3×). The combined organic extracts were dried over $MgSO_4$, concentrated, and the crude brown solid was used in the next step without purification. MS (m/z): 357.2 (M+1). Calc'd for $C_{16}H_{12}N_4O_4S$—356.06.

(d) Preparation of [(6-amino-(2H-benzo[d]1,3-dioxolan-5-yl))methyl](2-(4-pyridyl)(1,3-thiazol-4-yl))amine. A mixture of [(6-nitro-(2H-benzo[d]1,3-dioxolan-5-yl))methyl](2-(4-pyridyl)(1,3-thiazol-4-yl))amine (Step c) (1.50 g, 4.21 mmol), $NH_4Cl$ (0.12 g, 2.11 mmol), and iron powder (1.20 g, 21.06 mmol) in EtOH/$H_2O$ (1:1, 40 mL) was heated at reflux for 1 h. The mixture was filtered hot. The filtrate was concentrated, dissolved in water, and extracted with $CH_2Cl_2$ (3×). The combined organic extracts were washed with brine, dried over $MgSO_4$, concentrated, and the crude material was purified by flash column chromatography (2% MeOH/$CH_2Cl_2$) to afford a yellow solid. MS (m/z): 327.2 (M+1). Calc'd for $C_{16}H_{14}N_4O_2S$—326.08.

(e) Preparation of 7-(2-(4-pyridyl)-1,3-thiazol-4-yl)-5,7,8-trihydro-2H-1,3-dioxolano[4,5-g]quinazolin-6-one. To a stirred mixture of [(6-amino(2H-benzo[d]1,3-dioxolan-5-yl))methyl](2-(4-pyridyl)(1,3-thiazol-4-yl))amine (Step d) (0.35 g, 1.11 mmol) and CDI (0.54 g, 3.31 mmol) in anhydrous DMF (5 mL) was added NaH (60% oil dispersion, 0.15 g, 3.86 mmol) portionwise. After stirring at RT overnight, the reaction mixture was quenched by addition of $H_2O$. The tan solid was filtered, dried, and triturated in EtOH to afford a light-tan solid. The product was dissolved in MeOH and 4M HCl in dioxane (0.075 mL) was added. The solution was concentrated and the evaporated in vacuo to give an orange solid. MS (m/z): 353.2 (M+1). Anal. Calc'd For C₁₇H₁₂N₄O₃S·1.0HCl·1.0.5H₂O: C, 51.32; H, 3.51; N, 14.07; Found: C, 51.25; H, 3.40; N, 13.89.

EXAMPLE 21

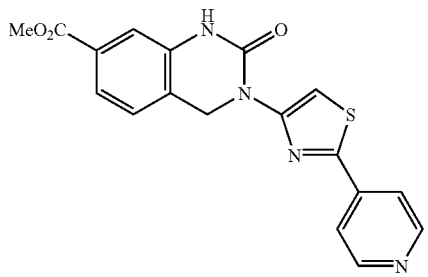

Methyl 2-oxo-3-(2-(4-pyridyl)(1,3-thiazol-4-yl))-1,3,4-trihydroquinazoline-7-carboxylate (a) Preparation of 3-nitro-4-{[prop-2-enyloxy-N-(2-(4-pyridyl)(1,3-thiazol-4-yl))carbonylamino]-methyl}benzoic acid. To a stirred suspension of NaH (60% oil dispersion, 0.29 g, 7.35 mmol) in anhydrous DMF (10 mL) was added prop-2-enyloxy-N-(2-(4-pyridyl)(1,3-thiazol-4-yl))carboxamide (Example 6c) (1.60 g, 6.13 mmol). After stirring at RT for 1 h, 3-nitro-4-bromomethylbenzoic acid (1.60 g, 6.13 mmol) was added. The solution was stirred at RT for 14 h, then quenched by the addition of H₂O, and the tan material was collected by filtration, air dried, and used in the next step. MS (m/z): 441.3 (M+1). Calc'd for C₂₀H₁₆N₄O₆S—440.08.

(b) Preparation of methyl 3-nitro-4-{[prop-2-enyloxy-N-(2-(4-pyridyl)(1,3-thiazol-4-yl))carbonylamino]methyl}benzoate. A solution of 3-nitro-4-{[prop-2-enyloxy-N-(2-(4-pyridyl)(1,3-thiazol-4-yl))carbonylamino]methyl}benzoic acid (Step a) in methanolic HCl (30 mL) was heated at reflux for 24 h. The mixture was cooled, concentrated, dissolved in H₂O, and neutralized by the addition of saturated aqueous K₂CO₃. A light-yellow solid was filtered and purified by flash chromatography on silica gel (1.3% MeOH/CH₂Cl₂) to give a yellow solid. MS (m/z): 455.3 (M+1). Calc'd for C₂₁H₁₈N₄O₆S—454.09.

(c) Preparation of methyl 3-nitro-4-{[(2-(4-pyridyl)(1,3-thiazol-4-yl))amino]methyl}benzoate. To a stirred mixture of methyl 3-nitro-4-{[prop-2-enyloxy-N-(2-(4-pyridyl)(1,3-thiazol-4-yl))carbonylamino]methyl}benzoate (Step b) (1.20 g, 2.73 mmol) and morpholine (2.40 g, 27.30 mmol) in anhydrous THF (20 mL) was added (Ph₃P)₄Pd (0.160 g, 0.14 mmol). The mixture was stirred at RT for 2 h. The solution was concentrated, dissolved in H₂O, and extracted with CH₂Cl₂ (3×). The combined organic extracts were dried over MgSO₄, concentrated, and purified by flash chromatography on silica gel (2% MeOH/CH₂Cl₂) to afford a light brown oil. MS (m/z) 371.3 (M+1). Calc'd for C₁₇H₁₄N₄O₄S—370.07.

(d) Preparation of methyl 3-amino-4-{[(2-(4-pyridyl)(1,3-thiazol-4-yl))amino]methyl}benzoate. A mixture of methyl 3-nitro-4-{[(2-(4-pyridyl)(1,3-thiazol-4-yl))amino]methyl}benzoate (Step c) (0.30 g, 0.81 mmol), NH₄Cl (0.022 g, 0.41 mmol), and iron powder (0.23 g, 4.05 mmol) in EtOH/H₂O (1:1, 10 mL) was heated at reflux for 1 h. The mixture was filtered hot, and the filtrate was concentrated, dissolved in water, and extracted with CH₂Cl₂ (3×). The combined organic extracts were washed with brine, dried over MgSO₄, concentrated, and the crude material was purified by flash chromatography (1.5% MeOH/CH₂Cl₂) to afford a brown solid. MS (m/z): 371.3 (M+1). Calc'd for C₁₇H₁₆N₄O₂S—340.10.

(e) Preparation of methyl 2-oxo-3-(2-(4-pyridyl)(1,3-thiazol-4-yl))-1,3,4-trihydroquinazoline-7-carboxylate. To a stirred mixture of methyl 3-amino-4-{[(2-(4-pyridyl)(1,3-thiazol-4-yl))amino]methyl}benzoate (Step d) (0.14 g, 0.41 mmol) and CDI (0.20 g, 1.24 mmol) in anhydrous DMF (5 mL) was added NaH (60% oil dispersion, 0.06 g, 1.44 mmol) portionwise. After stirring at RT overnight, the mixture was quenched by the addition of H₂O. The tan solid was filtered, dried, and triturated in EtOH to afford a light tan solid. The product was dissolved in MeOH and 4M HCl in p-dioxane (0.075 mL) was added. The solution was concentrated and the dried to give a tan solid. MS (m/z): 367.2 (M+1). Calc'd for C₁₈H₁₄N₄O₃S—366.08.

EXAMPLE 22

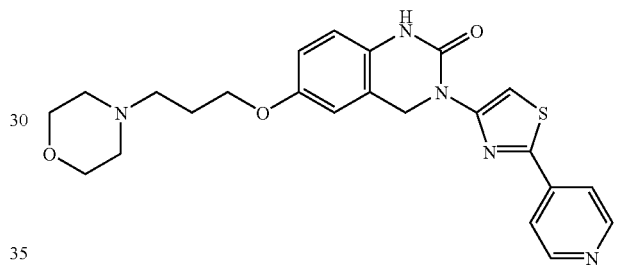

6-(3-Morpholin-4-ylpropoxy)-3-(2-(4-pyridyl)(1,3-thiazol-4-yl))-1,3,4-trihydroquinazolin-2-one (a) Preparation of 5-hydroxy-2-nitrobenzenecarbonitrile. A mixture of 3-chloro-6-nitrobenzonitrile (Aldrich, 10 g, 54.77 mmol), potassium acetate (8.06 g, 82.16 mmol), and 18-crown-6 ether (21.72 g, 82.16 mmol) in anhydrous CH₃CN (150 mL) was heated at reflux for 14 h. The mixture was cooled, dissolved in 50 mL of 1N NaOH, stirred for 2 h. The mixture was concentrated, extracted with ether. The aqueous layer was acidified with 10% HCl, and a tan solid was collected by filtration, which was air-dried.

(b) Preparation of 5-(3-morpholin-4-ylpropoxy)-2-nitrobenzenecarbonitrile. A mixture of 5-hydroxy-2-nitrobenzenecarbonitrile (Step a) (1.0 g, 6.10 mmol), K₂CO₃ (3.4 g, 24.38 mmol), and 1-(3-chloropropyl)morpholine (1.46 g, 7.32 mmol) in acetone (20 mL) was heated at reflux for 24 h. The mixture was cooled, concentrated, dissolved in H₂O, and extracted with CH₂Cl₂ (3×). The organic extracts were dried over MgSO₄, concentrated, and purified by flash column chromatography (2% MeOH/CH₂Cl₂) to give a light yellow oil.

(c) Preparation of [5-(3-morpholin-4-ylpropoxy)-2-nitrophenyl]methylamine. To a stirred solution of 5-(3-morpholin-4-ylpropoxy)-2-nitrobenzenecarbonitrile (Step b) in anhydrous THF (40 mL) was added 1.0M BH₃·THF (13 mL, 12.9 mmol) dropwise. The solution was stirred at RT for 3 h. The reaction was quenched by the addition of 10% aqueous HCl until pH=1, and the solution was heated at reflux for 2 h. The mixture was cooled, and extracted with Et$_2$O. The acidic aqueous layer was neutralized by saturated aqueous K$_2$CO$_3$, and extracted with CH$_2$Cl$_2$ (3×). The combined organic extracts were washed with brine, dried over MgSO$_4$, and concentrated to give a reddish oil.

(d) Preparation of ethyl 4-({[5-(3-morpholin-4-ylpropoxy)-2-nitrophenyl]methyl}amino)-2-(4-pyridyl)-1,3-thiazole-5-carboxylate. A mixture of ethyl 2-(4-pyridyl)-4-[(trifluoromethyl)sulfonyloxy]-1,3-thiazole-5-carboxylate (Example 14e) (0.10 g, 0.262 mmol) and [5-(3-morpholin-4-ylpropoxy)-2-nitrophenyl]methylamine (Step c) (0.081 g, 0.525 mmol) in anhydrous p-dioxane (3 mL) was heated at reflux for 24 h. The mixture was cooled, concentrated, and purified by flash column chromatography (1.5% MeOH/CH$_2$Cl$_2$) to afford a yellow foam. MS (m/z): 528.2 (M+1). Calc'd for C$_{25}$H$_{29}$N$_5$O$_6$S—527.18.

(e) Preparation of ethyl 4-({[2-amino-5-(3-morpholin-4-ylpropoxy)phenyl]methyl}amino)-2-(4-pyridyl)-1,3-thiazole-5-carboxylate. A mixture of ethyl 4-({[5-(3-morpholin-4-ylpropoxy)-2-nitrophenyl]methyl}amino)-2-(4-pyridyl)-1,3-thiazole-5-carboxylate (0.30 g, 0.569 mmol), NH$_4$Cl (0.022 g, 0.20 mmol), and iron powder (0.16 g, 2.85 mmol) in EtOH/H$_2$O (1:1, 10 mL) was heated at reflux for 1 h. The mixture was filtered hot. The filtrate was concentrated, dissolved in water, and extracted with CH$_2$Cl$_2$ (3×). The combined organic extracts were washed with brine, dried over MgSO$_4$, concentrated, and the crude material was purified by flash chromatography (5% MeOH/CH$_2$Cl$_2$) to afford a light brown oil. MS (m/z): 498.2 (M+1). Calc'd for C$_{25}$H$_{31}$N$_5$O$_4$S—497.21

(f) Preparation of ethyl 4-[6-(3-morpholin-4-ylpropoxy)-2-oxo(1,3,4-trihydroquinazolin-3-yl)]-2-(4-pyridyl)-1,3-thiazole-5-carboxylate. To a stirred mixture of ethyl 4-({[2-amino-5-(3-morpholin-4-ylpropoxy)phenyl]methyl}amino)-2-(4-pyridyl)-1,3-thiazole-5-carboxylate (Step e) (0.14 g, 0.41 mmol) and CDI (0.20 g, 1.24 mmol) in anhydrous DMF (5 mL) was added NaH (60% oil dispersion, 0.06 g, 1.44 mmol) portionwise. After stirring at RT overnight, the reaction mixture was quenched by the addition of H$_2$O. The tan solid was filtered, dried, and triturated in EtOH to afford a light tan solid. The compound was dissolved in MeOH, and 4M HCl in p-dioxane (0.075 mL) was added. The solution was concentrated and dried to give a tan solid. MS (m/z): 524.3 (M+1). Calc'd for C$_{26}$H$_{29}$N$_5$O$_5$S—523.19.

(g) Preparation of 6-(3-morpholin-4-ylpropoxy)-3-(2-(4-pyridyl)(1,3-thiazol-4-yl))-1,3,4-trihydroquinazolin-2-one. A mixture of ethyl 4-[6-(3-morpholin-4-ylpropoxy)-2-oxo(1,3,4-trihydroquinazolin-3-yl)]-2-(4-pyridyl)-1,3-thiazole-5-carboxylate (Step f) (0.076 g, 0.145 mmol) and 1N NaOH (0.29 mL, 0.29 mmol) in p-dioxane (2 mL) was stirred at RT for 16 h. The mixture was concentrated to dryness. To this solid was added concentrated H$_3$PO$_4$ (1 mL), and heated at reflux for 2 h. The mixture was cooled, H$_2$O was added, and the solution was neutralized by the addition of NH$_4$OH. The solid was filtered and purified by flash chromatography (4% MeOH/CH$_2$Cl$_2$) to afford a tan solid. MS (m/z): 452.3 (M+1). Calc'd for C$_{23}$H$_{25}$N$_5$O$_3$S—451.17.

EXAMPLE 23

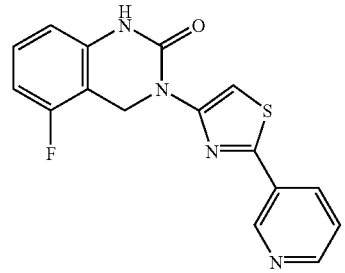

5-Fluoro-3-(2-(3-pyridyl)(1,3-thiazol-4-yl))-1,3,4-trihydroquinazolin-2-one (a) Preparation of ethyl 4-hydroxy-2-(3-pyridyl)-1,3-thiazole-5-carboxylate. To a stirred solution of thionicotinamide (Aldrich) (16.0 g, 115.0 mmol) in EtOH (300 mL) was added diethylbromomalonate (19.8 mL, 116.1 mmol) and pyridine (37.5 g, 463.7 mmol). The reaction mixture was heated at 80° C. for 16 h. The mixture was cooled and filtered. The filtrate was concentrated to minimal volume and the resulting precipitate was collected. The combined solids were air-dried and used in the next step without further purification.

(b) Preparation of ethyl 2-(3-pyridyl)-4-[(trifluoromethyl)sulfonyloxy]-1,3-thiazole-5-carboxylate. To a stirred, cooled (0° C.) mixture of ethyl 4-hydroxy-2-(3-pyridyl)-1,3-thiazole-5-carboxylate (Step a) (16.63 g, 66.49 mmol) and pyridine (13.2 mL, 166.23 mmol) in anhydrous CH$_2$Cl$_2$ (200 mL) was added Tf$_2$O dropwise. After stirring at RT for 14 h, the reaction was quenched by the addition of H$_2$O, and the layers were separated. The organic extracts were washed with brine, dried over MgSO$_4$, and concentrated to give an off white solid. MS (m/z): 383.3 (M+1). Calc'd for C$_{11}$H$_9$N$_2$O$_2$S—233.04.

(c) Preparation of ethyl 4-{[(6-fluoro-2-nitrophenyl)methyl]amino}-2-(3-pyridyl)-1,3-thiazole-5-carboxylate. A mixture of ethyl 2-(3-pyridyl)-4-[(trifluoromethyl)sulfonyloxy]-1,3-thiazole-5-carboxylate (Step b) (2.0 g, 5.23 mmol) and 2-amino-6-fluorobenzylamine (1.83 g, 13.08 mmol) in p-dioxane (40 mL) was heated at reflux for 24 h. The mixture was cooled, concentrated, and purified by flash chromatography (1% MeOH/CH$_2$Cl$_2$) to afford a yellow solid. MS (m/z): 373.3 (M+1). Calc'd for C$_{18}$H$_{15}$FN$_4$O$_4$S—402.08.

(d) Preparation of ethyl 4-{[(2-amino-6-fluorophenyl)methyl]amino}-2-(3-pyridyl)-1,3-thiazole-5-carboxylate. A mixture of ethyl 4-{[(6-fluoro-2-nitrophenyl)methyl]amino}-2-(3-pyridyl)-1,3-thiazole-5-carboxylate (Step c) (0.30 g, 0.81 mmol), NH$_4$Cl (0.022 g, 0.41 mmol), and iron powder (0.23 g, 4.05 mmol) in EtOH/H$_2$O (1:1, 10 mL) was heated at reflux for 1 h. The mixture was filtered hot. The filtrate was concentrated, dissolved in water, and extracted with CH$_2$Cl$_2$ (3×). The combined organic extracts were washed with brine, dried over MgSO$_4$, concentrated, and the crude material was purified by flash chromatography (1.5% MeOH/CH$_2$Cl$_2$) to afford a brown solid. MS (m/z): 373.3 (M+1). Calc'd for C$_{18}$H$_{17}$FN$_4$O$_2$S—372.11.

(e) Preparation of ethyl 4-(5-fluoro-2-oxo(1,3,4-trihydroquinazolin-3-yl))-2-(3-pyridyl)-1,3-thiazole-5-carboxylate. To a stirred mixture ethyl-2-(3-pyridyl)-1,3-thiazole-5-[[6- fluoro-2-amino]benzylamine]-4-carboxylate (Step d) (0.14 g, 0.41 mmol) and CDI (0.20 g, 1.24 mmol) in anhydrous DMF (5 mL) was added NaH (60% oil dispersion, 0.06 g, 1.44 mmol) portionwise. After stirring at RT overnight, the reaction was quenched by the addition of $H_2O$. The resulting solid was filtered, dried, and triturated in EtOH to afford a light tan solid. The compound was dissolved in MeOH and 4M HCl in p-dioxane (0.075 mL) was added. The solution was concentrated and dried to give a tan solid. MS (m/z): 399.3 (M+1). Anal. Calc'd For $C_{19}H_{15}FN_4O_3S$: C, 57.29; H, 3.77; N, 14.06; Found: C, 57.59; H, 4.02; N, 14.40.

(f) Preparation of 4-(5-fluoro-2-oxo(1,3,4-trihydroquinazolin-3-yl))-2-(3-pyridyl)-1,3-thiazole-5-carboxylic acid. A mixture of ethyl 4-(5-fluoro-2-oxo(1,3,4-trihydroquinazolin-3-yl))-2-(3-pyridyl)-1,3-thiazole-5-carboxylate (Step e) (0.076 g, 0.145 mmol) and 1N NaOH (0.29 mL, 0.29 mmol) in p-dioxane (2 mL) was stirred at RT for 16 h. The mixture was concentrated, dissolved in $H_2O$, neutralized by 2N HCl and filtered to give a light-yellow solid. MS (m/z): 371.4 (M+1). Anal. Calc'd for $C_{17}H_{11}FN_4O_3S$: C, 52.85; H, 3.57; N, 15.14; Found: C, 53.05; H, 3.27; N, 15.38.

(g) Preparation of 5-fluoro-3-(2-(3-pyridyl)(1,3-thiazol-4-yl))-1,3,4-trihydroquinazolin-2-one. A mixture of 4-(5-fluoro-2-oxo(1,3,4-trihydroquinazolin-3-yl))-2-(3-pyridyl)-1,3-thiazole-5-carboxylic acid (Step f) (0.30 g, 0.81 mmol) and conc. $H_3PO_4$ (5.0 mL) was heated neat for 1 h at 140° C. The mixture was cooled, diluted with $H_2O$, and basified with conc. $NH_4OH$. The solid was filtered, air-dried, and dissolved in MeOH, and 1.0 M HCl in ether (0.45 mL) was added. The mixture was concentrated to give a tan solid. MS (m/z): 327.4 (M+1) Calc'd For $C_{16}H_{11}FN_4OS.HCl$: C, 52.97; H, 3.33; N, 15.44; Found: C, 52.87; H, 3.45; N, 15.48.

EXAMPLE 24

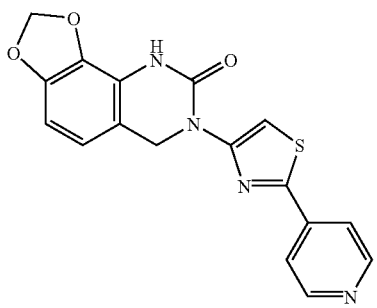

7-(2-(4-Pyridyl)-1,3-thiazol-4-yl)-6,7,9-trihydro-2H-1,3-dioxoleno[4,5-h]quinazolin-8-one (a) Preparation of (4-nitro-2H-benzo[d]1,3-dioxolan-5-yl)methan-1-ol. To a stirred solution of 4-nitro-piperonaldehyde (Lancaster, 1.0 g, 5.13 mmol) in EtOH (20 mL) was added $NaBH_4$ (0.96 g, 25.62 mmol) in small portions. The mixture was stirred 1 h at RT, and slowly quenched with 10% aqueous HCl. The mixture was extracted with EtOAc (3×). The organic extracts were washed with $NaHCO_3$, brine, dried over $MgSO_4$, and concentrated to give a yellow solid.

(b) Preparation of (4-nitro-2H-benzo[d]1,3-dioxolan-5-yl)methyl methylsulfonate. To a stirred mixture of (4-nitro-2H-benzo[d]1,3-dioxolan-5-yl)methan-1-ol (Step a) (1.0 g, 5.08 mmol) and TEA (0.92 mL, 6.61 mmol) in dry $CH_2Cl_2$ was added methanesulfonyl chloride (0.70 g, 6.09 mmol) dropwise. After stirring at RT for 2 h, the reaction mixture was quenched by $H_2O$, and the layers were separated. The organic layer was washed with brine, dried over $MgSO_4$, concentrated and purified by flash column chromatography (10% EtOAc/hexane) to give a yellow solid.

(c) Preparation of N-[(4-nitro(2H-benzo[3,4-d]1,3-dioxolen-5-yl))methyl]prop-2-enyloxy-N-(2-(4-pyridyl)(1,3-thiazol-4-yl))carboxamide. To a stirred suspension of NaH (60% oil dispersion, 0.09 g, 2.13 mmol) in anhydrous DMF (10 mL) was added prop-2-enyloxy-N-(2-(4-pyridyl) (1,3-thiazol-4-yl))carboxamide (Example 1b) (0.47 g, 1.78 mmol). After stirring at RT for 1 h, (4-nitro-2H-benzo[d]1,3-dioxolan-5-yl)methyl methylsulfonate (Step b) (0.48 g, 1.78 mmol) was added. The reaction mixture was stirred at RT for 14 h. The mixture was concentrated, dissolved in $H_2O$, and extracted with $CH_2Cl_2$ (3×). The organic extracts were combined, dried over $MgSO_4$, concentrated, and purified by flash column chromatography (1.3% MeOH/$CH_2Cl_2$) to afford a light-yellow solid. MS (m/z): 441.3 (M+1). Calc'd for $C_{20}H_{16}N_4O_6S$—440.08.

(d) Preparation of [(4-nitro-(2H-benzo[d]1,3-dioxolan-5-yl))methyl](2-(4-pyridyl)(1,3-thiazol-4-yl))amine. A mixture of N-[(4-nitro(2H-benzo[3,4-d]1,3-dioxolen-5-yl))methyl]-prop-2-enyloxy-N-(2-(4-pyridyl) (1,3-thiazol-4-yl)) carboxamide (Step c) (0.50 g, 1.14 mmol), $NH_4Cl$ (0.04 g, 0.57 mmol), and iron powder (0.32 g, 5.68 mmol) in EtOH/$H_2O$ (1:1, 40 mL) was heated at reflux for 2 h. The mixture was filtered hot. The filtrate was concentrated, dissolved in water, extracted with $CH_2Cl_2$ (3×). The combined organic extracts were washed with brine, dried over $MgSO_4$, concentrated, and the crude material was used in the next step without purification. MS (m/z): 357.2 (M+1). Calc'd for $C_{16}H_{12}N_4O_4S$—356.06.

(e) Preparation of [(4-amino-(2H-benzo[d]1,3-dioxolan-5-yl))methyl](2-(4-pyridyl)(1,3-thiazol-4-yl))amine. To a stirred mixture of [(4-nitro-(2H-benzo[d]1,3-dioxolan-5-yl))methyl](2-(4-pyridyl)(1,3-thiazol-4-yl))amine (Step d) (0.40 g, 1.12 mmol) and morpholine (0.98 g, 11.23 mmol) in anhydrous THF (10 mL) was added $(Ph_3P)_4Pd$ (0.13 g, 0.12 mmol). The mixture was stirred at RT overnight. The mixture was concentrated, dissolved in $H_2O$, extracted with $CH_2Cl_2$ (3×). The combined organic extracts were dried over $MgSO_4$, concentrated, and purified by flash column chromatography (1.5% MeOH/$CH_2Cl_2$) to give a brown solid. MS (m/z): 327.2 (M+1). Calc'd for $C_{16}H_{14}N_4O_2S$—326.08.

(f) Preparation of 7-(2-(4-pyridyl)-1,3-thiazol-4-yl)-6,7,9-trihydro-2H-1,3-dioxoleno[4,5-h]quinazolin-8-one. To a stirred mixture of [(4-amino-(2H-benzo[d]1,3-dioxolan-5-yl))methyl](2-(4-pyridyl)(1,3-thiazol-4-yl))amine (Step e) (0.35 g, 1.11 mmol) and CDI (0.54 g, 3.31 mmol) in anhydrous DMF (5 mL) was added NaH (60% oil dispersion, 0.15 g, 3.86 mmol) in portions. After stirring at RT overnight, the reaction mixture was quenched by $H_2O$. The tan solid was filtered, dried, and triturated in EtOH to afford a light tan solid. The product was dissolved in MeOH and 4M HCl in p-dioxane (0.075 mL) was added. The solution was concentrated and the dried to give an orange solid. MS (m/z): 353.5 (M+1). Anal. Calc'd For $C_{17}H_{12}N_5O_3S.HCl.0.25H_2O$: C, 43.43; H, 4.04; N, 11.19; Found: C, 43.56; H, 3.61; N, 11.09.

EXAMPLE 25

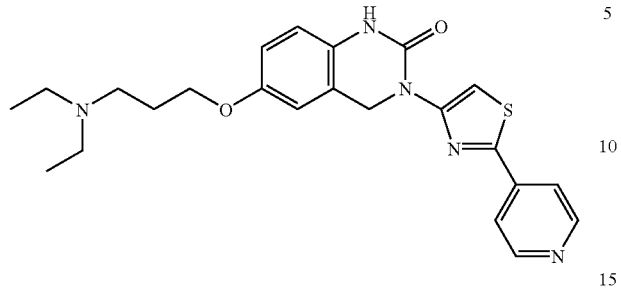

6-[3-(Diethylamino)propoxy]-3-(2-(4-pyridyl) (1,3-thiazol-4-yl))-1,3,4-trihydroquinazolin-2-one (a) Preparation of {3-[4-amino-3-(aminomethyl)phenoxy]-propyl}diethylamine. A solution of 2-nitro-5-[[3-[diethylamino]propyl]oxo]benzonitrile (Oakwood, Inc.) (2.50 g, 9.22 mmol) in MeOH (30 mL) was hydrogenated at RT with $H_2$ and 10% Pd/C (0.25 g) for 14 h. The catalyst was filtered, and the filtrate was concentrated to give a brown oil.

(b) Preparation of ethyl 4-[({2-amino-5-[3-(diethylamino)propoxy]phenyl}methyl)amino]-2-(4-pyridyl)-1,3-thiazole-5-carboxylate. A mixture of ethyl 2-(4-pyridyl)-4-[(trifluoromethyl)sulfonyloxy]-1,3-thiazole-5-carboxylate (Step a) (1.00 g, 2.62 mmol) and {3-[4-amino-3-(aminomethyl)phenoxy]propyl}-diethylamine (1.3 g, 5.23 mmol) in anhydrous dioxane (20 mL) was heated at reflux for 16 h. The mixture was cooled, concentrated, and purified by flash chromatography (7% MeOH/$CH_2Cl_2$) to afford a brown foam. MS (m/z): 484.2 (M+1). Calc'd for $C_{25}H_{33}N_5O_3S$—483.23.

(c) Preparation of ethyl 4-{6-[3-(diethylamino)propoxy]-2-oxo(1,3,4-trihydroquinazolin-3-yl)}-2-(4-pyridyl)-1,3-thiazole-5-carboxylate. To a stirred mixture of ethyl 4-[({2-amino-5-[3-(diethylamino)propoxy]phenyl}methyl)amino]-2-(4-pyridyl)-1,3-thiazole-5-carboxylate (Step b) (0.73 g, 1.51 mmol) and CDI (0.73 g, 4.53 mmol) in anhydrous DMF (10 mL) was added NaH (60% oil dispersion, 0.21 g, 5.29 mmol) portionwise. After stirring at RT overnight, the reaction was quenched by the addition of $H_2O$. The resulting tan solid was filtered, dried, and used in the next step without purification. MS (m/z): 510.2 (M+1). Calc'd for $C_{26}H_{31}N_5O_4S$—509.21.

(d) Preparation of 6-[3-(diethylamino)propoxy]-3-(2-(4-pyridyl)(1,3-thiazol-4-yl))-1,3,4-trihydroquinazolin-2-one. A mixture of ethyl 4-{6-[3-(diethylamino)propoxy]-2-oxo(1,3,4-trihydroquinazolin-3-yl)}-2-(4-pyridyl)-1,3-thiazole-5-carboxylate (Step c) (0.50 g, 0.982 mmol) and 5N NaOH (0.6 mL, 0.29 mmol) in p-dioxane (2 mL) was stirred at RT for 16 h. The mixture was concentrated, dissolved in $H_2O$, acidified, and concentrated to dryness. To the resulting solid was added concentrated $H_3PO_4$ (5 mL), and the solution was heated at reflux for 2 h. The mixture was cooled, quenched with $H_2O$, and neutralized by the addition of $NH_4OH$. The solid was filtered and purified by flash chromatography (7% MeOH/$CH_2Cl_2$) to afford a light-yellow solid. The solid was dissolved in MeOH, 1M HCl in ether (0.35 mL) was added, and the solution was concentrated to give an orange solid. MS (m/z): 438.2 (M+1). Calc'd for $C_{23}H_{27}N_5O_2S$—437.19.

EXAMPLE 26

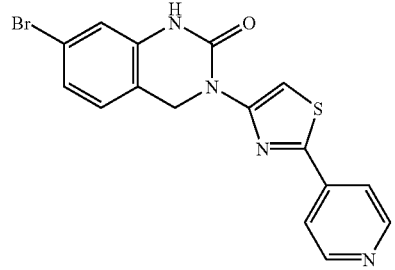

7-Bromo-3-(2-(4-pyridyl)(1,3-thiazol-4-yl))-1,3,4-trihydroquinazolin-2-one (a) Preparation of 4-bromo-1-(bromomethyl)-2-nitrobenzene. A mixture of methyl 2-methyl-3-nitrobenzoate (Aldrich) (10 g, 46.29 mmol), AIBN (1.90 g, 11.57 mmol), and NBS (9.90 g, 55.56 mmol) in anhydrous $CCl_4$ (200 mL) was heated at reflux for 72 h. The mixture was cooled and the resulting solid was filtered. The filtrate was concentrated, and then purified by flash chromatography (10% EtOAc/Hexane) to give a tan solid.

(b) Preparation of N-[(4-bromo-2-nitrophenyl)methyl]prop-2-enyloxy-N-(2-(4-pyridyl)(1,3-thiazol-4-yl))carboxamide. To a stirred suspension of NaH (60% oil dispersion, 0.47 g, 11.72 mmol) in anhydrous DMF (40 mL) was added prop-2-enyloxy-N-(2-(4-pyridyl) (1,3-thiazol-4-yl))carboxamide (Example 1b) (2.55 g, 9.77 mmol). After stirring at RT for 1 h, 4-bromo-1-(bromomethyl)-2-nitrobenzene (Step a) (2.88 g, 9.77 mmol) was added. The reaction mixture was stirred at RT for 14 h. The mixture was concentrated, dissolved in $H_2O$, and extracted with $CH_2Cl_2$ (3×). The organic extracts were combined, dried over $MgSO_4$, concentrated, and purified by flash chromatography (1% MeOH/$CH_2Cl_2$) to afford a brown foam. MS (m/z): 477.3 (M+2). Calc'd for $C_{19}H_{15}BrN_4O_4S$—474.00.

(c) Preparation of N-[(2-amino-4-bromophenyl)methyl]prop-2-enyloxy-N-(2-(4-pyridyl)(1,3-thiazol-4-yl))carboxamide. A mixture of N-[(4-bromo-2-nitrophenyl)methyl]prop-2-enyloxy-N-(2-(4-pyridyl) (1,3-thiazol-4-yl)) carboxamide (Step b) (1-80 g, 3.79 mmol), $NH_4Cl$ (0.10 g, 1.89 mmol), and iron powder (1.10 g, 18.94 mmol) in EtOH/$H_2O$ (1:1, 10 mL) was heated at reflux for 1 h. The mixture was filtered while hot. The filtrate was concentrated, dissolved in water, extracted with $CH_2Cl_2$ (3×). The combined organic extracts were washed with brine, dried over $MgSO_4$, concentrated, and the crude brown oil was used in the next step without further purification. MS (m/z): 447.3 (M+2). Calc'd for $C_{19}H_{17}BrN_4O_2S$—444.03.

(d) Preparation of [(2-amino-4-bromophenyl)methyl](2-(4-pyridyl)(1,3-thiazol-4-yl))amine. To a stirred mixture of N-[(2-amino-4-bromophenyl)methyl]prop-2-enyloxy-N-(2-(4-pyridyl)(1,3-thiazol-4-yl))carboxamide (Step c) (1.50 g, 3.37 mmol) and morpholine (2.293 g, 33.70 mmol) in anhydrous THF (30 mL) was added $(Ph_3P)_4Pd$ (0.20 g, 1.69 mmol). The mixture was stirred at RT for 2 h. The mixture was concentrated, dissolved in $H_2O$, extracted with $CH_2Cl_2$ (3×) The combined organic extracts were dried over $MgSO_4$, concentrated, and purified by flash column chromatography (1.5% MeOH/$CH_2Cl_2$) to afford a light brown solid. MS (m/z): 363.2 (M+2). Calc'd for $C_{15}H_{13}BrN_4S$—360.00.

(e) Preparation of 7-bromo-3-(2-(4-pyridyl)(1,3-thiazol-4-yl))-1,3,4-trihydroquinazolin-2-one. To a stirred mixture of [(2-amino-4-bromophenyl)methyl](2-(4-pyridyl)(1,3-thiazol-4-yl))amine (Step d) and CDI (1.21 g, 7.48 mmol) in anhydrous DMF (15 mL) was added NaH (60% oil dispersion, 0.35 g, 8.72 mmol) portionwise. After stirring at RT overnight, the reaction was quenched by the addition of H$_2$O. The tan solid was filtered, dried, and triturated in EtOH to afford an off white solid. The product was dissolved in MeOH and 1M HCl in Et$_2$O (2.2 mL) was added. The solution was concentrated and dried to give a tan solid. MS (m/z): 368.2 (M+2). Calc'd for C$_{16}$H$_{11}$, BrN$_4$OS—385.98.

EXAMPLE 27

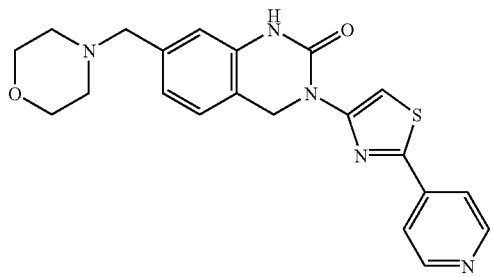

7-(Morpholin-4-ylmethyl)-3-(2-(4-pyridyl)(1,3-thiazol-4-yl))-1,3,4-trihydroquinazolin-2-one (a) Preparation of 4-(bromomethyl)-2-nitrobenzenecarbonitrile. This compound was prepared according to the method described in Example 6d from 3-nitro-p-tolunitrile (Aldrich) (10.40 g, 64.1 mmol), NBS (13.65 g, 76.7 mmol), and AIBN (1.1 g, 6.6 mmol). The crude material was purified by flash chromatography on silica gel using 15% EtOAc/Hexane to afford a light yellow solid.

(b) Preparation of 4-(morpholin-4-ylmethyl)-2-nitrobenzene carbonitrile. 4-(Bromomethyl)-2-nitrobenzene carbonitrile (1.92 g, 7.9 mmol) was dissolved in 40 mL of CH$_3$CN. Morpholine (1.0 mL, 11.4 mmol) was added and the reaction changed immediately from a light yellow to a orange-tan color. The reaction mixture was concentrated in vacuo. The crude residue was purified by flash chromatography on silica gel using CH$_2$Cl$_2$ to 96:4 CH$_2$Cl$_2$:MeOH as the eluant to give a light brown oil. MS m/z: 248 (M+1). Calc'd for C$_{12}$H$_{13}$N$_3$O$_3$—247.10.

(c) Preparation of [4-(morpholin-4-ylmethyl)-2-nitrophenyl]-methylamine. This compound was prepared according to the method described in Example 14c from 4-(morpholin-4-ylmethyl)-2-nitrobenzenecarbonitrile (Step b) (1.40 g, 5.7 mmol) and 1M BH$_3$.THF (25 mL, 25.0 mmol). The crude brown oil was purified by flash chromatography on silica gel using 98:2 CH$_2$Cl$_2$:MeOH as the eluant to give an opaque oil. MS m/z: 252 (M+1). Calc'd for C$_{12}$H$_{17}$N$_3$O$_3$—251.13.

(d) Preparation of ethyl 4-({[4-(morpholin-4-ylmethyl)-2-nitrophenyl]methyl}amino)-2-(3-pyridyl)-1,3-thiazole-5-carboxylate. This compound was prepared according to the method described in Example 14e from ethyl 2-(4-pyridyl)-4-[(trifluoromethyl)sulfonyloxy]-1,3-thiazole-5-carboxylate (863 mg, 3.4 mmol), [4-(morpholin-4-ylmethyl)-2-nitrophenyl]methylamine (Step c) (1.30 g, 3.4 mmol), and 40 mL of dioxane. The crude residue was purified by flash chromatography on silica gel using 7:3 CH$_2$Cl$_2$:EtOAc, then switching to 95:5 CH$_2$Cl$_2$:MeOH as the eluant to give a yellow solid. MS m/z: 484 (M+1). Calc'd for C$_{23}$H$_{25}$N$_5$O$_5$S—483.16.

(e) Preparation of ethyl 4-({[2-amino-4-(morpholin-4-ylmethyl)phenyl]methyl}amino)-2-(3-pyridyl)-1,3-thiazole-5-carboxylate. This compound was prepared according to the method described in Example 14g with ethyl 4-({[4-(morpholin-4-ylmethyl)-2-nitrophenyl]methyl}amino)-2-(4-pyridyl)-1,3-thiazole-5-carboxylate (Step d) (750 mg, 1.6 mmol), Fe powder (533 mg, 9.5 mmol) and NH$_4$Cl (54 mg, 1.0 mmol). A yellow solid was obtained. MS m/z: 454 (M+1). Calc'd for C$_{23}$H$_{27}$N$_5$O$_3$S—453.18.

(f) Preparation of ethyl 4-[7-(morpholin-4-ylmethyl)-2-oxo(1,3,4-trihydroquinazolin-3-yl)]-2-(4-pyridyl)-1,3-thiazole-5-carboxylate. This compound was prepared according to the method described in Example 10e from ethyl 4-({[2-amino-4-(morpholin-4-ylmethyl)phenyl]methyl}amino)-2-(4-pyridyl)-1,3-thiazole-5-carboxylate (Step e) (585 mg, 1.3 mmol), 60% NaH (180 mg, 4.5 mmol), and CDI (670 mg, 4.1 mmol). A yellow solid was obtained. MS m/z: 480 (M+1). Calc'd for C$_{24}$H$_{25}$N$_5$O$_4$S—479.16.

(g) Preparation of 7-(morpholin-4-ylmethyl)-3-(2-(4-pyridyl)(1,3-thiazol-4-yl))-1,3,4-trihydroquinazolin-2-one. This compound was prepared according to the method described in Example 14i using ethyl 4-[7-(morpholin-4-ylmethyl)-2-oxo(1,3,4-trihydroquinazolin-3-yl)]-2-(4-pyridyl)-1,3-thiazole-5-carboxylate (Step f) (460 mg, 1.0 mmol), and 1N NaOH (15 mL) and conc. H$_2$SO$_4$ (20 mL). The crude solid was purified by flash chromatography on silica gel using 98:2 to 96:4 CH$_2$Cl$_2$:MeOH as the eluant to give an orange solid. The orange solid was purified again by flash chromatography on silica gel using 95:5 CH$_2$Cl$_2$:MeOH as the eluant to give a white solid that contained some TEA. The above material was dissolved in 15 mL CH$_2$Cl$_2$ and washed with 1N HCl (aq), brine, dried over MgSO$_4$, and concentrated in vacuo to give a white solid. MP: 249–250° C. MS m/z: 408 (M+1). Anal. Calc'd for C$_{21}$H$_{21}$N$_5$O$_2$S.0.4H$_2$O: C, 60.82; H, 5.30; N, 16.89. Found C, 60.81; H, 5.24; N, 16.67.

EXAMPLE 28

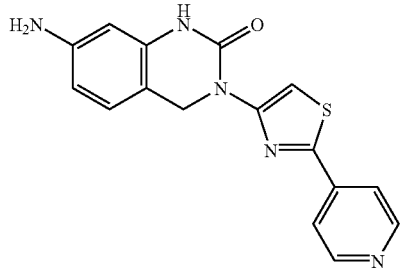

7-Amino-3-(2-(4-pyridyl)(1,3-thiazol-4-yl))-1,3,4-trihydroquinazolin-2-one (a) Preparation of (tert-butoxy)-N-(4-methyl-3-nitrophenyl)carboxamide. 4-Methyl-3-nitroaniline (1.05 g, 6.9 mmol) (Aldrich) was dissolved in 20 mL of THF. Na$_2$CO$_3$ (755 mg, 7.1 mmol) (Mallinckrodt) and tert-butyl dicarbonate (1.75 mL, 7.6 mmol) (Aldrich) were added and the solution was stirred overnight. The reaction mixture was filtered and the filtrate was concentrated in vacuo. The crude residue was purified by flash chromatography on silica gel using 15% EtOAc/Hexane as eluant to give a light yellow solid. MS m/z: 251 (M−1). Calc'd for $C_{12}H_{16}N_2O_4$—252.11.

(b) Preparation of (tert-butoxy)-N-[4-(bromomethyl)-3-nitrophenyl]carboxamide. This compound was prepared according to the method described in Example 6d using (tert-butoxy)-N-(4-methyl-3-nitrophenyl)carboxamide (4.75 g, 18.8 mmol), NBS (3.99 g, 22.4 mmol), and AIBN (0.30 g, 1.9 mmol). Additional AIBN (0.7 g) was added portionwise over 24 h to drive the reaction to completion. The crude product was purified by flash chromatography on silica gel using 7.5% EtOAc/Hexane to 20% EtOAc/Hexane to afford a light yellow solid.

(c) Preparation of (tert-butoxy)-N-(3-nitro-4-{[prop-2-enyloxy-N-(2-(4-pyridyl)(1,3-thiazol-4-yl))carbonylamino]-methyl}phenyl) carboxamide. This compound was prepared according to the method described in Example 6e using prop-2-enyloxy-N-(2-(4-pyridyl)(1,3-thiazol-4-yl)) carboxamide (Example 1b) (2.06 g, 7.9 mmol), 60% NaH (383 mg, 9.6 mmol), (tert-butoxy)-N-[4-(bromomethyl)-3-nitrophenyl]carboxamide (Step b) (2.61 g, 7.9 mmol), and 40 mL of anhydrous DMF. The crude was purified by flash chromatography on silica gel using 15% EtOAc/$CH_2Cl_2$ to give a brown solid. MS m/z: 512 (M+1). Calc'd for $C_{24}H_{25}N_5O_6S$—511.15.

(d) Preparation of (tert-butoxy)-N-(3-nitro-4-{[(2-(4-pyridyl)(1,3-thiazol-4-yl))amino]methyl}-phenyl)carboxamide. This compound was prepared according to the method described in Example 6f using (tert-butoxy)-N-(3-nitro-4-{[prop-2-enyloxy-N-(2-(4-pyridyl) (1,3-thiazol-4-yl))carbonylamino]-methyl}phenyl)carboxamide (Step c) (2.28 g, 4.4 mmol), morpholine (7.6 mL, 86.9 mmol), and $Pd(PPh_3)_4$ (750 mg, 0.7 mmol) to give a brown residue that was contaminated with $P(O)Ph_3$. This crude material was used without further purification.

(e) Preparation of N-(3-amino-4-{[(2-(4-pyridyl)(1,3-thiazol-4-yl))amino]methyl}phenyl)(tert-butoxy)carboxamide. This compound was prepared according to the method described in Example 8g using (tert-Butoxy)-N-(3-nitro-4-t[(2-(4-pyridyl)(1,3-thiazol-4-yl))amino]methyl}-phenyl) carboxamide (2.05 g, 4.8 mmol), Fe powder (1.35 g, 24.2 mmol), and $NH_4Cl$ (124 mg, 2.3 mmol). The crude oil was carried on without further purification. MS m/z: 398 (M+1). Calc'd for $C_{20}H_{23}N_5O_2S$—397.16.

(f) Preparation of 7-amino-3-(2-(4-pyridyl)(1,3-thiazol-4-yl))-1,3,4-trihydroquinazolin-2-one. The compound was prepared according to the method described in Example 10e using N—(3-amino-4-{[(2-(4-pyridyl)(1,3-thiazol-4-yl))-amino]methyl}phenyl) (tert-butoxy)carboxamide (Step e) (1.6 g, 4.0 mmol), CDI (1.6 g, 9.9 mmol), and 60% NaH (450 mg, 1.3 mmol). The crude solid contained both the aniline and BOC protected aniline. The crude material was purified by flash chromatography on silica gel using 97:3 $CH_2Cl_2$:MeOH to afford a mixture of the two products. The solid was dissolved in 8 mL $CH_2Cl_2$ The BOC protected product was not soluble and the solution was filtered to give the BOC protected amine as an off white solid. MS m/z: 424 (M+1). The filtrate was concentrated and the residue was purified by prep HPLC (MeCN:$H_2O$:0.1% TFA) to give the aniline product as a rust colored solid. MS m/z: 324 (M+1). Calc'd for $C_{16}H_{13}N_5OS$—323.08.

EXAMPLE 29

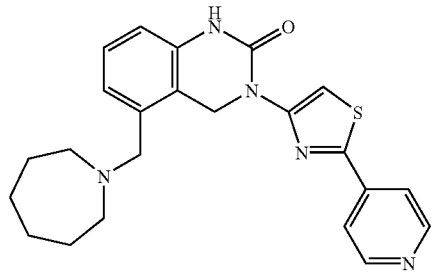

5-(Azaperhydroepinylmethyl)-3-(2-(4-pyridyl)(1,3-thiazol-4-yl))-1,3,4-trihydroquinazolin-2-one (a) Preparation of 6-(azaperhydroepinylmethyl)-2-nitrobenzenecarbonitrile. This compound was prepared according to the method described in Example 14b from 3-nitro-2-cyanobenzyl bromide (1.95 g, 8.1 mmol), hexamethyleneimine (Aldrich) (1.0 mL, 8.9 mmol), and 40 mL of acetonitrile. The crude solid was purified by flash chromatography on silica gel using $CH_2Cl_2$ initially to wash off the non-polar material, and then 70:30:2 $CH_2Cl_2$:EtOAc:MeOH as the eluant to afford a brown oil. MS m/z: 260 (M+1). Calc'd for $C_{14}H_{17}N_3O_2$—259.13.

(b) Preparation of [6-(azaperhydroepinylmethyl)-2-nitrophenyl]methylamine. This compound was prepared according to the method described in Example 14c from 6-(azaperhydroepinylmethyl)-2-nitro-benzenecarbonitrile (Step a) (1.40 g, 5.4 mmol) and 1M $BH_3$.THF (25 mL, 25 mmol) to give a light brown oil. MS m/z: 264 (M+1), Calc'd for $C_{14}H_{21}N_3O_2$—263.16.

(c) Preparation of ethyl 4-({[6-(azaperhydroepinylmethyl)-2-nitrophenyl]methyl}amino)-2-(4-pyridyl)-1,3-thiazole-5-carboxylate. This compound was prepared according to the method described in Example 14f from ethyl 2-(4-pyridyl)-4-[(trifluoromethyl)sulfonyloxy]-1,3-thiazole-5-carboxylate (Example) (1.62 g, 4.2 mmol) and [6-(azaperhydroepinylmethyl)-2-nitrophenyl]methylamine (Step b) (1.06 g, 4.3 mmol). The crude oil was purified by flash chromatography on silica gel using 95:5 $CH_2Cl_2$:MeOH as the eluant to give a brown oil. MS m/z: 496 (M+1). Calc'd for $C_2H_{29}N_5O_4S$—495.19.

(d) Preparation of ethyl 4-({[2-amino-6-(azaperhydroepinylmethyl)phenyl]-methyl}amino)-2-(4-pyridyl)-1,3-thiazole-5-carboxylate. This compound was prepared according to the method described in Example 14g from ethyl 4-({[6-(azaperhydroepinylmethyl)-2-nitrophenyl]methyl}amino)-2-(4-pyridyl)-1,3-thiazole-5-carboxylate (Step c) (1.7 g, 3.4 mmol), Fe powder (966 mg, 17.3 mmol), and $NH_4Cl$ (96 mg, 1.8 mmol) to give a brown residue. MS m/z: 466 (M+1). Calc'd for $C_{25}H_{31}N_5O_2S$—465.22.

(e) Preparation of ethyl 4-[5-(azaperhydroepinylmethyl)-2-oxo(1,3,4-trihydroquinazolin-3-yl)]-2-(4-pyridyl)-1,3-thiazole-5-carboxylate. This compound was prepared according to the method described in Example 10e from ethyl 4-({[2-amino-6-(azaperhydroepinylmethyl)-phenyl] methyl}-amino)-2-(4-pyridyl)-1,3-thiazole-5-carboxylate (Step d) (380 mg, 0.82 mmol), 60% NaH (115 mg, 2.9 mmol), CDI (408 mg, 2.5 mmol), and 20 mL of anhydrous DMF to give a brown solid. MS m/z: 492 (M+1). Calc'd for $C_{26}H_{29}N_5O_3S$—491.20.

(f) Preparation of 5-(azaperhydroepinylmethyl)-3-(2-(4-pyridyl)(1,3-thiazol-4-yl))-1,3,4-trihydroquinazolin-2-one. This compound was prepared according to the method described in Example 15 from Ethyl 4-[5-(azaperhydroepinylmethyl)-2-oxo(1,3,4-trihydroquinazolin-3-yl)]-2-(4-pyridyl)-1,3-thiazole-5-carboxylate (Step e) (609 mg, 1.3 mmol), 5 mL of 1N NaOH, and 20 mL of conc. $H_2SO_4$. The crude solid was purified by flash chromatography on silica gel using 95:5 $CH_2Cl_2$:MeOH. This resulting solid was dissolved in $CH_2Cl_2$ and washed (2×) with 1N HCl (aq). The combined aqueous layers were neutralized with 1N NaOH (aq) and extracted with $CH_2Cl_2$ (3×). The combined $CH_2Cl_2$ layers were washed with brine, dried over $MgSO_4$, and concentrated in vacuo to give an off white solid. MP: 202–204° C. MS m/z: 420 (M+1). Anal. Calc'd for $C_{23}H_{25}N_5OS$: C, 65.84; H, 6.01; N, 16.69. Found C, 65.70; H 6.10; N, 16.84.

EXAMPLE 30

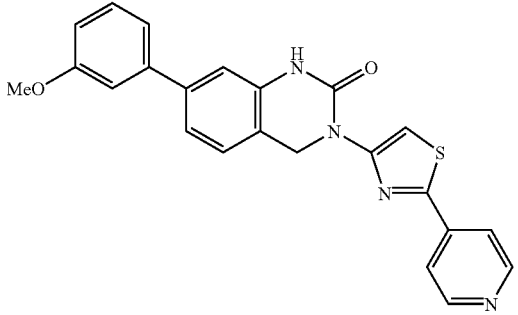

7-(3-Methoxyphenyl)-3-(2-(4-pyridyl)(1,3-thiazol-4-yl))-1,3,4-trihydroquinazolin-2-one (a) Preparation of 3-methoxy-1-(4-methyl-3-nitrophenyl)-benzene. This compound was prepared according to the method described in Example 12a from 4-bromo-2-nitrotoluene (Aldrich) (4.69 g, 21.7 mmol), 3-methoxyphenylboronic acid (Aldrich) (3.45 g, 22.7 mmol), 2M $Na_2CO_3$ (25 mL, 50.0 mmol), $Pd(PPh_3)_4$ (750 mg, 0.65 mmol), and 75 mL of toluene/20 mL of EtOH. The crude residue was purified by flash chromatography on silica gel using 95:5 Hexane:EtOAc to afford a light-yellow oil, which solidified upon standing.

(b) Preparation of 1-[4-(bromomethyl)-3-nitrophenyl]-3-methoxybenzene. This compound was prepared according to the method described in Example 6d using 3-methoxy-1-(4-methyl-3-nitrophenyl)benzene (Step a) (4.72 g, 19.4 mmol), NBS (4.16 g, 23.4 mmol), and AIBN (0.40 g, 2.4 mmol). The crude product was purified by flash chromatography on silica gel using 5% EtOAc/Hexane to afford a light yellow oil which solidified upon standing.

(c) Preparation of N-{[4-(3-methoxyphenyl)-2-nitrophenyl]-methyl}prop-2-enyloxy-N-(2-(4-pyridyl)(1,3-thiazol-4-yl))carboxamide. This compound was prepared according to the method described in Example 6e using prop-2-enyloxy-N-(2-(4-pyridyl) (1,3-thiazol-4-yl))carboxamide (Example 1b) (1.39 g, 5.3 mmol), 60% NaH (260 mg, 6.5 mmol), and 1-[4-(bromomethyl)-3-nitrophenyl]-3-methoxybenzene (Step b) (1.71 g, 5.3 mmol). The crude oil was purified by flash chromatography on silica gel using 99:1 $CH_2Cl_2$:MeOH as the eluant to afford a brown oil which solidified upon standing. MS m/z: 503 (M+1). Calc'd for $C_{26}H_{22}N_4O_5S$—502.13.

(d) Preparation of {[4-(3-methoxyphenyl)-2-nitrophenyl]-methyl}(2-(4-pyridyl)(1,3-thiazol-4-yl))amine. This compound was prepared according to the method described in Example 6f using N-{[4-(3-methoxyphenyl)-2-nitrophenyl]methyl}prop-2-enyloxy-N-(2-(4-pyridyl)(1,3-thiazol-4-yl))carboxamide (Step c) (2.03 g, 4.0 mmol), morpholine (3.5 mL, 40.0 mmol), and $Pd(PPh_3)_4$ (105 mg, 0.09 mmol). The crude oil was purified by flash chromatography on silica gel using 99:1 to 97:3 $CH_2Cl_2$:MeOH to give a red oil, which contained some $P(O)Ph_3$. This material was used without further purification. MS m/z: 419 (M+1). Calc'd for $C_{22}H_{18}N_4O_3S$—418.11.

(e) Preparation of {[2-amino-4-(3-methoxyphenyl)phenyl]-methyl}(2-(4-pyridyl)(1,3-thiazol-4-yl))amine. This compound was prepared according to the method described in Example 6g using {[4-(3-methoxyphenyl)-2-nitrophenyl]-methyl}(2-(4-pyridyl) (1,3-thiazol-4-yl))amine (1.12 g, 2.7 mmol), Fe powder (751 mg, 13.5 mmol), and $NH_4Cl$ (105 mg, 2.0 mmol) to give a red-brown solid. MS m/z: 389 (M+1). Calc'd for $C_{22}H_{20}N_4OS$—388.14.

(f) Preparation of 7-(3-methoxyphenyl)-3-(2-(4-pyridyl) (1,3-thiazol-4-yl))-1,3,4-trihydroquinazolin-2-one. This compound was prepared according to the method described in Example 10e using {[2-amino-4-(3-methoxyphenyl)phenyl]-methyl}(2-(4-pyridyl) (1,3-thiazol-4-yl))amine (Step e) (830 mg, 2.1 mmol), 60% NaH (298 mg, 7.5 mmol), and CDI (1.03 g, 6.3 mmol). The crude solid was recrystallized from EtOAc to give an off-white solid. MP: 256–258° C. MS m/z: 415 (M+1). Anal. Calc'd for $C_{23}H_{18}N_4O_2S$: C, 66.65; H, 4.38; N, 13.52. Found: C, 66.64; H, 4.46; N, 13.53.

EXAMPLE 31

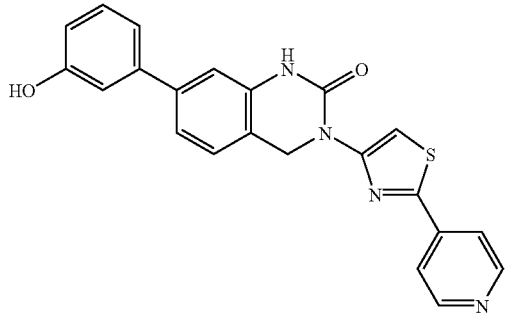

7-(3-Hydroxyphenyl)-3-(2-(4-pyridyl) (1,3-thiazol-4-yl))-1,3,4-trihydroquinazolin-2-one 60% NaH (198 mg, 4.95 mmol) was suspended in 10 mL of dry DMF and the mixture was cooled to 0° C. Ethanethiol (0.36 mL, 4.86 mmol) was added dropwise. After the addition was complete the reaction was stirred for 15 min at RT. 7-(3-Methoxyphenyl)-3-(2-(4-pyridyl)(1,3-thiazol-4-yl))-1,3,4-trihydroquinazolin-2-one (Example 30) (346 mg, 0.83 mmol) was dissolved in 20 mL of dry DMF and added dropwise to the solution of the sodium salt. The light orange solution was stirred and heated at reflux 4.5 h. The reaction mixture was cooled to RT and quenched with $H_2O$. The solution was stirred for 15 h at RT. The resulting precipitates were filtered and washed with H₂O and hexane to obtain the title compound as a light yellow solid. MP: 320–322° C. MS m/z: 401 (M+1). Anal. Calc'd for $C_{22}H_{16}N_4O_2S.0.2H_2O$: C, 65.40; H, 4.09; N, 13.87. Found: C, 65.07; H, 4.13; N, 13.53.

EXAMPLE 32

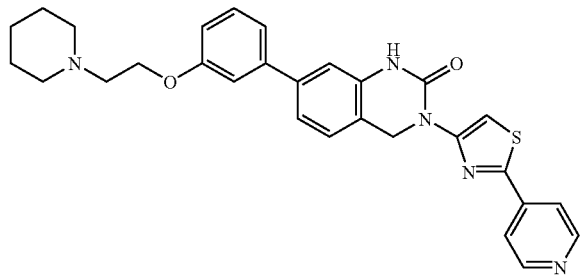

7-[3-(2-Piperidylethoxy)phenyl]-3-(2-(4-pyridyl)(1, 3-thiazol-4-yl))-1,3,4-trihydroquinazolin-2-one 7-(3-Hydroxyphenyl)-3-(2-(4-pyridyl)(1,3-thiazol-4-yl))-1,3,4-trihydroquinazolin-2-one (Example 31) (100 mg, 0.25 mmol) was dissolved in 10 mL of dry DMF and 60% NaH (19 mg, 0.48 mmol) was added. The reaction was stirred for 15 min at RT, and 1-(2-chloroethyl)piperidine hydrochloride was added. After stirring at RT for 1.5 h, the reaction was stirred at 80° C. for 4 h. The reaction was cooled to RT, and quenched with H₂O. After stirring for 2 h, the resulting precipitate was filtered and washed with H₂O and hexane. The crude solid was purified by flash chromatography on silica gel using 95:5 CH₂Cl₂:MeOH as the eluent to give an off-white solid. MP: 206–208° C. MS m/z: 512 (M+1). Anal. Calc'd for $C_{29}H_{29}N_5O_2S.1.2H_2O$: C, 65.32; H, 5.94; N, 13.13. Found: C, 65.12; H, 5.69; N, 13.00.

EXAMPLE 33

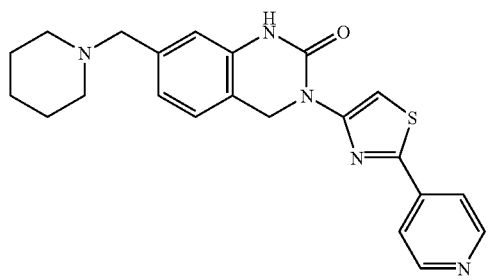

7-(Piperidylmethyl)-3-(2-(4-pyridyl)(1,3-thiazol-4-yl))-1,3,4-trihydroquinazolin-2-one (a) Preparation of 2-nitro-4-(piperidylmethyl)benzenecarbonitrile. This compound was prepared according to the method described in Example 26b from 3-nitro-4-cyanobenzyl bromide (1.82 g, 7.6 mmol) and piperidine (1.4 mL, 14.2 mmol). The crude residue was purified by flash chromatography on silica gel using 9:1 CH₂Cl₂:EtOAc as the eluant to give a light yellow oil. MS m/z: 246 (M+1). Calc'd for $C_{13}H_{15}N_3O_2$—245.12.

(b) Preparation of [2-nitro-4-(piperidylmethyl)phenyl]-methylamine. This compound was prepared according to the method described in Example 14c from 2-nitro-4-(piperidylmethyl)-benzenecarbonitrile (Step a) (1.25 g, 5.1 mmol) and 1M BH₃.THF (20 mL, 20.0 mmol) to give a brown oil. MS m/z: 250 (M+1). Calc'd for $C_{13}H_{19}N_3O_2$—249.15.

(c) Preparation of ethyl 4-({[2-nitro-4-(piperidylmethyl)-phenyl]-methyl}amino)-2-(4-pyridyl)-1,3-thiazole-5-carboxylate. This compound was prepared according to the method described in Example 14f from ethyl 2-(4-pyridyl)-4-[(trifluoromethyl)sulfonyloxy]-1,3-thiazole-5-carboxylate (Example 14e) (1.40 mg, 3.7 mmol) and [2-nitro-4-(piperidylmethyl)phenyl]-methylamine (Step b) (1.14 g, 4.6 mmol). The crude residue was purified by flash chromatography on silica gel using 97:3 CH₂Cl₂:MeOH to obtain an orange oil. MS m/z: 482 (M+1). Calc'd for $C_{24}H_{27}N_5O_4S$—481.18.

(d) Preparation of ethyl 4-({[2-amino-4-(piperidylmethyl)-phenyl]methyl}-amino)-2-(4-pyridyl)-1,3-thiazole-5-carboxylate. This compound was prepared according to the method described in Example 14g from ethyl 4-({[2-nitro-4-(piperidylmethyl)phenyl]methyl}-amino)-2-(4-pyridyl)-1,3-thiazole-5-carboxylate (Step c) (450 mg, 0.93 mmol), Fe powder (288 mg, 5.2 mmol) and NH₄Cl (35 mg, 0.70 mmol) to give a yellow solid. MS m/z: 452 (M+1). Calc'd for $C_{24}H_{29}N_5O_2S$—451.20.

(e) Preparation of ethyl 4-[2-oxo-7-(piperidylmethyl)(1, 3,4-trihydroquinazolin-3-yl)]-2-(4-pyridyl)-1,3-thiazole-5-carboxylate. This compound was prepared according to the method described in Example 10e from ethyl 4-({[2-amino-4-(piperidylmethyl)phenyl]methyl}-amino)-2-(4-pyridyl)-1, 3-thiazole-5-carboxylate (Step d) (350 mg, 0.78 mmol), 60% NaH (105 mg, 2.6 mmol), and CDI (377 mg, 2.3 mmol). The crude material was purified by flash chromatography on silica gel using 95:5 to 9:1 CH₂Cl₂:MeOH to give a yellow oily solid. MS m/z: 478 (M+1). Calc'd for $C_{25}H_{27}N_5O_3S$—477.18.

(f) Preparation of 7-(piperidylmethyl)-3-(2-(4-pyridyl)(1, 3-thiazol-4-yl))-1,3,4-trihydroquinazolin-2-one. This compound was prepared according to the method described in Example 14i using ethyl 4-[2-oxo-7-(piperidylmethyl) (1,3, 4-trihydroquinazolin-3-yl)]-2-(4-pyridyl)-1,3-thiazole-5-carboxylate (Step e) (150 mg, 0.31 mmol), and 1N NaOH (4 mL) and conc. H₂SO₄ (6 mL). The crude solid was purified by prep TLC chromatography on 1000 µm thick silica gel plates using 93:7 CH₂Cl₂:MeOH as the eluant and eluting twice to give a tan solid. MS m/z: 406 (M+1). Calc'd for $C_{22}H_{23}N_5OS$—405.16.

EXAMPLE 34

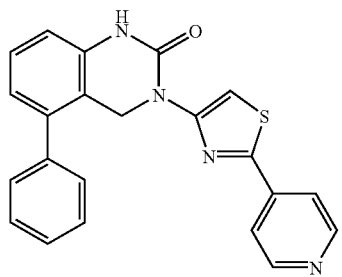

5-Phenyl-3-(2-(4-pyridyl)(1,3-thiazol-4-yl))-1,3,4-trihydroquinazolin-2-one (a) Preparation of 5-bromo-1-[(4-methoxyphenyl)methyl]-3-(2-(4-pyridyl)(1,3-thiazol-4-yl))-1,3,4-trihydroquinazolin-2-one. 5-Bromo-3-(2-(4-pyridyl) (1,3-thiazol-4-yl))-1,3,4-trihydroquinazolin-2-one (Example 6) (576 mg, 1.5 mmol) was suspended in 15 mL of anhydrous DMF and 60% NaH (74 mg, 1.9 mmol) was added portionwise over several minutes. The mixture was heated to 45° C. for 15 min to help dissolve the solids, then cooled to RT. After 1.5 h, 4-methoxybenzyl chloride (0.23 mL, 1.7 mmol) (Aldrich) was added dropwise. The reaction was stirred for 4 h, then $H_2O$ was added and the solution was stirred for 30 min. The reaction mixture was partitioned between $EtOAc:H_2O$ and the aqueous portion was extracted with EtOAc (3×). The combined EtOAc layers were washed with $H_2O$, brine, dried over $MgSO_4$, and concentrated in vacuo to give a reddish solid. MS m/z: 507. Calc'd for $C_{24}H_{19}BrN_4O_2S$—506.04.

(b) Preparation of 1-[(4-methoxyphenyl)methyl]-5-phenyl-3-(2-(4-pyridyl)(1,3-thiazol-4-yl))-1,3,4-trihydroquinazolin-2-one. 5-Bromo-1-[(4-methoxyphenyl)methyl]-3-(2-(4-pyridyl)(1,3-thiazol-4-yl))-1,3,4-trihydroquinazolin-2-one (Step a) (140 mg, 0.28 mmol) and phenylboronic acid (40 mg, 0.32 mmol) (Aldrich) were stirred in 9 mL of toluene/2 mL of EtOH. To this mixture was added 2M $Na_2CO_3$ (0.75 mL, 1.5 mmol), then $Pd(PPh_3)_4$ (10 mg, 0.01 mmol). The mixture was stirred at 80° C. overnight. The reaction mixture was cooled to RT and concentrated in vacuo. The crude solid was purified by flash chromatography on silica gel using 98:2 $CH_2Cl_2$:MeOH as the eluant to obtain an orange-red solid that contains some $P(O)Ph_3$. The above material was used for the next step without further purification.

(c) Preparation of 5-phenyl-3-(2-(4-pyridyl)(1,3-thiazol-4-yl))-1,3,4-trihydroquinazolin-2-one. 1-[(4-Methoxyphenyl)-methyl]-5-phenyl-3-(2-(4-pyridyl)(1,3-thiazol-4-yl))-1,3,4-trihydroquinazolin-2-one (Step b) (100 mg, 0.20 mmol) was dissolved in 10 mL of $CH_2Cl_2$. TFA (0.16 mL, 2.1 mmol) and anisole (0.22 mL, 2.0 mmol) were added, and the reaction was stirred at reflux for 30 h. The reaction was cooled to RT and concentrated in vacuo. The residue was dissolved in $CH_2Cl_2$ and washed with saturated $NaHCO_3$ (aq), brine, dried over $MgSO_4$, and concentrated in vacuo. The crude solid was purified by flash chromatography on silica gel using 95:5 $CH_2Cl_2$:MeOH as the eluant to obtain a light yellow solid. MS m/z: 385 (M+1). Calc'd for $C_{22}H_{16}N_4OS$—384.10.

EXAMPLE 35

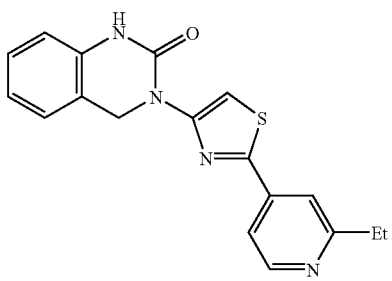

3-[2-(2-Ethyl-4-pyridyl)-1,3-thiazol-4-yl]-1,3,4-trihydroquinazolin-2-one (a) Preparation of ethyl 2-(2-ethyl-4-pyridyl)-1,3-thiazole-4-carboxylate. This compound was prepared according to the method described in Example 6a from ethionamide (Sigma) (4.05 g, 24.4 mmol) and ethyl bromopyruvate (3.3 mL, 23.7 mmol) to give a yellow solid. MS m/z: 263 (M+1). Calc'd for $C_{13}H_{14}N_2O_2S$—262.08.

(b) Preparation of 2-(2-ethyl-4-pyridyl)-1,3-thiazole-4-carboxylic acid. This compound was prepared according to the method described in Example 6b from ethyl 2-(2-ethyl-4-pyridyl)-1,3-thiazole-4-carboxylate (Step a) (6.9 g) and 1N NaOH (72 mL, 72.0 mmol) to give a yellow solid.

(c) Preparation of N-[2-(2-ethyl(4-pyridyl))(1,3-thiazol-4-yl)]prop-2-enyloxycarboxamide. This compound was prepared according to the method described in Example 6c from 2-(2-ethyl-4-pyridyl)-1,3-thiazole-4-carboxylic acid (Step b) (4.4 g, 18.8 mmol), TEA (3.2 mL, 23.0 mmol), DPPA (6.0 mL, 27.8 mmol), and allyl alcohol (12.5 mL, 183.8 mmol). The crude solid was purified by flash chromatography on silica gel using 8:2 $CH_2Cl_2$:EtOAc as the eluant to afford a yellow solid. MS m/z: 290 (M+1). Calc'd for $C_{14}H_{15}N_3O_2S$—289.09.

(d) Preparation of N-[2-(2-ethyl(4-pyridyl))(1,3-thiazol-4-yl)]-N-[(2-nitrophenyl)methyl]prop-2-enyloxycarboxamide. This compound was prepared according to the method described in Example 6d using N-[2-(2-ethyl(4-pyridyl))(1,3-thiazol-4-yl)]prop-2-enyloxycarboxamide (Step c) (1.26 g, 4.4 mmol), 60% NaH (215 mg, 5.4 mmol), and 2-nitrobenzyl bromide (955 mg, 4.4 mmol). The crude residue was purified by flash chromatography on silica gel using 99:1 $CH_2Cl_2$:MeOH as the eluant to afford a dark red-brown oil. MS m/z: 425 (M+1). Calc'd for $C_{21}H_{20}N_4O_4S$—424.12.

(e) Preparation of [2-(2-ethyl-4-pyridyl)(1,3-thiazol-4-yl)][(2-nitrophenyl)methyl]amine. N-[2-(2-Ethyl(4-pyridyl)) (1,3-thiazol-4-yl)]-N-[(2-nitrophenyl)methyl]prop-2-enyloxycarboxamide (1.58 g, 3.7 mmol), morpholine (3.25 mL, 37.2 mmol), and $Pd(PPh_3)_4$ (129 mg, 0.11 mmol) were stirred in anhydrous THF (25 mL) for 6 h. Poly(styrene-co-vinyl benzyl chloride-co-divinylbenzene) (100 mg) (Aldrich) was added to the reaction mixture to react with $P(O)Ph_3$. The reaction mixture was stirred for 15 min then filtered over a bed of Celite®. The filtrate was concentrated in vacuo, then dissolved in EtOAc and washed with $H_2O$. The aqueous layer was extracted with EtOAc (2×). The combined EtOAc layers were washed with brine, dried over $MgSO_4$, and concentrated in vacuo to give a dark brown oil that contained some morpholine. This material was used without further purification. MS m/z: 340. Calc'd for $C_{17}H_{16}N_4O_2S$—340.10.

(f) Preparation of [(2-aminophenyl)methyl][2-(2-ethyl(4-pyridyl))(1,3-thiazol-4-yl)]amine. This compound was prepared according to the method described in Example 6g using [2-(2-ethyl(4-pyridyl))(1,3-thiazol-4-yl)][(2-nitrophenyl)methyl]amine (Step e) (1.58 g), Fe powder (1.01 g, 18.1 mmol), and $NH_4Cl$ (110 mg, 2.1 mmol). The crude product was purified by flash chromatography on silica gel using 98:2 $CH_2Cl_2$:MeOH as the eluant to give a light-brown solid. MS m/z: 311 (M+1). Calc'd for $C_{17}H_{18}N_4S$—310.13.

(g) Preparation of 3-[2-(2-ethyl-4-pyridyl)-1,3-thiazol-4-yl]-1,3,4-trihydroquinazolin-2-one. This compound was prepared according to the method described in Example 10e using [(2-aminophenyl)methyl][2-(2-ethyl(4-pyridyl))(1,3-thiazol-4-yl)]amine (Step f) (550 mg, 1.8 mmol), 60% NaH (250 mg, 6.3 mmol), and CDI (877 mg, 5.4 mmol) to give an off-white solid. MP: 239–240° C. MS m/z: 337 (M+1). Anal. Calc'd for $C_{18}H_{16}N_4OS \cdot 0.1H_2O$: C, 63.92; H, 4.83; N, 16.57. Found: C, 63.75; H, 4.81; N, 16.40.

EXAMPLE 36

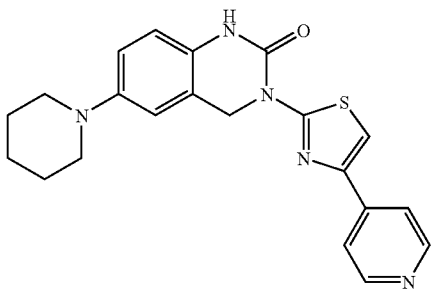

6-Piperidyl-3-(4-(4-pyridyl)(1,3-thiazol-2-yl))-1,3,4-trihydroquinazolin-2-one (a) Preparation of N-({[(2-nitro-5-piperidylphenyl)methyl]-amino}-thioxomethyl)benzamide. To a cooled (0° C.) solution of 1M $BH_3$.THF (Fluka) (25 mL, 25 mmol) was added a solution of 2-nitro-5-piperidyl-benzenecarbonitrile (J. Med. Chem. 1985, 28, 1387; 1.01 g, 4.4 mmol) in THF (10 mL) dropwise. After 0.25 h the reaction was warmed to RT. After an additional 18 h, one-half of the solvent was removed in vacuo. The concentrated solution was carefully added to 10% HCl (30 mL) and heated to reflux. After 2 h the solution was cooled to RT and the volatiles were removed in vacuo. The aqueous solution was washed with benzene, basified with 1 N NaOH and extracted with $CH_2Cl_2$. The combined organic extracts were washed with $H_2O$, dried over $Na_2SO_4$ and concentrated in vacuo. The residue was dissolved in $CHCl_3$ (40 mL) and to this solution was added benzoyl isothiocyanate (Aldrich) (0.55 mL) followed by $Et_3N$ (0.60 mL). The green-yellow solution was heated to 61° C. After 2 h the reaction was cooled to RT, concentrated in vacuo, and purified by flash chromatography with hexanes: EtOAc (9:1, 3:1, 7:3) as eluant to afford a yellow amorphous solid. MS m/z: 399 (M+1). Calc'd for $C_{20}H_{22}N_4O_3S$—398.14.

(b) Preparation of [(2-nitro-5-piperidylphenyl)methyl](4-(4-pyridyl)(1,3-thiazol-2-yl))amine. To a suspension of N-(([(2-nitro-5-piperidylphenyl)methyl]amino)thioxomethyl) benzamide (Step a) (427, 1.1 mmol) mg) in 70% aqueous MeOH was added $K_2CO_3$ (203 mg, 1.4 mmol) and the reaction was heated to reflux. After 1.5 h the reaction was cooled to RT and to the reaction mixture was added 2-bromo-1-(4-pyridyl)ethan-1-one hydrobromide (309 mg, 1.1 mmol) and the mixture was heated to 45° C. After 2 h the reaction mixture was cooled to RT and purified by flash chromatography with $CH_2Cl_2$:MeOH (99:1, 49:1) as eluant to afford a green-brown solid. MS m/z: 396 (M+1); 394(M−1). Calc'd for $C_{20}H_{21}N_5O_2S$—395.14.

(c) Preparation of 6-piperidyl-3-(4-(4-pyridyl)(1,3-thiazol-2-yl))-1,3,4-trihydroauinazolin-2-one. To a suspension of [(2-nitro-5-piperidylphenyl)methyl](4-(4-pyridyl)(1,3-thiazol-2-yl))amine (Step b) (154 mg, 0.4 mmol) in 70% aqueous EtOH was added $NH_4Cl$ (21 mg, 0.4 mmol) followed by Fe dust (91 mg, 1.6 mmol) and the reaction was heated to 74° C. After 1 h, the reaction was filtered through a pad of Celite® and the solution was concentrated in vacuo. The residue was azeotroped twice with benzene and dissolved in DMF (4 mL). To this solution was added CDI (Aldrich) (191 mg, 1.2 mmol) followed by 95% NaH (32 mg, 1.3 mmol) at RT, resulting in gas evolution. After 15 h, $H_2O$ (15 mL) was added and the precipitate was filtered, washed with $H_2O$ then EtOAc and dried in vacuo to give an off-white solid. Mp: >272° C. MS m/z: 392 (M+1); 390 (M−1). Anal. Calc'd for $C_{21}H_{21}N_5OS \cdot 0.25 H_2O$: C, 63.45; H, 5.49; N, 17.62. Found: C, 63.42; H, 5.38; N, 17.77.

EXAMPLE 37

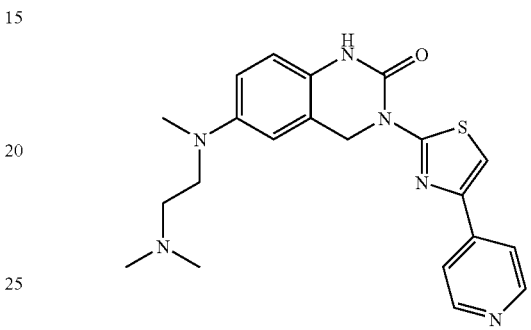

6-{[2-(Dimethylamino)ethyl](methyl)amino}-3-(4-(4-pyridyl)(1,3-thiazol-2-yl))-1,3,4-trihydroquinazolin-2-one (a) Preparation of 5-{[2-(dimethylamino)ethyl]methylamino}-2-nitrobenzenecarbonitrile. To a solution of 5-chloro-2-nitro-benzonitrile (Aldrich) (5.17 g, 28.3 mmol) in DMF (40 mL) was added N,N,N'-trimethylethylenediamine (Aldrich) (11.0 mL, 84.6 mmol) via syringe, and the reaction was heated at 50° C. After 2 h the reaction was poured into $H_2O$ (150 mL) and the precipitate was filtered, washed with $H_2O$ and dried to give a bright-yellow amorphous solid. MS m/z: 249 (M+1). Calc'd for $C_{12}H_{16}N_4O_2$—248.13.

(b) Preparation of [3-(aminomethyl)-4-nitrophenyl][2-(dimethylamino)ethyl]methylamine. To a cooled (0° C.) solution of 1M $BH_3$.THF (Fluka) (80 mL, 80.0 mmol) was added 5-([2-(dimethylamino)ethyl]-methylamino)-2-nitrobenzene carbonitrile (Step a) (4.01 g, 16.1 mmol) in portions over a period of 0.25 h. After 0.5 h, the reaction was warmed to RT. After 15 h, the solvent was concentrated to one-half its original volume. The concentrated solution was carefully added to 10% HCl (100 mL) and heated at reflux for 2 h. The solution was cooled to RT, and the volatiles were removed in vacuo. The aqueous solution was washed with benzene, basified with 5 N NaOH and extracted with $CH_2Cl_2$. The combined organics were washed with $H_2O$, dried over $Na_2SO_4$ and concentrated in vacuo to give a golden-brown oil. MS m/z: 253 (M+1).

(c) Preparation of N-({[(5-{[2-(dimethylamino)ethyl]methylamino}-2-nitrophenyl)methyl]amino)-thioxomethyl) benzamide. To a solution of [3-(aminomethyl)-4-nitrophenyl][2-(dimethylamino)ethyl]methylamine (Step b) (3.26 g, 12.9 mmol) in 100 mL $CHCl_3$ was added benzoyl isothiocyanate (Aldrich) (1.85 mL, 13.8 mmol) and the reaction solution was heated to 61° C. After 2 h the reaction was cooled to RT and concentrated in vacuo. The residue was dissolved in a minimum amount of $CHCl_3$ and this solution was added dropwise to 300 mL of toluene. The yellow precipitate that formed was filtered and filtrate was concentrated in vacuo. The residue was stirred vigorously overnight with hexanes and the solids were filtered, washed with hexanes, and dried in vacuo to give a yellow powder. MS m/z: 416 (M+1); 414 (M−1). Calc'd for $C_{20}H_{25}N_5O_3S$—415.17.

(d) Preparation of [2-(dimethylamino)ethyl]methyl(4-nitro-3-{[(4-(4-pyridyl)(1,3-thiazol-2-yl))amino]-methyl}phenyl)-amine. To a slurry of N-({[(5-([2-(dimethylamino)ethyl]-methylamino}-2-nitrophenyl)methyl]-amino}-thioxomethyl)benzamide (Step c) (1.09 g, 2.6 mmol) in 70% aqueous MeOH (31 mL) was added $K_2CO_3$ (416 mg, 3.0 mmol) and the reaction was heated to 65° C. After 1.5 h, the reaction was cooled to (45° C.) and 2-bromo-1-(4-pyridyl)ethan-1-one hydrobromide (838 mg, 3.0 mmol) was added. After 1 h, the reaction mixture was cooled to RT and purified by flash chromatography with $CH_2Cl_2$:2M $NH_3$ in MeOH (49:1, 19:1) as eluant to afford a yellow amorphous solid. MS m/z: 413 (M+1); 411 (M−1). Calc'd for $C_{20}H_{24}N_6O_2S$—412.17.

(e) Preparation of 6-{[2-(dimethylamino)ethyl]-(methyl)-amino}-3-(4-(4-pyridyl)(1,3-thiazol-2-yl))-1,3,4-trihydroquinazolin-2-one. To a suspension of 2-(dimethylamino)ethyl]methyl(4-nitro-3-{[(4-(4-pyridyl) (1,3-thiazol-2-yl))amino]-methyl}phenyl)amine (288 mg, 0.7 mmol) in 70% aqueous EtOH (14 mL) was added $NH_4Cl$ (45 mg, 0.8 mmol) followed by Fe dust (175 mg, 3.1 mmol) and the reaction was heated to 75° C. After 4 h the reaction was cooled to RT, filtered through a pad of Celite® and the solution concentrated in vacuo. The residue was azeotroped twice with benzene and dissolved in 10 mL DMF. To this solution was added CDI (343 mg) followed by 95% NaH (54 mg) at RT, resulting in gas evolution. After 15 h, $H_2O$ (25 mL) was added and the precipitate was filtered, washed with $H_2O$ and MeOH and dried in vacuo to give an off-white powder. Mp: 254–257° C. MS m/z: 409 (M+1). Anal. Calc'd for $C_{21}H_{24}N_6OS·0.5\ H_2O$: C, 60.41; H, 6.04; N, 20.13. Found: C, 60.15; H, 5.93; N, 20.04.

EXAMPLE 38

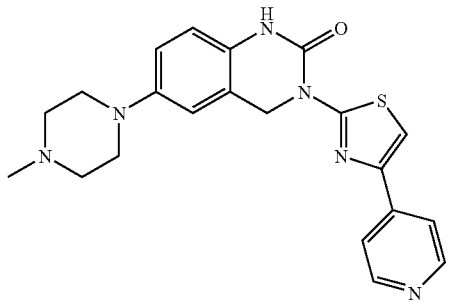

6-(4-Methylpiperazinyl)-3-(4-(4-pyridyl)(1,3-thiazol-2-yl))-1,3,4-trihydroquinazolin-2-one (a) Preparation of 5-(4-methylpiperazinyl)-2-nitrobenzene carbonitrile. To a solution of 5-chloro-2-nitro-benzonitrile (Aldrich) (9.70 g, 53.1 mmol) in 100 mL of DMF was added 1-methylpiperazine (Aldrich) (17.0 mL, 153.2 mmol) and the reaction was heated to 50° C. After 2 h, the reaction was poured into $H_2O$ (200 mL) and the precipitate was filtered, washed with $H_2O$ and dried to give a bright-yellow amorphous solid. MS m/z: 247 (M+1). Calc'd for $C_{12}H_{14}N_4O_2$—246.11.

(b) Preparation of [5-(4-methylpiperazinyl)-2-nitrophenyl]-methylamine. To a cooled (0° C.) solution of 1M $BH_3$.THF (Fluka) (79 mL, 79 mmol) was added 5-(4-methylpiperazinyl)-2-nitrobenzenecarbonitrile (Step a) (3.90 g, 16.0 mmol) in portions over a period of 0.25 h. After complete addition, the reaction was warmed to RT. After an additional 16 h the solvent was concentrated to one-half its original volume. The concentrated solution was carefully added to 10% HCl (100 mL) and heated to reflux for 3 h. After cooling to RT, the solids were filtered and the volatiles were removed in vacuo. The aqueous solution was basified with 5 N NaOH and extracted with $CH_2Cl_2$. The combined organics were dried over $Na_2SO_4$ and concentrated in vacuo to give a yellow oil. MS m/z: 251 (M+1). Calc'd for $C_{12}H_{18}N_4O_2$—250.14.

(c) Preparation of N-[({[5-(4-methylpiperazinyl)-2-nitrophenyl]methyl}amino)thioxomethyl]-benzamide. To a solution of [5-(4-methylpiperazinyl)-2-nitrophenyl]-methylamine (Step b) (2.85 g, 11.4 mmol) in 100 mL $CHCl_3$ was added benzoyl isothiocyanate (Aldrich) (1.70 mL, 12.6 mmol) and the reaction solution was heated to 61° C. After 3.5 h, the reaction was cooled to RT and purified by flash chromatography with $CH_2Cl_2$:2M $NH_3$ in MeOH (19:1) as eluant. The impure residue was stirred over hexanes and the solids were filtered and dried to afford a yellow amorphous solid. MS m/z: 414 (M+1); 412 (M−1). Calc'd for $C_{20}H_{23}N_5O_3S$—413.15.

(d) Preparation of {[5-(4-methylpiperazinyl)-2-nitrophenyl]-methyl}(4-(4-pyridyl)(1,3-thiazol-2-yl))amine. To a slurry of N-[({[5-(4-methylpiperazinyl)-2-nitrophenyl]methyl}-amino)-thioxomethyl]-benzamide (Step c) (1.47 g, 3.5 mmol) in 70% aqueous MeOH (50 mL) was added $K_2CO_3$ (550 mg, 3.9 mmol) and the reaction was heated to reflux. After 1.5 h, the reaction was cooled to 40° C., and 2-bromo-1-(4-pyridyl)ethan-1-one hydrobromide (990 mg, 3.5 mmol) was added. After 1 h, the reaction mixture was cooled to RT and purified by flash chromatography with $CH_2Cl_2$:MeOH (19:1) as eluant to afford a yellow-orange amorphous solid. MS m/z: 411 (M+1); 409 (M−1). Calc'd for $C_{20}H_{22}N_6O_2S$—410.15.

(e) Preparation of 6-(4-methylpiperazinyl)-3-(4-(4-pyridyl)(1,3-thiazol-2-yl))-1,3,4-trihydroquinazolin-2-one. To a suspension of {[5-(4-methylpiperazinyl)-2-nitrophenyl]-methyl}(4-(4-pyridyl) (1,3-thiazol-2-yl))amine (Step d) (614 mg, 1.5 mmol) in 70% aqueous EtOH (28 mL) was added $NH_4Cl$ (92 mg, 1.7 mmol) followed by Fe dust (411 mg, 7.4 mmol) and the reaction was heated to 75° C. After 2 h the reaction was cooled to RT, filtered through a pad of Celite® and the solution was concentrated in vacuo. The residue was azeotroped twice with benzene and dissolved in 15 mL DMF. To this solution was added CDI (729 mg, 4.5 mmol) followed by 95% NaH (109 mg, 4.5 mmol) at RT, resulting in gas evolution. After 15 h, $H_2O$ (50 mL) was added and the precipitate was filtered, washed with $H_2O$ and MeOH and dried in vacuo to give an off-white powder. Mp: 301–304° C. MS m/z: 407 (M+1); 405 (M−1). Calc'd for $C_{21}H_{22}N_6OS$—406.16.

EXAMPLE 39

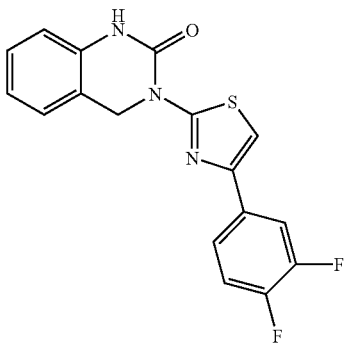

3-[4-(3,4-Difluorophenyl)-1,3-thiazol-2-yl]-1,3,4-trihydroquinazolin-2-one (a) Preparation of [4-(3,4-difluorophenyl)(1,3-thiazol-2-yl)][(2-nitrophenyl)methyl]amine. To a heated (40° C.) slurry of amino{[(2-nitrophenyl)methyl]amino}methane-1-thione (Example 16a) (624 mg, 2.9 mmol) in 50% aqueous MeOH (30 mL) was added 3,4-fluorophenacyl bromide (Maybridge) (689 mg, 2.9 mmol) and the reaction was stirred at 40° C. for 1 h. The reaction was cooled to RT and purified by flash chromatography with Hexanes:EtOAc (9:1, 4:1) as eluant to afford a yellow solid. MS m/z: 348 (M+1); 346 (M−1) Calc'd for $C_{16}H_{11}F_2N_3O_2S$—347.05.

(b) Preparation of 3-[4-(3,4-difluorophenyl)-1,3-thiazol-2-yl]-1,3,4-trihydroquinazolin-2-one. To a suspension of [4-(3,4-difluorophenyl)(1,3-thiazol-2-yl)][(2-nitrophenyl)-methyl]amine (Step a) (860 mg, 2.5 mmol) in 70% aqueous EtOH (28 mL) was added $NH_4Cl$ (148 mg, 2.8 mmol) followed by Fe dust (683 mg, 12.2 mmol) and the reaction was heated to 75° C. After 2 h, the reaction was cooled to RT, filtered through a pad of Celite® and the solution was concentrated in vacuo. The residue was azeotroped twice with benzene and dissolved in 20 mL DMF. To this solution was added CDI (997 mg, 6.1 mmol) followed by 95% NaH (178 mg, 7.4 mmol) at RT, resulting in gas evolution. After 15 h, $H_2O$ (50 mL) was added and the precipitate was filtered, washed with $H_2O$, MeOH and EtOAc and dried in vacuo to give a white solid. Mp: 289–293° C. MS m/z: 344 (M+1); 342 (M−1). Anal. Calc'd for $C_{17}H_{11}F_2N_3OS.0.10$ $H_2O$: C, 59.15; H, 3.27; N, 12.08. Found: C, 59.09; H, 3.21; N, 12.17.

EXAMPLE 40

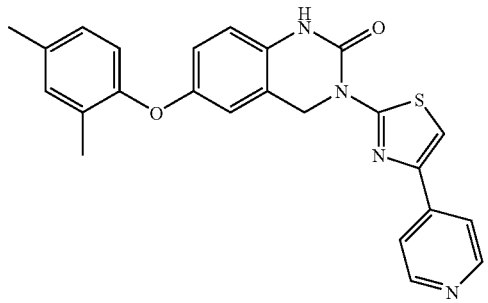

6-(2,4-Dimethylphenoxy)-3-(4-(4-pyridyl)(1,3-thiazol-2-yl))-1,3,4-trihydroquinazolin-2-one (a) Preparation of 5-(2,4-dimethylphenoxy)-2-nitrobenzene carbonitrile. To a suspension of 2,4-dimethylphenol (Aldrich) (3.6 mL, 29.8 mmol) and 95% NaH (717 mg, 29.8 mmol) in 30 mL DMF was added 5-fluoro-2-nitrobenzonitrile (Combi-Blocks) (4.45 g, 26.8 mmol). The reaction mixture was heated at 50° C. for 4 h, then poured into 120 mL of $H_2O$. The precipitate was filtered, washed with $H_2O$ and dried in vacuo to give a yellow amorphous solid that was used without further purification. MS m/z: 286 (M+1). Calc'd for $C_{15}H_{12}N_2O_3$—268.08.

(b) Preparation of N-[({[5-(2,4-dimethylphenoxy)-2-nitrophenyl]methyl}amino)thioxomethyl]-benzamide. To a cooled (0° C.) solution of 1M $BH_3$.THF (Fluka) (100 mL, 100 mmol) was added 5-(2,4-dimethylphenoxy)-2-nitrobenzene carbonitrile (Step a) (4.03 g, 15.0 mmol) in portions. After complete addition, the reaction was warmed to RT. After 18 h the solvent was concentrated to one-half its original volume. The concentrated solution was carefully added to 10% HCl (100 mL) and heated to reflux for 2 h. The solution was cooled to RT and the volatiles were removed in vacuo. The aqueous solution was basified with 5N NaOH and extracted with $CH_2Cl_2$. The combined organics were washed with $H_2O$, dried over $Na_2SO_4$ and concentrated in vacuo. The residue was dissolved in 100 mL $CHCl_3$ and to the suspension was added benzoyl isothiocyanate (2.0 mL, 15 mmol). After heating to 61° C. for 2 h the reaction was cooled to RT and purified by flash chromatography with hexanes:EtOAc (9:1, 17:3, 3:1, 0:1) as eluant. MS m/z: 436 (M+1); 434 (M−1). Calc'd for $C_{23}H_{21}N_3O_4S$—435.13.

(c) Preparation of {[5-(2,4-dimethylphenoxy)-2-nitrophenyl]-methyl}(4-(4-pyridyl)(1,3-thiazol-2-yl))amine. To a solution of N-[({[5-(2,4-dimethylphenoxy)-2-nitrophenyl]methyl}-amino)thioxomethyl]-benzamide (Step b) (956 mg, 2.2 mmol) in 70% aqueous MeOH (50 mL) was added $K_2CO_3$ (367 mg, 2.7 mmol) and the reaction was heated to reflux. After 3 h, the reaction was cooled to 40° C. and 2-bromo-1-(4-pyridyl)ethan-1-one hydrobromide (624 mg, 2.2 mmol) was added. After 1.5 h, the reaction mixture was cooled to RT, concentrated in vacuo and purified by flash chromatography with hexanes:EtOAc (9:1, 3:1, 1:1) as eluant to afford an orange foam. MS m/z: 433 (M+1); 431 (M−1). Calc'd for $C_{23}H_{20}N_4O_3S$—432.13.

(d) Preparation of 6-(2,4-dimethylphenoxy)-3-(4-(4-pyridyl)-(1,3-thiazol-2-yl))-1,3,4-trihydroquinazolin-2-one. To a suspension of {[5-(2,4-dimethylphenoxy)-2-nitrophenyl]-methyl}(4-(4-pyridyl)(1,3-thiazol-2-yl))amine (Step c) (125 mg, 0.3 mmol) in 80% aqueous EtOH (6 mL) was added $NH_4Cl$ (20 mg, 0.4 mmol) followed by Fe dust (82 mg, 1.5 mmol) and the reaction was heated to 78° C. After 2 h, the reaction was cooled to RT, filtered through a pad of Celite® and the solution was concentrated in vacuo. The residue was azeotroped twice with benzene and dissolved in 5 mL DMF. To this solution was added CDI (138 mg, 0.9 mmol) followed by 95% NaH (27 mg, 1.1 mmol) at RT, resulting in gas evolution. After 16 h, $H_2O$ (10 mL) was added and the precipitate was filtered, washed with $H_2O$ and MeOH and dried in vacuo to give a pale yellow powder. The crude solid was purified by flash chromatography with $CH_2Cl_2$:MeOH (39:1) as eluant to afford a white solid. Mp: 254–258° C. MS m/z: 429 (M+1); 427 (M−1). Calc'd for $C_{24}H_{20}N_4O_2S$— Exact Mass: 428.13

EXAMPLE 41

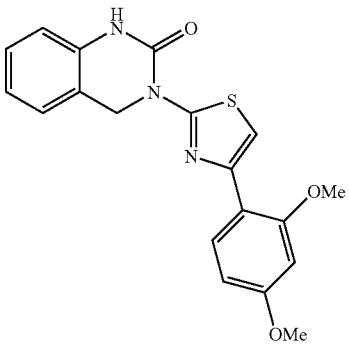

3-[4-(2,4-Dimethoxyphenyl)-1,3-thiazol-2-yl]-1,3,4-trihydroquinazolin-2-one (a) Preparation of [4-(2,4-dimethoxyphenyl)(1,3-thiazol-2-yl)][(2-nitrophenyl)methyl]amine. To a slurry of amino{[(2-nitrophenyl)methyl]amino}methane-1-thione (Example 16a) (539 mg, 2.6 mmol) in 50% aqueous MeOH (50 mL) was added 2-bromo-2″,4″-dimethoxy-acetophenone (Aldrich) (554 mg, 2.1 mmol) and the reaction was heated to 40° C. After 2 h, the reaction was cooled to RT and purified by flash chromatography with hexanes:EtOAc:CH$_2$Cl$_2$:MeOH (3:1:0:0, 0:0:19:1) as eluant to afford a yellow foam. MS m/z: 372 (M+1); 370 (M−1). Calc'd for C$_{18}$H$_{17}$N$_3$O$_4$S—371.09.

(b) Preparation of 3-[4-(2,4-dimethoxyphenyl)-1,3-thiazol-2-yl]-1,3,4-trihydroquinazolin-2-one. To a solution of [4-(2,4-dimethoxyphenyl)(1,3-thiazol-2-yl)][(2-nitrophenyl)-methyl]amine (Step a) (484 mg, 1.3 mmol) and NH$_4$Cl (71 mg, 1.3 mmol) in 70% aqueous EtOH (20 mL) was added iron dust (348 mg, 6.2 mmol) and the reaction was heated to 78° C. After 1.5 h, the reaction was cooled to RT, filtered through a pad of Celite® and the solution was concentrated in vacuo. The residue was azeotroped twice with benzene and dissolved in 15 mL of DMF. To this solution was added CDI (520 mg, 3.2 mmol) followed by 95% NaH (96 mg, 4.0 mmol) at RT, resulting in gas evolution. After 15 h, H$_2$O (30 mL) was added and the precipitate was filtered, washed with H$_2$O and MeOH and dried in vacuo to give a white solid. Mp: 283–288° C. MS m/z: 368 (M+1); 366 (M−1). Anal. Calc'd for C$_{19}$H$_{17}$N$_3$O$_3$S.0.1 MeOH: C, 61.90; H, 4.73; N, 11.34. Found: C, 61.87; H, 4.76; N, 11.33.

EXAMPLE 42

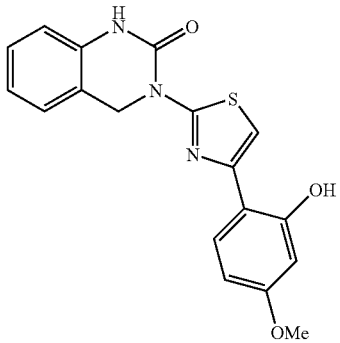

3-[4-(2-Hydroxy-4-methoxyphenyl)-1,3-thiazol-2-yl]-1,3,4-trihydroquinazolin-2-one To a slurry of 95% NaH (43 mg, 1.8 mmol) in DMF was added ethanethiol (Aldrich) (0.12 mL, 1.6 mmol) resulting in a yellow homogenous solution. After 5 min, 3-[4-(2,4-dimethoxyphenyl)-1,3-thiazol-2-yl]-1,3,4-trihydroquinazolin-2-one (Example 41) (112 mg, 0.3 mmol) was added and the solution heated to 150° C. After 2.5 h, the reaction was cooled to RT, concentrated in vacuo and purified by flash chromatography with CH$_2$Cl$_2$:MeOH (39:1, 19:1) as eluant to give an off-white amorphous solid. MS m/z: 354 (M+1); 352 (M−1). Anal. Calc'd for C$_{18}$H$_{15}$N$_3$O$_3$S: C, 61.18; H, 4.28; N, 11.89. Found: C, 60.96; H, 4.43; N, 11.87.

EXAMPLE 43

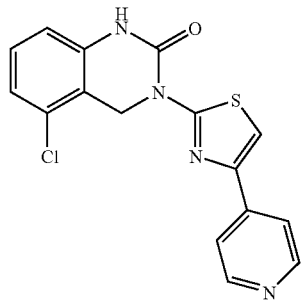

5-Chloro-3-(4-(4-pyridyl)(1,3-thiazol-2-yl))-1,3,4-trihydroquinazolin-2-one (a) Preparation of (2-chloro-6-nitrophenyl)methylamine. To a cooled (0° C.) solution of 1M BH$_3$.THF (Fluka) (100 mL, 100 mmol) was added 5-chloro-2-nitrobenzonitrile (3.69 g, 20 mmol) in three portions. After complete addition, the reaction was warmed to RT. After 15 h, the solvent was concentrated to one-half its original volume. The concentrated solution was carefully added to 10% HCl (100 mL) and heated to reflux. After 2.5 h, the solution was cooled to RT and the volatiles were removed in vacuo. The aqueous solution was basified with 1N NaOH and extracted with CH$_2$Cl$_2$. The combined organics were dried over Na$_2$SO$_4$ and concentrated in vacuo to afford a red oil. MS m/z: 187 (M+1). Calc'd for C$_7$H$_7$ClN$_2$O$_2$—186.02.

(b) Preparation of N-({[(2-chloro-6-nitrophenyl)methyl]amino}thioxomethyl)benzamide. To solution of (2-chloro-6-nitrophenyl)methylamine (Step a) (3.19 g, 17 mmol) in 100 mL CHCl$_3$ was added benzoyl isothiocyanate (2.3 mL, 17 mmol) and the reaction was heated to 61° C. After 2.5 h, the reaction was cooled to RT and purified by flash chromatography with hexanes:EtOAc (9:1, 4:1, 13:7, 1:1) as eluant to give an off-white amorphous solid. MS m/z: 348 (M−1). Calc'd for C$_{15}$H$_{12}$ClN$_3$O$_3$S—349.03.

(c) Preparation of [(2-chloro-6-nitrophenyl)methyl](4-(4-pyridyl)(1,3-thiazol-2-yl))amine. To a solution of N-({[(2-chloro-6-nitrophenyl)methyl]amino}thioxomethyl)benzamide (Step b) (1.22 g, 3.5 mmol) in 70% aqueous MeOH (50 mL) was added K$_2$CO$_3$ (567 mg, 4.1 mmol) and the reaction was heated to reflux. After 1.5 h, the reaction was cooled (40° C.) and 2-bromo-1-(4-pyridyl)ethan-1-one hydrobromide (992.4 mg, 3.5 mmol) was added. After 1.5 h, the reaction mixture was cooled to RT and purified by flash chromatography with hexanes:EtOAc:CH₂Cl₂:MeOH (9:1:0:0, 3:1:0:0, 1:1:0:0, 0:0:49:1) as eluant to afford an off-white amorphous solid. MS m/z: 347 (M+1); 345 (M−1). Calc'd for $C_{15}H_{11}ClN_4O_2S$—346.03.

(d) Preparation of 5-chloro-3-(4-(4-pyridyl)(1,3-thiazol-2-yl))-1,3,4-trihydroquinazolin-2-one. To a solution of [(2-chloro-6-nitrophenyl)methyl](4-(4-pyridyl) (1,3-thiazol-2-yl))amine (Step c) (89 mg, 0.3 mmol) and NH₄Cl (26 mg, 0.5 mmol) in 83% aqueous EtOH (6 mL) was added iron dust (95 mg, 1.7 mmol) and the reaction was heated to 78° C. After 2 h, the reaction was cooled to RT, filtered through a pad of Celite® and the solution was concentrated in vacuo. The residue was azeotroped twice with benzene and dissolved in 5 mL of DMF. To this solution was added CDI (137 mg, 0.8 mmol) followed by 95% NaH (22 mg, 0.9 mmol) at RT, resulting in gas evolution. After 16 h, H₂O (30 mL) was added and the precipitate was filtered, washed with H₂O and MeOH and dried in vacuo. The crude material was purified by flash chromatography with CH₂Cl₂:MeOH (39:1) as eluant to afford an off-white solid. Mp: >300° C. MS m/z: 342 (M+1). MALDI-FTMS Exact Mass Calc'd for $C_{16}H_{11}ClN_4OS$: 343.0415. Found: 343.0413.

EXAMPLE 44

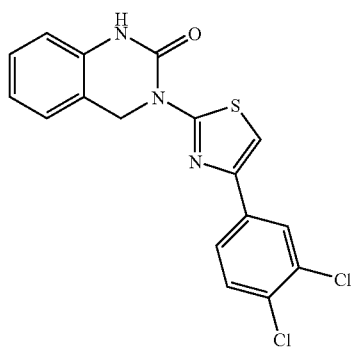

3-[4-(3,4-Dichlorophenyl)-1,3-thiazol-2-yl]-1,3,4-trihydroquinazolin-2-one (a) Preparation of [4-(3,4-dichlorophenyl)(1,3-thiazol-2-yl)][(2-nitrophenyl)methyl]amine. To a slurry of amino{[(2-nitrophenyl)methyl]amino}methane-1-thione (Example 16a) (515 mg, 2.4 mmol) in 50% aqueous MeOH (30 mL) was added 3,4-dichlorophenacyl bromide (Maybridge) (660 mg, 2.5 mmol) and the reaction was heated to 45° C. After 2 h, the reaction was cooled to RT and purified by flash chromatography with hexanes:EtOAc (3:1) as eluant to afford an orange foam. MS m/z: 382, 380 (M+1); 380, 378 (M−1). Calc'd for $C_{16}H_{11}Cl_2N_3O_2S$—378.99.

(b) Preparation of 3-[4-(3,4-dichlorophenyl)-1,3-thiazol-2-yl]-1,3,4-trihydroquinazolin-2-one. To a solution of [4-(3,4-dichlorophenyl)(1,3-thiazol-2-yl)][(2-nitrophenyl)-methyl]-amine (Step a) (668 mg, 1.8 mmol) and NH₄Cl (95 mg, 1.8 mmol) in 70% aqueous EtOH (20 mL) was added iron dust (443 mg, 7.9 mmol) and the reaction was heated to 78° C. After 1.5 h, the reaction was filtered through a pad of Celite® while hot and the solution was concentrated in vacuo. The residue was azeotroped twice with benzene and dissolved in 20 mL DMF. To this solution was added CDI (745 mg, 4.6 mmol) followed by 95% NaH (136 mg, 5.7 mmol) at RT, resulting in gas evolution. After 15 h, H₂O (40 mL) was added and the precipitate was filtered, washed with H₂O and MeOH and dried in vacuo to give an off-white solid. Mp: 295–299° C. MS m/z: 374 (M−1). Anal. Calc'd for $C_{17}H_{11}Cl_2N_3OS$: C, 54.26; H, 2.95; N, 11.17; Cl, 18.84. Found: C, 54.14; H, 2.94; N, 11.05; Cl, 19.01.

EXAMPLE 45

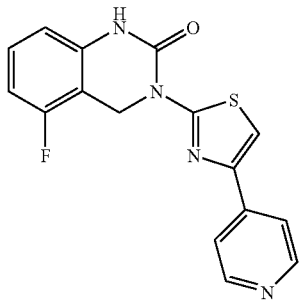

5-Fluoro-3-(4-(4-pyridyl)(1,3-thiazol-2-yl))-1,3,4-trihydroquinazolin-2-one (a) Preparation of [(2-amino-6-fluorophenyl)methyl](4-(4-pyridyl)(1,3-thiazol-2-yl))amine. A flask charged with 2-amino-6-fluorobenzylamine (Lancaster) (1.05 g, 7.5 mmol) and 2-chloro-4-(4-pyridyl)-1,3-thiazole (384 mg, 1.9 mmol) was heated at 80° C. for 16 h. The temperature was increased to 100° C. for an additional 5 h, then cooled to RT and purified by flash chromatography with Hexanes:EtOAc (3:1, 1:1) as eluant to afford a pale-yellow solid. MS m/z: 301 (M+1); 299 (M−1). Calc'd for $C_{15}H_{13}FN_4S$—300.08.

(b) Preparation of 5-fluoro-3-(4-(4-pyridyl)(1,3-thiazol-2-yl))-1,3,4-trihydroquinazolin-2-one. To a solution of [(2-amino-6-fluorophenyl)methyl](4-(4-pyridyl)(1,3-thiazol-2-yl))amine (Step a) (240 mg, 0.8 mmol) in 8.0 mL DMF was added CDI (259 mg, 1.6 mmol) followed by 95% NaH (45 mg, 1.9 mmol) at RT, resulting in gas evolution. After 15 h, the precipitate was filtered, washed with H₂O, MeOH, and CH₂Cl₂, and dried in vacuo to give a white solid. Mp: >300° C. MS m/z: 327 (M+1); 325 (M−1). Anal. Calc'd for $C_{16}H_{11}FN_4OS$: C, 58.88; H, 3.40; N, 17.17. Found: C, 58.62; H, 3.41; N, 17.06.

EXAMPLE 46

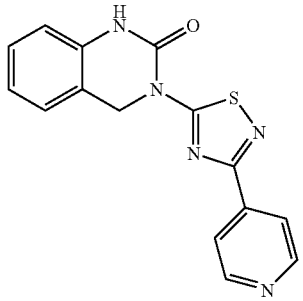

3-(3-(4-Pyridyl)-1,2,4-thiadiazol-5-yl)-1,3,4-trihydroquinazolin-2-one (a) Preparation of 5-chloro-3-(4-pyridyl)-1,2,4-thiadiazole. To a cooled (10–15° C.) suspension of 3-(4-pyridyl)-1,2,4-thiadiazole-5-ylamine (EP 0641797 A1, 1995) (765 mg, 4.3 mmol) in 13 mL glacial AcOH and conc. HCl (3 mL) was added copper turnings (Aldrich) (81 mg). To this suspension was added a solution of NaNO$_2$ (312 mg, 4.5 mmol) in H$_2$O (1 mL) dropwise over a period of 0.5 h. After 4 h, a solution of NaNO$_2$ (312 mg, 4.5 mmol) in H$_2$O (1 mL) was added while maintaining a temperature <15° C. After 1 h, the reaction was poured into H$_2$O (40 mL) and extracted with CHCl$_3$. The combined organics were washed with saturated NaHCO$_3$, dried over Na$_2$SO$_4$, and concentrated in vacuo to give a white powder. MS m/z: 198 (M+1). Calc'd for C$_7$H$_4$ClN$_3$S—196.98.

(b) Preparation of 3-(3-(4-pyridyl)-1,2,4-thiadiazol-5-yl)-1,3,4-trihydroquinazolin-2-one. To a solution of 5-chloro-3-(4-pyridyl)-1,2,4-thiadiazole (Step a) (202 mg, 1.0 mmol) in 10 mL THF was added 2-amino-benzylamine (Aldrich) (122 mg, 1.0 mmol) at RT. After 2 h, the reaction was heated at 60° C. After 15 h, the reaction was cooled to RT and the solvent was removed in vacuo. The residue was dissolved in 10 mL DMF and to this solution was added CDI (Aldrich) (352 mg, 2.2 mmol) followed by 95% NaH (58 mg, 2.4 mmol) at RT. After 18 h, H$_2$O (20 mL) was added and the white precipitate was washed consecutively with H$_2$O, MeOH and CH$_2$Cl$_2$. The crude material was purified by flash chromatography with CH$_2$Cl$_2$:MeOH (39:1, 19:1) as eluant to give a white solid. Mp: >290° C. MS m/z: 310 (M+1); 308 (M–1). MALDI-FTMS Calc'd for C$_{15}$H$_{11}$N$_5$OS: 310.0757. Found: 310.0744.

EXAMPLE 47

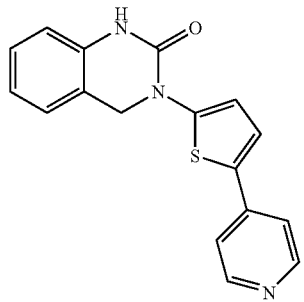

3-(5-(4-Pyridyl)-2-thienyl)-1,3,4-trihydroquinazolin-2-one (a) Preparation of methyl 5-(4-pyridyl)thiophene-2-carboxylate. To a solution of methyl 5-bromothiophene-2-carboxylate (4.02 g, 18 mmol) and 4-pyridine boronic acid (Frontier) (2.0 g, 16 mmol) in 150 mL DME was added PdCl$_2$dppf.CH$_2$Cl$_2$ (Strem) (1.27 g, 1.7 mmol) followed by 12 mL 2M Na$_2$CO$_3$ solution. The reaction was heated to reflux for 16 h and cooled to RT. The solvent was removed in vacuo, partitioned between EtOAc/H$_2$O and filtered. The organic layer was extracted with 1N HCl (3×50 mL) and the combined acidic layers were neutralized with 1N NaOH. The resulting precipitate was extracted with EtOAc (3×50 mL), dried in vacuo, and concentrated to give a pale green powder. MS m/z: 220 (M+1). Calc'd for C$_{11}$H$_9$NO$_2$S—219.04.

(b) Preparation of 5-(4-pyridyl)thiophene-2-carboxylic acid. To a solution of methyl 5-(4-pyridyl)thiophene-2-carboxylate (Step a) (2.44 g, 11.1 mmol) in 130 mL EtOH was added 1N NaOH (30 mL) at RT. After 2 h the solvent was removed in vacuo. The residue was dissolved in 100 mL H$_2$O and acidified with 1N HCl to pH 5. The resulting white precipitate was filtered, washed with H$_2$O and dried in vacuo to give an off-white powder. MS m/z: 206 (M+1); 204 (M–1). Calc'd for C$_{10}$H$_7$NO$_2$S—205.02.

(c) Preparation of prop-2-enyloxy-N-(5-(4-pyridyl)(2-thienyl))carboxamide. To a suspension of 5-(4-pyridyl)thiophene-2-carboxylic acid (Step b) (1.21 g, 6.0 mmol) in 50 mL toluene was added Et$_3$N (1.0 mL, 7.2 mmol) at RT. After 1 h, DPPA (Aldrich) (2.1 mL, 9.7 mmol) was added. After an additional hour the reaction was heated to 80° C. After 1 h, allyl alcohol (4.0 mL, 62 mmol) was added and the reaction was cooled to 70° C. After 15 h at this temperature, the reaction was cooled to RT, concentrated in vacuo and purified by flash chromatography with Hexanes:EtOAc:CH$_2$Cl$_2$:MeOH (3:1:0:0, 1:1:0:0, 0:0:99:1) as eluant to give a pale-yellow amorphous solid. MS m/z: 261 (M+1); 259 (M–1). Calc'd for C$_{13}$H$_{12}$N$_2$O$_2$S—260.06.

(d) Preparation of N-[(2-nitrophenyl)methyl]prop-2-enyloxy-N-(5-(4-pyridyl)(2-thienyl))carboxamide. To a RT slurry of 95% NaH (101 mg, 4.2 mmol) in DMF (20 mL) was added dropwise a solution of prop-2-enyloxy-N-(5-(4-pyridyl) (2-thienyl))-carboxamide (Step c) (882 mg, 3.4 mmol) in DMF (15 mL). After 1 h, a solution of 2-nitrobenzyl bromide (Aldrich) (814 mg, 3.8 mmol) in DMF (10 mL) was added. After 16.5 h, the reaction was concentrated in vacuo and purified by flash chromatography with Hexanes:EtOAc:CH$_2$Cl$_2$:MeOH (3:1:0:0, 1:1:0:0, 0:0:19:1) as eluant to give a pale-yellow amorphous solid. MS m/z: 396 (M+1); 394 (M–1). Calc'd for C$_{20}$H$_{117}$N$_3$O$_4$S—395.09.

(e) Preparation of [(2-nitrophenyl)methyl] (5-(4-pyridyl) (2-thienyl))amine. To solution of N-[(2-nitrophenyl)-methyl]prop-2-enyloxy-N-(5-(4-pyridyl) (2-thienyl)) carboxamide (776 mg, 2.0 mmol) and morpholine (Aldrich) (1.8 mL, 21 mmol) in THF (20 mL) was added Pd(Ph$_3$P)$_4$ (Strem) (128 mg, 0.1 mmol) at RT. After 16.5 h, the reaction was concentrated in vacuo and purified by flash chromatography with Hexanes:EtOAc (3:1, 1:1, 1:4) as eluant to give a red foam. MS m/z: 312 (M+1); 310 (M–1). Calc'd for C$_{16}$H$_{13}$N$_3$O$_2$S—311.07.

(f) Preparation of 3-(5-(4-pyridyl)-2-thienyl)-1,3,4-trihydroquinazolin-2-one. To a solution of [(2-nitrophenyl)-methyl](5-(4-pyridyl) (2-thienyl))amine (Step e) (535 mg, 1.7 mmol) and NH$_4$Cl (95 mg, 1.8 mmol) in 70% aqueous EtOH (20 mL) was added iron dust (482 mg, 8.6 mmol) and the reaction was heated to 78° C. After 1 h, the reaction was filtered through a pad of Celite®, washed with hot EtOH and the solution was concentrated in vacuo. The residue was azeotroped twice with benzene and dissolved in DMF (20 mL). To this solution was added (Aldrich) (754 mg, 4.6 mmol) followed by 95% NaH (132 mg, 5.5 mmol) at RT, resulting in gas evolution. After 16 h, H$_2$O (40 mL) was added and the precipitate was filtered, washed with H$_2$O and MeOH and dried in vacuo to give an off-white solid. Mp: 301–305° C. MS m/z: 308 (M+1); 306 (M–1). Anal. Calc'd for C$_{17}$H$_{13}$N$_3$OS.0.1 H$_2$O: C, 66.04; H, 4.30; N, 13.59. Found: C, 66.21; H, 4.50; N, 13.55.

EXAMPLE 48

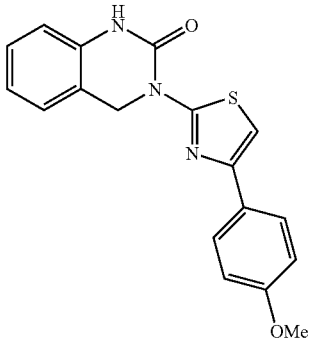

3-[4-(4-Methoxyphenyl)-1,3-thiazol-2-yl]-1,3,4-trihydroquinazolin-2-one (a) Preparation of [(2-aminophenyl)methyl][4-(4-methoxyphenyl)(1,3-thiazol-2-yl)]amine. To a heated (50° C.) suspension of 2-bromo-4'-methoxyacetophenone (Aldrich) (2.36 g, 10.3 mmol) and KSCN (1.27 g, 13.1 mmol) in EtOH (25 mL) was added 2-aminobenzylamine (Aldrich) (1.23 g, 10.0 mmol). After 18 h, the reaction was cooled to RT and the solvent was removed in vacuo. The residue was partitioned between water and $CH_2Cl_2$ and the aqueous layer was extracted with $CH_2Cl_2$. The combined organics were dried over $Na_2SO_4$ and purified by column chromatography to yield a yellow oil. MS m/z: 312 (M+1); 310 (M−1). Calc'd for $C_{17}H_{17}N_3OS$—311.11.

(b) Preparation of 3-[4-(4-methoxyphenyl)-1,3-thiazol-2-yl]-1,3,4-trihydroquinazolin-2-one. To a solution of [(2-aminophenyl)methyl][4-(4-methoxyphenyl)(1,3-thiazol-2-yl)]amine (1.36 g, 4.4 mmol) in THF (40 mL) was added CDI (Aldrich) (1.42 g, 8.8 mmol) followed by 60% NaH (402 mg, 10.0 mmol) at RT, resulting in gas evolution. After 6 h, saturated $NH_4Cl$ was added and a precipitate was filtered, washed with $H_2O$ and hexanes and dried in vacuo to give an off-white solid. Mp: 275–278° C. MS m/z: 338 (M+1). Calc'd for $C_{18}H_{15}N_3O_2S$—337.09.

EXAMPLE 49

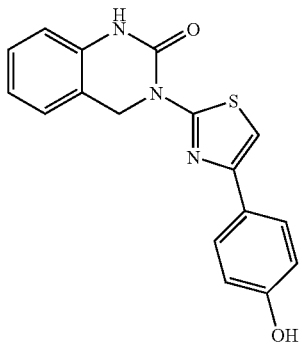

3-[4-(4-Hydroxyphenyl)-1,3-thiazol-2-yl]-1,3,4-trihydroquinazolin-2-one

To a slurry of 60% NaH (212 mg, 5.3 mmol) in DMF (10 mL) was added ethanethiol (Aldrich) (0.38 mL, 5.1 mmol) dropwise resulting in gas evolution. After 5 min, 3-[4-(4-methoxyphenyl)-1,3-thiazol-2-yl]-1,3,4-trihydroquinazolin-2-one (Example 48) (297 mg, 0.9 mmol) was added and the reaction was heated to 150° C. After 4 h, the reaction was cooled to RT and the solvent was removed in vacuo to one-half of its original volume. Saturated $NH_4Cl$ was added giving a precipitate that was filtered, washed with $H_2O$ and dried in vacuo. The crude material was purified by reverse phase HPLC to give a tan amorphous solid. Mp: 288–291° C. Anal. Calc'd for $C_{17}H_{13}N_3O_2S$: C, 63.14; H, 4.05; N, 12.99. Found: C, 62.84; H, 3.97; N, 12.95.

EXAMPLE 50

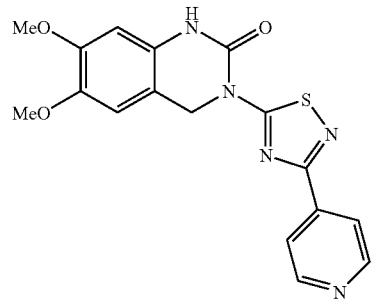

6,7-Dimethoxy-3-(3-(4-pyridyl)(1,2,4-thiadiazol-5-yl))-1,3,4-trihydroquinazolin-2-one (a) Preparation of [(2-amino-4,5-dimethoxyphenyl)methyl](3-(4-pyridyl)(1,2,4-thiadiazol-5-yl))amine. A solution of 5-chloro-3-(4-pyridyl)-1,2,4-thiadiazole (Example 46a) (207 mg, 1.05 mmol) and 2-(aminomethyl)-4,5-dimethoxyphenylamine (223 mg, 1.22 mmol) in THF (10 mL) was heated at 60° C. for 22 h. The reaction was cooled to RT, the solvent was removed in vacuo and the residue was purified by flash chromatography with EtOAc:Hexanes:2M $NH_3$ in MeOH:$CH_2Cl_2$ (1:4:0:0, 1:1:0:0, 0:0:1:19, 0:0:1:9) as eluant to afford an off-white amorphous solid. MS m/z: 344 (M+1); 342 (M−1). Calc'd for $C_{16}H_{17}N_5O_2S$—343.11.

(b) Preparation of 6,7-dimethoxy-3-(3-(4-pyridyl)(1,2,4-thiadiazol-5-yl))-1,3,4-trihydroquinazolin-2-one. To a RT solution of [(2-amino-4,5-dimethoxyphenyl)methyl](3-(4-pyridyl)(1,2,4-thiadiazol-5-yl))amine (Step a) (165 mg, 0.5 mmol) and CDI (Aldrich) (155 mg, 1.0 mmol) in DMF (5 mL) was added 60% NaH (40 mg, 7.5 mmol) resulting in gas evolution. After 18 h, saturated $NH_4Cl$ was added to the mixture. The solids were filtered, washed with water and hexanes, and dried in vacuo. The crude material was purified by reverse phase HPLC to give a yellow solid. MS m/z: 370 (M+1); 368 (M−1). Calc'd for $C_{17}H_{15}N_5O_3S$—369.09.

EXAMPLE 51

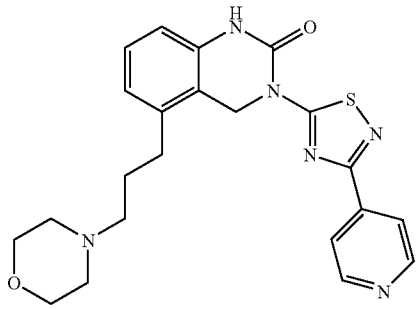

5-(2-Morpholin-4-ylethoxy)-3-(3-(4-pyridyl)(1,2,4-thiadiazol-5-yl))-1,3,4-trihydroquinazolin-2-one (a) Preparation of 2-(2-morpholin-4-ylethoxy)-6-nitrobenzene-carbonitrile. To a slurry 60% NaH (214 mg, 5.4 mmol) in THF (40 mL) was added N-(2-hydroxyethyl)morpholine (Acros) (0.65 mL, 5.4 mmol) resulting in gas evolution. After 30 min, this solution was added to a cooled (0° C.) solution of 2,6-dinitrobenzene-carbonitrile (J. Med. Chem. 1990, 434) (790 mg, 4.1 mmol) in THF (30 mL). The reaction was warmed to RT. After 2 h, the reaction solvent was removed in vacuo and the residue was purified by flash chromatography with 2M $NH_3$ in MeOH:$CH_2Cl_2$ (0:1, 1:39) as eluant to afford a tan amorphous solid. MS m/z: 278 (M+1). Calc'd for $C_{13}H_{15}N_3O_4$—277.11.

(b) Preparation of {([2-amino-6-(2-morpholin-4-ylethoxy)-phenyl]methyl}(3-(4-pyridyl)(1,2,4-thiadiazol-5-yl))amine. To a cooled (−10° C.) solution of 2-(2-morpholin-4-ylethoxy)-6-nitrobenzene-carbonitrile (Step a) (9.37 mg, 3.4 mmol) in THF (10 mL) was added 1M $BH_3$.THF (Fluka) (18 mL, 18.0 mmol). The reaction was warmed to RT. After 15 h, the solvent was concentrated to one-half its original volume. The concentrated solution was carefully added to 10% HCl (40 mL) and heated at 55° C. for 2 h. The solution was cooled to RT and washed with EtOAc. The aqueous solution was basified with 5N NaOH and extracted with $CH_2Cl_2$ and $CHCl_3$. The combined organics were dried over $Na_2SO_4$ and concentrated in vacuo to give a brown gum. MS m/z: 282 (M+1). To a solution of [2-(2-morpholin-4-ylethoxy)-6-nitrophenyl]methylamine (662 mg, 2.4 mmol) and $NH_4Cl$ (130 mg, 2.4 mmol) in 5:1 EtOH:$H_2O$ was added Fe dust (606 mg, 11 mol). The reaction was heated to 60° C. After 1 h, AcOH (0.5 mL) and a four drops of 1N HCl were added. After an additional 2 h, the reaction was cooled to RT and filtered through a pad of Celite®. The solvent was removed in vacuo and the residue warmed to 60° C. in MeOH in the presence of charcoal. The charcoal was filtered, the solvent removed in vacuo and the crude material dried. To a solution the 2-(aminomethyl)-3-(2-morpholin-4-ylethoxy)phenylamine (2.4 mmol) was added 5-chloro-3-(4-pyridyl)-1,2,4-thiadiazole (Example 46a) (407 mg, 2.1 mmol) in THF (20 mL) and the reaction was heated at 60° C. for 20 h. The reaction was cooled to RT, the solvent was removed in vacuo, and the residue was purified by flash chromatography with 2M $NH_3$ in MeOH:$CH_2Cl_2$ (0:1, 1:9) as eluant to afford pale yellow glass. MS m/z: 413 (M+1); 411 (M−1). Calc'd for $C_{13}H_{15}N_3O_4$—277.11.

(c) Preparation of 5-(2-morpholin-4-ylethoxy)-3-(3-(4-pyridyl)(1,2,4-thiadiazol-5-yl))-1,3,4-trihydroquinazolin-2-one. To a solution of {[2-amino-6-(2-morpholin-4-ylethoxy)phenyl]methyl}(3-(4-pyridyl)(1,2,4-thiadiazol-5-yl))amine (Step b) (190 mg, 0.5 mmol) and CDI (Aldrich) (150 mg, 0.9 mmol) in DMF (5 mL) was added 60% NaH (40 mg, 1.0 mmol) resulting in gas evolution. After 17 h, saturated $NH_4Cl$ was added and the solids were filtered, washed successively with saturated $NH_4Cl$, hexanes, water and MeOH and dried in vacuo. The residue was purified by reverse phase HPLC to give an off-white solid. Mp: 259–260° C. MS m/z: 439 (M+1); 437 (M−1). Anal. Calc'd for $C_{21}H_{22}N_6O_3S.2.5$ $CF_3CO_2H.1$ $H_2O$: C, 42.11; H, 3.60; N, 11.34; F, 19.22. Found: C, 41.74; H, 3.52; N, 11.75; F, 19.56.

EXAMPLE 52

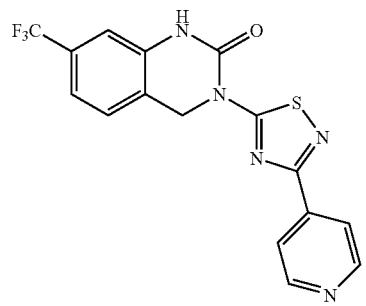

3-(3-(4-Pyridyl)(1,2,4-thiadiazol-5-yl))-7-(trifluoromethyl)-1,3,4-trihydroquinazolin-2-one (a) Preparation of [2-nitro-4-(trifluoromethyl)phenyl]-methylamine. To a cooled (0° C.) solution of 1M $BH_3$.THF (Fluka) (40 mL, 40 mmol) was added 2-nitro-4-(trifluoromethyl)benzene-carbonitrile (Lancaster) (1.69 g, 8 mmol). The reaction was warmed to RT. After 18 h, the solvent was concentrated to one-half its original volume. The concentrated solution was carefully added to 10% HCl (80 mL) and heated to 55° C. for 3 h. The solution was cooled to RT and washed with EtOAc. The aqueous solution was basified with 5N NaOH and extracted with $CH_2Cl_2$. The combined organics were dried over $Na_2SO_4$ and concentrated in vacuo to give a yellow liquid. MS m/z: 221 (M+1). Calc'd for $C_8H_7F_3N_2O_2$—220.05.

(b) Preparation of 3-(3-(4-pyridyl)(1,2,4-thiadiazol-5-yl))-7-(trifluoromethyl)-1,3,4-trihydroquinazolin-2-one. To a solution of [2-nitro-4-(trifluoromethyl)phenyl]-methylamine (Step a) (1.5 g, 6.9 mmol) and $NH_4Cl$ (364 mg, 6.8 mmol) in 70% aqueous EtOH (70 mL) was added Fe dust (2.0 g, 35 mmol), and the reaction was heated to 74° C. After 3 h, the reaction was filtered through a pad of Celite® while hot. The solvent was removed in vacuo and the residue was azeotroped with benzene. The crude material was dissolved in THF (30 mL) and 5-chloro-3-(4-pyridyl)-1,2,4-thiadiazole (Example 46a) (445 mg, 2.2 mmol) was added. The reaction was heated at 60° C. for 22 h, the solvent was removed in vacuo and residue was purified by flash chromatography with 2M $NH_3$ in MeOH:$CH_2Cl_2$ (0:1, 1:39, 1:49) as eluant. MS m/z: 369 (M+1); 367 (M−1). To a solution of {[2-amino-4-(trifluoromethyl)phenyl]methyl}(3-(4-pyridyl)(1,2,4-thiadiazol-5-yl))amine (2.2 mmol) and CDI (Aldrich) (533 mg, 3.3 mmol) in DMF (10 mL) was added 60% NaH (138 mg, 3.5 mmol) resulting in gas evolution. After 17 h, saturated NH₄Cl was added and the solids were filtered, washed successively with saturated NH₄Cl, hexanes, water and MeOH and dried in vacuo to afford pale-purple solid. Mp: >300° C. MS m/z: 378 (M+1); 376 (M−1). Calc'd for $C_{16}H_{10}F_3N_5OS$—377.06.

EXAMPLE 53

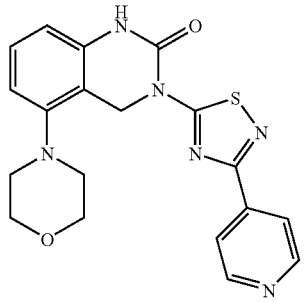

5-Morpholin-4-yl-3-(3-(4-pyridyl)(1,2,4-thiadiazol-5-yl))-1,3,4-trihydroquinazolin-2-one (a) Preparation of (2-morpholin-4-yl-6-nitrophenyl)-methylamine. To a cooled (0° C.) solution of 1M BH₃.THF (Fluka) (13 mL, 13.0 mmol) was added 6-nitro-2-morpholin-4-ylbenzenecarbonitrile (prepared by the method described in Example 51a) (610 mg, 2.6 mmol). The reaction was warmed to RT. After 18 h, the solvent was concentrated to one-half its original volume. The concentrated solution was carefully added to 10% HCl (20 mL) and heated at 55° C. for 2 h. The solution was cooled to RT and washed with EtOAc. The aqueous solution was basified with 5N NaOH and extracted with CH₂Cl₂. The combined organics were dried over Na₂SO₄ and concentrated in vacuo to give an orange-yellow oil. MS m/z: 238 (M+1). Calc'd for $C_{11}H_{15}N_3O_3$—237.11.

(b) Preparation of 5-morpholin-4-yl-3-(3-(4-pyridyl)(1,2,4-thiadiazol-5-yl))-1,3,4-trihydroquinazolin-2-one. To a solution of (2-morpholin-4-yl-6-nitrophenyl)methylamine (Step a) (487 mg, 2.1 mmol) and NH₄Cl (146 mg, 2.7 mmol) in 70% aqueous EtOH was added Fe dust (608 mg, 11 mol), and was heated at 74° C. After 2 h, the reaction was filtered through a pad of Celite® while hot. The solvent was removed in vacuo and the residue was azeotroped with benzene. The crude amine was dissolved in 30 mL THF and 5-chloro-3-(4-pyridyl)-1,2,4-thiadiazole (Example 46a) (412 mg, 2.1 mmol) was added. The reaction was heated at 60° C. for 23 h and the solvent was removed in vacuo. The residue was dissolved in THF and to this solution was added CDI (Aldrich) (518 mg, 3.2 mmol) followed by 60% NaH (134 mg, 3.3 mmol) resulting in gas evolution. After 17 h, saturated NH₄Cl was added and the solids were filtered, washed successively with saturated NH₄Cl, hexanes, H₂O, and MeOH and dried in vacuo to afford a white solid. Mp: >300° C. MS m/z: 395 (M+1); 393 (M−1). Anal. Calc'd for $C_{19}H_{18}N_6O_2S$: C, 57.85; H, 4.60; N, 21.31. Found: C, 57.68; H, 4.72; N, 21.24.

EXAMPLE 54

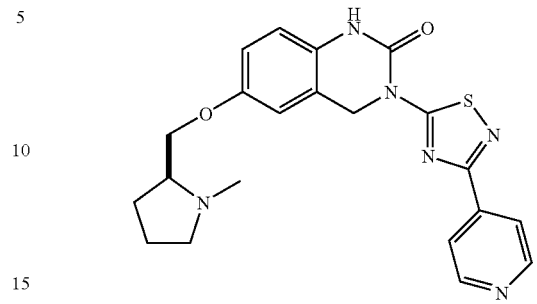

6-[((2S)-1-Methylpyrrolidin-2-yl)methoxy]-3-(3-(4-pyridyl)-(1,2,4-thiadiazol-5-yl))-1,3,4-trihydroquinazolin-2-one (a) Preparation of 5-[((2S)-1-methylpyrrolidin-2-yl)methoxy]-2-nitrobenzenecarbonitrile. To a slurry of 60% NaH (956 mg, 24 mmol) in THF (100 mL) was added (S)-(−)-1-methyl-2-pyrolidinemethanol (Aldrich) (2.8 mL, 24 mmol) resulting in gas evolution. After 30 min, 5-fluoro-2-nitrobenzonitrile (Combi Blocks) (3.3 g, 20 mmol) was added. After 3 h the reaction solvent was removed in vacuo and the residue was partitioned between CH₂Cl₂ and H₂O. The aqueous layer was extracted with CH₂Cl₂ and the combined organics were dried over Na₂SO₄ and concentrated in vacuo to give a red oil. MS m/z: 262 (M+1). Calc'd for $C_{13}H_{15}N_3O_3$—261.11.

(b) Preparation of {5-[((2S)-1-methylpyrrolidin-2-yl)methoxy]-2-nitrophenyl}methylamine. To a cooled (0° C.) solution of 1M BH₃.THF (Fluka) (100 mL, 100 mmol) was added 5-[((2S)-1-methylpyrrolidin-2-yl)methoxy]-2-nitrobenzenecarbonitrile (Step a) (5.1 g, 20 mmol). The reaction was warmed to RT. After 16 h, the solvent was concentrated to one-half its original volume. The concentrated solution was carefully added to 10% HCl (100 mL) and heated at 50° C. for 2 h. The solution was cooled to RT and washed with Et₂O and EtOAc. The aqueous solution was basified with 5N NaOH and extracted with CH₂Cl₂. The combined organics were dried over Na₂SO₄ and concentrated in vacuo to give a red-orange oil. MS m/z: 266 (M+1). Calc'd for $C_{13}H_{19}N_3O_3$—265.14.

(c) Preparation of ({5-[((2S)-1-methylpyrrolidin-2-yl)methoxy]-2-aminophenyl}methyl)(3-(4-pyridyl)(1,2,4-thiadiazol-5-yl))amine. A solution of {5-[((2S)-1-methylpyrrolidin-2-yl)methoxy]-2-nitrophenyl}methylamine (Step b) (1.13 g, 4.2 mmol) and 10% Pd/C (290 mg) in MeOH (50 mL) was equipped with a balloon filled with H₂ and the reaction was stirred at RT. After 6 h, the reaction was filtered through a pad of Celite® and the solvent was removed in vacuo. MS m/z: 498 (M+1); 496 (M−1). A solution of the 4-[((2S)-1-methylpyrrolidin-2-yl)methoxy]-2-(aminomethyl)phenylamine (851 mg, 3.6 mmol) and 5-chloro-3-(4-pyridyl)-1,2,4-thiadiazole (Example 46a) (638 mg, 3.2 mmol) in 1,4-dioxanes (32 mL) was heated at 70° C. After 18 h, the reaction was cooled to RT, diluted with MeOH and purified by flash chromatography with 2M NH₃ in MeOH:CH₂Cl₂:CHCl₃ (0:1:0, 1:49:0, 1:19:0, 1:13:0, 1:0:9) as eluant to afford an orange foam. MS m/z: 397 (M+1); 395 (M−1). Calc'd for $C_{20}H_{24}N_6OS$—396.17.

(d) Preparation of 6-[((2S)-1-methylpyrrolidin-2-yl)methoxy]-3-(3-(4-pyridyl)(1,2,4-thiadiazol-5-yl))-1,3,4-trihydroquinazolin-2-one. To a solution of ({5-[((2S)-1-methylpyrrolidin-2-yl)methoxy]-2-aminophenyl}methyl)(3-(4-pyridyl)(1,2,4-thiadiazol-5-yl))amine (Step c) (583 mg, 1.5 mol) in THF (20 mL) was added CDI (Aldrich) (375 mg, 2.3 mmol) followed by 60% NaH (87 mg, 2.2 mmol) resulting in gas evolution. After 15 h, H$_2$O was added and the solids were filtered, washed successively with H$_2$O and MeOH, and dried in vacuo to afford a tan solid. Mp: >275° C. MS m/z: 423 (M+1). Anal. Calc'd for C$_{21}$H$_{22}$N$_6$O$_2$S: C, 59.70; H, 5.25; N, 19.89. Found: C, 59.91; H, 5.32; N, 19.57.

EXAMPLE 55

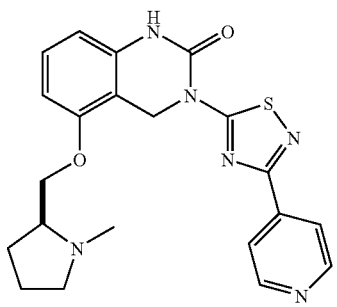

5-[((2S)-1-Methylpyrrolidin-2-yl)methoxy]-3-(3-(4-pyridyl)-(1,2,4-thiadiazol-5-yl))-1,3,4-trihydroquinazolin-2-one (a) Preparation of 2-[((2S)-1-methylpyrrolidin-2-yl)methoxy]-6-nitrobenzenecarbonitrile. To a cooled (0° C.) slurry 60% NaH (360 mg, 9.0 mmol) in THF (100 mL) was added (S)-(−)-1-methyl-2-pyrolidinemethanol (Aldrich) (1.1 mL, 9.2 mmol) resulting in gas evolution. After 30 min, this solution was added to a cooled (0° C.) solution of 2,6-dinitrobenzenecarbonitrile (*J. Med. Chem.* 1990, 434) (1.3 g, 20 mmol) in THF (50 mL). After 2 h, the reaction solvent was removed in vacuo and the residue was purified by flash chromatography with 2M NH$_3$ in MeOH:CH$_2$Cl$_2$ (1:24) as eluant to afford an orange oil. MS m/z: 262 (M+1). Calc'd for C$_{13}$H$_{15}$N$_3$O$_3$—261.11.

(b) Preparation of {2-[((2S)-1-methylpyrrolidin-2-yl)methoxy]-6-nitrophenyl}methylamine. To a cooled (0° C.) solution of 1M BH$_3$.THF (Fluka) (30 mL, 30 mmol) was added 2-[((2S)-1-methylpyrrolidin-2-yl)methoxy]-6-nitrobenzenecarbonitrile (Step a) (1.0 g, 3.8 mmol). The reaction was warmed to RT. After 15 h, the solvent was concentrated to one-half its original volume. The concentrated solution was carefully added to 10% HCl (30 mL) and heated at 60° C. for 1 h. The solution was cooled to RT and washed with EtOAc. The aqueous solution was basified with 5N NaOH and extracted with CH$_2$Cl$_2$. The combined organic layers were dried over Na$_2$SO$_4$, concentrated in vacuo and purified by flash chromatography with 2M NH$_3$ in MeOH:CH$_2$Cl$_2$ (0:1, 1:33, 1:19, 1:9) as eluant to afford an orange oil. MS m/z: 266 (M+1). Calc'd for C$_{13}$H$_{19}$N$_3$O$_3$—265.14.

(c) Preparation of ({6-[((2S)-1-methylpyrrolidin-2-yl)methoxy]-2-aminophenyl}methyl)(3-(4-pyridyl)(1,2,4-thiadiazol-5-yl))amine. A solution of {2-[((2S)-1-methylpyrrolidin-2-yl)methoxy]-6-nitrophenyl}methylamine (Step b) (307 mg, 1.2 mmol) and 10% Pd/C (80 mg) in MeOH (10 mL) was equipped with a balloon filled with H$_2$ and the reaction was stirred at RT. After 16 h, the reaction was filtered through a pad of Celite® and the solvent was removed in vacuo to give a yellow oil. A solution of the 3-[((2S)-1-methylpyrrolidin-2-yl)methoxy]-2-(aminomethyl)phenylamine (204 mg, 0.9 mmol) and 5-chloro-3-(4-pyridyl)-1,2,4-thiadiazole (Example 46a) (176 mg, 0.9 mmol) in 1,4-dioxanes (2 mL) was heated at 70° C. After 18 h, the reaction was cooled to RT, diluted with MeOH and purified by flash chromatography with 2M NH$_3$ in MeOH:CH$_2$Cl$_2$:CHCl$_3$ (0:1:0, 1:49:0, 1:19:0, 1:13:0, 1:0:9) as eluant to afford a yellow foam. MS m/z: 397 (M+1); 395 (M−1). Calc'd for C$_{20}$H$_{24}$N$_6$OS—396.17.

(d) Preparation of 5-[((2S)-1-methylpyrrolidin-2-yl)methoxy]-3-(3-(4-pyridyl)(1,2,4-thiadiazol-5-yl))-1,3,4-trihydroquinazolin-2-one. To a solution of ({6-[((2S)-1-methylpyrrolidin-2-yl)methoxy]-2-aminophenyl}methyl)(3-(4-pyridyl)(1,2,4-thiadiazol-5-yl))amine (Step c) (122 mg, 0.3 mol) in THF (3 mL) was added CDI (Aldrich) (76 mg, 0.5 mmol) followed by 60% NaH (29 mg, 0.7 mmol) resulting in gas evolution. After 15 h, saturated NH$_4$Cl was added and the solvent was removed in vacuo. The residue was washed with MeOH and dried in vacuo. The crude material was purified by reverse phase HPLC to afford a white solid. Mp: >250° C. MS m/z: 423 (M+1); 421 (M−1). Calc'd for C$_{21}$H$_{22}$N$_6$O$_2$S—422.15.

EXAMPLE 56

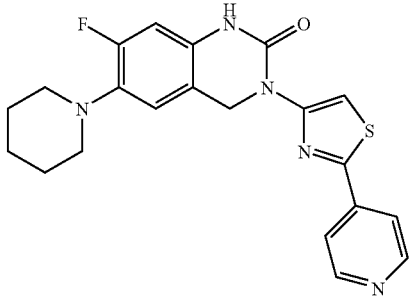

7-Fluoro-6-piperidyl-3-(2-(4-pyridyl)(1,3-thiazol-4-yl))-1,3,4-trihydroquinazolin-2-one (a) Preparation of methyl 4,5-difluoro-2-nitrobenzoate. 4,5-Difluoro-2-nitro benzoic acid (8.55 g, 42.1 mmol) was heated at reflux in SOCl$_2$ (50 mL). After 17 h, the SOCl$_2$ was removed in vacuo and the resulting oil was treated with a solution of MeOH (100 mL) and TEA (8 mL). After stirring for 2 h, the solvent was removed in vacuo, and the resulting residue was dissolved in CH$_2$Cl$_2$ and washed with H$_2$O (2×) and brine. The CH$_2$Cl$_2$ layer was dried with MgSO$_4$ and concentrated in vacuo to give a light-green solid.

(b) Preparation of methyl 4-fluoro-2-nitro-5-piperidylbenzoate. To a solution of methyl 4,5-difluoro-2-nitrobenzoate (Step a) (7.6 g, 35.0 mmol) in CH$_3$CN (100 mL) was added pyridine (5.6 mL, 69.2 mmol) and piperidine (3.5 mL, 35.4 mmol). The solution was stirred at RT for 1.5 h and at 65° C. for 7 h. The reaction was cooled to RT and concentrated in vacuo. The residue was dissolved in EtOAc, washed with H$_2$O and brine, dried over MgSO$_4$, and concentrated in vacuo to give a dark-red oil. MS: m/z 283 (M+1). Calc'd for C$_{13}$H$_{15}$FN$_2$O$_4$—282.10.

(c) Preparation of (4-fluoro-2-nitro-5-piperidylphenyl)-methan-1-ol. To a solution of methyl 4-fluoro-2-nitro-5-piperidylbenzoate (Step b) (7.74 g, 27.4 mmol) in anhydrous $Et_2O$ (100 mL) at 0° C. was added MeOH (3.3 mL, 81.5 mmol) and 2M solution of $LiBH_4$ in THF (45.0 mL, 90 mmol) dropwise over 20 minutes. The reaction mixture was warmed to RT and stirred overnight. The reaction was then cooled to 0° C. again, quenched with $H_2O$ and neutralized with 1N HCl (aq). The mixture was partitioned and the aqueous layer extracted with $Et_2O$ (2×). The combined ether layers were washed with brine, dried over $MgSO_4$, and concentrated in vacuo to give a brown solid that was carried on without further purification.

(d) Preparation of [2-fluoro-5-(iodomethyl)-4-nitrophenyl]-piperidine. (4-Fluoro-2-nitro-5-piperidylphenyl) methan-1-ol (Step c) (8.5 g, 27.4 mmol) was dissolved in $CH_2Cl_2$ (50 mL) and TEA (7.0 mL, 50.2 mmol). The solution was cooled to 0° C. and methanesulfonyl chloride (3.1 mL, 40.0 mmol) was added dropwise over several minutes. After 16 h, TLC showed the reaction was not complete and additional methanesulfonyl chloride (0.3 mL, 3.9 mmol) was added. After stirring for an additional 24 h, the reaction mixture was partitioned between $CH_2Cl_2$ and $H_2O$. The $CH_2Cl_2$ was washed with $H_2O$, brine, dried over $MgSO_4$, and concentrated in vacuo to give a yellow solid. MS: m/z 273 (M+1). Calc'd for $C_{12}H_{14}FIN_2O_2$—364.01. The yellow solid (1.54 g, 5.7 mmol) was dissolved in 100 mL of acetone and treated with NaI (0.85 g, 5.7 mmol). After 24 h, the reaction mixture was concentrated in vacuo and the residue was dissolved in $CH_2Cl_2$ and washed with $H_2O$ (2×). The $CH_2Cl_2$ layer was dried over $MgSO_4$ and concentrated in vacuo to give a dark oil.

(e) Preparation of N-[(4-fluoro-2-nitro-5-piperidylphenyl)-methyl]prop-2-enyloxy-N-(2-(4-pyridyl)(1,3-thiazol-4-yl))carboxamide. Prop-2-enyloxy-N-(2-(4-pyridyl)(1,3-thiazol-4-yl))carboxamide (Example 6c) (1.38 g, 5.0 mmol) was dissolved in 50 mL of anhydrous DMF. 60% NaH (0.24 g, 5.9 mmol) was added portionwise and the solution was stirred at RT for 0.5 h. A solution of [2-fluoro-5-(iodomethyl)-4-nitrophenyl]piperidine (Step d) (1.81 g, 5.0 mmol) in anhydrous DMF (10 mL) was added dropwise over 1.5 min. The reaction was heated at 80° C. for 20 h. After cooling to RT the reaction mixture was partitioned between EtOAc and $H_2O$. The aqueous layer was extracted with EtOAc (3×). The combined EtOAc layers were washed with $H_2O$, brine, dried over $MgSO_4$, and concentrated in vacuo. The crude residue was purified by flash chromatography on silica gel using 8:2 $CH_2Cl_2$:EtOAc as eluant to afford a yellow solid. MS: m/z 514 (M+1). Calc'd for $C_{24}H_{24}FN_5O_4S$—497.15.

(f) Preparation of [(2-amino-4-fluoro-5-piperidylphenyl)-methyl](2-(4-pyridyl)(1,3-thiazol-4-yl))amine. N-[(4-fluoro-2-nitro-5-piperidylphenyl)methyl]prop-2-enyloxy-N-(2-(4-pyridyl)(1,3-thiazol-4-yl))carboxamide (Step e) (810 mg, 1.58 mmol) was dissolved in a solution of EtOH (50 mL) and $H_2O$ (20 mL). Iron powder (460 mg, 8.2 mmol) and $NH_4Cl$ (50 mg, 0.9 mmol) were added and the reaction mixture stirred at 80° C. for 1.5 h. The reaction was filtered while hot through a bed of Celite®, and the Celite® was rinsed liberally with EtOAc and MeOH. The filtrate was concentrated in vacuo to leave a residue, which was extracted with EtOAc (2×). The combined EtOAc layers were washed with brine, dried over $MgSO_4$, and concentrated in vacuo to a dark brown residue. MS: m/z 484 (M+1). The residue was dissolved in 40 mL of dioxane and 4M HCl in dioxane (3 mL, 12 mmol) was added. The solution was stirred at RT for 19 h, and concentrated in vacuo. The solid was dissolved in $CH_2Cl_2$ and 1N NaOH (aq). The aqueous layer was extracted with $CH_2Cl_2$ and the combined organic layers were washed with brine, dried over $MgSO_4$, and concentrated in vacuo to give a dark brown solid. MS: m/z 384 (M+1). Calc'd for $C_{20}H_{22}FN_5S$—383.16.

(g) Preparation of 7-fluoro-6-piperidyl-3-(2-(4-pyridyl)-(1,3-thiazol-4-yl))-1,3,4-trihydroquinazolin-2-one. To a solution of (2-amino-4-fluoro-5-piperidin-1-yl-benzyl)-(2-pyrindin-4-yl-thiazol-4-yl)-amine (Step f) (0.58 g, 1.5 mmol), CDI (0.73 g, 4.5 mmol), and 30 mL of anhydrous DMF was added 60% NaH (0.21 g, 5.3 mmol) portionwise over several minutes. The solution was stirred at RT for 17 h and quenched with 50 mL of $H_2O$. The solution was stirred for 5 min, then filtered. The light-brown solid was washed with $H_2O$ (2×) and hexanes (2×). The solid was suspended in hexane (20 mL) and stirred overnight. After filtration, a light-brown solid was obtained. Mp: 312–314° C. MS: m/z 410 (M+1). Calc'd for $C_{21}H_{20}FN_5OS$—409.14. Anal. Calc'd for $C_{21}H_{20}FN_5OS \cdot 0.5H_2O$: C, 60.27; H, 5.06; N, 16.74. Found C, 60.67; H, 5.02; N, 16.70.

EXAMPLE 57

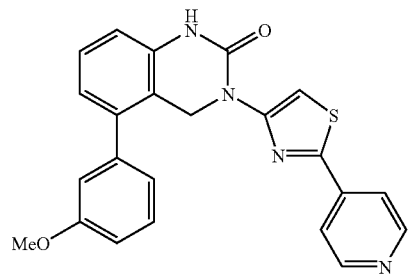

5-(3-Methoxyphenyl)-3-(2-(4-pyridyl)(1,3-thiazol-4-yl))-1,3,4-trihydroquinazolin-2-one (a) Preparation of 5-(3-methoxyphenyl)-1-[(4-methoxyphenyl)-methyl]-3-(2-(4-pyridyl)(1,3-thiazol-4-yl))-1,3,4-trihydroquinazolin-2-one. To a solution of 5-bromo-1-[(4-methoxyphenyl)methyl]-3-(2-(4-pyridyl)(1,3-thiazol-4-yl))-1,3,4-trihydroquinazolin-2-one (Example 34a) (0.18 g, 0.4 mmol), 3-methoxyphenylboronic acid (95 mg, 0.6 mmol), 2M $Na_2CO_3$ (0.75 mL, 1.5 mmol), and 8 mL of toluene/2 mL of EtOH was added $Pd(PPh_3)_4$ (29 mg, 0.03 mmol). The reaction was stirred at 80° C. overnight, then cooled to RT and concentrated in vacuo. The residue was taken up in $CH_2Cl_2$ and washed with $H_2O$. The aqueous layer was extracted with $CH_2Cl_2$ (2×). The combined organic layers were washed with brine, dried over $MgSO_4$, and concentrated in vacuo. The resulting residue was purified by flash chromatography on silica gel using 40% EtOAc/hexane to give an oil that solidified upon standing. MS: m/z 535 (M+1). Calc'd for $C_{31}H_{26}N_4O_3S$—534.17.

(b) Preparation of 5-(3-methoxyphenyl)-3-(2-(4-pyridyl) (1,3-thiazol-4-yl))-1,3,4-trihydroquinazolin-2-one. To a solution of 5-(3-methoxyphenyl)-1-[(4-methoxyphenyl)methyl]-3-(2-(4-pyridyl) (1,3-thiazol-4-yl))-1,3,4-trihydroquinazolin-2-one (Step a) (150 mg, 0.3 mmol), anisole (0.31 mL, 2.9 mmol), and dichloroethane (10 mL) was added TFA (0.22 mL, 2.9 mmol). The solution was stirred at 80° C. for 6 h, and then additional anisole (0.31 mL, 2.9 mmol) and TFA (0.22 mL, 2.9 mmol) were added. After stirring for 9 days the reaction was cooled to RT. The residue was dissolved in CH$_2$Cl$_2$, washed with saturated NaHCO$_3$ and H$_2$O, and dried over MgSO$_4$. The solution was concentrated in vacuo and the resulting residue was purified by flash chromatography on silica gel using 3% MeOH/CH$_2$Cl$_2$ to give a crude solid. The solid was dissolved in CH$_2$Cl$_2$/MeOH and precipitated upon standing. The solution was placed in the freezer for 2 h before filtering. The solid was washed with cold MeOH to give a solid. MP: 250–252° C. MS: m/z 415 (M+1). Calc'd for C$_{23}$H$_{18}$N$_4$O$_2$S—414.12. Anal. Calc'd. C$_{23}$H$_{18}$N$_4$O$_2$S: C, 66.65; H, 4.38; N, 13.52. Found: C, 66.38; H, 4.39; N, 13.51.

EXAMPLE 58

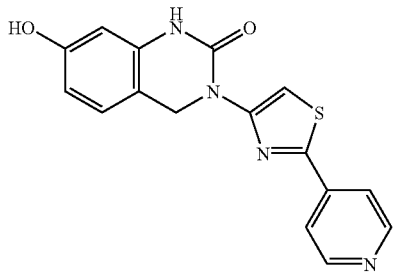

7-Hydroxy-3-(2-(4-pyridyl)(1,3-thiazol-4-yl))-1,3,4-trihydroquinazolin-2-one (a) Preparation of 1-methyl-2-nitro-4-(1,1,2,2-tetramethyl-1-silapropoxy)benzene. To a solution of 4-methyl-3-nitrophenol (25.15 g, 164.2 mmol, Aldrich) and imidazole (28.01 g, 411.4 mmol, Aldrich) in CH$_2$Cl$_2$ (500 mL) was added TBSCl 7(27.0 g, 179.1 mmol, Aldrich). After stirring at RT overnight, MeOH (40 mL) was added and the solution was stirred for 20 min. The solution was concentrated in vacuo to give an oil, which was dissolved in CH$_2$Cl$_2$, washed with H$_2$O and brine, dried over MgSO$_4$, and concentrated in vacuo to give a golden oil.

(b) Preparation of 1-(bromomethyl)-2-nitro-4-(1,1,2,2-tetramethyl-1-silapropoxy)benzene. To a solution of 1-methyl-2-nitro-4-(1,1,2,2-tetramethyl-1-silapropoxy)benzene (Step a) (20.0 g, 74.8 mmol) in CCl$_4$ (250 mL) at 80° C. was added NBS (17.30 g, 97.2 mmol) and AIBN (1.30 g, 7.9 mmol). After stirring at 80° C. for 15 h, the reaction was cooled to RT, then filtered and concentrated in vacuo. The yellow oil was purified by flash chromatography on silica gel using 2.5% EtOAc/hexane as the eluant to give a light yellow oil.

(c) Preparation of 2-(4-pyridyl)-1,3-thiazole-4-ylamine. To a solution of prop-2-enyloxy-N-(2-(4-pyridyl)(1,3-thiazol-4-yl))carboxamide (Example 6c) (8.0 g, 30.0 mmol) in THF (300 mL) was added morpholine (26.0 mL, 297.3 mmol) and Pd(PPh$_3$)$_4$ (2.0 g, 1.7 mmol). The solution was stirred at RT overnight and concentrated in vacuo. The resulting residue was taken up in EtOAc and washed with H$_2$O. The aqueous layer was extracted with EtOAc (4×). The combined EtOAc layers were washed with H$_2$O and brine, dried over MgSO$_4$, and concentrated in vacuo. The residue was purified by flash chromatography on silica gel using 97:3 CH$_2$Cl$_2$:MeOH to give an orange solid.

(d) Preparation of 3-nitro-4-{[(2-(4-pyridyl)(1,3-thiazol-4-yl)) amino]methyl}phenol. To a solution of 2-(4-pyridyl)-1,3-thiazole-4-ylamine (Step c) (4.30 g, 24.3 mmol) in anhydrous DMF (100 mL) was added 60% NaH (1.14 g, 28.5 mmol) portionwise over several minutes. After the addition was completed, the reaction was stirred for 45 min then a solution of 1-(bromomethyl)-2-nitro-4-(1,1,2,2-tetramethyl-1-silapropoxy)benzene (Step b) (7.98 g, 22.8 mmol) in anhydrous DMF (10 mL) was added dropwise over several minutes. The reaction was stirred at 80° C. overnight. The reaction was cooled to RT and quenched with H$_2$O. The reaction was partitioned between EtOAc and H$_2$O. The aqueous layer was extracted with EtOAc (3×). The combined EtOAc layers were washed with brine, dried over MgSO$_4$, and concentrated in vacuo. The crude residue was purified by flash chromatography on silica gel using 40% EtOAc/hexane to give an orange solid. MS: m/z 329 (M+1). Calc'd for C$_{15}$H$_{12}$N$_4$O$_3$S—328.06.

(e) Preparation of {[2-nitro-4-(1,1,2,2-tetramethyl-1-silapropoxy)phenyl]methyl}(2-(4-pyridyl)(1,3-thiazol-4-yl)) amine. To a solution of 3-nitro-4-{[(2-(4-pyridyl)(1,3-thiazol-4-yl))amino]methyl}phenol (Step d) (2.95 g, 9.0 mmol) and imidazole (1.54 g, 22.6 mmol) in anhydrous DMF (80 mL) was added a 50% solution of TBSCl in CH$_2$Cl$_2$ (4.0 mL, 13.9 mmol). After 1 h, MeOH was added and the resulting mixture was stirred for an additional 5 min. The solution was concentrated to half of its original volume in vacuo, diluted with H$_2$O and extracted with EtOAc (4×). The combined EtOAc layers were washed with H$_2$O and brine, dried over MgSO$_4$, and concentrated in vacuo to give an oil which contained some DMF, but was carried on. MS: m/z 443 (M+1). Calc'd for C$_{21}$H$_{26}$N$_4$O$_3$SSi—442.15.

(f) Preparation of {[2-amino-4-(1,1,2,2-tetramethyl-1-silapropoxy)phenyl]methyl}(2-(4-pyridyl)(1,3-thiazol-4-yl)) amine. To a solution of {[2-nitro-4-(1,1,2,2-tetramethyl-1-silapropoxy)phenyl]methyl}(2-(4-pyridyl)(1,3-thiazol-4-yl))amine (Step e) and 100 mL of EtOH/40 mL of H$_2$O was added Iron powder (2.53 g, 45.3 mmol) and NH$_4$Cl (0.29 g, 5.5 mmol). The reaction was stirred at 80° C. until TLC showed complete conversion. The reaction was filtered while hot through a bed of Celite® and the filtrate concentrated to an aqueous solution. The aqueous solution was extracted with EtOAc and the combined EtOAc layers were washed with brine, dried over MgSO$_4$, and concentrated in vacuo. The crude residue was purified by flash chromatography on silica gel using 40% EtOAc/hexane to give an orange solid. MS: m/z 413 (M+1). Calc'd for C$_{21}$H$_{28}$N$_4$OSSi—412.18.

(g) Preparation of 3-(2-(4-pyridyl)(1,3-thiazol-4-yl))-7-(1,1,2,2-tetramethyl-1-silapropoxy)-1,3,4-trihydroquinazolin-2-one. To a solution of {[2-amino-4-(1,1,2,2-tetramethyl-1-silapropoxy)phenyl]methyl}(2-(4-pyridyl)(1,3-thiazol-4-yl))amine (Step f) (0.77 g, 1.9 mmol), CDI (0.91 g, 5.6 mmol), and 30 mL of anhydrous DMF was added 60% NaH (0.25 g, 6.3 mmol) portionwise over several minutes. After stirring at RT for 15 h the reaction was quenched with 100 mL of H$_2$O. The aqueous solution was extracted with EtOAc (4×). The combined EtOAc layers were washed with H$_2$O and brine, dried over MgSO$_4$, and concentrated in vacuo. The crude brown oil was purified by flash chromatography on silica gel using 2% MeOH/CH$_2$Cl$_2$ to obtain a light-brown solid. MS: m/z 439 (M+1). Calc'd for C$_{16}$H$_{12}$N$_4$O$_2$S—324.07.

(h) Preparation of 7-hydroxy-3-(2-(4-pyridyl)(1,3-thiazol-4-yl))-1,3,4-trihydroquinazolin-2-one. To a solution of 3-(2-(4-pyridyl)(1,3-thiazol-4-yl))-7-(1,1,2,2-tetramethyl-1-silapropoxy)-1,3,4-trihydroquinazolin-2-one (Step g) (77 mg, 0.2 mmol) in THF (10 mL) was added 1M TBAF (0.2 mL, 0.2 mmol). After stirring for 2 h at RT, the solution was concentrated in vacuo. The resulting residue was taken up in CH₂Cl₂ and washed with H₂O and brine. The combined aqueous layers were filtered and the resulting solid was washed with H₂O to give a light-brown solid. MS: m/z 325 (M+1). Calc'd for C₁₆H₁₂N₄O₂S—324.07.

EXAMPLE 59

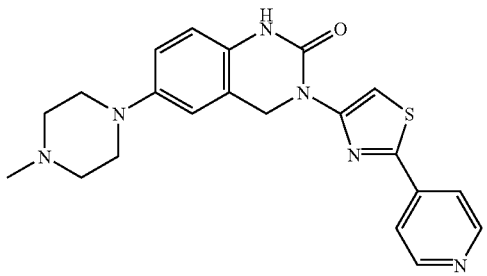

6-(4-Methylpiperazinyl)-3-(2-(4-pyridyl)(1,3-thiazol-4-yl))-1,3,4-trihydro-quinazolin-2-one (a) Preparation of 2-amino-5-(4-methylpiperazinyl)benzene carbonitrile. A mixture of 5-(4-methylpiperazinyl)-2-nitrobenzene carbonitrile (prepared by the method described in Example 54a) (3.31 g, 13.41 mmol), NH₄Cl (0.36 g, 6.70 mmol), and iron powder (3.75 g, 67.04 mole) in EtOH/H₂O (2:1, 80 mL) was heated at reflux for 1 h. The mixture was filtered while hot. The filtrate was concentrated, dissolved in water and extracted with CH₂Cl₂ (3×). The combined organic extracts were dried over MgSO₄ and concentrated to afford a brown oil. MS (m/z): 217.3 (M+1). Calc'd for C₁₂H₁₆N₄—216.14.

(b) Preparation of 2-(aminomethyl)-4-(4-methylpiperazinyl)-phenylamine. To a stirred solution of 2-amino-5-(4-methylpiperazinyl)benzenecarbonitrile (Step a) (1.7 g, 7.86 mmol) in dried THF (15 mL) was added 1M BH₃.THF (27.5 mL, 27.5 mmol) dropwise. After stirring for 2 h at RT, the mixture was cooled to 0° C. and quenched slowly with 10% aqueous HCl until pH=1. The resulting mixture was heated at reflux for 2 h. After cooling to RT, the mixture was washed with Et₂O. The aqueous layer was neutralized with 5N NaOH, extracted with CH₂Cl₂ (3×). The organic layers were dried over MgSO₄, and concentrated to give a light-yellow oil. MS (m/z): 206.3 (M+1). Calc'd for C₁₂H₂₀N₄—220.17.

(c) Preparation of ethyl 4-([{2-amino-5-(4-methylpiperazinyl)phenyl]methyl}amino)-2-(4-pyridyl)-1,3-thiazole-5-carboxylate. A mixture of ethyl 2-(4-pyridyl)-4-[(trifluoromethyl)-sulfonyloxy]-1,3-thiazole-5-carboxylate (Example 14e) (0.87 g, 2.27 mmol) and 2-(aminomethyl)-4-(4-methylpiperazinyl)phenylamine (Step b) (1.0 g, 4.54 mmol) in dried dioxane (15 mL) was heated at reflux for 24 h. The mixture was cooled to RT, concentrated, and purified by flash column chromatography (5% MeOH/CH₂Cl₂) to afford a light-brown oil. MS (m/z): 453.6 (M+1). Calc'd for C₂₃H₂₈N₆O₂S—452.20.

(d) Preparation of ethyl 4-[6-(4-methylpiperazinyl)-2-oxo (1,3,4-trihydroquinazolin-3-yl)]-2-(4-pyridyl)-1,3-thiazole-5-carboxylate. To a stirred mixture of ethyl 4-({[2-amino-5-(4-methylpiperazinyl)phenyl]methyl}amino)-2-(4-pyridyl)-1,3-thiazole-5-carboxylate (Step c) (0.70 g, 1.56 mmol) and CDI (0.76 g, 4.69 mmol) in dried DMF (10 mL) was added NaH (60% oil dispersion, 0.22 g, 5.46 mmol). After stirring at RT for 16 h, the mixture was quenched with H₂O, extracted with CH₂Cl₂ (3×), dried over MgSO₄, concentrated, and purified by flash column chromatography (8% MeOH/CH₂Cl₂) to give a light brown solid. MS (m/z): 479.6 (M+1). Calc'd for C₂₄H₂₆N₆O₃S—478.18.

(e) Preparation of 6-(4-methylpiperazinyl)-3-(2-(4-pyridyl)(1,3-thiazol-4-yl))-1,3,4-trihydro-quinazolin-2-one. To a stirred solution of ethyl 4-[6-(4-methylpiperazinyl)-2-oxo (1,3,4-trihydroquinazolin-3-yl)]-2-(4-pyridyl)-1,3-thiazole-5-carboxylate (Step d) (0.13 g, 0.27 mmol) in dioxane (2 mL) was added 5N NaOH (0.2 mL, 0.82 mmol) and stirred for 18 h. The mixture was cooled, acidified with 10% aqueous HCl until pH=1 and heated at reflux for 48 h. The resulting mixture was cooled to RT and concentrated in vacuo. The residue was dissolved in H₂O, neutralized with 5N NaOH, and filtered to obtain a tan solid which was dissolved in MeOH/CH₂Cl₂(1:1, 4 mL), added 2M HCl in Et₂O, concentrated, and triturated in MeOH to afford an off-white solid. MS (m/z): 407.5 (M+1). Calc'd for C₂₁H₂₂N₆OS—406.16.

EXAMPLE 60

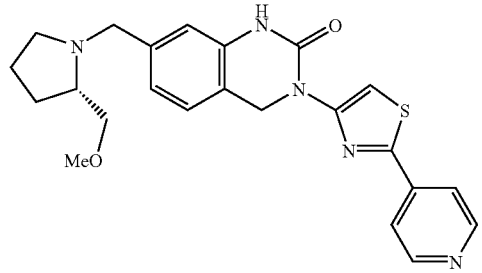

7-{[(2S)-2-(Methoxymethyl)pyrrolidinyl]methyl}-3-(2-(4-pyridyl)(1,3-thiazol-4-yl))-1,3,4-trihydro-quinazolin-2-one (a) Preparation of 4-(bromomethyl)-2-nitrobenzene carbonitrile. A mixture of 4-methyl-2-nitro benzonitrile (20 g, 123.34 mmol), NBS (26.34 g, 148.01 mmol), and AIBN (4.05 g, 24.67 mmol) in anhydrous CCl₄ (200 mL) was heated at reflux for 36 h. The mixture was cooled and filtered. The filtrate was concentrated to give a brown oil.

(b) Preparation of 4-{[(2S)-2-(methoxymethyl)pyrrolidinyl]-methyl}-2-nitrobenzenecarbonitrile. A mixture of (S)-(+)-2-methymethoxylpyrrolidine (5.8 g, 50.36 mmol) and 4-(bromomethyl)-2-nitrobenzenecarbonitrile (Step a) (6.07 g, 25.18 mol) in dried THF (30 mL) was stirred at RT for 2 h. The mixture was concentrated and purified by flash column chromatography (35% EtOAc/Hexane) to afford a yellow oil. MS (m/z): 276.3 (M+1). Calc'd for C₁₄H₁₇N₃O₃—275.13.

(c) Preparation of (4-{[(2S)-2-(methoxymethyl)pyrrolidinyl]-methyl}-2-nitrophenyl)methylamine. To a stirred solution of 4-{[(2S)-2-(methoxymethyl)pyrrolidinyl]methyl}-2-nitrobenzenecarbonitrile (Step b) (2.82 g, 10.25 mmol) in dried THF (20 mL) was added 1.0 M BH₃.THF (36 mL, 36 mmol) dropwise. The reaction mixture was heated at reflux for 1 h. After cooling, the resulting mixture was slowly treated with 10% aqueous HCl until pH 1, then heated at reflux for 2 h. The resulting mixture was cooled to RT and washed with Et₂O. The aqueous layer was basified with 5N NaOH and extracted with CH₂Cl₂ (3×). The organic extracts were dried over MgSO₄, concentrated, and purified by flash column chromatography (5% MeOH/CH₂Cl₂) to afford a light-brown oil. MS (m/z): 265.3 (M+1). Calc'd for C₁₄H₂₁N₃O₃—279.16.

(d) Preparation of ethyl 4-{[(4-{[(2S)-2-(methoxymethyl)-pyrrolidinyl]methyl}-2-nitrophenyl)-methyl]amino}-2-(4-pyridyl)-1,3-thiazole-5-carboxylate. A mixture of (4-{[(2S)-2-(methoxymethyl)pyrrolidinyl]methyl}-2-nitrophenyl)-methylamine (Step c) (11.44 g, 5.16 mmol) and ethyl 2-(4-pyridyl)-4-[(trifluoromethyl)sulfonyloxy]-1,3-thiazole-5-carboxylate (Example 14e) (0.99 g, 2.58 mmol) in dried dioxane (20 mL) was heated at reflux for 16 h. The mixture was cooled, concentrated, and purified by flash column chromatography (5% MeOH/CH₂Cl₂) to give a brown oil. MS (m/z): 512.1 (M+1). Calc'd for C₂₅H₂₉N₅O₅S—511.19.

(e) Preparation of ethyl 4-{[(4-{[(2S)-2-(methoxymethyl)-pyrrolidinyl]methyl}-2-aminophenyl)-methyl]amino}-2-(4-pyridyl)-1,3-thiazole-5-carboxylate. A mixture of ethyl 4-{[(4-{[(2S)-2-(methoxymethyl)pyrrolidinyl]methyl}-2-nitrophenyl)methyl]amino}-2-(4-pyridyl)-1,3-thiazole-5-carboxylate (Step d) (0.80 g, 1.57 mmol), iron powder (0.44 g, 7.83 mmol), and NH₄Cl (0.04 g, 0.78 mmol) in EtOH/H₂O (1:1, 40 mL) was heated at reflux for 1 h. The mixture was cooled and extracted with CH₂Cl₂ (3×). The organic extracts were dried over MgSO₄, concentrated, and the residue was purified by flash column chromatography (7% MeOH/CH₂Cl₂) to give a yellow foam. MS (m/z): 482.6 (M+1). Calc'd for C₂₅H₃₁N₅O₃S—481.21.

(f) Preparation of ethyl 4-(7-{[(2S)-2-(methoxymethyl)-pyrrolidinyl]methyl}-2-oxo(1,3,4-trihydroquinazolin-3-yl))-2-(4-pyridyl)-1,3-thiazole-5-carboxylate. To a stirred mixture of ethyl 4-{[(4-{[(2S)-2-(methoxymethyl)-pyrrolidinyl]methyl}-2-aminophenyl)methyl]amino}-2-(4-pyridyl)-1,3-thiazole-5-carboxylate (Step e) (0.34 g, 0.71 mmol) and CDI (0.34 g, 2.12 mmol) in anhydrous DMF (8 mL) was added NaH (60% oil dispersion, 0.10 g, 2.47 mmol). After stirring at RT for 16 h, the mixture was quenched with H₂O, extracted with CH₂Cl₂ (3×), dried over MgSO₄, and concentrated. The residue was purified by flash column chromatography (7% MeOH/CH₂Cl₂) to give a light-yellow oil. MS (m/z): 508.6 (M+1). Calc'd for C₂₆H₂₉N₅O₄S—507.19.

(g) Preparation of 7-{[(2S)-2-(methoxymethyl)pyrrolidinyl]-methyl}-3-(2-(4-pyridyl)(1,3-thiazol-4-yl))-1,3,4-trihydroquinazolin-2-one hydrochloride. To a stirred solution of ethyl 4-(7-{[(2S)-2-(methoxymethyl)-pyrrolidinyl]methyl}-2-oxo(1,3,4-trihydroquinazolin-3-yl))-2-(4-pyridyl)-1,3-thiazole-5-carboxylate (Step f) (0.15 g, 0.32 mmol) in dioxane (2 mL) was added 5N NaOH (0.2 mL, 0.94 mmol) and stirred for 18 h. The mixture was cooled, acidified with 10% aqueous HCl until pH=1 and heated at reflux for 48 h. The reaction mixture was cooled, concentrated, dissolved in H₂O, neutralized with 5N NaOH, and extracted with CH₂Cl₂ (3×). The organic extracts were dried over MgSO₄, concentrated, and purified by flash column chromatography (5% MeOH/CH₂Cl₂) to give a tan solid which was dissolved in MeOH and added 2M HCl in Et₂O (0.3 mL), and concentrated to afford a tan solid. MS (m/z): 436.6 (M+1). Calc'd for C₂₃H₂₅N₅O₂S—435.17.

EXAMPLE 61

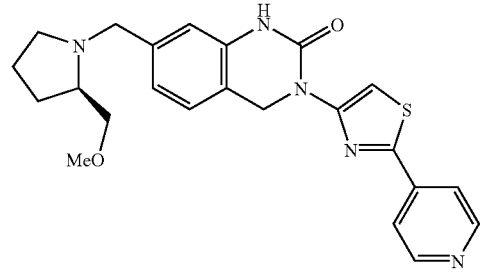

7-{[(2R)-2-(Methoxymethyl)pyrrolidinyl]methyl}-3-(2-(4-pyridyl)(1,3-thiazol-4-yl))-1,3,4-trihydroquinazolin-2-one (a) Preparation of 4-{[(2R)-2-(methoxymethyl)pyrrolidinyl]-methyl}-2-nitrobenzenecarbonitrile. A mixture of (R)-(+)-2-methymethoxylpyrrolidine (3.82 g, 33.18 mmol) and Et₃N (3.40 g, 33.18 mmol) in anhydrous THF (60 mL) was added 4-bromomethyl-2-nitrobenzonitrile (8.0 g, 33.18 mmol) and stirred at RT for 2 h. The mixture was filtered, and the filtrate was concentrated and purified by flash column chromatography (35% EtOAc/Hexane) to afford a brown oil. MS (m/z): 276.3 (M+1). Calc'd for C₁₄H₁₇N₃O₃—275.13.

(b) Preparation of (4-{[(2R)-2-(methoxymethyl)pyrrolidinyl]-methyl}-2-nitrophenyl)methylamine. To a stirred solution of 4-{[(2R)-2-(methoxymethyl)pyrrolidinyl]methyl}-2-nitrobenzenecarbonitrile (Step a) (2.50 g, 9.09 mmol) in dried THF (15 mL) was added 1.0M BH₃.THF (31.8 mL, 31.8 mmol) dropwise. The reaction was heated at reflux for 1 h. After cooled to RT, the mixture was slowly quenched with 10% aqueous HCl until pH=1, and heated at reflux for 2 h. The resulting reaction was cooled and washed with Et₂O. The aqueous layer was basified with 5N NaOH and extracted with CH₂Cl₂ (3×). The organic extracts were dried over MgSO₄ and concentrated to afford a reddish oil. MS (m/z): 265.3 (M+1). Calc'd for C₁₄H₂₁N₃O₃—279.16.

(c) Preparation of ethyl 4-{[(4-{[(2R)-2-(methoxymethyl)-pyrrolidinyl]methyl}-2-nitrophenyl)-methyl]amino}-2-(4-pyridyl)-1,3-thiazole-5-carboxylate. A mixture of (4-{[(2R)-2-(methoxymethyl)pyrrolidinyl]methyl}-2-nitrophenyl)methylamine (Step b) (1.60 g, 5.76 mmol) and ethyl 2-(4-pyridyl)-4-[(trifluoromethyl)sulfonyloxy]-1,3-thiazole-5-carboxylate (Example 14e) (1.0 g, 2.62 mmol) in dioxane (20 mL) was heated at reflux for 24 h. The mixture was cooled, concentrated, and purified by flash column chromatography (1% MeOH/CH₂Cl₂) to give a brown oil. MS (m/z): 512.1 (M+1). Calc'd for C₂₅H₂₉N₅O₅S—511.19.

(d) Preparation of ethyl 4-{[(4-{[(2R)-2-(methoxymethyl)-pyrrolidinyl]methyl}-2-aminophenyl)-methyl]amino}-2-(4-pyridyl)-1,3-thiazole-5-carboxylate. A mixture of ethyl 4-{[(4-{[(2R)-2-(methoxymethyl)pyrrolidinyl]methyl}-2-nitrophenyl)methyl]amino}-2-(4-pyridyl)-1,3-thiazole-5-carboxylate (Step c) (1.12 g, 2.01 mmol), iron powder (0.56 g, 10.05 mmol), and NH₄Cl (0.05 g, 1 mmol) in EtOH/H₂O (1:1, 40 mL) was heated at reflux for 1 h. The mixture was cooled and extracted with CH$_2$Cl$_2$ (3×). The organic extracts were dried over MgSO$_4$, concentrated, and purified by flash column chromatography (4% MeOH/ CH$_2$Cl$_2$) to give a yellow foam. MS (m/z): 482.6 (M+1). Calc'd for C$_{25}$H$_{31}$N$_5$O$_3$S—481.21.

(e) Preparation of ethyl 4-(7-{[(2R)-2-(methoxymethyl)-pyrrolidinyl]methyl}-2-oxo(1,3,4-trihydroquinazolin-3-yl))-2-(4-pyridyl)-1,3-thiazole-5-carboxylate. To a stirred mixture of ethyl 4-{[(4-{[(2R)-2-(methoxymethyl)-pyrrolidinyl]methyl}-2-aminophenyl)methyl]amino}-2-(4-pyridyl)-1,3-thiazole-5-carboxylate (0.40 g, 0.83 mmol) and CDI (0.40 g, 2.50 mmol) in dried DMF (10 mL) was added NaH (60% oil dispersion, 0.12 g, 2.91 mmol). After stirring at RT for 16 h, the mixture was quenched with H$_2$O, extracted with CH$_2$Cl$_2$ (3×), dried over MgSO$_4$, and concentrated to give a yellow oil. MS (m/z): 508.6 (M+1). Calc'd for C$_{26}$H$_{29}$N$_5$O$_4$S—507.19.

(f) Preparation of 7-{[(2R)-2-(methoxymethyl)pyrrolidinyl]-methyl}-3-(2-(4-pyridyl)(1,3-thiazol-4-yl))-1,3,4-trihydroquinazolin-2-one hydrochloride. To a stirred solution of ethyl 4-(7-{[(2R)-2-(methoxymethyl)-pyrrolidinyl]methyl}-2-oxo(1,3,4-trihydroquinazolin-3-yl))-2-(4-pyridyl)-1,3-thiazole-5-carboxylate (Step e) (0.15 g, 0.30 mmol) in dioxane (2 mL) was added 5 N NaOH (0.2 mL, 0.94 mmol) and stirred for 18 h. The mixture was cooled, acidified with 10% aqueous HCl until pH 1, then heated at reflux for 48 h. The reaction mixture was cooled, concentrated, dissolved in H$_2$O, neutralized with 5N NaOH, and extracted with CH$_2$Cl$_2$ (3×). The organic extracts were dried over MgSO$_4$, concentrated, and purified by flash column chromatography (5% MeOH/CH$_2$Cl$_2$) to give a tan solid which was dissolved in MeOH. 2M HCl in Et$_2$O (0.3 mL) was added, and the mixture was concentrated to afford a tan solid. MS (m/z): 436.6 (M+1). Calc'd for C$_{23}$H$_{25}$N$_5$O$_2$S—435.17.

EXAMPLE 62

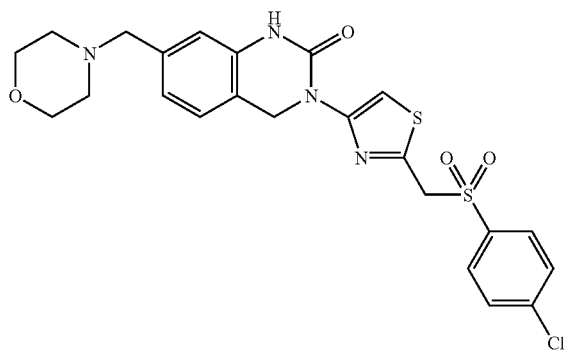

3-(2-{[(4-Chlorophenyl)sulfonyl]methyl}(1,3-thiazol-4-yl))-7-(morpholin-4-ylmethyl)-1,3,4-trihydroquinazolin-2-one (a) Preparation of 4-(morpholin-4-ylmethyl)-2-nitrobenzenecarbonitrile. A mixture of morpholine (27.8 g, 319.4 mmol) and 4-bromomethyl-2-nitro benzonitrile (35.0 g, 145.18 mmol) in anhydrous THF (200 mL) was stirred at RT for 2 h. The mixture was filtered. The filtrate was concentrated and purified by flash column chromatography (35% EtOAc/Hexane) to afford a yellow oil. MS (m/z): 248.3 (M+1). Calc'd for C$_{12}$H$_{13}$N$_3$O$_3$—247.10.

(b) Preparation of [4-(morpholin-4-ylmethyl)-2-nitrophenyl]methylamine. To a stirred solution of 4-(morpholin-4-ylmethyl)-2-nitrobenzenecarbonitrile (Step a) (13.5 g, 54.61 mmol) in anhydrous THF (100 mL) was added 1.0 M BH$_3$.THF (191 mL, 191.14 mmol) dropwise. The reaction was heated at reflux for 1 h and then cooled to RT. The resulting mixture was slowly quenched with 10% aqueous HCl until pH=1, and heated at reflux for 2 h. The resulting reaction was cooled and washed with ether. The aqueous layer was basified with 5N NaOH, and extracted with CH$_2$Cl$_2$ (3×). The organic extracts were dried over MgSO$_4$ and concentrated to afford a reddish oil. MS (m/z): 252.3 (M+1). Calc'd for C$_{12}$H$_{17}$N$_3$O$_3$—251.13.

(c) Preparation of ethyl 2-{[(4-chlorophenyl)sulfonyl]methyl}-4-({[4-(morpholin-4-ylmethyl)-2-nitro-phenyl]methyl}amino)-1,3-thiazole-5-carboxylate. A mixture of [4-(morpholin-4-ylmethyl)-2-nitrophenyl]methylamine (Step b) (3.21 g, 12.76 mmol) and ethyl 2-{[(4-chlorophenyl)sulfonyl]methyl}-4-[(trifluoromethyl)sulfonyloxy]-1,3-thiazole-5-carboxylate (3.0 g, 6.08 mmol) in anhydrous dioxane (30 mL) was heated at reflux for 16 h. The mixture was cooled, concentrated, and purified by flash column chromatography (2% MeOH/CH$_2$Cl$_2$) to give an orange foam. MS (m/z): 596.1 (M+1). Calc'd for C$_{25}$H$_{27}$ClN$_4$O$_7$S$_2$—Exact Mass: 594.10.

(d) Preparation of ethyl 4-({[2-amino-4-(morpholin-4-ylmethyl)phenyl]methyl}amino)-2-{[(4-chlorophenyl)-sulfonyl]methyl}-1,3-thiazole-5-carboxylate. A mixture of ethyl 2-{[(4-chlorophenyl)sulfonyl]methyl}-4-({[4-(morpholin-4-ylmethyl)-2-nitrophenyl]methyl}-amino)-1,3-thiazole-5-carboxylate (Step c) (1.20 g, 2.02 mmol), iron powder (0.56 g, 10.09 mmol), and NH$_4$Cl (0.05 g, 1.01 mmol) in EtOH/H$_2$O (1:1, 50 mL) was heated at reflux for 1 h. The mixture was cooled and extracted with CH$_2$Cl$_2$ (3×). The organic extracts were dried over MgSO$_4$ and concentrated to afford a yellow foam. MS (m/z): 566.1 (M+1). Calc'd for C$_{25}$H$_{29}$ClN$_4$O$_5$S$_2$—564.13.

(e) Preparation of ethyl 2-{[(4-chlorophenyl)sulfonyl]methyl}-4-[7-(morpholin-4-ylmethyl)-2-oxo(1,3,4-trihydroquinazolin-3-yl)]-1,3-thiazole-5-carboxylate. To a stirred mixture of ethyl 4-({[2-amino-4-(morpholin-4-ylmethyl)-phenyl]methyl}amino)-2-{[(4-chlorophenyl)sulfonyl]methyl}-1,3-thiazole-5-carboxylate (Step d) (1.09 g, 1.93 mmol) and CDI (0.94 g, 5.79 mmol) in dried DMF (20 mL) was added NaH (60% oil dispersion, 0.27 g, 6.76 mmol). After stirring at RT for 16 h, the mixture was quenched with H$_2$O, extracted with CH$_2$Cl$_2$ (3×), dried over MgSO$_4$, concentrated, and purified by flash column chromatography (2% MeOH/CH$_2$Cl$_2$) to give a light-yellow oil. MS (m/z): 592.1 (M+1). Calc'd for C$_{26}$H$_{27}$ClN$_4$O$_6$S$_2$—590.11.

(f) Preparation of 3-(2-{[(4-chlorophenyl)sulfonyl]-methyl}(1,3-thiazol-4-yl))-7-(morpholin-4-ylmethyl)-1,3,4-trihydroquinazolin-2-one. To a stirred solution of ethyl 2-{[(4-chlorophenyl)sulfonyl]methyl}-4-[7-(morpholin-4-ylmethyl)-2-oxo(1,3,4-trihydroquinazolin-3-yl)]-1,3-thiazole-5-carboxylate (Step e) (0.70 g, 1.19 mmol) in dioxane (10 mL) was added 5 N NaOH (0.7 mL, 3.56 mmol) and stirred for 18 h. The mixture was acidified with 10% aqueous HCl until pH 1 and heated at reflux for 48 h. The reaction mixture was cooled, concentrated, dissolved in $H_2O$, neutralized with 5N NaOH, and extracted with $CH_2Cl_2$ (3×) The combined organic extracts were dried over $MgSO_4$, concentrated, and purified by flash column chromatography (5% $MeOH/CH_2Cl_2$) to give a tan solid. MS (m/z): 520.1 (M+1). Calc'd for $C_{23}H_{23}ClN_4O_4S_2$—518.08.

EXAMPLE 63

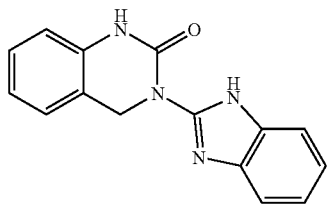

3-Benzimidazol-2-yl-1,3,4-trihydroquinazolin-2-one

A mixture of 2-aminobenzylamine (500 mg, 4.1 mmol) and 2-chlorobenzoimidazole (305 mg, 2.0 mmol) was heated at 110° C. for 18 h. The resulting solid was dissolved in $CH_2Cl_2$ (30 mL) and washed with $H_2O$ (30 mL). The organic layer was separated, dried over $Na_2SO_4$, and concentrated to provide crude benzimidazole-amine (200 mg) which was treated with CDI (500 mg, 3.0 mmol) in anhydrous DMF (15 mL). After stirring at RT for 18 h, the reaction mixture was concentrated and the viscous residue was triturated with $CH_2Cl_2$. The precipitates were filtered and recrystallized from DMSO (3 mL) and $CH_2Cl_2$ (0.5 mL) to afford the title compound as an off-white solid. MS m/z: 265 (M+H$^+$). Anal. Calc'd for $C_{15}H_{12}N_4O$: C, 68.17; H, 4.58; N, 21.20; O, 6.05; Found C, 68.35; H, 4.71; N, 21.27; O, 6.04.

Other compounds included in this invention are set forth in Table 1 below.

TABLE 1

| # | R¹ | R² | Q |
|---|---|---|---|
| 64 | 4-methyl-piperazine-1-carbonyl | H | 4-pyridyl |
| 65 | 4-methyl-piperazin-1-ylmethyl | H | 4-pyridyl |
| 66 | [(2-dimethylamino-ethyl)-methyl-amino]-methyl | H | 4-pyridyl |
| 67 | 3,5-dimethyl-piperazin-1-ylmethyl | H | 4-pyridyl |
| 68 | pyrrolidin-1-ylmethyl | H | 4-pyridyl |
| 69 | 4-methyl-piperazine-1-carbonyl | Ph | 4-pyridyl |
| 70 | 4-methyl-piperazin-1-ylmethyl | Ph | 4-pyridyl |
| 71 | [(2-dimethylamino-ethyl)-methyl-amino]-methyl | Ph | 4-pyridyl |
| 72 | 3,5-dimethyl-piperazin-1-ylmethyl | Ph | 4-pyridyl |
| 73 | pyrrolidin-1-ylmethyl | Ph | 4-pyridyl |
| 74 | H | H | ($CH_2SO_2$)-phenyl |
| 75 | H | H | ($CH_2SO_2$)-2-thienyl |
| 76 | H | H | ($CH_2SO_2$)-2-pyridyl |
| 77 | H | H | (NMeSO2)-phenyl |
| 78 | H | H | (NMeSO2)-2-thienyl |
| 79 | H | H | (NMeSO2)-2-pyridyl |

TABLE 2

| # | R¹ | Q |
|---|----|---|
| 80 | 4-methyl-piperazine-1-carbonyl | 4-pyridyl |
| 81 | 4-methyl-piperazin-1-ylmethyl | 4-pyridyl |
| 82 | [(2-dimethylamino-ethyl)-methyl-amino]-methyl | 4-pyridyl |
| 83 | 3,5-dimethyl-piperazin-1-ylmethyl | 4-pyridyl |
| 84 | pyrrolidin-1-ylmethyl | 4-pyridyl |

TABLE 3

| # | R¹ | Q |
|---|----|---|
| 85 | 4-methyl-piperazine-1-carbonyl | 4-pyridyl |
| 86 | 4-methyl-piperazin-1-ylmethyl | 4-pyridyl |
| 87 | [(2-dimethylamino-ethyl)-methyl-amino]-methyl | 4-pyridyl |
| 88 | 3,5-dimethyl-piperazin-1-ylmethyl | 4-pyridyl |
| 89 | pyrrolidin-1-ylmethyl | 4-pyridyl |

TABLE 4

| # | R¹ | Q |
|---|----|---|
| 90 | 4-methyl-piperazin-1-yl | 4-pyridyl |
| 91 | (2-dimethylamino-ethyl)-methyl-amino | 4-pyridyl |
| 92 | pyrrolidin-1-yl | 4-pyridyl |
| 93 | 2-piperidin-1-yl-ethoxy | 4-pyridyl |
| 94 | 2-morpholin-4-yl-ethoxy | 4-pyridyl |

EXAMPLE 95

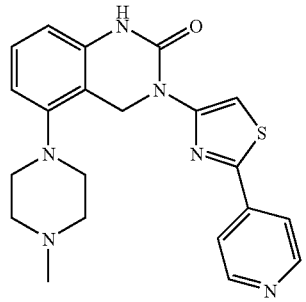

5-(Methylpiperazin-1-yl)-3-(2-(4-pyridyl)(1,3-thiazol-4-yl))-1,3,4-trihydroquinazolin-2-one (a) Preparation of [6-(methylpiperazin-1-yl)-2-nitrophenyl]methylamine. This compound was prepared according to the method described in Example 14(c) by employing 2-(4-methylpiperazin-1-yl)-6-nitrobenzonitrile (J. Med. Chem., 1981, 24, 742–748). MS m/z: 251.2 (M+1).

(b) Preparation of ethyl 4-({[methylpiperazin-1-yl)-2-nitrophenyl]methyl}amino)-2-(4-pyridyl)-1,3-thiazole-5-carboxylate. This compound was prepared according to the method described in Example 14(f) by employing [6-(methylpiperazin-1-yl)-2-nitrophenyl]methylamine (Step a) and ethyl 2-(4-pyridyl)-4-[(trifluoromethyl)sulfonyloxy]-1,3-thiazole-5-carboxylate. MS m/z: 483.2 (M+1).

(c) Preparation of ethyl 4-({[2-amino-6-(methylpiperazin-1-yl)phenyl]methyl}amino)-2-(4-pyridyl)-1,3-thiazole-5-carboxylate. This compound was prepared according to the method described in Example 14(g) with ethyl 4-({[methylpiperazin-1-yl)-2-nitrophenyl]methyl}amino)-2-(4-pyridyl)-1,3-thiazole-5-carboxylate (Step b). MS m/z: 453.2 (M+1).

(d) Preparation of ethyl 4-[5-(methylpiperazin-1-yl)-2-oxo(1,3,4-trihydroquinazolin-3-yl)]-2-(4-pyridyl)-1,3-thiazole-5-carboxylate. This compound was prepared according to the method described in Example 10(e) from ethyl 4-({[2-amino-6-(methylpiperazin-1-yl)phenyl]methyl}-amino)-2-(4-pyridyl)-1,3-thiazole-5-carboxylate (Step c). MS m/z: 479.1 (M+1).

(e) Preparation of 5-(methylpiperazin-1-yl)-3-(2-(4-pyridyl)(1,3-thiazol-4-yl))-1,3,4-trihydroquinazolin-2-one. This compound was prepared according to the method described in Example 14(i) with ethyl 4-[5-(methylpiperazin-1-yl)-2-oxo(1,3,4-trihydroquinazolin-3-yl)]-2-(4-pyridyl)-1,3-thiazole-5-carboxylate (Step d). MS m/z: 407.0 (M+1).

The pharmacological properties of the compounds of this invention may be confirmed by a number of pharmacological assays. The exemplified pharmacological assays which follow have been carried out with the compounds according to the invention and their salts. The compounds of invention exhibited more than 10% cdk5/p25 or cdk2/cyclin inhibition at 10 μM.

Biological Evaluation

Protocols for Cyclin E2/CDK2

Cloning of Cdk2 and Cyclin 2/Generation of Cdk2 and Cyclin 2 Recombinant Baculovirus The following oligonucleotide primers flanking the coding sequence of the human Cdk2 cDNA clone were used to amplify the gene and place EcoRI and HindIII restriction sites at the 5' and 3' ends of the gene respectively. [5' oligo-5'-AAGCGCGCGGAATTCATAAATATGGAGAAC-TTCCAAAAGGTGGAA-3' (SEQ ID NO: 1); 3' oligo-5'-CTCGACAAGCTTATTAGAGTCGAAGATGGGGTAC-3' (SEQ ID NO: 2)]

The following oligonucleotide primers flanking the coding sequence of the human CycE2 cDNA clone were used to amplify the gene and-place XhoI and SphI restriction sites at the 5' and 3' ends of the gene respectively. A His tag was also placed at the N-terminus of the CycE2 protein. [5' oligo-5'-CCCGGGATCTCGAGATAAATATGCAT-CATCATCATCATTCAAGACGAAGTAGC-CGTTTACAA-3' (SEQ ID NO: 3); 3' oligo-5'-CCCGGTACCGCATGCTTAGTGTTTTCCTGGTGGTTT-TTC-3' (SEQ ID NO: 4)]

CycE-2 and Cdk2 PCR fragments were subcloned into the vector pFastBacDual (Gibco/LifeTechnologies) using the restriction sites indicated above. Recombinant virus was made following protocols supplied by the manufacturer.

Expression of Cyclin 2/CDK2 in Insect Cells

Hi5 cells were grown to a cell density of $1\times10^6$ cells per ml in 800 ml of Excell 405 media (JRH). Cells were infected with virus at a multiplicity of 1. Infected cultures were incubated with shaking at 28° C. Cells were harvested by centrifugation.

Cloning of Cdk5 and p25/Generation of CDK5 and p25 Recombinant Baculovirus

Based on the reported sequences of human CDK5 and p35, GenBank accession numbers X66364 and X80343 respectively, oligonucleotide primers flanking the coding sequence of each gene were used to amplify CDK5 (5'-GCGATGCAGAAATACGAGAAACT-3' (SEQ ID NO: 5); 5'-CCCCACTGTCTCACCCTCTCAA-3' (SEQ ID NO: 6)) and p35 (5'-CGGTGAGCGGTTTTATCCC-TCC-3' (SEQ ID NO: 7); 5'-GCATTGAATCCTTGAGCCATGACG-3' (SEQ ID NO: 12)) from a human fetal brain cDNA library (Clontech). p25, a C-terminal proteolytic fragment corresponding to amino acids 99–307 of full-length p35 (Lew, et. al), was PCR subcloned from the p35 sequence using oligonucleotide primers (5'-CGGGATCCATGGCCCAGC-CCCCACCGGCCCA-3' (SEQ ID NO: 8); 5'-CCAAGCTTTCACCGATCCAGGCCTAG-3' (SEQ ID NO: 9)). The p25 PCR product (629 bp) was cloned into the pFastBacHTb baculovirus expression vector (Gibco BRL) using BamHI and HindIII. CDK5 was PCR subcloned using oligonucleotide primers (5'-CGGGATCC-GCCACCATG-CAGAAATACGAGAAACTGG-3' (SEQ ID NO: 10); 5'-GGACTAGTCTAGGGCGGAC-AGAAGTCG-3' (SEQ ID NO: 11)). The CDK5 PCR product (879 bp) was cloned into the pFastBac1 baculovirus expression vector (Gibco BRL) using BamHII and SpeI. Recombinant baculovirus expressing human Cdk5 and N-terminally six histidine tagged p25 were generated using the Bac-to-Bac system (Gibco BRL).

Expression of P25/CDK5 in Insect Cells

Coinfections of Hi5 cells by recombinant baculovirus containing the P25 gene and another containing the CDK5 gene were done at a multiplicity of infection of 5 (each virus). The Hi5 cultures were set to a cell concentration of $1\times10^6$ cells per ml in 800 ml of Excell media by JRH. The cultures were grown in 2.6 L fernbach flasks with shaking (110 rpm) at 27° C. for 60 h. The cells were harvested by centrifugation.

Purification of Complexes

All steps were performed at 4° C. Insect cells expressing either cyclin E2/CDK2 or p25/CDK5 were lysed using a microfluidizer (Microfluidics Corporation.) The lysis buffer contained 10 mM Hepes, 150 mM NaCl, 20 mM $MgCl_2$, 20 mm imidazole, 0.5 mM EDTA, 10% glycerol, 25 µg/ml Aprotinin, 25 µg/ml Leupeptin, 1 mM Pefabloc, pH 7.5). Total protein was determined on the resulting lysate using the Bradford method with a BSA standard curve. Protamine sulfate was added to the lysate to give a final 30:1 protein:protamine sulfate, incubated for 15–20 min and centrifuged at 14000×g for 30 min to remove insoluble material. Ni-NTA superflow resin (Qiagen Inc) was equilibrated in lysis buffer and incubated with the centrifugation supernatant for 1 h while rotating. The slurry was packed in a glass column and washed until a stable UV baseline was reached. Proteins were eluted with a linear gradient of 20–300 mM imidazole over 15 column volumes. Fractions were analyzed by SDS-PAGE and Western blot. Appropriate fractions were pooled, total protein determined, and submitted for kinase assay.

CDK2 Kinase Assay

CDK2 kinase assays were carried out with inhibitor (dissolved in DMSO) in a total volume of 50 µl with 1 nM enzyme (His-tagged cyclin 2/CDK2), 1 µM Histone-H1 (Gibco), 25 µM ATP, 20 µCi/ml $^{33}$P-ATP (Amersham; 2500 Ci/mmole) in kinase buffer (50 mM Tris-HCl, pH 7.5, 5 mM $MgCl_2$, 1 mM EGTA, 5 mM DTT, 200 g/ml BSA and 20 mM β-glycerophosphate for 60 min at 25° C. Reactions were stopped by the addition of an equal volume of 30% trichloroacetic acid (Sigma). Precipitates were formed by incubation at 4° C. for 60 min then collected by filtration on Millipore® filter plates (MAFC NOB10). MicroScint-20 (40 µL, Packard) was added, and counted on a Packard Top-Count®. Raw cpms were analyzed with a four-parameter logistic fit using the Levenburg Marquardt algorithm (Xlfit software IDBS LTD). Kinetic parameters were calculated by non-linear regression analysis using Grafit (Erithacus Software LTD). Riscovitine (BIOMOL Research Labs Inc., Plymouth Meeting, Pa.) and staurosporin (Sigma, St. Louis Mo.) were used as standards.

CDK5 Kinase Assay

CDK5 kinase assays were carried out with inhibitor (dissolved in DMSO) in a total volume of 50 µl with 1 nM enzyme (His-tagged p25/CDK5), 1 µM Histone-H1 (Gibco), 25 µM ATP, 20 µCi/ml $^{33}$P-ATP (Amersham; 2500 Ci/mmole) in kinase buffer (50 mM Tris-HCl, pH 7.5, 5 mM $MgCl_2$, 1 mM EGTA, 5 mM DTT, 200 µg/ml BSA and 20 mM β-glycerophosphate) for 60 min at 25° C. Reactions were stopped by the addition of an equal volume of 30% trichloroacetic acid (Sigma). Precipitates were formed by incubation at 4° C. for 60 min then collected by filtration on Millipore® filter plates (MAFC NOB10). MicroScint-20 (40 µL, Packard) was added, and counted on a Packard Top-Count®. Raw cpms were analyzed with a four-parameter logistic fit using the Levenburg Marquardt algorithm (Xlfit software IDBS LTD). Kinetic parameters were calculated by non-linear regression analysis using Grafit (Erithacus Software LTD). Riscovitine (BIOMOL Research Labs Inc., Plymouth Meeting, Pa.) and staurosporin (Sigma) were used as standards.

Examples 1–2, 4, 5–16, 20, 24, 26–34, 36, 43, 45, 49, 51, 55–58 and 95 exhibited cdk2/cyclin kinase activity with $IC_{50}$ values less than 1 µM. The compounds of examples 1–2, 5–16, 18, 20–21, 24, 26–35, 38, 43, 45–46, 49–50, 52–55, 57–59, and 61 exhibited cdk5/p25 kinase activity with $IC_{50}$ values less than 1 µM.

Cell Proliferation Assay

Cell proliferation was measured using a calorimetric immunoassay (B/M Roche #164 7229), based on the measurement of pyrimidine analog BrdU incorporation during DNA synthesis in proliferating cells. Cells, e.g., human PC-3 prostate carconima cells, huFSF normal human foreskin fibroblast cells, HCT 116 human colon carcinoma cells or HT 29 human colon carcinoma cells, were cultured in a 96-well plate for 24 h, until a cell count of $3 \times 10^3$ to $6 \times 10^3$ cells per well in duplicate wells were achieved, in a well volume of 200 µl. The media was changed and 1 µl of 200× control inhibitors or compounds was added to each well. Cells are incubated for 48 h at 37° C. The cells were labeled with BrdU for 4 h at 37° C. The labeling medium was removed and in one step, the cells were fixed and the DNA was denatured (30 min at RT). Anti-BrdU-POD antibody was added to bind to the BrdU incorporated in newly synthesized cellular DNA (60–90 min at RT). The cells were washed 3×with washing buffer, substrate (100 µl) was added and the cells were incubated for 10 min at RT. The substrate reaction was stopped by adding 25 µl of 1M $H_2SO_4$. The amount of BrdU incorporated was quantified by measuring the absorbance at 450 nm using ELISA reader. $IC_{50}$'s were calculated using GraFit (Sigma). Examples 2, 15, 28, 31–32 and 34 inhibited cell proliferation with $IC_{50}$ values less than 5 µM.

Ischemic Stroke Model: Middle Cerebral Artery Occlusion (MCAO) In Vivo

The compounds' effect on treating stroke was measured in a MCAO rat model. (L. Belayev et al., Stroke, 27, 1616–23 (1996). Male Sprague-Dawley rats (300–330 g body weight) were anesthetized with halothane and MCAO was induced by inserting a poly-L-lysine coated monofilament suture to the beginning of the middle cerebral artery (MCA). After various time points (60, 90 or 120 min), the intraluminal suture was carefully removed to start reperfusion. Physiological conditions (blood $O_2$, $CO_2$, pH, glucose, blood pressure) were monitored and kept stable during the surgery. The compound was dissolved in 20% Captisol in phosphate buffered saline and administered (orally, IV or IP) 90 min after ischemia onset, at the beginning of reperfusion. Further dosing occurred at 4–8 h and twice a day thereafter.

The use of behavioral tests was directly analogous to the clinical neurological examination for assessing ischemic deficits and rates of behavioral recovery. The battery consisted of four tests: (1) postural reflex test, (2) forelimb placing test (J B Bederson et al., Stroke, 17:472–76 (1986) (L. Belayev et al., Stroke, 26:2313–20 (1995), (3) contralateral foot fault index (A. Tamura et al., J. Cereb Blood Flow Metab., 1:53–60 (1981) (D M Freeney, Science, 217:855–57 (1982), and (4) cylinder asymmetry (T A Jones and T. Schallert, J. Neurosci., 14:2140–52 (1994). Tests were performed once a day for three days and then once a week for a period of 30 days. These tests are useful in assessing neurological deficits for short-term studies; the cylinder asymmetry test appeared to be the most useful for long term experiments.

At the end of the experiment, the infarct volume was measured (J B Bederson et al., Stroke, 17:1304–8 (1986) (K A Osborne et al, J. Neurol Neurosurg. Psychiatry, 50:402 (1987) (R A Swanson et al., J. Cereb. Blood Flow Metab., 10:290–3 (1990). The brains were removed and sliced coronally at 1 mm thickness. The brain slices were stained with 2% (w/vol) 2,3,5-triphenyltetrazolium chloride (TTC) which stains the infarcted areas of the brain in white and allows for the measurement of infarct volume by an image-analysis system. Edema volume that contributes to infarct volume was subtracted by comparison with the total volume of the contralateral hemisphere.

Formulations

Also embraced within this invention is a class of pharmaceutical compositions comprising the active compounds of Formula I-V in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg body weight, preferably between about 0.5 and about 50 mg/kg body weight and most preferably between about 0.1 to 20 mg/kg body weight, may be appropriate. The daily dose can be administered in one to four doses per day.

For therapeutic purposes, the active compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs.

The compounds of this invention can also be administered by a transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The foregoing is merely illustrative of the invention and is not intended to limit the invention to the disclosed compounds. Variations and changes which are obvious to one skilled in the art are intended to be within the scope and nature of the invention which are defined in the appended claims.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups from the genus.

From the foregoing description, one skilled in the art can easily ascertain the essential characteristics of this invention, and without departing from the spirit and scope thereof, can make various changes and modifications of the invention to adapt it to various usages and conditions.

All mentioned references, patents, applications and publications, are hereby incorporated by reference in their entirety, as if here written. The references provided are not admitted to be prior art.

What is claimed is:

1. A compound of formula I

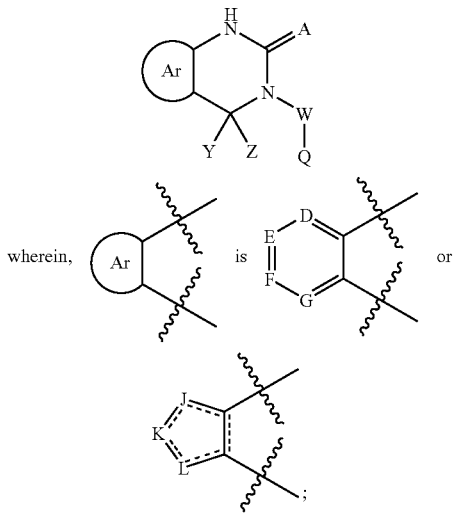

wherein, Ar is 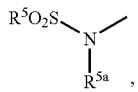 or wherein A is O or S;
wherein D is selected from $CR^1$, $CR^2$, $CR^3$, $CR^4$ and N;
wherein E is selected from $CR^1$, $CR^2$, $CR^3$, $CR^4$ and N;
wherein F is selected from $CR^1$, $CR^2$, $CR^3$, $CR^4$ and N;
wherein G is selected from $CR^1$, $CR^2$, $CR^3$, $CR^4$ and N;
wherein J is selected from $NR^6$, S, O, $CR^1$, $CR^2$, $CR^3$ and $CR^4$;
wherein K is selected from $NR^6$, S, O, $CR^1$, $CR^2$, $CR^3$ and $CR^4$;
wherein L is selected from $NR^6$, S, O, $CR^1$, $CR^2$, $CR^3$ and $CR^4$;
wherein Q is selected from H, hydroxy, $-N(R^5)_2$, $-NR^5C(O)R^5$, $-(C_1-C_8)$alkyl-$OR^5$, $-(C_1-C_8)$alkyl-$S(O)_nR^5$, substituted aryl, an unsubstituted or substituted monocyclic or bicyclic, non-aromatic carbocyclic ring, an unsubstituted or substituted monocyclic or bicyclic, heteroaryl and an unsubstituted or substituted monocyclic or bicyclic, non-aromatic heterocyclic ring, wherein the ring is unsubstituted or substituted with one or more groups selected from H, halo, aryl, alkynyl, alkenyl, $-OR^5$, $-N(R^5)_2$, $-(C_1-C_8)$alkyl-$N(R^5)_2$, $-(C_1-C_8)$alkyl-$S(O)_nR^5$, $-N(R^5)_2(C_1-C_8)$alkyl-$N(R^5)_2$, lower alkoxyalkyl, $-S(O)_nR^5$, $-NR^5S(O)_nR^5$, cyano, $(C_1-C_8)$alkyl, lower cyanoalkyl, lower alkylaminoalkoxy, lower aminoalkoxyalkyl $(C_3-C_{10}$cycloalkyl, nitro, optionally substituted 4–7 membered heterocyclyl, optionally substituted phenoxyalkyl, optionally substituted heterocyclyloxyalkyl, $-SO_2NR^5R^5$, $-NR^5SO_2R^5$, $-C(O)N(R^5)_2$, $-CO_2R^5$, $-CO_2NR^5R^5$, $-SO_2NHC(O)R^5$, optionally substituted phenylalkyl, optionally substituted heterocyclylalkyl, $-NR^5C(O)N(R^5)_2$, $-NR^5C(O)R^5$, $-NR^5CO_2R^5$ and $-C(O)R^5$; wherein W is selected from thienyl, thiazolyl, oxazolyl, imidazolyl, pyrrolyl, furyl, pyrazolyl, isoxazolyl, thiadiazolyl, triazolyl and isothiazolyl that is unsubstituted or substituted with one or more groups selected from halo, aryl, cycloalkyl, $-OR^5$, $(C_2-C_8)$alkenyl, $(C_2-C_8)$alkynyl, $-N(R^5)_2$, $-(C_1-C_8)$alkyl-$N(R^5)_2$, $-SO_2NR^5R^5$, $-(C_1-C_8)$alkyl-$SO_2R^5$, $-(C_1-C_8)$alkyl-$SO_2-(C_1-C_8)$alkyl-$R^5$, $-C_1-C_8)$alkyl-$SO_2-(C_1-C_8)$aryl, $-(C_1-C_8)$alkyl-$SO_2-(C_1-C_8)$heteroaryl, $(C_1-C_8)$alkyl, $(C_3-C_{10})$cycloalkyl, nitro, cyano, optionally substituted 5–6 membered heterocyclyl, formyl, alkylcarbonyl, cycloalkylcarbonyl, heterocyclylcarbonyl, arylcarbonyl, $-NR^5S(O)_n R^5$, $-C(O)N(R^5)_2$, $-CO_2R^5$, optionally substituted phenylalkyl, optionally substituted heterocyclylalkyl, $-NR^5C(O)N(R^5)_2$, $-NR^5C(O)R^5$ and $-NR^5CO_2R^5$;

wherein Y is selected from H, $-N(R^{5a})_2$, $-SR^{5a}$, $-OR^{5a}$, and $-C(R^{5a})_3$;

wherein Z is selected from H, $-N(R^{5a})_2$, $-SR^{5a}$, $-OR^{5a}$, and $-C(R^{5a})_3$;

wherein n is 0, 1 or 2;

wherein $R^1$, $R^2$, $R^3$, and $R^4$ are independently selected from H, $-OR^5$, alkylenedioxy, halo, optionally substituted aryl, alkenyl, alkynyl, $-NR^5_2$, $-(C_1-C_8)$alkyl-$N(R^5)_2$, $-S(O)_n-NR^5R^5$, $-S(O)_nR^5$, $(C_1-C_8)$alkyl, $(C_1-C_8)$haloalkyl, hydroxy-$(C_1-C_8)$alkyl, optionally substituted $(C_3-C_{10})$cycloalkyl, nitro, cyano, optionally substituted 4–10 membered heterocyclyl, $-C(O)R^5$, $-NR^5SO_2R^5$, $-C(O)N(R^5)_2$, $-CO_2R^5$, optionally substituted arylalkyl, optionally substituted 4–10 membered heterocyclylalkyl, $-NR^5C(O)N(R^5)_2$, $-NR^5C(O)R^5$ and $-NR^5CO_2R^5$; wherein $R^1$ and $R^2$ may be joined to form a 5–10 membered saturated or unsaturated carbocyclic or heterocyclic ring; wherein $R^2$ and $R^3$ may be joined to form a 5–10 membered saturated or unsaturated carbocyclic or heterocyclic ring; or wherein $R^3$ and $R^4$ may be joined to form a 5–10 membered saturated or unsaturated carbocyclic or heterocyclic ring;

wherein $R^5$ is independently selected from H, lower alkyl, optionally substituted aryl, optionally substituted aralkyl, optionally substituted heterocyclyl, optionally substituted heterocyclylalkyl, optionally substituted $C_3-C_6$ cycloalkyl, optionally substituted $C_3-C_6$ cycloalkyl-alkyl, lower alkyl-$NR^5$-lower alkyl, and lower haloalkyl;

wherein $R^{5a}$ is independently selected from H, and $(C_1-C_6)$alkyl;

wherein $R^6$ is selected from H, $(C_1-C_2)$alkyl, and a lone pair of electrons;

wherein each alkyl, aryl, heteroaryl, heterocyclyl, cycloalkyl, alkynyl, alkynyl, and alkoxy moiety of any $R^1$, $R^2$, $R^3$, $R^4$, or can optionally join with another adjacent or vicinal $R^1$, $R^2$, $R^3$, $R^4$, or $R^5$ form a 3–7 membered ring; and wherein each aryl, heteroaryl, cycloalkyl, and heterocyclyl moiety of any $R^1$, $R^2$, $R^3$, $R^4$, $R^5$, Y, Z, Q, and W is optionally substituted with one or more groups selected from halo, $-NH_2$, $-OH$, $-CO_2H$, $(C_1-C_6)$alkylamino, $(C_1-C_6)$alkoxy, $(C_1-C_6)$alkoxyalkyl, $(C_1-C_6)$alkyl, di$(C_1-C_6)$alkylamino, phenyl, and heterocyclyl;

provided Q is not pyridinium; further provided the compound is not 3-(2-pyridin-3-yl-thiazol-4-yl)-3,4-dihydro-1H-quinazolin-2-one or 6-methyl-3-(2-pyridin-2-yl-thiazol-4-yl)-3,4-dihydro-1H-quinazolin-2-one, and pharmaceutically acceptable salt thereof.

2. Compound of claim 1 wherein Q is selected from hydroxy, $-N(R^5)_2$, $R^5SO_2-(C_1-C_6)$alkyl,

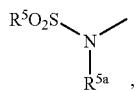

substituted phenyl, substituted or unsubstituted 5–6 membered heteroaryl, substituted or unsubstituted ($C_3$–$C_6$) cycloalkyl, and substituted or unsubstituted non-aromatic heterocyclyl.

3. Compound of claim 2 wherein A is O; wherein Q is selected from hydroxy, —N($R^5$)$_2$, $R^5SO_2$—($C_1$–$C_6$)alkyl,

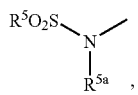

substituted phenyl, substituted or unsubstituted 5–6 membered heteroaryl, substituted or unsubstituted ($C_3$–$C_6$) cycloalkyl, and substituted or unsubstituted non-aromatic heterocyclyl.

4. Compound of claim 3, and pharmaceutically acceptable salt thereof,
wherein Ar is selected from phenyl, pyridyl and thiazolyl, wherein Ar is optionally substituted with one or more radicals selected from —$OR^5$, halo, optionally substituted phenyl, $C_2$–$C_6$-alkenyl, $C_2$–$C_6$-alkynyl, —N($R^5$)$_2$, —($C_1$–$C_6$)alkyl-N($R^5$)$_2$, —S(O)$_n$—N($R^5$)$_2$, —S(O)$_n$$R^5$, ($C_1$–$C_6$)alkyl, ($C_1$–$C_4$)haloalkyl, hydroxy-($C_1$–$C_4$)alkyl, ($C_3$–$C_6$)cycloalkyl, nitro, cyano, hydroxy-($C_1$–$C_4$)-alkylamino, ($C_{11}$–$C_2$)-alkylamino-($C_1$–$C_2$)-alkylamino, ($C_1$–$C_2$)-alkylamino-($C_1$–$C_2$)-alkoxy, optionally substituted 4–6 membered heterocyclyl, —C(O)$R^5$, —$NR^5SO_2R^5$, —C(O)N($R^5$)$_2$, —$CO_2R^5$, optionally substituted phenyl-($C_1$–$C_4$)aminoalkyl, optionally substituted phenyl-($C_1$–$C_6$)alkyl, optionally substituted 4–7 membered heterocyclyl-$C_1$–$C_6$-alkyl, —$NR^5C(O)N(R^5)_2$, —$NR^5C(O)R^5$ and —$NR^5CO_2R^5$;
wherein Q is selected from —N($R^5$)$_2$, $R^5SO_2$—($C_1$–$C_3$) alkyl,

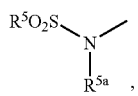

substituted phenyl, and
substituted or unsubstituted 5–6-membered heteroaryl;
wherein Y is selected from H, —N($R^{5a}$)$_2$, —$OR^{5a}$ and ($C_1$–$C_3$)alkyl;
wherein Z is selected from H, —N($R^{5a}$)$_2$, —$OR^{5a}$, and ($C_1$–$C_3$)alkyl;
wherein $R^5$ is independently selected from H, ($C_1$–$C_6$) alkyl, optionally substituted phenyl, optionally substituted phenyl-($C_1$–$C_4$)alkyl, optionally substituted 4–10 membered heterocyclyl, optionally substituted 4–10 membered heterocyclyl-($C_1$–$C_4$)alkyl, optionally substituted $C_3$–$C_6$ cycloalkyl, optionally substituted $C_3$–$C_6$ cycloalkyl-($C_1$–$C_4$)alkyl, ($C_1$–$C_2$)-alkyl$NR^{5a}$—($C_1$–$C_4$)-alkyl, and ($C_1$–$C_4$)haloalkyl;
wherein $R^{5a}$ is independently selected from H, and ($C_1$–$C_6$)alkyl; and wherein each aryl, heteroaryl, and cycloalkyl moiety is optionally substituted with one or more groups selected from halo, —$NH_2$, —OH, —$CO_2H$, ($C_1$–$C_4$)alkylamino, ($C_1$–$C_2$)alkoxy, ($C_1$–$C_2$)alkoxyalkyl, ($C_1$–$C_4$) alkyl, di($C_1$–$C_4$)alkylamino, pyrrolidinyl, piperazinyl, piperidinyl, morpholinyl, and azetidinyl.

5. Compound of claim 4, and pharmaceutically acceptable salt thereof, wherein W is selected from thiazolyl and thiadiazolyl; wherein Ar is phenyl optionally substituted with one or more radicals selected from hydroxy, ($C_1$–$C_4$) alkyl-O—, optionally substituted phenyl-($C_1$–$C_4$)alkyl-O—, optionally substituted 4–6 membered heterocyclyl-($C_1$–$C_4$) alkyl-O—, optionally substituted phenyl-O—, $C_{1-2}$-alkylenedioxy, halo, optionally substituted phenyl, —$NH_2$, —$NR^{5a}$—($C_1$–$C_5$)alkyl, optionally substituted 4–6 membered heterocyclyl-$NR^{5a}$, optionally substituted 4–6 membered heterocyclyl-($C_1$–$C_4$)alkyl-$NR^{5a}$—, optionally substuted ($C_3$–$C_6$)cycloalkyl-($C_1$–$C_4$)alkyl-$NR^{5a}$—, —($C_1$–$C_2$) alkyl-$NH_2$, —($C_1$–$C_2$)alkyl-$NR^{5a}$—($C_1$–$C_2$)alkyl, —$SO_2NR^5R^5$, ($C_1$–$C_4$)alkylsulfonyl, ($C_1$–$C_4$)alkylthio, ($C_1$–$C_4$)alkyl, ($C_1$–$C_2$)haloalkyl, hydroxy-($C_1$–$C_2$)alkyl, hydroxy-($C_1$–$C_4$)-alkylamino, [(($C_1$–$C_2$)alkyl)$_2$N—($C_1$–$C_4$)-alkyl]-$NR^{5a}$—, ($C_1$–$C_2$)alkyl-$NR^{5a}$—($C_1$–$C_4$)-alkyl-O—, ($C_3$–$C_6$)cycloalkyl, optionally substituted 4–6 membered heterocyclyl-sulfonyl, optionally substituted heterocyclyl selected from pyrrolidinyl, piperazinyl, piperidinyl, and morpholinyl, —C(O)$R^5$, —$NR^{5a}SO_2R^5$, —C(O)N ($R^5$)$_2$, —$CO_2R^5$, optionally substituted phenyl-($C_1$–$C_4$) aminoalkyl, optionally substituted phenyl-($C_1$–$C_2$)alkyl, optionally substituted 5–7 membered heterocyclyl-$C_1$–$C_4$-alkyl, —$NR^{5a}C(O)R^5$ and —$NR^{5a}CO_2R^{5a}$;
wherein Q is selected from —N($R^5$)$_2$, $R^{5b}SO_2$—($C_1$–$C_2$) alkyl,

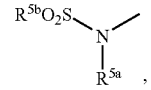

substituted phenyl and
substituted or unsubstituted 6 membered heteroaryl;
wherein Y is selected from H, and ($C_1$–$C_3$)alkyl;
wherein Z is selected from H and ($C_1$–$C_3$)alkyl;
wherein $R^5$ is independently selected from H, ($C_1$–$C_6$) alkyl, $C_1$–$C_6$)aminoalkyl optionally substituted with optionally substituted phenyl, optionally substituted $C_3$–$C_6$ cycloalkyl, $C_3$–$C_6$ cycloalkyl-($C_1$–$C_4$)alkyl, optionally substituted phenyl, optionally substituted phenyl-($C_1$–$C_3$)alkyl, optionally substituted 4–6 membered heterocyclyl-($C_1$–$C_4$)alkyl, ($C_1$–$C_2$)haloalkyl, and optionally substituted 4–6 membered heterocyclyl;
wherein $R^{5a}$ is independently selected from H, and ($C_1$–$C_6$)alkyl; and
wherein each aryl, heteroaryl, and cycloalkyl moiety is optionally substituted with one or more groups selected from chloro, fluoro, —$NH_2$, —OH, —$CO_2H$, ($C_1$–$C_2$) alkylamino, methoxymethyl, ($C_1$–$C_2$)alkyl, di($C_1$–$C_2$) alkylamino, pyrrolidinyl, piperazinyl, piperidinyl, morpholinyl and azetidinyl.

6. Compound of claim 5, and pharmaceutically acceptable salt thereof, wherein W is selected from thiazolyl and thiadiazolyl; wherein Ar is phenyl optionally substituted with one or more radicals selected from (tert-butoxycarbonyl)amino, cyclopropylmethylamino, 3-hydroxypropylamino, 2-(piperidin-1-yl)ethylamino, 2-(pyrrolidin-1-yl) ethylamino, 2-(morpholin-4-yl)ethylamino, 3-(piperidin-1- yl)propylamino, 3-(pyrrolidin-1-yl)propylamino, 3-(morpholin-4-yl)propylamino, N-methyl-N-(2-piperid-1-ylethyl)amino, N-methyl-N-(2-pyrrolidin-1-ylethyl)amino, N-methyl-N-(2-morpholin-4-ylethyl)amino, ((2S)-2-amino-3-phenylpropyl)amino, 4-methylpiperazin-1-ylamino, 4-methylpiperazin-1-yl, 3-aminopyrrolidin-1-yl, (diethylamino)ethylamino, 3,5-dimethylpiperazin-1-yl, (4-piperidylmethyl)amino, (2-methylbutyl)amino, 2-(dimethylamino)ethoxy, 2-(methylamino)ethoxy, ((2R)pyrrolidin-2-yl)methoxy, ((2R)-1-methylpyrrolidin-2-yl)methoxy, 2-(piperid-1-yl)ethoxy, 2-(piperazin-1-yl)ethoxy, 2-morpholin-4-ylethoxy, 3-(N,N-diethylamino)propoxy, optionally substituted phenoxy, 3-(morpholin-4-yl)propoxy, methylenedioxy, hydroxy, benzyloxy, methoxy, chloro, fluoro, bromo, optionally substituted phenyl, amino, methylamino, diethylamino, aminomethyl, dimethylaminoethyl, N-(N',N'-diethylaminoethyl)-N-methylamino, aminosulfonyl, piperazinylsulfonyl, methylthio, methylsulfonyl, methyl, cyclopropyl, pyrrolidinyl, piperazinyl, 4-methylpiperazinyl, piperidinyl, morpholinyl, methylcarbonyl, phenylcarbonyl, piperidinylcarbonyl, trifluoromethyl, hydroxymethyl, hydroxyethyl, diethylaminocarbonyl, carboxy, methoxycarbonyl, optionally substituted benzyl, 1-azepanylmethyl, (2-methoxymethylpyrrolidin-1-yl)methyl, piperazinylmethyl, 4-methylpiperazinylmethyl, piperidinylmethyl, and morpholinylmethyl;

wherein Q is selected from amino, 2-pyridylamino, 3-pyridylamino, 4-pyridylamino, phenylsulfonylamino, N-methyl-N-(2-pyridylsulfonyl)amino, N-methyl-N-(3-pyridylsulfonyl)amino, N-methyl-N-(4-pyridylsulfonyl)amino, N-methyl-N-(2-thienylsulfonyl)amino, N-methyl-N-(phenylsulfonyl)amino, 2-pyridylsulfonylmethyl, 3-pyridylsulfonylmethyl, 4-pyridylsulfonylmethyl, 2-thienylsulfonylmethyl, phenylsulfonylmethyl, 2-furylmethylsulfonylmethyl, 3-trifluoromethylbenzyl-sulfonylmethyl, methylsulfonylmethyl, tert-butyl-sulfonylmethyl, 4-fluorophenyl-methylsulfonylmethyl, 4-chlorophenyl-methylsulfonylmethyl, phenyl substituted with one or more substituents selected from H, hydroxyl, chloro, fluoro, methoxy, amino, aminomethyl, methylsulfonyl, methyl, cyano, trifluoromethyl, and pyrrolyl, unsubstituted pyridyl, and pyridyl substituted with one or more substituents selected from chloro, fluoro, —NH₂, —OH, —CO₂H, methylamino, methyl, ethyl, diethyl-amino, pyrrolidinyl, piperazinyl, piperidinyl, morpholinyl and azetidinyl;

wherein Y is H; and wherein Z is H.

7. A compound of claim 1 having Formula II

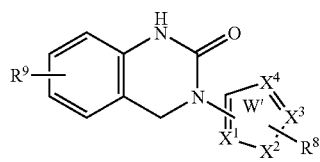

II wherein $X^1$ is C, $CR^{10}$ or N; wherein $X^2$ is selected from NH, N(CH₃), S and O; wherein $X^3$ is C, $CR^{10}$ or N; wherein $X^4$ is C, $CR^{10}$ or N; provided at least one of $X^1$, $X^2$, $X^3$ and $X^4$ is not N, NH or N(CH₃);

wherein $R^8$ is selected from —N($R^{11}$)₂, $R^{11}$S(O)ₙ—(C₁–C₈)alkyl,

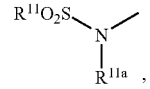

substituted phenyl, optionally substituted pyridyl, optionally substituted pyrazinyl, optionally substituted pyrimidinyl and optionally substituted pyridazinyl;

wherein $R^9$ is one or more substituents selected from H, hydroxy, (C₁–C₄)alkyl-O—, optionally substituted phenyl-C₁–C₄)alkyl-O—, optionally substituted 4–6 membered heterocyclyl-(C₁–C₄)alkyl-O—, optionally substituted phenyl-O—, C₁₋₂-alkylenedioxy, halo, optionally substituted phenyl, —NH₂, —NR$^{11a}$—(C₁–C₅)alkyl optionally substituted 4–6 membered heterocyclyl-NR$^{11a}$—, optionally substituted 4–6 membered heterocyclyl-(C₁–C₄)alkyl-NR$^{11a}$—, optionally substituted (C₃–C₆)cycloalkyl-(C₁–C₄)alkyl-NR$^{11a}$—, —(C₁–C₂)alkyl-NH₂, —(C₁–C₂)alkyl-NR$^{11a}$—(C₁–C₂)alkyl, —SO₂NR$^{11}$R$^{11}$, (C₁–C₄)alkylsulfonyl, (C₁–C₄)alkylthio, (C₁–C₄)alkyl, (C₁–C₂)haloalkyl, hydroxy-(C₁–C₂)alkyl, hydroxy-(C₁–C₄)-alkylamino, [((C¹–C₂)alkyl)₂N—(C₁–C₄)-alkyl]-NR$^{11a}$ —, (C₁–C₂)-alkylNR$^{11a}$—(C₁–C₄)-alkyl-O—, (C₃–C₆)cycloalkyl, optionally substituted 4–6 membered heterocyclyl-sulfonyl, optionally substituted heterocyclyl selected from pyrrolidinyl, piperazinyl, piperidinyl, and morpholinyl, —C(O)R$^{11}$, —NR$^{11a}$SO₂R$^{11}$, —C(O)N(R$^{11}$)₂, —CO₂R$^{11}$, optionally substituted phenyl-(C₁–C₄)aminoalkyl, optionally substituted phenyl-(C₁–C₂)alkyl, optionally substituted 5–7 membered heterocyclyl-C₁–C₄-alkyl, —NR$^{11a}$C(O)R$^{11}$ and —NR$^{11a}$CO₂R$^{11a}$;

wherein n is 0, 1 or 2;

wherein OR$^{10}$ is selected from H, halo, aryl, cycloalkyl, —O$^{11}$, (C₂–C₈)alkenyl, (C₂–C₈)alkynyl, —N(R$^{11}$)₂, —(C₁–C₈)alkyl-N(R$^{11}$)₂, —SO₂NR$^{11}$R$^{11}$, (C₁–C₈)alkyl, cycloalkylalkyl, nitro, cyano, heteroaryl, optionally substituted 5–6 membered heterocyclyl, formyl, alkylcarbonyl, cycloalkylcarbonyl, arylcarbonyl, heterocyclylcarbonyl, —NR$^{11a}$SO₂R$^{11}$, optionally substituted phenylalkyl, optionally substituted heteroarylalkyl, —NR$^{11a}$C(O)N(R$^{11}$)₂, —NR$^{11a}$C(O)R$^{11}$ and —NR$^{11a}$CO₂R$^{11}$;

wherein each R$^{11}$ is independently selected from H, (C₁–C₆)alkyl, (C₁–C₆)aminoalkyl optionally substituted with optionally substituted phenyl, optionally substituted phenyl, optionally substituted phenyl-(C₁–C₄)alkyl, optionally substituted 4–6 membered heterocyclyl, optionally substituted 4–6 membered heterocyclyl-(C₁–C₄)alkyl, C₃–C₆ cycloalkyl, C₃–C₆ cycloalkyl-(C₁–C₄)alkyl and (C₁–C₂)haloalkyl;

wherein each R$^{11a}$ is independently selected from H and methyl; and wherein each phenyl, cycloalkyl, and heterocyclyl moiety is optionally substituted with one or more groups selected from halo, —NH₂, —OH, —CO₂H, (C₁–C₄)alkylamino, (C₁–C₄)alkyl, di(C₁–C₄)alkylamino, (C₁–C₄)haloalkyl, pyrrolidinyl, piperazinyl, piperidinyl, morpholinyl, and azetidinyl;

and pharmaceutically acceptable derivatives thereof;

provided the compound is not 3-(2-pyridin-3-yl-thiazol-4-yl)-3,4-dihydro-1H-quinazolin-2-one or 6-methyl-3-(2-pyridin-2-yl-thiazol-4-yl)-3,4-dihydro-1H-quinazolin-2-one.

8. A compound of claim 7 wherein $X^2$ is S; wherein $R^8$ is selected from amino, 2-pyridylamino, 3-pyridylamino, 4-pyridylamino, phenylsulfonylamino, N-methyl-N-(2-pyridylsulfonyl)amino, N-methyl-N-(3-pyridylsulfonyl)amino, N-methyl-N-(4-pyridylsulfonyl)amino, N-methyl-N-(2-thienylsulfonyl)amino, N-methyl-N-(phenylsulfonyl)amino, 2-pyridylsulfonylmethyl, 3-pyridylsulfonylmethyl, 4-pyridylsulfonylmethyl, 2-thienylsulfonylmethyl, phenylsulfonylmethyl, 2-furylmethylsulfonylmethyl, 3-trifluoromethylphenylmethylsulfonylmethyl, methylsulfonylmethyl, tert-butylsulfonylmethyl, 4-fluorophenyl-methylsulfonylmethyl, 4-chlorophenyl-methylsulfonylmethyl, unsubstituted phenyl, phenyl substituted with one or more substituents selected from hydroxyl, chloro, fluoro, methoxy, amino, aminomethyl, methylsulfonyl, methyl, cyano, trifluoromethyl, and pyrrolyl, unsubstituted 4-pyridyl, and 4-pyridyl substituted with one or more substituents selected from chloro, fluoro, —$NH_2$, —OH, —$CO_2H$, methylamino, methyl, ethyl, diethyl-amino, pyrrolidinyl, piperazinyl, piperidinyl, morpholinyl and azetidinyl;

wherein $R^9$ is one or more radicals selected from H, (tert-butoxycarbonyl)amino, cyclopropylmethylamino, 3-hydroxypropylamino, 2-(piperidin-1-yl)ethylamino, 2-(pyrrolidin-1-yl)ethylamino, 2-(morpholin-4-yl)ethylamino, 3-(piperidin-1-yl)propylamino, 3-(pyrrolidin-1-yl)propylamino, 3-(morpholin-4-yl)propylamino, N-methyl-N-(2-piperid-1-ylethyl)amino, N-methyl-N-(2-pyrrolidin-1-ylethyl)amino, N-methyl-N-(2-morpholin-4-ylethyl)amino, ((2S)-2-amino-3-phenylpropyl)amino, 4-methylpiperazin-1-ylamino, 4-methylpiperazin-1-yl, 3-aminopyrrolidin-1-yl, (diethylamino)ethylamino, 3,5-dimethylpiperazin-1-yl, (4-piperidylmethyl)amino, (2-methylbutyl)amino, 2-(dimethylamino)ethoxy, 2-(methylamino)ethoxy, ((2R)pyrrolidin-2-yl)methoxy, ((2R)-1-methylpyrrolidin-2-yl)methoxy, 2-(piperid-1-yl)ethoxy, 2-(piperazin-1-yl)ethoxy, 2-morpholin-4-ylethoxy, 3-(N,N-diethylamino)propoxy, optionally substituted phenoxy, 3-(morpholin-4-yl)propoxy, methylenedioxy, hydroxy, benzyloxy, methoxy, chloro, fluoro, bromo, optionally substituted phenyl, amino, methylamino, diethylamino, aminomethyl, dimethylaminoethyl, N-(N',N'-diethylaminoethyl)-N-methylamino, aminosulfonyl, piperazinylsulfonyl, methylthio, methylsulfonyl, methyl, cyclopropyl, pyrrolidinyl, piperazinyl, 4-methylpiperazinyl, piperidinyl, morpholinyl, methylcarbonyl, phenylcarbonyl, piperidinylcarbonyl, trifluoromethyl, hydroxymethyl, hydroxyethyl, diethylaminocarbonyl, carboxy, methoxycarbonyl, optionally substituted benzyl, 1-azepanylmethyl, (2-methoxymethylpyrrolidin-1-yl)methyl, piperazinylmethyl, 4-methylpiperazinylmethyl, piperidinylmethyl, and morpholinylmethyl; and wherein $R^{10}$ is H; and pharmaceutically acceptable salt thereof.

9. A compound of claim 1 and pharmaceutically acceptable salt thereof selected from:

3-(2-(4-pyridyl)-1,3-thiazol-4-yl)-1,3,4-trihydroquinazolin-2-one;
methyl 2-oxo-3-(2-(4-pyridyl)(1,3-thiazol-4-yl))-1,3,4-trihydroquinazoline-5-carboxylate;
5-methoxy-3-(2-(4-pyridyl)(1,3-thiazol-4-yl))-1,3,4-trihydroquinazolin-2-one;
5-bromo-3-(2-(4-pyridyl)(1,3-thiazol-4-yl))-1,3,4-trihydroquinazolin-2-one;
6-methyl-3-(2-(4-pyridyl)(1,3-thiazol-4-yl))-1,3,4-trihydroquinazolin-2-one;
5-methyl-3-(2-(4-pyridyl)(1,3-thiazol-4-yl))-1,3,4-trihydroquinazolin-2-one;
7-fluoro-3-(2-(4-pyridyl)(1,3-thiazol-4-yl))-1,3,4-trihydroquinazolin-2-one;
6-fluoro-3-(2-(4-pyridyl)(1,3-thiazol-4-yl))-1,3,4-trihydroquinazolin-2-one;
5-chloro-3-(2-(4-pyridyl)(1,3-thiazol-4-yl))-1,3,4-trihydroquinazolin-2-one;
7-phenyl-3-(2-(4-pyridyl)(1,3-thiazol-4-yl))-1,3,4-trihydroquinazolin-2-one;
5-fluoro-3-(2-(4-pyridyl)(1,3-thiazol-4-yl))-1,3,4-trihydroquinazolin-2-one;
5-(morpholin-4-ylmethyl)-3-(2-(4-pyridyl)(1,3-thiazol-4-yl))-1,3,4-trihydroquinazolin-2-one;
5-(piperidylmethyl)-3-(2-(4-pyridyl)(1,3-thiazol-4-yl))-1,3,4-trihydroquinazolin-2-one;
3-(4-(4-pyridyl)-1,3-thiazol-2-yl)-1,3,4-trihydroquinazolin-2-one;
3-(4-(3-pyridyl)-1,3-thiazol-2-yl)-1,3,4-trihydroquinazolin-2-one;
7-(2-(4-pyridyl)-1,3-thiazol-4-yl)-5,7,8-trihydro-2H-1,3-dioxolano[4,5-g]quinazolin-6-one;
methyl 2-oxo-3-(2-(4-pyridyl)(1,3-thiazol-4-yl))-1,3,4-trihydroquinazoline-7-carboxylate;
7-(2-(4-pyridyl)-1,3-thiazol-4-yl)-6,7,9-trihydro-2H-1,3-dioxoleno[4,5-h]quinazolin-8-one;
7-bromo-3-(2-(4-pyridyl)(1,3-thiazol-4-yl))-1,3,4-trihydroquinazolin-2-one;
7-(morpholin-4-ylmethyl)-3-(2-(4-pyridyl)(1,3-thiazol-4-yl))-1,3,4-trihydroquinazolin-2-one;
7-amino-3-(2-(4-pyridyl)(1,3-thiazol-4-yl))-1,3,4-trihydroquinazolin-2-one;
5-(azaperhydroepinylmethyl)-3-(2-(4-pyridyl)(1,3-thiazol-4-yl))-1,3,4-trihydroquinazolin-2-one;
7-(3-methoxyphenyl)-3-(2-(4-pyridyl)(1,3-thiazol-4-yl))-1,3,4-trihydroquinazolin-2-one;
7-(3-hydroxyphenyl)-3-(2-(4-pyridyl)(1,3-thiazol-4-yl))-1,3,4-trihydroquinazolin-2-one;
7-[3-(2-piperidylethoxy)phenyl]-3-(2-(4-pyridyl)(1,3-thiazol-4-yl))-1,3,4-trihydroquinazolin-2-one;
7-(piperidylmethyl)-3-(2-(4-pyridyl)(1,3-thiazol-4-yl))-1,3,4-trihydroquinazolin-2-one;
5-phenyl-3-(2-(4-pyridyl)(1,3-thiazol-4-yl))-1,3,4-trihydroquinazolin-2-one;
3-[2-(2-ethyl-4-pyridyl)-1,3-thiazol-4-yl]-1,3,4-trihydroquinazolin-2-one;
6-(4-methylpiperazinyl)-3-(4-(4-pyridyl)(1,3-thiazol-2-yl))-1,3,4-trihydroquinazolin-2-one;
5-chloro-3-(4-(4-pyridyl)(1,3-thiazol-2-yl))-1,3,4-trihydroquinazolin-2-one;
5-fluoro-3-(4-(4-pyridyl)(1,3-thiazol-2-yl))-1,3,4-trihydroquinazolin-2-one;
3-(3-(4-pyridyl)-1,2,4-thiadiazol-5-yl)-1,3,4-trihydroquinazolin-2-one;
3-[4-(4-hydroxyphenyl)-1,3-thiazol-2-yl]-1,3,4-trihydroquinazolin-2-one;
6,7-dimethoxy-3-(3-(4-pyridyl)(1,2,4-thiadiazol-5-yl))-1,3,4-trihydroquinazolin-2-one;
3-(3-(4-pyridyl)(1,2,4-thiadiazol-5-yl))-7-(trifluoromethyl)-1,3,4-trihydroquinazolin-2-one;
5-morpholin-4-yl-3-(3-(4-pyridyl)(1,2,4-thiadiazol-5-yl))-1,3,4-trihydroquinazolin-2-one;
6-[((2S)-1-methylpyrrolidin-2-yl)methoxy]-3-(3-(4-pyridyl)(1,2,4-thiadiazol-5-yl))-1,3,4-trihydroquinazolin-2-one;

5-[((2S)-1-methylpyrrolidin-2-yl)methoxy]-3-(3-(4-pyridyl)(1,2,4-thiadiazol-5-yl))-1,3,4-trihydroquinazolin-2-one;

5-(3-methoxyphenyl)-3-(2-(4-pyridyl)(1,3-thiazol-4-yl))-1,3,4-trihydroquinazolin-2-one;

7-hydroxy-3-(2-(4-pyridyl)(1,3-thiazol-4-yl))-1,3,4-trihydroquinazolin-2-one;

6-(4-methylpiperazinyl)-3-(2-(4-pyridyl)(1,3-thiazol-4-yl))-1,3,4-trihydro-quinazolin-2-one; and 7-{[(2R)-2-(methoxymethyl)pyrrolidinyl]methyl}-3-(2-(4-pyridyl)(1,3-thiazol-4-yl))-1,3,4-trihydroquinazolin-2-one.

10. A compound of claim 1 having Formula III

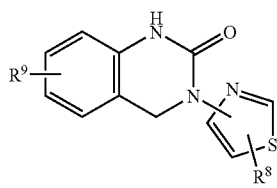

III wherein the thiazole ring is substituted in positions 2 and 4;

wherein $R^8$ is selected from pyridyl, pyrazinyl, pyrimidinyl and pyridazinyl; wherein $R^8$ is unsubstituted or substituted with one or more substituents selected from chloro, fluoro, —$NH_2$, —OH, —$CO_2H$, ($C_1$–$C_2$)alkylamino, ($C_1$–$C_2$)alkyl, di($C_1$–$C_2$)alkylamino, ($C_1$–$C_2$)alkylamino($C_1$–$C_2$)alkyl, hydroxy-($C_1$–$C_2$)alkylamino, 5–6-membered heterocyclyloxy, 5–6-membered heterocyclyl-($C_1$–$C_2$)alkoxy, ($C_1$–$C_2$)alkoxy, phenyl, pyrrolidinyl, piperazinyl, piperidinyl, morpholinyl and azetidinyl;

wherein $R^9$ is one or more substituents selected from H, hydroxy, ($C_1$–$C_4$)alkyl-O—, optionally substituted phenyl-$C_1$–$C_4$)alkyl-O—, optionally substituted 4–6 membered heterocyclyl-($C_1$–$C_4$)alkyl-O—, optionally substituted phenyl-O—, $C_{1-2}$-alkylenedioxy, halo, optionally substituted phenyl, —$NH_2$, —$NR^{11a}$—($C_1$–$C_5$)alkyl optionally substituted 4–6 membered heterocyclyl-$NR^{11a}$—, optionally substituted 4–6 membered heterocyclyl-($C_1$–$C_4$)alkyl-$NR^{11a}$, optionally substituted ($C_3$–$C_6$)cycloalkyl-($C_1$–$C_4$)alkyl-$NR^{11a}$—, —($C_1$–$C_2$)alkyl-$NH_2$, —($C_1$–$C_2$)alkyl-$NR^{11a}$—($C_1$–$C_2$)alkyl, —$SO_2NR^{11}R^{11}$, ($C_1$–$C_4$)alkylsulfonyl, ($C_1$–$C_4$)alkylthio, ($C_1$–$C_4$)alkyl, ($C_1$–$C_2$)haloalkyl, hydroxy-($C_1$–$C_2$)alkyl, hydroxy-($C_1$–$C_4$)-alkylamino, [(($C_1$–$C_2$)alkyl)$_2$N—($C_1$–$C_4$)-alkyl]-$NR^{11a}$—, ($C_1$–$C_2$)-alkyl$NR^{11a}$—($C_1$–$C_4$)-alkyl-O—, ($C_3$–$C_6$)cycloalkyl, optionally substituted 4–6 membered heterocyclyl-sulfonyl, optionally substituted heterocyclyl selected from pyrrolidinyl, piperazinyl, piperidinyl, and morpholinyl, —C(O)$^{11}$, —$NR^{11a}SO_2R^{11}$, —C(O)N($R^{11}$)$_2$, —$CO_2^{11}$, optionally substituted phenyl-($C_1$–$C_4$)aminoalkyl, optionally substituted phenyl-($C_1$–$C_2$)alkyl, optionally substituted 5–7 membered heterocyclyl-$C_1$–$C_4$-alkyl, —$NR^{11a}C(O)R^{11}$ and —$NR^{11a}CO_2R^{11a}$;

wherein $R^{11}$ is selected from H, ($C_1$–$C_6$)alkyl, $C_1$–$C_6$ aminoalkyl optionally substituted with optionally substituted phenyl, optionally substituted phenyl, optionally substituted phenyl-($C_1$–$C_4$)alkyl, optionally substituted 4–6 membered heterocyclyl, optionally substituted 4–6 membered heterocyclyl-($C_1$–$C_4$)alkyl, ($C_3$–$C_6$)cycloalkyl, ($C_3$–$C_6$)cycloalkyl-($C_1$–$C_4$)alkyl and ($C_1$–$C_2$)haloalkyl;

wherein each $R^{11a}$ is independently selected from H and methyl; and wherein each phenyl, cycloalkyl and heterocyclyl moiety is optionally substituted with one or more groups selected from halo, —$NH_2$, —OH, —$CO_2H$, ($C_1$–$C_4$)alkylamino, ($C_1$–$C_4$)alkyl, di($C_1$–$C_4$)alkylamino, ($C_1$–$C_4$)haloalkyl, pyrrolidinyl, piperazinyl, piperidinyl, morpholinyl, and azetidinyl;

and pharmaceutically acceptable salt thereof;

provided the compound is not 3-(2-pyridin-3-yl-thiazol-4-yl)-3,4-dihydro-1H-quinazolin-2-one or 6-methyl-3-(2-pyridin-2-yl-thiazol-4-yl)-3,4-dihydro-1H-quinazolin-2-one.

11. A compound of claim 10 wherein $R^8$ is unsubstituted 4-pyridyl or 4-pyridyl substituted with one or more substituents selected from chloro, fluoro, —$NH_2$, —OH, —$CO_2H$, methylamino, methyl, ethyl, diethyl-amino, pyrrolidinyl, piperazinyl, piperidinyl, morpholinyl and azetidinyl; and wherein $R^9$ is one or more radicals selected from H, (tert-butoxycarbonyl)amino, cyclopropylmethylamino, 3-hydroxypropylamino, 2-(piperidin-1-yl)ethylamino, 2-(pyrrolidin-1-yl)ethylamino, 2-(morpholin-4-yl)ethylamino, 3-(piperidin-1-yl)propylamino, 3-(pyrrolidin-1-yl)propylamino, 3-(morpholin-4-yl)propylamino, N-methyl-N-(2-piperid-1-ylethyl)amino, N-methyl-N-(2-pyrrolidin-1-ylethyl)amino, N-methyl-N-(2-morpholin-4-ylethyl)amino, ((2S)-2-amino-3-phenylpropyl)amino, 4-methylpiperazin-1-ylamino, 4-methylpiperazin-1-yl, 3-aminopyrrolidin-1-yl, (diethylamino)ethylamino, 3,5-dimethylpiperazin-1-yl, (4-piperidylmethyl)amino, (2-methylbutyl)amino, 2-(dimethylamino)ethoxy, 2-(methylamino)ethoxy, ((2R)pyrrolidin-2-yl)methoxy, ((2R)-1-methylpyrrolidin-2-yl)methoxy, 2-(piperid-1-yl)ethoxy, 2-(piperazin-1-yl)ethoxy, 2-morpholin-4-ylethoxy, 3-(N,N-diethylamino)propoxy, optionally substituted phenoxy, 3-(morpholin-4-yl)propoxy, methylenedioxy, hydroxy, benzyloxy, methoxy, chloro, fluoro, bromo, optionally substituted phenyl, amino, methylamino, diethylamino, aminomethyl, dimethylaminoethyl, N-(N',N'-diethylaminoethyl)-N-methylamino, aminosulfonyl, piperazinylsulfonyl, methylthio, methylsulfonyl, methyl, cyclopropyl, pyrrolidinyl, piperazinyl, 4-methylpiperazinyl, piperidinyl, morpholinyl, methylcarbonyl, phenylcarbonyl, piperidinylcarbonyl, trifluoromethyl, hydroxymethyl, hydroxyethyl, diethylaminocarbonyl, carboxy, methoxycarbonyl, optionally substituted benzyl, 1-azepanylmethyl, (2-methoxymethylpyrrolidin-1-yl)methyl, piperazinylmethyl, 4-methylpiperazinylmethyl, piperidinylmethyl, and morpholinylmethyl; and pharmaceutically acceptable salt thereof.

12. A compound of claim 1 having Formula IV

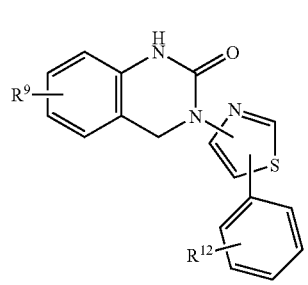

IV wherein the thiazole ring is substituted in positions 2 and 4;

wherein $R^9$ is one or more radicals selected from H, hydroxy, $(C_1-C_4)$alkyl-O—, optionally substituted phenyl-$C_1-C_4$)alkyl-O—, optionally substituted 4–6 membered heterocyclyl-$(C_1-C_4)$alkyl-O—, optionally substituted phenyl-O—, $C_{1-2}$-alkylenedioxy, halo, optionally substituted phenyl, —$NH_2$, —$NR^{11a}$—$(C_1-C_5)$alkyl optionally substituted 4–6 membered heterocyclyl-$NR^{11a}$—, optionally substituted 4–6 membered heterocyclyl-$(C_1-C_4)$alkyl-$NR^{11a}$—, optionally substituted $(C_3-C_6)$cycloalkyl-$(C_1-C_4)$alkyl-$NR^{11a}$—$(C_1-C_2)$alkyl-$NH_2$, —$(C_1-C_2)$alkyl-$NR^{11a}$—$(C_1-C_2)$alkyl, —$SO_2NR^{1111}$, $(C_1-C_4)$alkylsulfonyl, $(C_1-C_4)$alkylthio, $(C_1-C_4)$alkyl, $(C_1-C_2)$haloalkyl, hydroxy-$(C_1-C_2)$alkyl, hydroxy-$(C_1-C_4)$-alkylamino, $[((C_1-C_2)$alkyl$)_2N$—$(C_1-C_4)$-alkyl]-$NR^{11a}$—, $(C_1-C_2)$-alkyl$NR^{11a}$—$(C_1-C_4)$-alkyl-O—, $(C_3-C_6)$cycloalkyl, optionally substituted 4–6 membered heterocyclyl-sulfonyl, optionally substituted heterocyclyl selected from pyrrolidinyl, piperazinyl, piperidinyl, and morpholinyl, —$C(O)^{11}$, —$NR^{11a}SO_2R^{11}$, —$C(O)N(R^{11})_2$, —$CO_2^{11}$, optionally substituted phenyl-$(C_1-C_4)$aminoalkyl, optionally substituted phenyl-$(C_1-C_2)$alkyl, optionally substituted 5–7 membered heterocyclyl-$C_1-C_4$-alkyl, —$NR^{11a}C(O)R^{11}$ and —$NR^{11a}CO_2R^{11a}$;

wherein each $R^{11}$ is independently selected from H, $(C_1-C_6)$alkyl, $C_1-C_6$)aminoalkyl optionally substituted with optionally substituted phenyl, optionally substituted phenyl, optionally substituted phenyl-$(C_1-C_4)$alkyl, optionally substituted 4–6 membered heterocyclyl, optionally substituted 4–6 membered heterocyclyl-$(C_1-C_4)$alkyl, $(C_3-C_6)$cycloalkyl, $(C_3-C_6)$cycloalkyl-$(C_1-C_4)$alkyl and $(C_1-C_2)$haloalkyl;

wherein each $R^{11a}$ is independently selected from H and methyl;

wherein $R^{12}$ is one or more substituents selected from hydroxyl, halo, aryl, $(C_2-C_4)$alkynyl, $(C_2-C_4)$alkenyl, —$OR^{11}$, —$N(R^{11})_2$, —$(C_1-C_4)$alkyl-$N(R^{11})_2$, lower alkyloxyalkyl, $R^{11}$—$SO_2$—, $(C_1-C_4)$alkyl, cyano, nitro, lower cyanoalkyl, lower haloalkyl, lower hydroxyalkyl, lower aminoalkyl, lower alkylaminoalkyl, lower alkylaminoalkoxy, lower aminoalkoxyalkyl, $(C_3-C_6)$cycloalkyl, optionally substituted 4–6 membered heterocyclyl, optionally substituted phenoxyalkyl, optionally substituted heterocyclyloxyalkyl, —$SO_2NR^{11}R^{11}$, —$NR^{11}SO_2^{11}$, —$C(O)N(R^{11})_2$, —$CO_2R^{11}$, —$CO_2NR^{11}R^{11}$, —$SO_2NHC(O)R^{11}$, optionally substituted phenyl-$(C_1-C_4)$alkyl, optionally substituted heterocyclyl-$(C_1-C_4)$alkyl, —$NR^{11}C(O)N(R^{11})_2$, —$NR^{11}C(O)R^{11}$, —$NR^{11}CO_2R^{11}$ and —$C(O)R^{11}$; and wherein each phenyl, cycloalkyl, and heterocyclyl moiety is optionally substituted with one or more groups selected from halo, —$NH_2$, —OH, —$CO_2H$, $(C_1-C_4)$alkylamino, $(C_1-C_4)$alkyl, di$(C_1-C_4)$alkylamino, $(C_1-C_4)$haloalkyl, pyrrolidinyl, piperazinyl, piperidinyl, morpholinyl, and azetidinyl;

and pharmaceutically acceptable salt thereof.

13. A compound of claim 12 wherein $R^9$ is one or more radicals selected from H, (tert-butoxycarbonyl)amino, ((2R)-1-methylpyrrolidin-2-yl)methoxy, 3-(N,N-diethylamino)propoxy, optionally substituted phenoxy, 3-(morpholin-4-yl)propoxy, hydroxy, methylenedioxy, methoxy, bromo, chloro, fluoro, optionally substituted phenyl, amino, N-(N',N'-diethylaminoethyl)-N-methylamino, trifluoromethyl, methyl, 4-methylpiperazinyl, piperidinyl, morpholinyl, N,N-diethylaminocarbonyl, methoxycarbonyl, carboxy, 1-azepanylmethyl, 4-methylpiperazinylmethyl, (2-methoxymethylpyrrolidin-1-yl)methyl, piperidinylmethyl, and morpholinylmethyl; and wherein $R^{12}$ is one or more radicals selected from hydroxyl, chloro, fluoro, and methoxy; and pharmaceutically acceptable salt thereof.

14. A compound of claim 1 having Formula Va or Vb

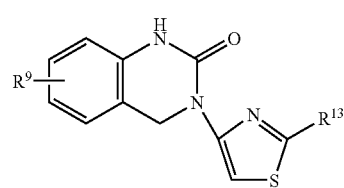

Va

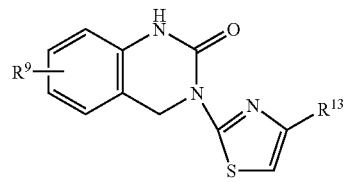

Vb wherein $R^9$ is one or more radicals selected from H, hydroxy, $(C_1-C_4)$alkyl-O—, optionally substituted phenyl-$C_1-C_4$)alkyl-O—, optionally substituted 4–6 membered heterocyclyl-$(C_1-C_4)$alkyl-O—, optionally substituted phenyl-O—, $C_{1-2}$-alkylenedioxy, halo, optionally substituted phenyl, —$NH_2$, —$NR^{11a}$—$(C_1-C_5)$alkyl, optionally substituted 4–6 membered heterocyclyl-$NR^{11a}$—, optionally substituted 4–6 membered heterocyclyl-$(C_1-C_4)$alkyl-$NR^{11a}$—, optionally substituted $(C_3-C_6)$cycloalkyl-$(C_1-C_4)$alkyl-$NR^{11a}$, —$(C_1-C_2)$alkyl-$NH_2$, —$(C_1-C_2)$alkyl-$NR^{11a}$—$(C_1-C_2)$alkyl, —$SO_2NR^{11}R^{11}$, $(C_1-C_4)$alkylsulfonyl, $(C_1-C_4)$alkylthio, $(C_1-C_4)$alkyl, $(C_1-C_2)$haloalkyl, hydroxy-$(C_1-C_2)$alkyl, hydroxy-$(C_1-C_4)$-alkylamino, $[((C_1-C_2)$alkyl$)_2N$—$(C_1-C_4)$-alkyl]-$NR^{11a}$—, $(C_1-C_2)$-alkyl$NR^{11a}$—$(C_1-C_4)$-alkyl-O—, $(C_3-C_6)$cycloalkyl, optionally substituted 4–6 membered heterocyclyl-sulfonyl, optionally substituted heterocyclyl selected from pyrrolidinyl, piperazinyl, piperidinyl, and morpholinyl, —$C(O)^{11}$, —$NR^{11a}SO_2R^{11}$, —$C(O)N(R^{11})_2$, —$CO_2^{11}$, optionally substituted phenyl-$(C_1-C_4)$aminoalkyl, optionally substituted phenyl- ($C_1$–$C_2$)alkyl, optionally substituted 5–7 membered heterocyclyl-$C_1$–$C_4$-alkyl, —$NR^{11a}C(O)R^{11}$ and —$NR^{11a}CO_2R^{11a}$;

wherein each $R^{11}$ is independently selected from H, ($C_1$–$C_6$)alkyl, $C_1$–$C_6$)aminoalkyl optionally substituted with optionally substituted phenyl, optionally substituted phenyl, optionally substituted phenyl-($C_1$–$C_4$)alkyl, optionally substituted 4–6 membered heterocyclyl, optionally substituted 4–6 membered heterocyclyl-($C_1$–$C_4$)alkyl, ($C_3$–$C_6$)cycloalkyl, ($C_3$–$C_6$)cycloalkyl-($C_1$–$C_4$)alkyl and ($C_1$–$C_2$)haloalkyl;

wherein each $R^{11a}$ is independently selected from H and methyl;

wherein $R^{13}$ is selected from 6-membered nitrogen containing heteroaryl and $R^{11}$sulfonyl-($C_{1-2}$)alkyl; and wherein each phenyl, cycloalkyl, and heterocyclyl moiety is optionally substituted with one or more groups selected from halo, —$NH_2$, —OH, —$CO_2H$, ($C_1$–$C_4$)alkylamino, ($C_1$–$C_4$)alkyl, di($C_1$–$C_4$)alkylamino, ($C_1$–$C_4$)haloalkyl, pyrrolidinyl, piperazinyl, piperidinyl, morpholinyl, and azetidinyl;

and pharmaceutically acceptable salt thereof;

provided the compound is not 3-(2-pyridin-3-yl-thiazol-4-yl)-3,4-dihydro-1H-quinazolin-2-one or 6-methyl-3-(2-pyridin-2-yl-thiazol-4-yl)-3,4-dihydro-1H-quinazolin-2-one.

15. Compound of claim 14 wherein $R^9$ is one or more radicals selected from H, (tert-butoxycarbonyl)amino, ((2R)-1-methylpyrrolidin-2-yl)methoxy, 3-(N,N-diethylamino)propoxy, optionally substituted phenoxy, 3-(morpholin-4-yl)propoxy, hydroxy, methylenedioxy, methoxy, bromo, chloro, fluoro, optionally substituted phenyl, amino, N-(N',N'-diethylaminoethyl)-N-methylamino, trifluoromethyl, methyl, 4-methylpiperazinyl, piperidinyl, morpholinyl, N,N-diethylaminocarbonyl, methoxycarbonyl, carboxy, 1-azepanylmethyl, 4-methylpiperazinylmethyl, (2-methoxymethylpyrrolidin-1-yl)methyl, piperidinylmethyl, and morpholinylmethyl; and wherein $R^{13}$ is selected from 4-pyridyl, 3-ethyl-4-pyridyl, and 4-chlorophenylsulfonylmethyl; and pharmaceutically acceptable derivatives thereof.

16. A compound of claim 14 wherein $R^{13}$ is 4-pyridyl; and pharmaceutically acceptable salt thereof.

17. A compound of claim 1 wherein W is

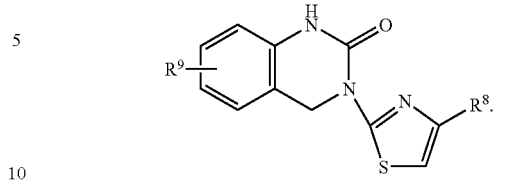

18. A compound of claim 7 having the formula

19. A compound of claim 7 having the formula

20. A compound of claim 10 having the formula

21. A compound of claim 10 having the formula

22. A compound of claim 12 having the formula

23. A compound of claim 12 having the formula

24. A pharmaceutical composition comprising a pharmaceutically acceptable carrier and a compound of any one of claims 1 and 2–23.

* * * * *